United States Patent
Romero et al.

(10) Patent No.: US 9,518,065 B2
(45) Date of Patent: Dec. 13, 2016

(54) IRAK INHIBITORS AND USES THEREOF

(71) Applicant: NIMBUS IRIS, INC., Cambridge, MA (US)

(72) Inventors: Donna Romero, Chesterfield, MO (US); Craig E. Masse, Cambridge, MA (US); Shaughnessy Robinson, Westerly, RI (US); Jeremy Robert Greenwood, Brooklyn, NY (US); Geraldine C. Harriman, Charlestown, RI (US)

(73) Assignee: Nimbus Iris, Inc., Cambridge, MA (US)

( * ) Notice: Subject to any disclaimer, the term of this patent is extended or adjusted under 35 U.S.C. 154(b) by 0 days.

(21) Appl. No.: 14/496,501

(22) Filed: Sep. 25, 2014

(65) Prior Publication Data

US 2015/0094305 A1    Apr. 2, 2015

Related U.S. Application Data

(60) Provisional application No. 61/883,497, filed on Sep. 27, 2013.

(51) Int. Cl.
| | | |
|---|---|---|
| *A01N 43/90* | (2006.01) | |
| *A61K 31/519* | (2006.01) | |
| *C07D 239/00* | (2006.01) | |
| *C07D 471/00* | (2006.01) | |
| *C07D 487/00* | (2006.01) | |
| *C07D 491/00* | (2006.01) | |
| *C07D 513/04* | (2006.01) | |
| *C07D 519/00* | (2006.01) | |

(52) U.S. Cl.
CPC ........... *C07D 513/04* (2013.01); *A61K 31/519* (2013.01); *C07D 519/00* (2013.01)

(58) Field of Classification Search
None
See application file for complete search history.

(56) References Cited

U.S. PATENT DOCUMENTS

| | | | |
|---|---|---|---|
| 3,627,766 A | 12/1971 | Eichenberger et al. | |
| 5,948,911 A | 9/1999 | Pamukcu et al. | |
| 6,297,238 B1 | 10/2001 | Doyle et al. | |
| 6,482,948 B1 | 11/2002 | Yamada et al. | |
| 6,734,180 B1 | 5/2004 | Nunokawa et al. | |
| 7,829,570 B2 | 11/2010 | Hirst et al. | |
| 7,947,693 B2 | 5/2011 | Nordvall et al. | |
| 8,053,438 B2 | 11/2011 | Allen et al. | |
| 8,058,285 B2 | 11/2011 | Reichelt et al. | |
| 8,247,418 B2 | 8/2012 | Allen et al. | |
| 8,288,397 B2 | 10/2012 | Branstetter et al. | |
| 8,318,718 B2 | 11/2012 | Allen et al. | |
| 8,329,700 B2 | 12/2012 | Allen et al. | |
| 8,637,527 B2 | 1/2014 | Branstetter et al. | |
| 8,703,941 B2 | 4/2014 | Romero et al. | |
| 9,067,948 B2 | 6/2015 | Harriman et al. | |
| 9,085,586 B2 | 7/2015 | Romero et al. | |
| 9,175,007 B2 | 11/2015 | Greenwood et al. | |
| 9,212,190 B2 | 12/2015 | Harriman et al. | |
| 9,340,554 B2 | 5/2016 | Romero et al. | |
| 2002/0058667 A1 | 5/2002 | Castelhano et al. | |
| 2003/0119829 A1 | 6/2003 | Stolle et al. | |
| 2007/0155777 A1 | 7/2007 | Burkitt et al. | |
| 2008/0004253 A1 | 1/2008 | Branstetter et al. | |
| 2008/0176871 A1 | 7/2008 | Girardet et al. | |
| 2009/0163545 A1 | 6/2009 | Goldfarb | |
| 2009/0247554 A1 | 10/2009 | Dong et al. | |
| 2010/0041676 A1 | 2/2010 | Hirst et al. | |
| 2010/0063047 A1 | 3/2010 | Borchardt et al. | |
| 2010/0143341 A1 | 6/2010 | Taylor et al. | |
| 2010/0227853 A1 | 9/2010 | Hoffman et al. | |
| 2012/0015962 A1 | 1/2012 | Arora et al. | |
| 2012/0046278 A1 | 2/2012 | Herdewijn et al. | |
| 2012/0277209 A1 | 11/2012 | Allen et al. | |
| 2012/0283238 A1 | 11/2012 | Romero et al. | |
| 2013/0190297 A1 | 7/2013 | De Jonghe et al. | |
| 2013/0231328 A1 | 9/2013 | Harriman et al. | |
| 2014/0018343 A1 | 1/2014 | Romero et al. | |
| 2014/0018357 A1 | 1/2014 | Harriman et al. | |
| 2014/0018361 A1 | 1/2014 | Harriman et al. | |
| 2016/0002256 A1 | 1/2016 | Harriman et al. | |
| 2016/0002257 A1 | 1/2016 | Romero et al. | |
| 2016/0068543 A1 | 3/2016 | Greenwood et al. | |
| 2016/0193216 A1 | 7/2016 | Harriman et al. | |

FOREIGN PATENT DOCUMENTS

| | | | |
|---|---|---|---|
| EP | 1167367 A1 | 1/2002 | |
| JP | 3109012 B2 | 11/2000 | |

(Continued)

OTHER PUBLICATIONS

International Search Report and Written Opinion issued by the United States Patent and Trademark Office as International Searching Authority for International Application No. PCT/US2014/057444 mailed Dec. 12, 2014 (10 pages).

(Continued)

*Primary Examiner* — Jeffrey H Murray
(74) *Attorney, Agent, or Firm* — Andrea L. C. Reid; Dechert LLP

(57) ABSTRACT

The present invention provides compounds of the general formula I:

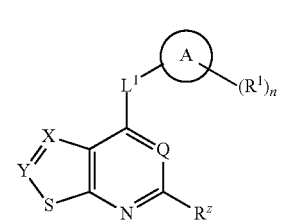

or a pharmaceutically acceptable salt thereof, wherein each variable is as defined and described herein, as inhibitors of one or more interleukin-1 receptor-associated kinases ("IRAK").

14 Claims, No Drawings

(56) References Cited

FOREIGN PATENT DOCUMENTS

| | | |
|---|---|---|
| WO | WO-00/05234 A1 | 2/2000 |
| WO | WO-02088138 A1 | 11/2002 |
| WO | WO-03057149 A2 | 7/2003 |
| WO | WO-2004041285 A1 | 5/2004 |
| WO | WO-2004089312 A2 | 10/2004 |
| WO | WO-2005037213 A2 | 4/2005 |
| WO | WO-2006010567 A1 | 2/2006 |
| WO | WO-2006136402 A1 | 12/2006 |
| WO | WO-2007/117995 A2 | 10/2007 |
| WO | WO-2008/005303 A2 | 1/2008 |
| WO | WO-2008152390 A1 | 12/2008 |
| WO | WO-2009/078999 A1 | 6/2009 |
| WO | WO-2010/057121 A1 | 5/2010 |
| WO | WO-2010/057126 A1 | 5/2010 |
| WO | WO-2011029054 | 3/2011 |
| WO | WO-2011072127 A1 | 6/2011 |
| WO | WO-2012007375 A1 | 1/2012 |
| WO | WO-2012012712 | 1/2012 |
| WO | WO-2012097013 A1 | 7/2012 |
| WO | WO-2013078126 A1 | 5/2013 |
| WO | WO-2013106535 | 7/2013 |
| WO | WO-2014011902 A1 | 1/2014 |
| WO | WO-2014011906 | 1/2014 |
| WO | WO-2014011911 | 1/2014 |
| WO | WO-2014110114 | 7/2014 |
| WO | WO-2014194201 A2 | 12/2014 |
| WO | WO-2014194242 A2 | 12/2014 |
| WO | WO-2014194245 A2 | 12/2014 |

OTHER PUBLICATIONS

Agrawal et al., "Ligand-Based Pharmacophore Detection and Screening of Potential Glitazones," Current Enzyme Inhibition, vol. 8, No. 1, No Month Listed 2012 (pp. 22-46).

Ananthan et al., "High-throughput screening for inhibitors of Mycobacterium tuberculosis H37Rv," Tuberculosis, vol. 89, No. 5, Sep. 2009 (pp. 334-353).

Bahia et al., "Interleukin-1 receptor associated kinase inhibitors: Potential therapeutic agents for inflammatory-and-immune-related disorders," Cellular Signalling, vol. 27, No Month Listed 2015 (pp. 1039-1055).

Bogolubsky et al., "Synthesis of Thieno[2,3-d]pyrimidin-2-ylmethanamine Combinatorial Library with Four Diversity Points Supporting Information," Journal of Combinatorial Chemistry, vol. 9, No. 4, No Month Listed 2007 (pp. 661-667).

CAS STN Abstract, RN 1185175-64-7 & 1008036-50-7 (Pub. Mar. 14, 2008 & Sep. 16, 2009).

Database Registry [Online], Chemical Abstracts Service, XP002746325, retrieved from STN Database accession No. 944643-89-4 *compounds 944643-89-4*, Columbus, Ohio, No Month Listed 2007 (1 page).

Database Registry [Online], Chemical Abstracts Service, XP002746326, retrieved from STN Database accession No. 665010-65-1 *compounds 665010-65-1*, Columbus, Ohio, No Month Listed 2004 (1 page).

Database Registry [Online], Chemical Abstracts Service, XP002746327, retrieved from STN Database accession No. 382641-25-0 *compounds 382641-25-0*, Columbus, Ohio, No Month Listed 2002 (1 page).

Extended European Search Report issued by the European Patent Office for European Patent Application No. 12734553.6 dated Sep. 24, 2014 (13 pages).

Extended European Search Report issued by the European Patent Office for European Patent Application No. 13817066.7 mailed Oct. 30, 2015 (8 pages).

Extended European Search Report issued by the European Patent Office for European Patent Application No. 13817012.1 mailed Apr. 20, 2016 (7 pages).

Iaroshenko et al., "3-Formylchromones, Acylpyruvates, and Chalcone as Valuable Substrates for the Syntheses of Fused Pyridines," Synthesis, No. 16, Aug. 2010 (pp. 2749-2758).

International Search Report and Written Opinion issued by the United States Patent and Trademark Office as International Searching Authority for International Application No. PCT/US2012/020845 mailed May 16, 2012 (7 pages).

International Search Report and Written Opinion issued by the United States Patent and Trademark Office as International Searching Authority for International Application No. PCT/US2013/020981 mailed Mar. 18, 2013 (8 pages).

International Search Report and Written Opinion issued by the United States Patent and Trademark Office as International Searching Authority for International Application No. PCT/US2013/050108 mailed Dec. 16, 2013 (20 pages).

International Search Report and Written Opinion issued by the United States Patent and Trademark Office as International Searching Authority for International Application No. PCT/US2013/050113 mailed Dec. 9, 2013 (18 pages).

International Search Report and Written Opinion issued by the United States Patent and Trademark Office as International Searching Authority for International Application No. PCT/US2013/050120 mailed Dec. 9, 2013 (25 pages).

International Search Report and Written Opinion issued by the United States Patent and Trademark Office as International Searching Authority for International Application No. PCT/US2014/010652 mailed Apr. 30, 2014 (7 pages).

Kadoshima-Yamaoka et al., "ASB16165, a novel inhibitor for phosphodiesterase 7A (PDE7A), suppresses IL-12-induced IFN-gamma production by mouse activated T lymphocytes," Immunology Letters, vol. 122, No. 2, No Month Listed 2009 (pp. 193-197).

Mohammad Emad Azaba, "Utility of the Enaminonitrile Moiety in the Synthesis of Some Biologically Active Thienopyrimidine Derivates," Phosphorus, Sulfur, and Silicon, vol. 183, No Month Listed 2008 (pp. 1766-1782).

Modica et al., "Synthesis and binding properties of novel selective 5-HT3 receptor ligand," Bioorganic & Medicinal Chemistry, vol. 12, No Month Listed 2004 (pp. 3891-3901).

Ngo et al., Oncogenically active MYD88 mutations in human lymphoma, Nature, vol. 470, No. 7332, Feb. 2011 (pp. 115-119).

No Author Listed, "Drugs Approved for Melanoma," National Cancer retrieved from internet <http://www.cancer.gov/cancertopics/druginfo/melanoma> accessed 2013 (2 pages).

No Author Listed, "Understanding Psoriasis—Treatment," WebMD, retrieved from internet <http://www.webmd.com/skin-problems-and-treatments/psoriasis/understanding-psoriasis-treatment> accessed 2014 (4 pages).

Noravyan et al., "Synthesis and anticonvulsive activity of 4-alkyl (or aryl) amino-6,6-dimethyl-5,6-dihydro-8H-pyrano (or thiopyrano) [3,4-b] thieno [5,4-d]pyrimidines," Khimiko-Farmatsevticheskii Zhurnal, vol. 11, No. 9, No Month Listed 1977 (pp. 38-42).

Patani et al., "Bioisosterism: A Rational Approach in Drug Design," Chemical Review, vol. 96, No Month Listed 1996 (pp. 3147-3176).

Sauter et al., "Syntheses of fully aromatic pyrido[4',3':4,5]thieno[2,3-d]pyrimidine derivatives," ACH-Models in Chemistry, vol. 131, No. 3-4, No Month Listed 1994 (pp. 489-498).

Song et al., "The kinase activities of interleukin-1 receptor associated kinase (IRAK)-1 and 4 are redundant in the control of inflammatory cytokine expression in human cells," Molecular Immunology, vol. 46, No. 7, No Month Listed 2009 (pp. 1458-1466).

Wagner et al., "Synthese neuer Pyrido[3',2':4,5]thieno[3,2-d]1,2,3-triazin-Derivate als Antianaphylaktika," Pharmazie, vol. 48, No. 7, No Month Listed 1993 (6 pages) with English Abstract.

Wang, "IRAK-4 Inhibitors for Inflammation," Current Topics in Medicinal Chemistry, vol. 9, No. 8, No Month Listed 2009 (pp. 724-737).

IRAK INHIBITORS AND USES THEREOF

CROSS-REFERENCE TO RELATED APPLICATIONS

The present application claims priority to U.S. provisional patent application Ser. No. 61/883,497, filed Sep. 27, 2013, the entirety of which is incorporated herein by reference.

TECHNICAL FIELD OF THE INVENTION

The present invention relates to compounds and methods useful for inhibiting one or more interleukin-1 receptor-associated kinases ("IRAK"). The invention also provides pharmaceutically acceptable compositions comprising compounds of the present invention and methods of using said compositions in the treatment of various disorders.

BACKGROUND OF THE INVENTION

The search for new therapeutic agents has been greatly aided in recent years by a better understanding of the structure of enzymes and other biomolecules associated with diseases. One important class of enzymes that has been the subject of extensive study is the protein kinase family.

Protein kinases constitute a large family of structurally related enzymes that are responsible for the control of a variety of signal transduction processes within the cell. Protein kinases are thought to have evolved from a common ancestral gene due to the conservation of their structure and catalytic function. Almost all kinases contain a similar 250-300 amino acid catalytic domain. The kinases may be categorized into families by the substrates they phosphorylate (e.g., protein-tyrosine, protein-serine/threonine, lipids, etc.).

In general, protein kinases mediate intracellular signaling by effecting a phosphoryl transfer from a nucleoside triphosphate to a protein acceptor that is involved in a signaling pathway. These phosphorylation events act as molecular on/off switches that can modulate or regulate the target protein biological function. These phosphorylation events are ultimately triggered in response to a variety of extracellular and other stimuli. Examples of such stimuli include environmental and chemical stress signals (e.g., osmotic shock, heat shock, ultraviolet radiation, bacterial endotoxin, and $H_2O_2$), cytokines (e.g., interleukin-1 (IL-1), interleukin-8 (IL-8) and tumor necrosis factor $\alpha$ (TNF-$\alpha$)), and growth factors (e.g., granulocyte macrophage-colony-stimulating factor (GM-CSF), and fibroblast growth factor (FGF)). An extracellular stimulus may affect one or more cellular responses related to cell growth, migration, differentiation, secretion of hormones, activation of transcription factors, muscle contraction, glucose metabolism, control of protein synthesis, and regulation of the cell cycle.

Many diseases are associated with abnormal cellular responses triggered by kinase-mediated events. These diseases include, but are not limited to, autoimmune diseases, inflammatory diseases, bone diseases, metabolic diseases, neurological and neurodegenerative diseases, cancer, cardiovascular diseases, allergies and asthma, Alzheimer's disease, and hormone-related diseases. Accordingly, there remains a need to find protein kinase inhibitors useful as therapeutic agents.

SUMMARY OF THE INVENTION

It has now been found that compounds of this invention, and pharmaceutically acceptable compositions thereof, are effective as inhibitors of IRAK kinases. Such compounds have the general formula I:

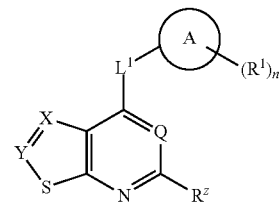

or a pharmaceutically acceptable salt thereof, wherein each variable is as defined and described herein.

Compounds of the present invention, and pharmaceutically acceptable compositions thereof, are useful for treating a variety of diseases, disorders or conditions, associated with regulation of signaling pathways implicating IRAK kinases. Such diseases, disorders, or conditions include those described herein.

Compounds provided by this invention are also useful for the study of IRAK enzymes in biological and pathological phenomena; the study of intracellular signal transduction pathways occurring in bodily tissues; and the comparative evaluation of new IRAK inhibitors or other regulators of kinases, signaling pathways, and cytokine levels in vitro or in vivo.

DETAILED DESCRIPTION OF CERTAIN EMBODIMENTS

1. General Description of Certain Embodiments of the Invention

Compounds of the present invention, and compositions thereof, are useful as inhibitors of one or more IRAK protein kinases. In some embodiments, a provided compound inhibits IRAK-1 and IRAK-4.

The binding pocket of IRAK-4 contains a plurality of hydration sites, each of which is occupied by a single molecule of water. Each of these water molecules has a stability rating associated with it. As used herein, the term "stability rating" refers to a numerical calculation which incorporates the enthalpy, entropy, and free energy values associated with each water molecule. This stability rating allows for a measurable determination of the relative stability of water molecules that occupy hydration sites in the binding pocket of IRAK-4.

Water molecules occupying hydration sites in the binding pocket of IRAK-4 having a stability rating of >2.5 kcal/mol are referred to as "unstable waters."

Without wishing to be bound by any particular theory, it is believed that displacement or disruption of an unstable water molecule (i.e., a water molecule having a stability rating of >2.5 kcal/mol), or replacement of a stable water (i.e., a water molecule having a stability rating of <1 kcal/mol), by an inhibitor results in tighter binding of that inhibitor. Accordingly, inhibitors designed to displace one or more unstable water molecules (i.e., those unstable water molecules not displaced by any known inhibitor) will be a tighter binder and, therefore, more potent inhibitor as compared to an inhibitor that does not displace unstable water molecules.

It was surprisingly found that provided compounds displace or disrupt one or more unstable water molecules. In some embodiments, a provided compound displaces or disrupts at least two unstable water molecules.

In certain embodiments, the present invention provides a compound of formula I:

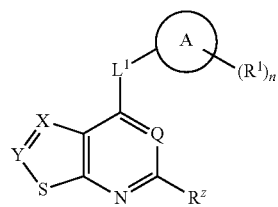

or a pharmaceutically acceptable salt thereof, wherein:
Q is CH, C—CN, or N;
X is C-L²(R⁴)ₚ—Rˣ and Y is N; or
X is N and Y is C—Rˣ;
Ring A is a 3-7 membered saturated or partially unsaturated carbocyclic ring or a 4-7 membered saturated or partially unsaturated heterocyclic ring having 1-3 heteroatoms independently selected from nitrogen, oxygen, or sulfur;
each R¹ and R¹' is independently —R², halogen, —CN, —NO₂, —OR, —SR, —N(R)₂, —S(O)₂R, —S(O)₂N(R)₂, —S(O)R, —C(O)R, —C(O)OR, —C(O)N(R)₂, —C(O)N(R)OR, —N(R)C(O)OR, —N(R)C(O)N(R)₂, Cy, or —N(R)S(O)₂R; or R¹ is selected from one of the following formulas:

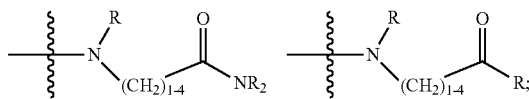

or
two R¹ groups are taken together with their intervening atoms to form an optionally substituted 4-7 membered fused, spiro-fused, or bridged bicyclic ring having 0-2 heteroatoms independently selected from nitrogen, oxygen, or sulfur;
each Cy is independently an optionally substituted ring selected from a 3-7 membered saturated or partially unsaturated carbocyclic ring or a 4-10 membered saturated or partially unsaturated heterocyclic ring having 1-3 heteroatoms independently selected from nitrogen, oxygen, or sulfur;
each R is independently hydrogen, or an optionally substituted group selected from $C_{1-6}$ aliphatic, phenyl, 4-7 membered saturated or partially unsaturated heterocyclic having 1-2 heteroatoms independently selected from nitrogen, oxygen, or sulfur, or 5-6 membered heteroaryl ring having 1-4 heteroatoms independently selected from nitrogen, oxygen, or sulfur, or:
two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, or sulfur;
each R² is independently an optionally substituted group selected from $C_{1-6}$ aliphatic, phenyl, 4-7 membered saturated or partially unsaturated heterocyclic having 1-2 heteroatoms independently selected from nitrogen, oxygen, or sulfur, or 5-6 membered heteroaryl ring having 1-4 heteroatoms independently selected from nitrogen, oxygen, or sulfur;

each R⁴ is independently halogen, —CN, —NO₂, —OR, —SR, —N(R)₂, —S(O)₂R, —S(O)₂N(R)₂, —S(O)R, —C(O)R, —C(O)OR, —C(O)N(R)₂, —N(R)C(O)R, —N(R)C(O)N(R)₂, —C(O)N(R)OR, —N(R)C(O)OR, —N(R)S(O)₂N(R)₂, —N(R)S(O)₂R, or an optionally substituted group selected from $C_{1-6}$ aliphatic, phenyl, 4-7 membered saturated or partially unsaturated heterocyclic having 1-2 heteroatoms independently selected from nitrogen, oxygen, or sulfur, or 5-6 membered heteroaryl ring having 1-4 heteroatoms independently selected from nitrogen, oxygen, or sulfur;
Rˣ is hydrogen, —R², —CN, —NO₂, halogen, —C(O)N(R)₂, —C(O)OR, —C(O)R, —N(R)₂, —NH[Ar], —OR, or —S(O)₂N(R)₂;
R$^z$ is hydrogen, —R², —CN, —NO₂, halogen, —C(O)N(R)₂, —C(O)OR, —C(O)R, —N(R)₂, —NH[Ar], —OR, or —S(O)₂N(R)₂;
[Ar] is a phenyl or heteroaromatic ring substituted by m instances of R¹';
L¹ is a covalent bond or a $C_{1-6}$ bivalent hydrocarbon chain wherein one or two methylene units of the chain are optionally and independently replaced by —N(R)—, —N(R)C(O)—, —C(O)N(R)—, —N(R)S(O)₂—, —S(O)₂N(R)—, —O—, —C(O)—, —OC(O)—, —C(O)O—, —S—, —S(O)— or —S(O)₂—;
L² is a covalent bond or a $C_{1-6}$ bivalent hydrocarbon chain wherein one or two methylene units of the chain are optionally and independently replaced by —N(R)—, —N(R)C(O)—, —C(O)N(R)—, —N(R)S(O)₂—, —S(O)₂N(R)—, —O—, —C(O)—, —OC(O)—, —C(O)O—, —S—, —S(O)— or —S(O)₂—;
m is 0-4;
n is 0-4; and
p is 0-2.

2. Compounds and Definitions

Compounds of the present invention include those described generally herein, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle," "cycloaliphatic" or "cycloalkyl"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms.

In some embodiments, "cycloaliphatic" (or "carbocycle" or "cycloalkyl") refers to a monocyclic $C_3$-$C_6$ hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

As used herein, the term "bridged bicyclic" refers to any bicyclic ring system, i.e. carbocyclic or heterocyclic, saturated or partially unsaturated, having at least one bridge. As defined by IUPAC, a "bridge" is an unbranched chain of atoms or an atom or a valence bond connecting two bridgeheads, where a "bridgehead" is any skeletal atom of the ring system which is bonded to three or more skeletal atoms (excluding hydrogen). In some embodiments, a bridged bicyclic group has 7-12 ring members and 0-4 heteroatoms independently selected from nitrogen, oxygen, or sulfur. Such bridged bicyclic groups are well known in the art and include those groups set forth below where each group is attached to the rest of the molecule at any substitutable carbon or nitrogen atom. Unless otherwise specified, a bridged bicyclic group is optionally substituted with one or more substituents as set forth for aliphatic groups. Additionally or alternatively, any substitutable nitrogen of a bridged bicyclic group is optionally substituted. Exemplary bridged bicyclics include:

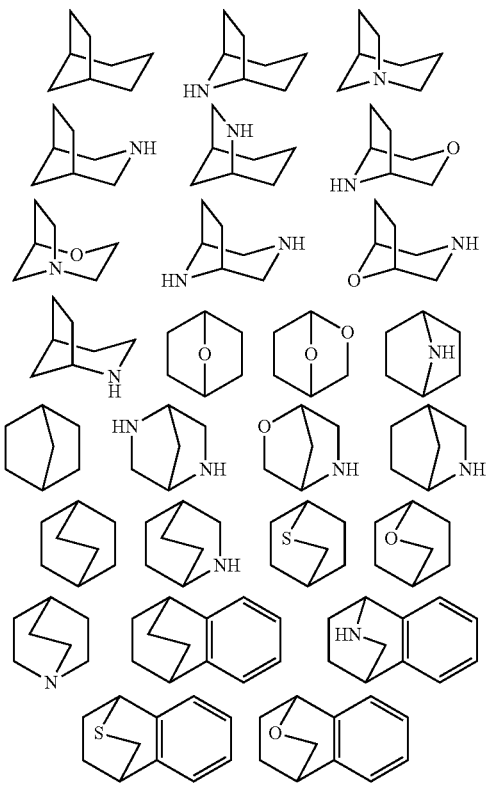

The term "lower alkyl" refers to a $C_{1-4}$ straight or branched alkyl group. Exemplary lower alkyl groups are methyl, ethyl, propyl, isopropyl, butyl, isobutyl, and tert-butyl.

The term "lower haloalkyl" refers to a $C_{1-4}$ straight or branched alkyl group that is substituted with one or more halogen atoms.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or $NR^+$ (as in N-substituted pyrrolidinyl)).

The term "unsaturated," as used herein, means that a moiety has one or more units of unsaturation.

As used herein, the term "bivalent $C_{1-8}$ (or $C_{1-6}$) saturated or unsaturated, straight or branched, hydrocarbon chain", refers to bivalent alkylene, alkenylene, and alkynylene chains that are straight or branched as defined herein.

The term "alkylene" refers to a bivalent alkyl group. An "alkylene chain" is a polymethylene group, i.e., $-(CH_2)_n-$, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

As used herein, the term "cyclopropylenyl" refers to a bivalent cyclopropyl group of the following structure:

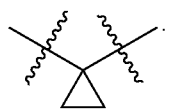 [SMILES: *C1(*)CC1]

The term "halogen" means F, Cl, Br, or I.

The term "aryl" used alone or as part of a larger moiety as in "aralkyl," "aralkoxy," or "aryloxyalkyl," refers to monocyclic or bicyclic ring systems having a total of five to fourteen ring members, wherein at least one ring in the system is aromatic and wherein each ring in the system contains 3 to 7 ring members. The term "aryl" may be used interchangeably with the term "aryl ring." In certain embodiments of the present invention, "aryl" refers to an aromatic ring system which includes, but not limited to, phenyl, biphenyl, naphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-," used alone or as part of a larger moiety, e.g., "heteroaralkyl," or "heteroaralkoxy," refer to groups having 5 to 10 ring atoms, preferably 5, 6, or 9 ring atoms; having 6, 10, or 14 π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle," "heterocyclyl," "heterocyclic radical," and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^+$NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; —$(CH_2)_{0-4}R^\circ$; —$(CH_2)_{0-4}OR^\circ$; —$O(CH_2)_{0-4}R^\circ$, —O—$(CH_2)_{0-4}C(O)OR^\circ$; —$(CH_2)_{0-4}CH(OR^\circ)_2$; —$(CH_2)_{0-4}SR^\circ$; —$(CH_2)_{0-4}Ph$, which may be substituted with $R^\circ$; —$(CH_2)_{0-4}O(CH_2)_{0-1}Ph$ which may be substituted with $R^\circ$; —CH=CHPh, which may be substituted with $R^\circ$; —$(CH_2)_{0-4}O(CH_2)_{0-1}$-pyridyl which may be substituted with $R^\circ$; —$NO_2$; —CN; —$N_3$; —$(CH_2)_{0-4}N(R^\circ)_2$; —$(CH_2)_{0-4}N(R^\circ)C(O)R^\circ$; —$N(R^\circ)C(S)R^\circ$; —$(CH_2)_{0-4}N(R^\circ)C(O)NR^\circ_2$; —$N(R^\circ)C(S)NR^\circ_2$; —$(CH_2)_{0-4}N(R^\circ)C(O)OR^\circ$; —$N(R^\circ)N(R^\circ)C(O)R^\circ$; —$N(R^\circ)N(R^\circ)C(O)NR^\circ_2$; —$N(R^\circ)N(R^\circ)C(O)OR^\circ$; —$(CH_2)_{0-4}C(O)R^\circ$; —$C(S)R^\circ$; —$(CH_2)_{0-4}C(O)OR^\circ$; —$(CH_2)_{0-4}C(O)SR^\circ$; —$(CH_2)_{0-4}C(O)OSiR^\circ_3$; —$(CH_2)_{0-4}OC(O)R^\circ$; —$OC(O)(CH_2)_{0-4}SR$—, $SC(S)SR^\circ$; —$(CH_2)_{0-4}SC(O)R^\circ$; —$(CH_2)_{0-4}C(O)NR^\circ_2$; —$C(S)NR^\circ_2$; $C(S)SR^\circ$; —$SC(S)SR^\circ$, —$(CH_2)_{0-4}OC(O)NR^\circ_2$; —$C(O)N(OR^\circ)R^\circ$; —$C(O)C(O)R^\circ$; —$C(O)CH_2C(O)R^\circ$; —$C(NOR^\circ)R^\circ$; —$(CH_2)_{0-4}SSR^\circ$; —$(CH_2)_{0-4}S(O)_2R^\circ$; —$(CH_2)_{0-4}S(O)_2OR^\circ$; —$(CH_2)_{0-4}OS(O)_2R^\circ$; —$S(O)_2NR^\circ_2$; —$(CH_2)_{0-4}S(O)R^\circ$; —$N(R^\circ)S(O)_2NR^\circ_2$; —$N(R^\circ)S(O)_2R^\circ$; —$N(OR^\circ)R^\circ$; —$C(NH)NR^\circ_2$; —$P(O)_2R^\circ$; —$P(O)R^\circ_2$; —$OP(O)R^\circ_2$; —$OP(O)(OR^\circ)_2$; $SiR^\circ_3$; —$(C_{1-4}$ straight or branched)alkylene)O—$N(R^\circ)_2$; or —$(C_{1-4}$ straight or branched)alkylene)C(O)O—$N(R^\circ)_2$, wherein each $R^\circ$ may be substituted as defined below and is independently hydrogen, $C_{1-6}$ aliphatic, —$CH_2Ph$, —$O(CH_2)_{0-1}Ph$, —$CH_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of $R^\circ$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on $R^\circ$ (or the ring formed by taking two independent occurrences of $R^\circ$ together with their intervening atoms), are independently halogen, —$(CH_2)_{0-2}R^\bullet$, -(halo$R^\bullet$), —$(CH_2)_{0-2}OH$, —$(CH_2)_{0-2}OR^\bullet$, —$(CH_2)_{0-2}CH(OR^\bullet)_2$; —O(halo$R^\bullet$), —CN, —$N_3$, —$(CH_2)_{0-2}C(O)R^\bullet$, —$(CH_2)_{0-2}C(O)OH$, —$(CH_2)_{0-2}C(O)OR^\bullet$, —$(CH_2)_{0-2}SR^\bullet$, —$(CH_2)_{0-2}SH$, —$(CH_2)_{0-2}NH_2$, —$(CH_2)_{0-2}NHR^\bullet$, —$(CH_2)_{0-2}NR^\bullet_2$, —$NO_2$, —$SiR^\bullet_3$, —$OSiR^\bullet_3$, —$C(O)SR^\bullet$, —$(C_{1-4}$ straight or branched alkylene)C(O)O$R^\bullet$, or —$SSR^\bullet$ wherein each $R^\bullet$ is unsubstituted or where preceded by "halo" is substituted only with one or more halogens, and is independently selected from $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur. Suitable divalent substituents on a saturated carbon atom of $R^\circ$ include =O and =S.

Suitable divalent substituents on a saturated carbon atom of an "optionally substituted" group include the following: =O, =S, =$NNR^*_2$, =$NNHC(O)R^*$, =$NNHC(O)OR^*$, =$NNHS(O)_2R^*$, =$NR^*$, =$NOR^*$, —$O(C(R^*_2))_{2-3}O$—, or —S(C(R*$_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R$^•$, -(haloR$^•$), —OH, —OR$^•$, —O(haloR$^•$), —CN, —C(O)OH, —C(O)OR$^•$, —NH$_2$, —NHR$^•$, —NR$^•_2$, or —NO$_2$, wherein each R$^•$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^†$, —NR$^†_2$, —C(O)R$^†$, —C(O)OR$^†$, —C(O)C(O)R$^†$, —C(O)CH$_2$C(O)R$^†$, —S(O)$_2$R$^†$, —S(O)$_2$NR$^†_2$, —C(S)NR$^†_2$, —C(NH)NR$^†_2$, or —N(R$^†$)S(O)$_2$R$^†$; wherein each R$^†$ is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R$^†$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R$^†$ are independently halogen, —R$^•$, -(haloR$^•$), —OH, —OR$^•$, —O(haloR$^•$), —CN, —C(O)OH, —C(O)OR$^•$, —NH$_2$, —NHR$^•$, —NR$^•_2$, or —NO$_2$, wherein each R$^•$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and N$^+$(C$_{1-4}$alkyl)$_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}$C- or $^{14}$C-enriched carbon are within the scope of this invention. Such compounds are useful, for example, as analytical tools, as probes in biological assays, or as therapeutic agents in accordance with the present invention. In certain embodiments, R$^x$, of a provided compound comprises one or more deuterium atoms.

As used herein, the term "inhibitor" is defined as a compound that binds to and/or inhibits IRAK-4 with measurable affinity. In certain embodiments, an inhibitor has an IC$_{50}$ and/or binding constant of less than about 50 μM, less than about 1 μM, less than about 500 nM, less than about 100 nM, less than about 10 nM, or less than about 1 nM.

A compound of the present invention may be tethered to a detectable moiety. It will be appreciated that such compounds are useful as imaging agents. One of ordinary skill in the art will recognize that a detectable moiety may be attached to a provided compound via a suitable substituent. As used herein, the term "suitable substituent" refers to a moiety that is capable of covalent attachment to a detectable moiety. Such moieties are well known to one of ordinary skill in the art and include groups containing, e.g., a carboxylate moiety, an amino moiety, a thiol moiety, or a hydroxyl moiety, to name but a few. It will be appreciated that such moieties may be directly attached to a provided compound or via a tethering group, such as a bivalent saturated or unsaturated hydrocarbon chain. In some embodiments, such moieties may be attached via click chemistry. In some embodiments, such moieties may be attached via a 1,3-cycloaddition of an azide with an alkyne, optionally in the presence of a copper catalyst. Methods of using click chemistry are known in the art and include those described by Rostovtsev et al., Angew. Chem. Int. Ed. 2002, 41, 2596-99 and Sun et al., Bioconjugate Chem., 2006, 17, 52-57.

As used herein, the term "detectable moiety" is used interchangeably with the term "label" and relates to any moiety capable of being detected, e.g., primary labels and secondary labels. Primary labels, such as radioisotopes (e.g., tritium, $^{32}$P, $^{33}$P, $^{35}$S, or $^{14}$C), mass-tags, and fluorescent labels are signal generating reporter groups which can be detected without further modifications. Detectable moieties also include luminescent and phosphorescent groups.

The term "secondary label" as used herein refers to moieties such as biotin and various protein antigens that require the presence of a second intermediate for production of a detectable signal. For biotin, the secondary intermediate may include streptavidin-enzyme conjugates. For antigen labels, secondary intermediates may include antibody-enzyme conjugates. Some fluorescent groups act as secondary labels because they transfer energy to another group in the process of nonradiative fluorescent resonance energy transfer (FRET), and the second group produces the detected signal.

The terms "fluorescent label", "fluorescent dye", and "fluorophore" as used herein refer to moieties that absorb light energy at a defined excitation wavelength and emit light energy at a different wavelength. Examples of fluorescent labels include, but are not limited to: Alexa Fluor dyes (Alexa Fluor 350, Alexa Fluor 488, Alexa Fluor 532, Alexa Fluor 546, Alexa Fluor 568, Alexa Fluor 594, Alexa Fluor 633, Alexa Fluor 660 and Alexa Fluor 680), AMCA, AMCA-S, BODIPY dyes (BODIPY FL, BODIPY R6G, BODIPY TMR, BODIPY TR, BODIPY 530/550, BODIPY 558/568, BODIPY 564/570, BODIPY 576/589, BODIPY 581/591, BODIPY 630/650, BODIPY 650/665), Carboxyrhodamine 6G, carboxy-X-rhodamine (ROX), Cascade Blue, Cascade Yellow, Coumarin 343, Cyanine dyes (Cy3, Cy5, Cy3.5, Cy5.5), Dansyl, Dapoxyl, Dialkylaminocoumarin, 4',5'-Dichloro-2',7'-dimethoxy-fluorescein, DM-NERF, Eosin, Erythrosin, Fluorescein, FAM, Hydroxycoumarin, IRDyes (IRD40, IRD 700, IRD 800), JOE, Lissamine rhodamine B, Marina Blue, Methoxycoumarin, Naphthofluorescein, Oregon Green 488, Oregon Green 500, Oregon Green 514, Pacific Blue, PyMPO, Pyrene, Rhodamine B, Rhodamine 6G, Rhodamine Green, Rhodamine Red, Rhodol Green, 2',4',5',7'-Tetra-bromosulfone-fluorescein, Tetramethyl-rhodamine (TMR), Carboxytetramethylrhodamine (TAMRA), Texas Red, Texas Red-X.

The term "mass-tag" as used herein refers to any moiety that is capable of being uniquely detected by virtue of its mass using mass spectrometry (MS) detection techniques. Examples of mass-tags include electrophore release tags such as N-[3-[4'-[(p-Methoxytetrafluorobenzyl)oxy]phenyl]-3-methylglyceronyl]isonipecotic Acid, 4'-[2,3,5,6-Tetrafluoro-4-(pentafluorophenoxyl)]methyl acetophenone, and their derivatives. The synthesis and utility of these mass-tags is described in U.S. Pat. Nos. 4,650,750, 4,709,016, 5,360, 8191, 5,516,931, 5,602,273, 5,604,104, 5,610,020, and 5,650,270. Other examples of mass-tags include, but are not limited to, nucleotides, dideoxynucleotides, oligonucleotides of varying length and base composition, oligopeptides, oligosaccharides, and other synthetic polymers of varying length and monomer composition. A large variety of organic molecules, both neutral and charged (biomolecules or synthetic compounds) of an appropriate mass range (100-2000 Daltons) may also be used as mass-tags.

The terms "measurable affinity" and "measurably inhibit," as used herein, means a measurable change in an IRAK protein kinase activity between a sample comprising a compound of the present invention, or composition thereof, and an IRAK protein kinase, and an equivalent sample comprising an IRAK protein kinase, in the absence of said compound, or composition thereof.

3. Description of Exemplary Embodiments

As described above, in certain embodiments, the present invention provides a compound of formula I:

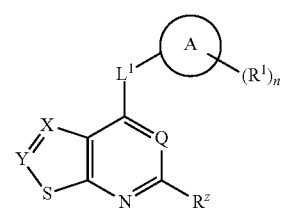

or a pharmaceutically acceptable salt thereof, wherein:
Q is CH, C—CN, or N;
X is C-L$^2$(R$^4$)$_p$—R$^x$ and Y is N; or
X is N and Y is C—R$^x$;
Ring A is a 3-7 membered saturated or partially unsaturated carbocyclic ring or a 4-7 membered saturated or partially unsaturated heterocyclic ring having 1-3 heteroatoms independently selected from nitrogen, oxygen, or sulfur;
each R$^1$ and R$^{1'}$ is independently —R$^2$, halogen, —CN, —NO$_2$, —OR, —SR, —N(R)$_2$, —S(O)$_2$R, —S(O)$_2$N(R)$_2$, —S(O)R, —C(O)R, —C(O)OR, —C(O)N(R)$_2$, —C(O)N(R)OR, —N(R)C(O)OR, —N(R)C(O)N(R)$_2$, Cy, or —N(R)S(O)$_2$R; or R$^1$ is selected from one of the following formulas:

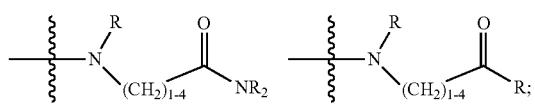

or
two R$^1$ groups are taken together with their intervening atoms to form an optionally substituted 4-7 membered fused, spiro-fused, or bridged bicyclic ring having 0-2 heteroatoms independently selected from nitrogen, oxygen, or sulfur;
each Cy is independently an optionally substituted ring selected from a 3-7 membered saturated or partially unsaturated carbocyclic ring or a 4-10 membered saturated or partially unsaturated heterocyclic ring having 1-3 heteroatoms independently selected from nitrogen, oxygen, or sulfur;
each R is independently hydrogen, or an optionally substituted group selected from C$_{1-6}$ aliphatic, phenyl, 4-7 membered saturated or partially unsaturated heterocyclic having 1-2 heteroatoms independently selected from nitrogen, oxygen, or sulfur, or 5-6 membered heteroaryl ring having 1-4 heteroatoms independently selected from nitrogen, oxygen, or sulfur, or:
two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, or sulfur;

each $R^2$ is independently an optionally substituted group selected from $C_{1-6}$ aliphatic, phenyl, 4-7 membered saturated or partially unsaturated heterocyclic having 1-2 heteroatoms independently selected from nitrogen, oxygen, or sulfur, or 5-6 membered heteroaryl ring having 1-4 heteroatoms independently selected from nitrogen, oxygen, or sulfur;

each $R^4$ is independently halogen, —CN, —NO$_2$, —OR, —SR, —N(R)$_2$, —S(O)$_2$R, —S(O)$_2$N(R)$_2$, —S(O)R, —C(O)R, —C(O)OR, —C(O)N(R)$_2$, —N(R)C(O)R, —N(R)C(O)N(R)$_2$, —C(O)N(R)OR, —N(R)C(O)OR, —N(R)S(O)$_2$N(R)$_2$, —N(R)S(O)$_2$R, or an optionally substituted group selected from $C_{1-6}$ aliphatic, phenyl, 4-7 membered saturated or partially unsaturated heterocyclic having 1-2 heteroatoms independently selected from nitrogen, oxygen, or sulfur, or 5-6 membered heteroaryl ring having 1-4 heteroatoms independently selected from nitrogen, oxygen, or sulfur;

$R^x$ is hydrogen, —$R^2$, —CN, —NO$_2$, halogen, —C(O)N(R)$_2$, —C(O)OR, —C(O)R, —N(R)$_2$, —NH[Ar], —OR, or —S(O)$_2$N(R)$_2$;

$R^z$ is hydrogen, —$R^2$, —CN, —NO$_2$, halogen, —C(O)N(R)$_2$, —C(O)OR, —C(O)R, —N(R)$_2$, —NH[Ar], —OR, or —S(O)$_2$N(R)$_2$;

[Ar] is a phenyl or heteroaromatic ring substituted by m instances of $R^{1'}$;

$L^1$ is a covalent bond or a $C_{1-6}$ bivalent hydrocarbon chain wherein one or two methylene units of the chain are optionally and independently replaced by —N(R)—, —N(R)C(O)—, —C(O)N(R)—, —N(R)S(O)$_2$—, —S(O)$_2$N(R)—, —O—, —C(O)—, —OC(O)—, —C(O)O—, —S—, —S(O)— or —S(O)$_2$—;

$L^2$ is a covalent bond or a $C_{1-6}$ bivalent hydrocarbon chain wherein one or two methylene units of the chain are optionally and independently replaced by —N(R)—, —N(R)C(O)—, —C(O)N(R)—, —N(R)S(O)$_2$—, —S(O)$_2$N(R)—, —O—, —C(O)—, —OC(O)—, —C(O)O—, —S—, —S(O)— or —S(O)$_2$—;

m is 0-4;
n is 0-4; and
p is 0-2.

As defined generally above, Q is CH, C—CN, or N. In some embodiments, Q is CH. In some embodiments, Q is C—CN. In some embodiments Q is N.

As defined generally above, X is C-$L^2(R^4)_p$—$R^x$ and Y is N; or X is N and Y is C—$R^x$. In some embodiments, X is C-$L^2(R^4)_p$—$R^x$ and Y is N. In some embodiments, X is N and Y is C—$R^x$.

As defined generally above, the Ring A group of formula I is a 3-7 membered saturated or partially unsaturated carbocyclic ring or a 4-7 membered saturated or partially unsaturated heterocyclic ring having 1-3 heteroatoms independently selected from nitrogen, oxygen, or sulfur. In some embodiments, Ring A is a 3-7 membered saturated or partially unsaturated carbocyclic ring. In certain embodiments, Ring A is a 4-7 membered saturated or partially unsaturated heterocyclic ring having 1-3 heteroatoms independently selected from nitrogen, oxygen, or sulfur.

In some embodiments, Ring A is a 3-7 membered saturated carbocyclic ring. In certain embodiments, Ring A is cyclopentyl or cyclohexyl. In some embodiments, Ring A is cyclohexyl.

One of skill in the art will appreciate that a when Ring A is a disubstituted cycloalkyl ring, said ring can have cis or trans relative stereochemistry. In some embodiments, Ring A is a trans-1,4-disubstituted cycloalkyl ring. In some embodiments, Ring A is a trans-1,4-disubstituted cyclohexyl ring.

In certain embodiments, Ring A is a 4-7 membered saturated heterocyclic ring having 1-3 heteroatoms independently selected from nitrogen, oxygen, or sulfur. In certain embodiments, Ring A is a 5-6 membered saturated heterocyclic ring having 1-3 heteroatoms independently selected from nitrogen, oxygen, or sulfur. In certain embodiments, Ring A is piperidinyl, piperazinyl, morpholinyl, thiomorpholinyl, tetrahydropyranyl, or tetrahydrofuranyl. In some embodiments, when Ring A is a 4-7 membered saturated heterocyclic ring, $L^1$ is a covalent bond. In some embodiments, when Ring A is a 4-7 membered saturated heterocyclic ring, $L^1$ is not a covalent bond.

As defined generally above, the n group of formula I is 0-4. In some embodiments, n is 0. In other embodiments, n is 1-4. In certain embodiments, n is 1 or 2.

As defined generally above, each $R^1$ group of formula I is independently —$R^2$, halogen, —CN, —NO$_2$, —OR, —CH$_2$OR, —SR, —N(R)$_2$, —S(O)$_2$R, —S(O)$_2$N(R)$_2$, —S(O)R, —C(O)R, —C(O)OR, —C(O)N(R)$_2$, —C(O)N(R)—OR, —N(R)C(O)R, —N(R)C(O)N(R)$_2$, Cy, or —N(R)S(O)$_2$R; or $R^1$ is selected from one of the following formulas:

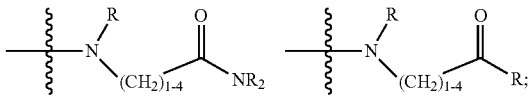

or two $R^1$ groups are taken together with their intervening atoms to form an optionally substituted 4-7 membered fused, spiro-fused, or bridged bicyclic ring having 0-2 heteroatoms independently selected from nitrogen, oxygen, or sulfur.

In certain embodiments, $R^1$ is —$R^2$, —OR, —N(R)$_2$, —C(O)OR, —C(O)N(R)$_2$, —C(O)N(R)—OR, —SO$_2$N(R)$_2$, Cy, or —N(R)C(O)OR. In some embodiments, $R^1$ is —C(O)NH$_2$, —C(O)NHCH$_3$, —C(O)NH—OH, —CH$_3$, —CH$_2$CH$_3$, —S(O)$_2$t-butyl, —OH, —C(O)OH, —NH$_2$, —NHCH$_3$, —N(CH$_3$)$_2$, —N(CH$_2$CH$_3$)$_2$, —NHC(O)CH$_3$, or —CH$_2$-phenyl. In certain embodiments, $R^1$ is selected from one of the following formulas:

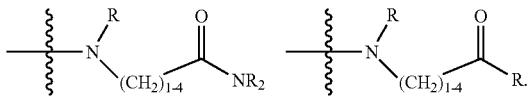

In certain embodiments, $R^1$ is Cy. In certain embodiments, $R^1$ is —N(R)$_2$. In some embodiments, $R^1$ is dimethylamino. In some embodiments, $R^1$ is ethylamino. Exemplary $R^1$ groups include those depicted in Table 1.

In some embodiments, the present invention provides a compound of formula I wherein two $R^1$ groups are taken together with their intervening atoms to form an optionally substituted 4-7 membered fused, spiro-fused, or bridged bicyclic ring having 0-2 heteroatoms independently selected from nitrogen, oxygen, or sulfur. In certain embodiments, two $R^1$ groups on adjacent carbon atoms are taken together to form an optionally substituted 4-7 membered ring fused to Ring A. In other embodiments, two $R^1$ groups on the same carbon atom are taken together to form an optionally substituted 4-7 membered spiro-fused ring. In other embodiments, two $R^1$ groups on non-adjacent carbon atoms are taken together to form an optionally substituted bridged bicyclic ring with Ring A.

As defined generally above, each Cy is independently an optionally substituted ring selected from a 3-7 membered saturated or partially unsaturated carbocyclic ring or a 4-10 membered saturated or partially unsaturated heterocyclic ring having 1-3 heteroatoms independently selected from nitrogen, oxygen, or sulfur.

In some embodiments, a Cy is an optionally substituted 3-7 membered saturated carbocyclic ring. In certain embodiments, a Cy is an optionally substituted 4-10 membered saturated heterocyclic ring containing 1-2 heteroatoms independently selected from nitrogen, oxygen or sulfur. In certain embodiments a Cy is an optionally substituted spirobicyclic 7-10 membered heterocyclic ring. In certain embodiments a Cy is an optionally substituted 4-7 membered monocyclic heterocyclic ring. In certain embodiments, a Cy is optionally substituted morpholinyl, pyrrolidinyl, azetidinyl, piperidinyl or piperazinyl. In some embodiments, a Cy is morpholinyl. In some embodiments, a Cy is 4,4-difluoropiperidinyl. In some embodiments, a Cy is tetrahydrothiopyran-1,1-dioxide-4-yl. In some embodiments, a Cy is 2-oxa-7-azaspiro[3.5]nonane.

One of ordinary skill in the art will appreciate that an $R^1$ substituent on a saturated carbon of Ring A forms a chiral center. In some embodiments, that chiral center is in the (R) configuration. In other embodiments, that chiral center is in the (S) configuration.

As defined generally above, $R^x$ is hydrogen, —$R^2$, —CN, —$NO_2$, halogen, —C(O)N(R)$_2$, —C(O)OR, —C(O)R, —N(R)$_2$, —NH[Ar], —OR, or —S(O)$_2$N(R)$_2$. In some embodiments, $R^x$ is hydrogen. In some embodiments, $R^x$ is, —$R^2$, —CN, —$NO_2$, halogen, —C(O)N(R)$_2$, —C(O)OR, —C(O)R, —N(R)$_2$, —NH[Ar], —OR, or —S(O)$_2$N(R)$_2$. In some embodiments, $R^x$ is, —$R^2$, —CN, —$NO_2$, halogen, —C(O)N(R)$_2$, —C(O)OR, —C(O)R, —OR, or —S(O)$_2$N(R)$_2$. In some embodiments, $R^x$ is —OR. In some embodiments, $R^x$ is —C(O)NR$_2$. In some embodiments, $R^x$ is optionally substituted $C_{1-6}$ aliphatic. In some embodiments, $R^x$ is methyl. In some embodiments, $R^x$ is ethyl. In some embodiments, $R^x$ is trifluoromethyl.

As defined generally above, the $L^1$ group of formula I is a covalent bond or a $C_{1-6}$ bivalent hydrocarbon chain wherein one or two methylene units of the chain are optionally and independently replaced by —N(R)—, —N(R)C(O)—, —C(O)N(R)—, —N(R)S(O)$_2$—, —S(O)$_2$N(R)—, —O—, —C(O)—, —OC(O)—, —C(O)O—, —S—, —S(O)— or —S(O)$_2$—. In some embodiments, $L^1$ is a covalent bond. In other embodiments, $L^1$ is a $C_{1-6}$ bivalent hydrocarbon chain wherein one or two methylene units of the chain are optionally and independently replaced by —N(R)—, —N(R)C(O)—, —C(O)N(R)—, —N(R)S(O)$_2$—, —S(O)$_2$N(R)—, —O—, —C(O)—, —OC(O)—, —C(O)O—, —S—, —S(O)— or —S(O)$_2$—.

In some embodiments, $L^1$ is —NH— (i.e., a $C_1$ bivalent hydrocarbon chain wherein the methylene unit is replaced by —NH—), —O—, —CH$_2$O—, —OCH$_2$—, —NHC(O)—, —CH$_2$NH—, or —NHCH$_2$—. In some embodiments, $L^1$ is —O—. In some embodiments, $L^1$ is —N(R)—. In some embodiments, $L^1$ is —OCH$_2$—. In some embodiments, $L^1$ is —N(R)CH$_2$—. Exemplary $L^1$ groups include those depicted in Table 1.

As defined generally above, $L^2$ is a covalent bond or a $C_{1-6}$ bivalent hydrocarbon chain wherein one or two methylene units of the chain are optionally and independently replaced by —N(R)—, —N(R)C(O)—, —C(O)N(R)—, —N(R)S(O)$_2$—, —S(O)$_2$N(R)—, —O—, —C(O)—, —OC(O)—, —C(O)O—, —S—, —S(O)— or —S(O)$_2$—.

In certain embodiments $L^2$ is a covalent bond. In some embodiments $L^2$ is a $C_{1-3}$ bivalent hydrocarbon chain wherein one or two methylene units of the chain are optionally and independently replaced by —C(O)N(R)—, —O—, —C(O)—, —S—, —S(O)— or —S(O)$_2$—. In certain embodiments, $L^2$ is methylene. In certain embodiments, $L^2$ is ethylene.

As defined generally above, each $R^4$ is independently halogen, —CN, —$NO_2$, —OR, —SR, —N(R)$_2$, —S(O)$_2$R, —S(O)$_2$N(R)$_2$, —S(O)R, —C(O)R, —C(O)OR, —C(O)N(R)$_2$, —N(R)C(O)R, —N(R)C(O)N(R)$_2$, —C(O)N(R)OR, —N(R)C(O)OR, —N(R)S(O)$_2$N(R)$_2$, —N(R)S(O)$_2$R, or an optionally substituted group selected from $C_{1-6}$ aliphatic, phenyl, 4-7 membered saturated or partially unsaturated heterocyclic having 1-2 heteroatoms independently selected from nitrogen, oxygen, or sulfur, or 5-6 membered heteroaryl ring having 1-4 heteroatoms independently selected from nitrogen, oxygen, or sulfur.

In some embodiments, each $R^4$ is independently CN, —OR, —SR, —S(O)R, —S(O)$_2$R, —C(O)N(R)$_2$, —N(R)C(O)R, or an optionally substituted group selected from $C_{1-6}$ aliphatic, phenyl, 4-7 membered saturated or partially unsaturated heterocyclic having 1-2 heteroatoms independently selected from nitrogen, oxygen, or sulfur, or 5-6 membered heteroaryl ring having 1-4 heteroatoms independently selected from nitrogen, oxygen, or sulfur. In certain embodiments, each $R^4$ is independently —CN, —OR, —SR, —S(O)R, —S(O)$_2$R, —C(O)N(R)$_2$, or —N(R)C(O)R. In certain embodiments $R^4$ is an optionally substituted group selected from $C_{1-6}$ aliphatic, 4-7 membered saturated or partially unsaturated heterocyclic having 1-2 heteroatoms independently selected from nitrogen, oxygen, or sulfur, or 5-6 membered heteroaryl ring having 1-4 heteroatoms independently selected from nitrogen, oxygen, or sulfur. In certain embodiments $R^4$ is hydroxyl. In certain embodiments $R^4$ is —C(O)N(R)$_2$. In certain embodiments, $R^4$ is halogen. In certain embodiments, $R^4$ is fluorine.

As defined generally above, [Ar] is a phenyl or heteroaromatic ring substituted by m instances of $R^{1'}$. In some embodiment [Ar] is a phenyl ring substituted by m instances of $R^{1'}$. In some embodiments, [Ar] is a heteroaromatic ring substituted by m instances of $R^{1'}$. In some embodiments, [Ar] is a 5-membered heteroaromatic ring substituted by m instances of $R^{1'}$. In some embodiments, [Ar] is an 6-membered heteroaromatic ring substituted by m instances of $R^{1'}$. In some embodiments, [Ar] is a pyrazole ring substituted by m instances of $R^{1'}$. In some embodiments [Ar] is an optionally substituted phenyl or heteroaromatic ring. In some embodiments, [Ar] is an optionally substituted phenyl ring. In some embodiments, [Ar] is an unsubstituted phenyl ring. In some embodiments, [Ar] is a substituted phenyl ring. In some embodiments, [Ar] is an optionally substituted heteroaromatic ring. In some embodiments, [Ar] is an optionally substituted 5-membered heteroaromatic ring. In some embodiments, [Ar] is an optionally substituted 6-membered heteroaromatic ring. In some embodiments, [Ar] is an optionally substituted pyrazole ring. Exemplary [Ar] groups include those depicted in Table 1.

As defined generally above, each $R^{1'}$ is independently —$R^2$, halogen, —CN, —$NO_2$, —OR, —SR, —N(R)$_2$, —S(O)$_2$R, —S(O)$_2$N(R)$_2$, —S(O)R, —C(O)R, —C(O)OR, —C(O)N(R)$_2$, —C(O)N(R)OR, —N(R)C(O)OR, —N(R)C(O)N(R)$_2$, Cy, or —N(R)S(O)$_2$R.

In some embodiments, $R^{1'}$ is optionally substituted $C_{1-6}$ aliphatic. In some embodiments, $R^{1'}$ is optionally substituted $C_{1-3}$ alkyl. In some embodiments, $R^{1'}$ is tetrahydropyran-4-yl-methyl. In some embodiments, $R^{1'}$ is Cy. In some embodiments, $R^{1'}$ is tetrahydropyran. In some embodiments, $R^{1'}$ is tetrahydrothiopyran-1,1-dioxide. Exemplary $R^{1'}$ groups include those depicted in Table 1.

As defined generally above, m is 0-4. In some embodiments m is 0. In some embodiments m is 1-4. In certain embodiments, m is 1. In certain embodiments, m is 2.

As defined generally above, n is 0-4. In some embodiments n is 0. In some embodiments n is 1-4. In certain embodiments, n is 1. In certain embodiments, n is 2.

As defined generally above, p is 0-2. In some embodiments p is 0. In some embodiments p is 1. In certain embodiments, p is 2.

In some embodiments, the compound of formula I is not selected from the following compounds:

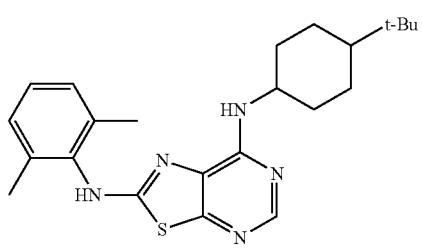

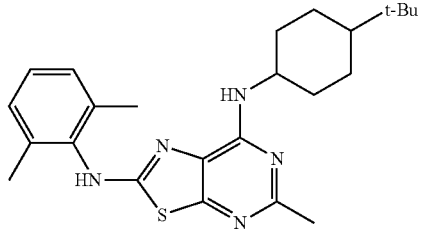

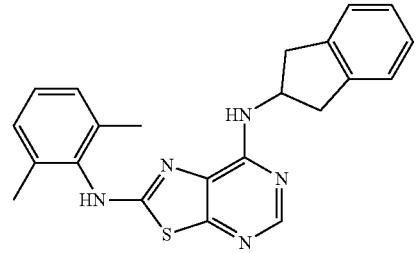

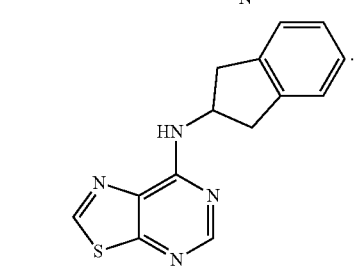

In certain embodiments, the present invention provides a compound of formula I, wherein Q is N, thereby forming a compound of formula II:

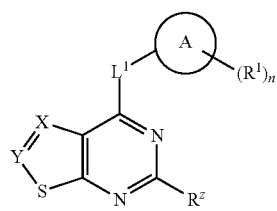

or a pharmaceutically acceptable salt thereof, wherein each of X, Y, Ring A, $L^1$, $R^1$, $R^z$, and n is as defined above and described in embodiments herein, both singly and in combination.

In certain embodiments, the present invention provides a compound of formula II of formulae III or IV:

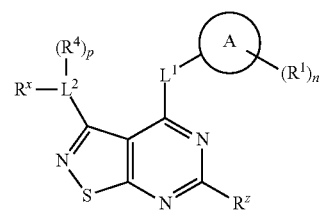

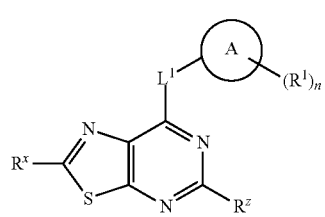

or a pharmaceutically acceptable salt thereof, wherein each of Ring A, $L^1$, $L^2$, $R^1$, $R^4$, $R^x$, $R^z$, n, and p is as defined above and described in embodiments herein, both singly and in combination.

In certain embodiments, the present invention provides a compound of formula III or IV wherein $L^1$ is NH, thereby forming a compound of formulae III-i or IV-i:

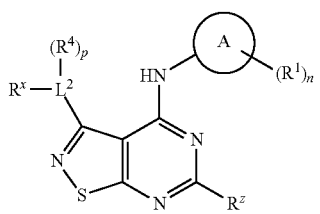

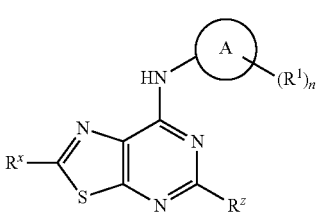

or a pharmaceutically acceptable salt thereof, wherein each of Ring A, $L^2$, $R^1$, $R^4$, $R^x$, $R^z$, n, and p is as defined above and described in embodiments herein, both singly and in combination.

In some embodiments, the present invention provides a compound of formula IV-i wherein $R^x$ is optionally substituted $C_{1-6}$ aliphatic.

In certain embodiments, the present invention provides a compound of formula III or IV, wherein n is 1, and Ring A is trans-substituted cyclohexyl, thereby forming a compound of formulae V or VI:

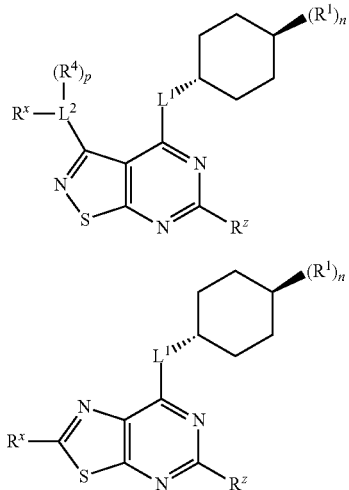

V

VI or a pharmaceutically acceptable salt thereof, wherein each of $L^1$, $L^2$, $R^1$, $R^4$, $R^x$, $R^z$, n, and p is as defined above and described in embodiments herein, both singly and in combination.

In certain embodiments, the present invention provides a compound of formula V or VI, wherein $L^1$ is —O—, thereby forming a compound of formulae VII or VIII:

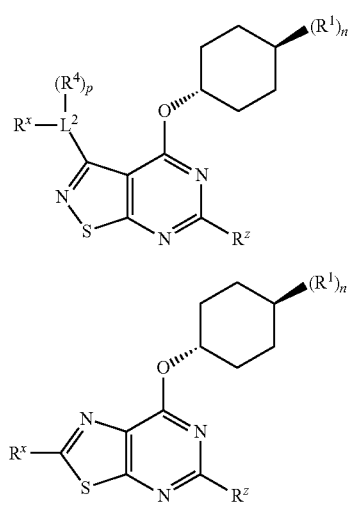

VII

VIII or a pharmaceutically acceptable salt thereof, wherein each of $L^2$, $R^1$, $R^4$, $R^x$, $R^z$, n, and p is as defined above and described in embodiments herein, both singly and in combination.

In certain embodiments, the present invention provides a compound of formula V or VI, wherein $L^1$ is —NH—, thereby forming a compound of formulae IX or X:

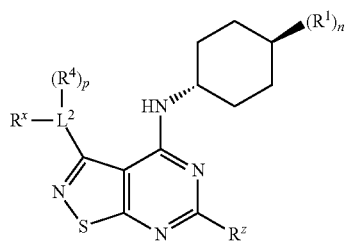

IX

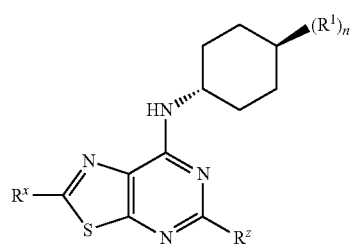

X or a pharmaceutically acceptable salt thereof, wherein each of $L^2$, $R^1$, $R^4$, $R^x$, $R^z$, n, and p is as defined above and described in embodiments herein, both singly and in combination.

In some embodiments, the present invention provides a compound of formulae III, IV, V, VI, V, VI, VII, VIII, IX, or X wherein $R^z$ is —NH[Ar]. In some embodiments, the present invention provides a compound of formulae III, IV, V, VI, V, VI, VII, VIII, IX, or X wherein $R^z$ is hydrogen. In some embodiments, the present invention provides a compound of formulae III, IV, V, VI, V, VI, VII, VIII, IX, or X wherein $R^z$ is —$R^2$, —CN, —$NO_2$, halogen, —C(O)N(R)$_2$, —C(O)OR, —C(O)R, —N(R)$_2$, —NH[Ar], —OR, or —S(O)$_2$N(R)$_2$.

In some embodiments, the present invention provides a compound of formulae III, IV, V, VI, V, VI, VII, VIII, IX, or X wherein [Ar] is phenyl substituted by m instances of $R^{1'}$. In some embodiments, the present invention provides a compound of formulae III, IV, V, VI, V, VI, VII, VIII, IX, or X wherein [Ar] is heteroaryl substituted by m instances of $R^{1'}$. In some embodiments, the present invention provides a compound of formulae III, IV, V, VI, V, VI, VII, VIII, IX, or X wherein [Ar] is 5-membered heteroaryl substituted by m instances of $R^{1'}$. In some embodiments, the present invention provides a compound of formulae III, IV, V, VI, V, VI, VII, VIII, IX, or X wherein [Ar] is 6-membered heteroaryl substituted by m instances of $R^{1'}$.

In certain embodiments, the present invention provides a compound of formula I, wherein Q is C, thereby forming a compound of formula XI:

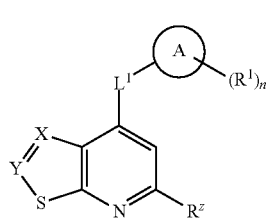

XI or a pharmaceutically acceptable salt thereof, wherein each of X, Y, Ring A, $L^1$, $R^1$, $R^z$, and n is as defined above and described in embodiments herein, both singly and in combination.

In certain embodiments, the present invention provides a compound of formula XI of formulae XII or XIII:

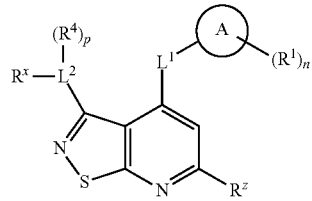
III

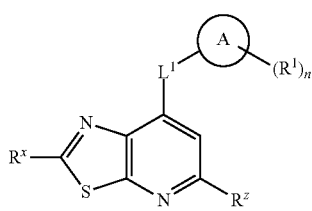
IV or a pharmaceutically acceptable salt thereof, wherein each of Ring A, $L^1$, $L^2$, $R^1$, $R^4$, $R^x$, $R^z$, n, and p is as defined above and described in embodiments herein, both singly and in combination.

In certain embodiments, the present invention provides a compound of formula XII or XIII, wherein n is 1, and Ring A is trans-substituted cyclohexyl, thereby forming a compound of formulae XIV or XV:

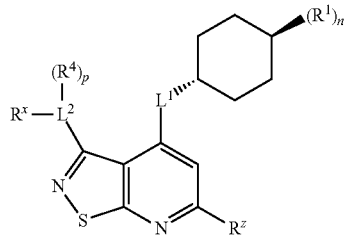
XIV

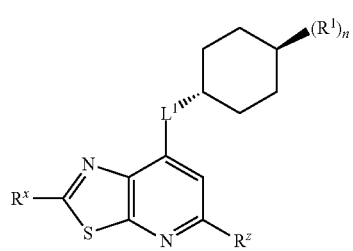
XV or a pharmaceutically acceptable salt thereof, wherein each of $L^1$, $L^2$, $R^1$, $R^4$, $R^x$, $R^z$, n, and p is as defined above and described in embodiments herein, both singly and in combination.

In certain embodiments, the present invention provides a compound of formula XIV or XV, wherein $L^1$ is —O—, thereby forming a compound of formulae XVI or XVII:

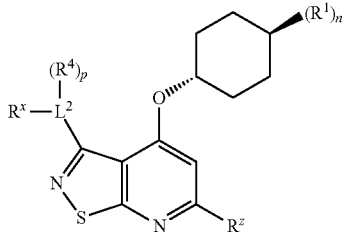
XVI

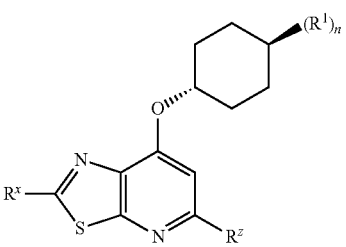
XVII or a pharmaceutically acceptable salt thereof, wherein each of $L^2$, $R^1$, $R^4$, $R^x$, $R^z$, n, and p is as defined above and described in embodiments herein, both singly and in combination.

In certain embodiments, the present invention provides a compound of formula XVI or XVII, wherein $L^1$ is —NH—, thereby forming a compound of formulae XVIII or XIX:

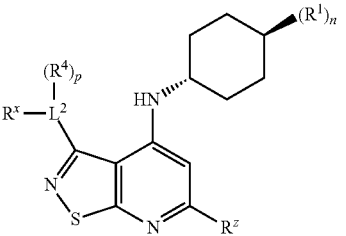
XVIII

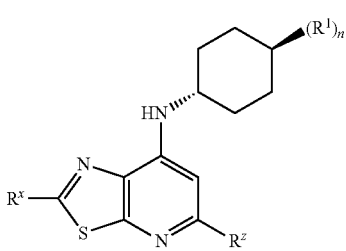
XIX or a pharmaceutically acceptable salt thereof, wherein each of $L^2$, $R^1$, $R^4$, $R^x$, $R^z$, n, and p is as defined above and described in embodiments herein, both singly and in combination.

In certain embodiments, the present invention provides a compound of formula I, wherein Ring A is trans-substituted cyclohexyl, thereby forming a compound of formula XX:

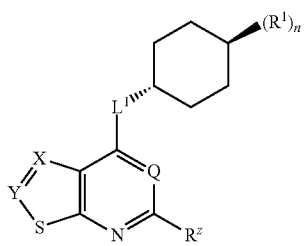

XX or a pharmaceutically acceptable salt thereof, wherein each of Q, X, Y, L¹, R$^z$, R¹, and n is as defined above and described in embodiments herein, both singly and in combination.

In some embodiments, the present invention provides a compound of formula XX wherein Q is N. In some embodiments, the present invention provides a compound of formula XX wherein Q is C. In some embodiments, the present invention provides a compound of formula XX wherein Q is N, and R$^z$ is —NH[Ar]. In some embodiments, the present invention provides a compound of formula XX wherein Q is C, and R$^z$ is —NH[Ar].

Exemplary compounds of the invention are set forth in Table 1, below.

TABLE 1

Exemplary Compounds

Compound

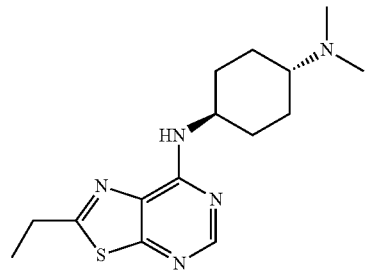 [SMILES: CCc1nc2c(N[C@H]3CC[C@H](N(C)C)CC3)ncnc2s1]

I-1

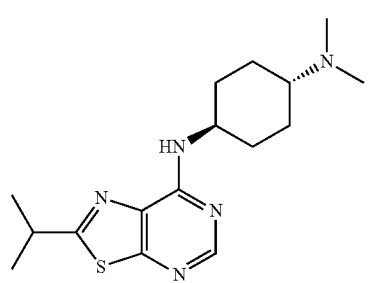 [SMILES: CC(C)c1nc2c(N[C@H]3CC[C@H](N(C)C)CC3)ncnc2s1]

I-2

TABLE 1-continued

Exemplary Compounds

Compound

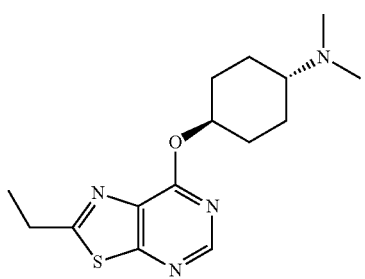 [SMILES: CCc1nc2c(O[C@H]3CC[C@H](N(C)C)CC3)ncnc2s1]

I-3

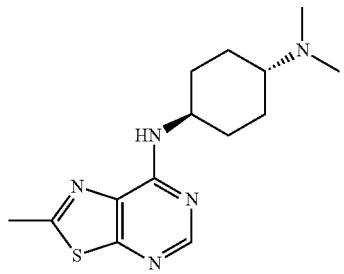

I-4

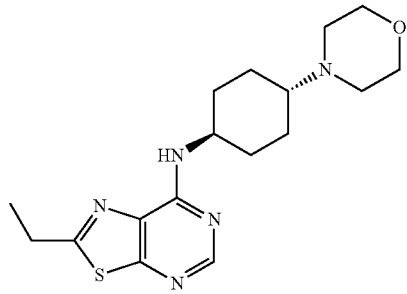 [SMILES: CCc1nc2c(N[C@H]3CC[C@H](N4CCOCC4)CC3)ncnc2s1]

I-5

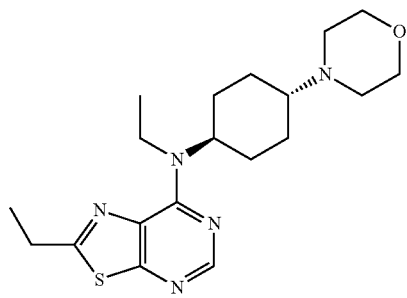 [SMILES: CCc1nc2c(N(CC)[C@H]3CC[C@H](N4CCOCC4)CC3)ncnc2s1]

I-6

TABLE 1-continued
Exemplary Compounds
Compound
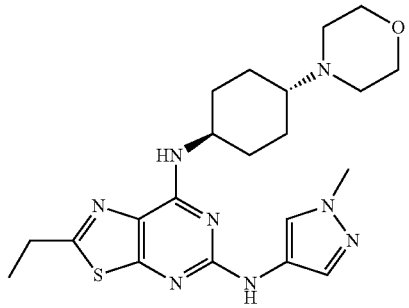 [SMILES: CCc1nc2c(N[C@H]3CC[C@H](N4CCOCC4)CC3)nc(Nc3cnn(C)c3)nc2s1]
I-7
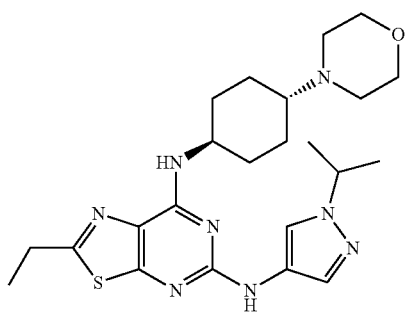 [SMILES: CCc1nc2c(N[C@H]3CC[C@H](N4CCOCC4)CC3)nc(Nc3cnn(C(C)C)c3)nc2s1]
I-8
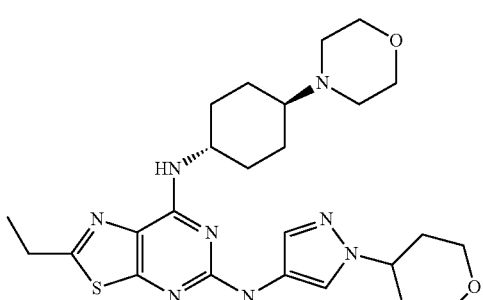
I-9
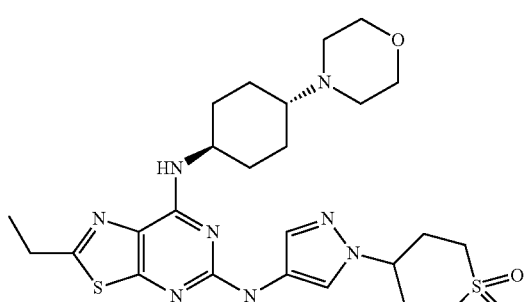
I-10
TABLE 1-continued
Exemplary Compounds
Compound
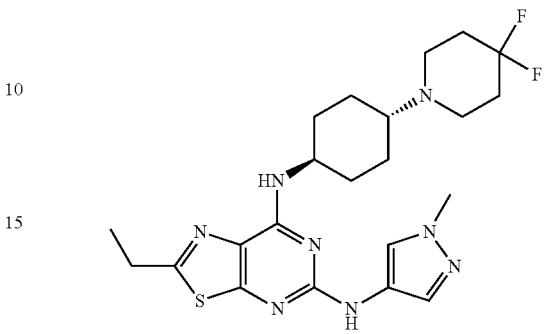
I-11
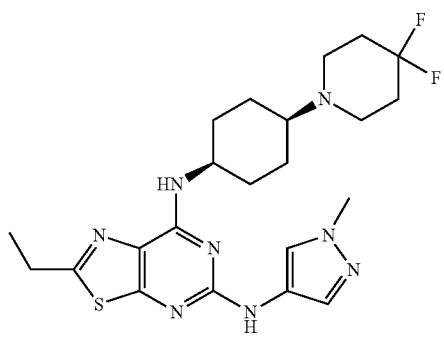 [SMILES: CCc1nc2c(N[C@H]3CC[C@@H](N4CCC(F)(F)CC4)CC3)nc(Nc3cnn(C)c3)nc2s1]
I-12
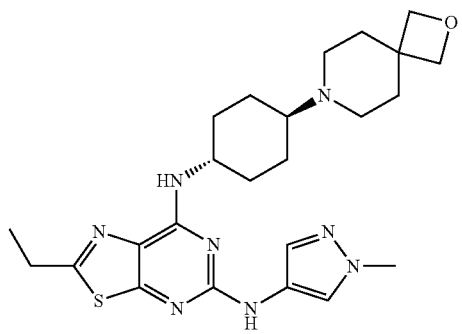
I-13
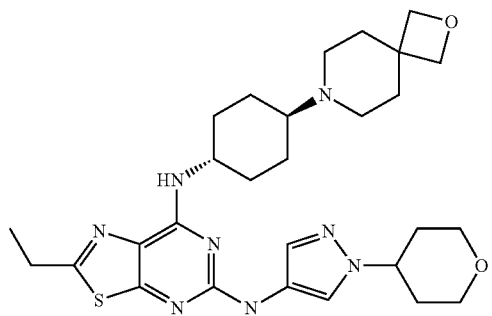
I-14

TABLE 1-continued
Exemplary Compounds
Compound
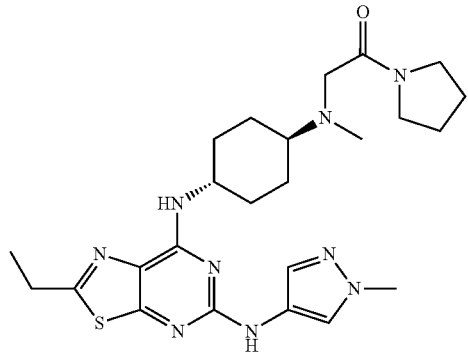
I-15
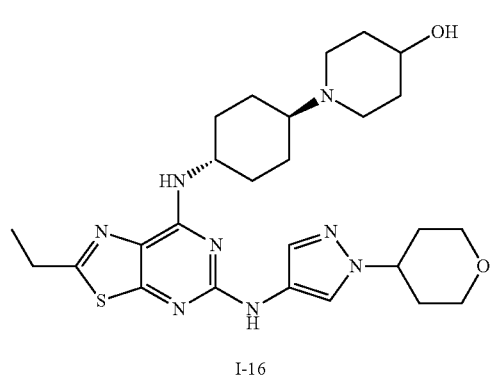
I-16
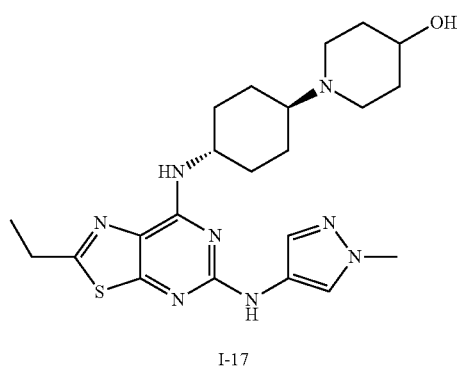
I-17
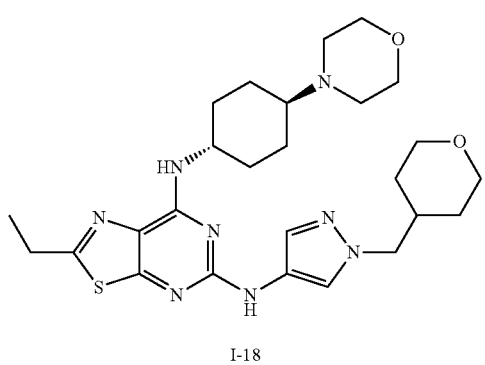
I-18
TABLE 1-continued
Exemplary Compounds
Compound
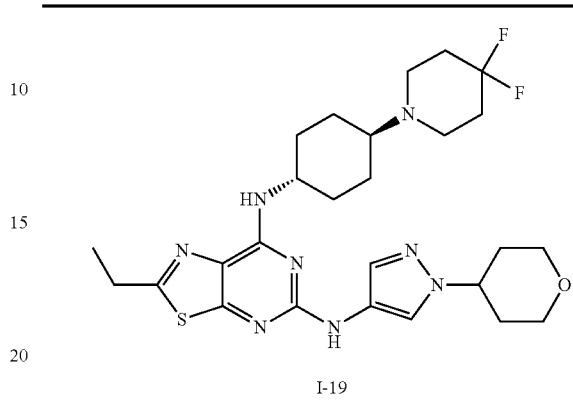
I-19
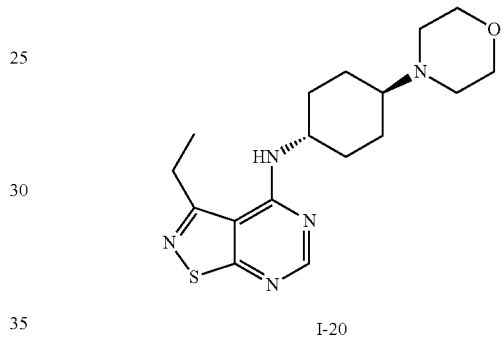
I-20
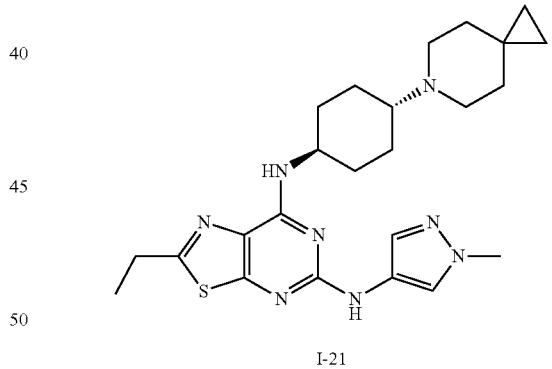
I-21
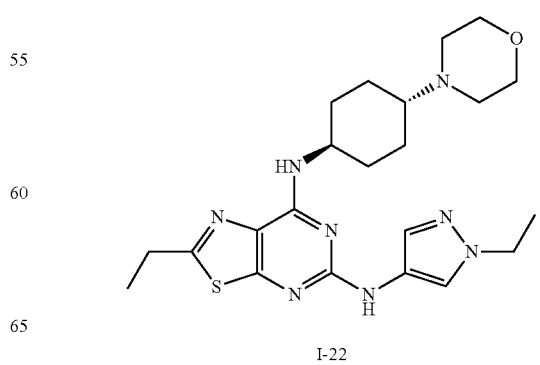
I-22

TABLE 1-continued
Exemplary Compounds
Compound
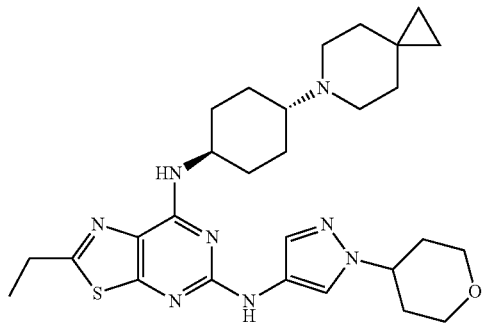
I-23
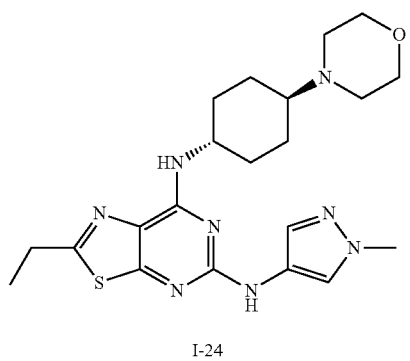
I-24
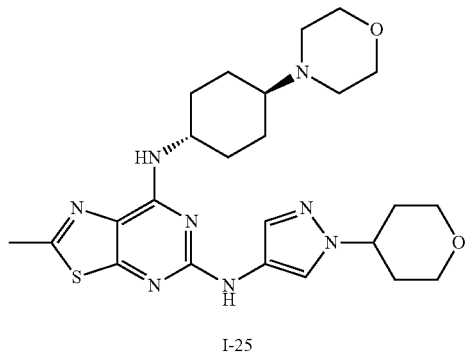
I-25
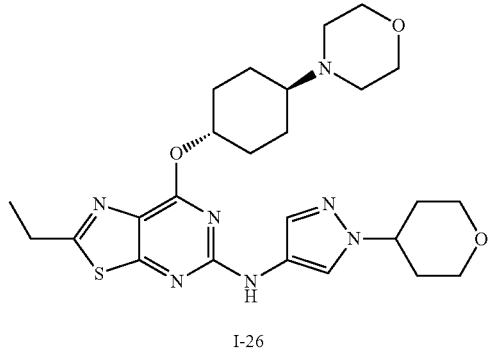
I-26
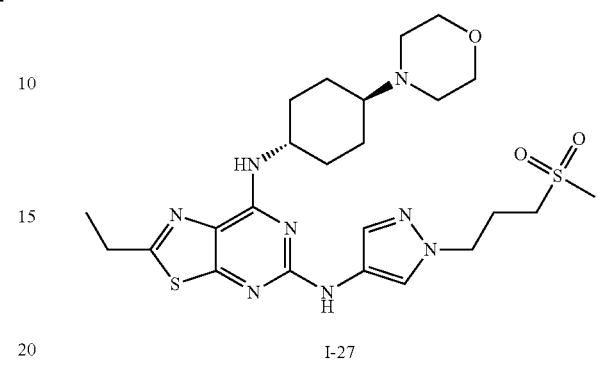
I-27
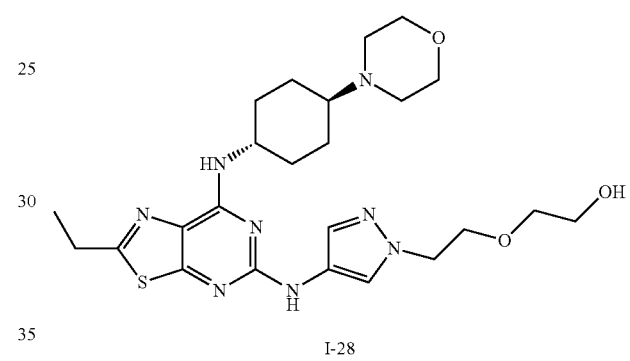
I-28
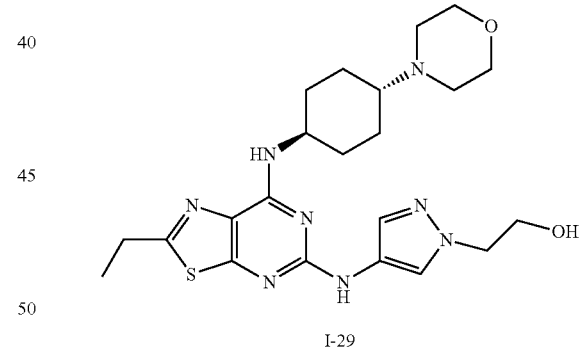
I-29
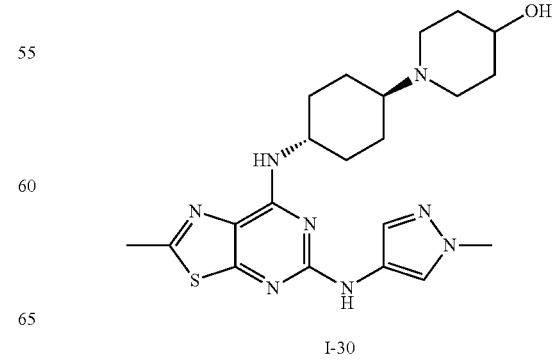
I-30

TABLE 1-continued
Exemplary Compounds
Compound
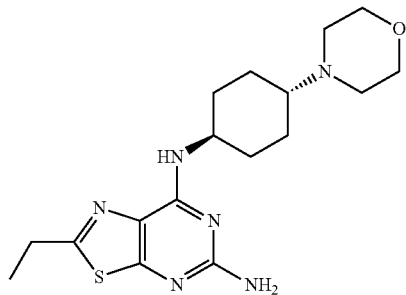
I-31
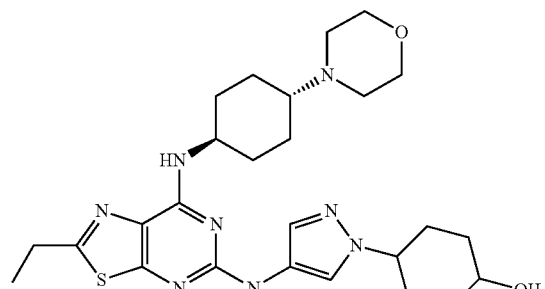
I-32
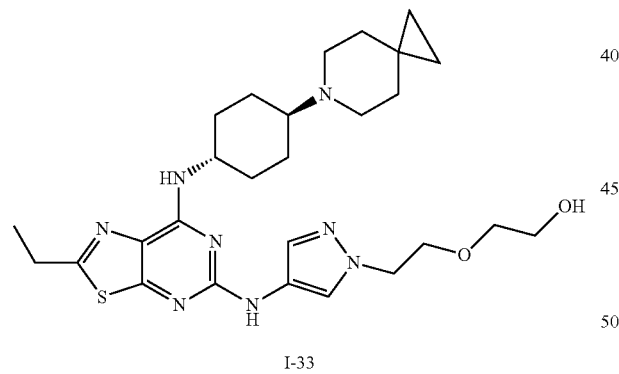
I-33
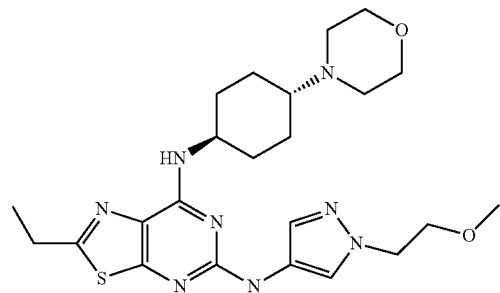
I-34
TABLE 1-continued
Exemplary Compounds
Compound
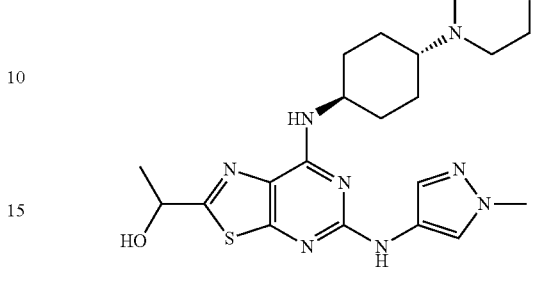
I-35
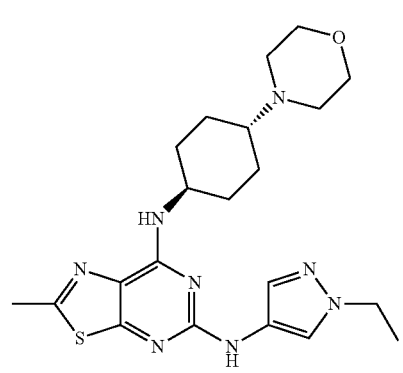
I-36
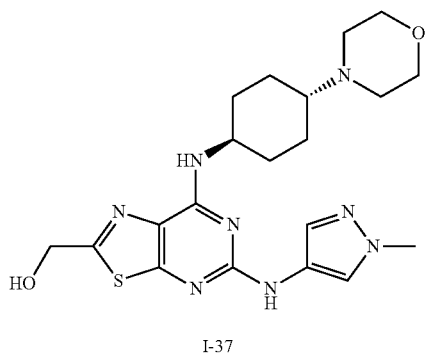
I-37
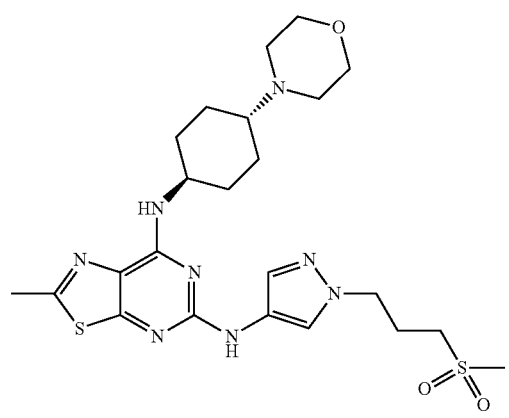
I-38

TABLE 1-continued
Exemplary Compounds
Compound
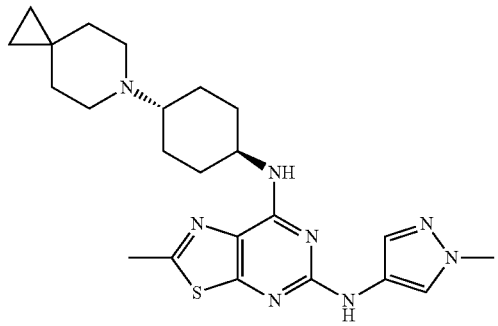
I-39
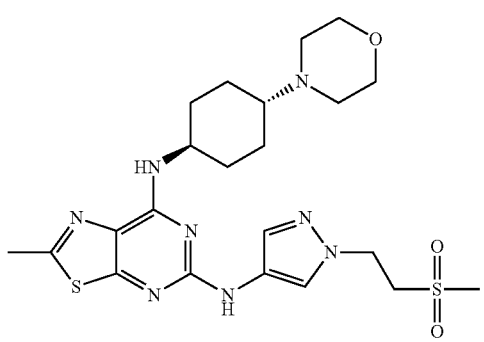
I-40
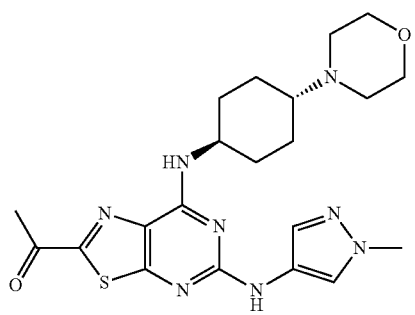
I-41
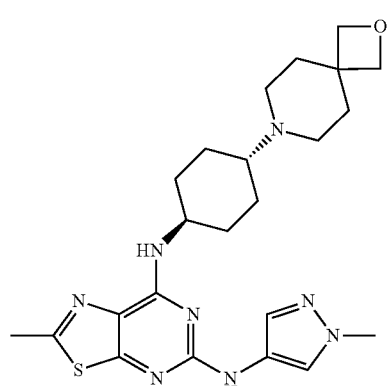
I-42
TABLE 1-continued
Exemplary Compounds
Compound
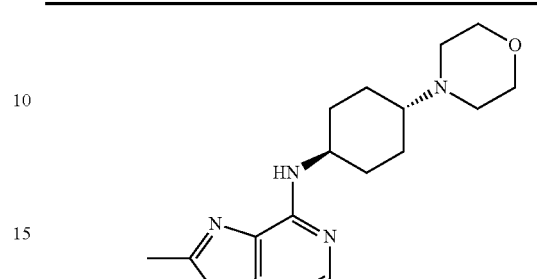
I-43
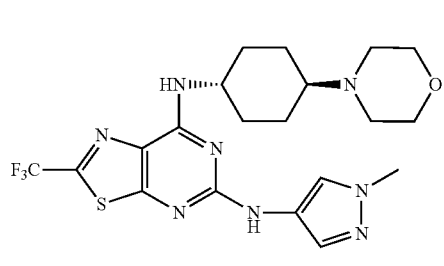
I-44
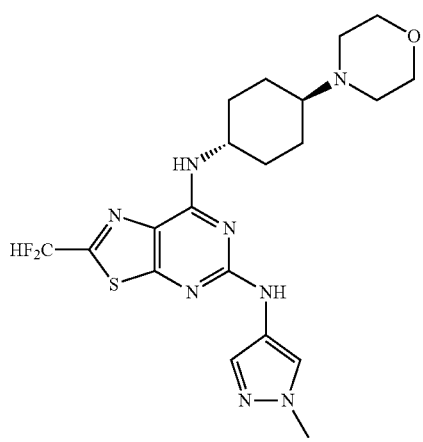
I-45
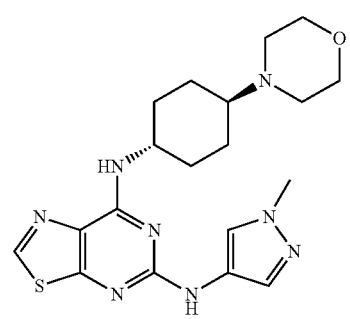
I-46

TABLE 1-continued
Exemplary Compounds
Compound
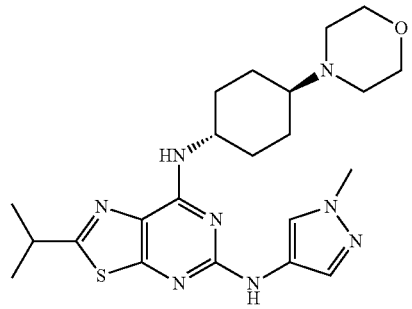
I-47
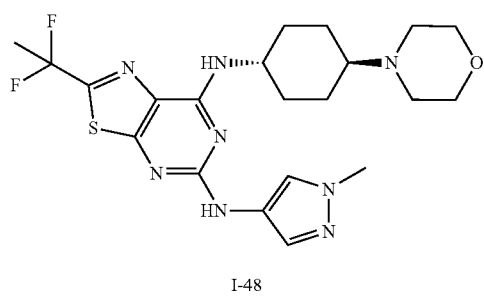
I-48
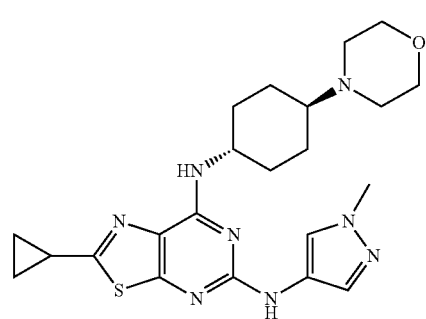
I-49
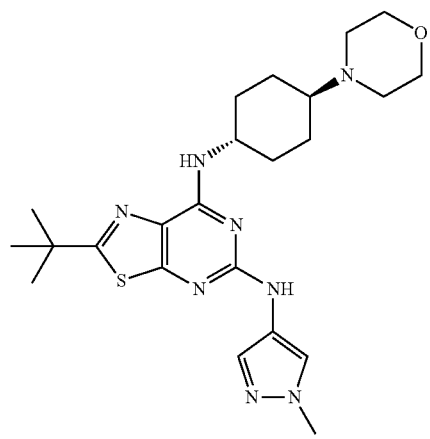
I-50
TABLE 1-continued
Exemplary Compounds
Compound
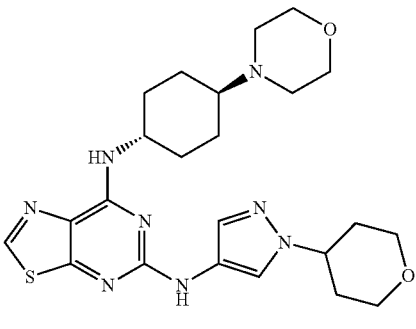
I-51
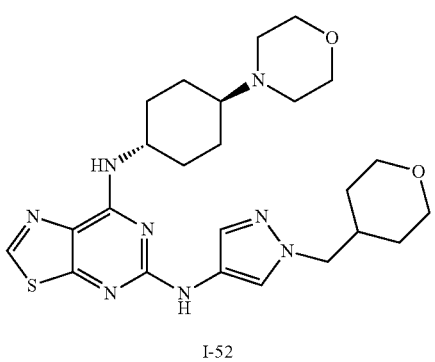
I-52
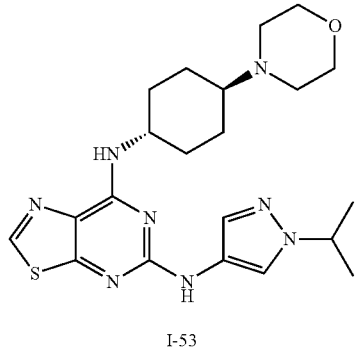
I-53
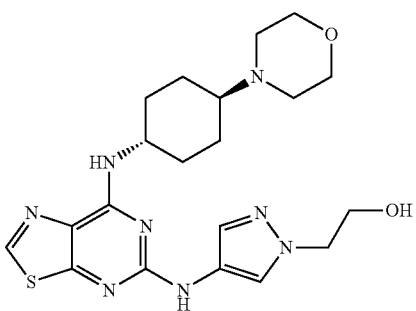
I-54

TABLE 1-continued

Exemplary Compounds

Compound

I-55

I-56

I-57

I-58

In some embodiments, the present invention provides a compound set forth in Table 1, above, or a pharmaceutically acceptable salt thereof.

Without wishing to be bound by any particular theory, it is believed that proximity of an inhibitor compound, or pendant moiety of an inhibitor compound, to the water of interest facilitates displacement or disruption of that water by the inhibitor compound, or pendant moiety of an inhibitor compound. In some embodiments, a water molecule displaced or disrupted by an inhibitor compound, or pendant moiety of an inhibitor compound, is an unstable water molecule.

In certain embodiments, the present invention provides a complex comprising IRAK-4 and an inhibitor, wherein at least one unstable water of IRAK-4 is displaced or disrupted by the inhibitor. In some embodiments, at least two unstable waters selected are displaced or disrupted by the inhibitor.

4. General Methods of Providing the Present Compounds

The compounds of this invention may be prepared or isolated in general by synthetic and/or semi-synthetic methods known to those skilled in the art for analogous compounds and by methods described in detail in the Examples, herein.

In the Schemes below, where a particular protecting group ("PG"), leaving group ("LG"), or transformation condition is depicted, one of ordinary skill in the art will appreciate that other protecting groups, leaving groups, and transformation conditions are also suitable and are contemplated. Such groups and transformations are described in detail in *March's Advanced Organic Chemistry Reactions, Mechanisms, and Structure*, M. B. Smith and J. March, 5$^{th}$ Edition, John Wiley & Sons, 2001, *Comprehensive Organic Transformations*, R. C. Larock, 2$^{nd}$ Edition, John Wiley & Sons, 1999, and *Protecting Groups in Organic Synthesis*, T. W. Greene and P. G. M. Wuts, 3$^{rd}$ edition, John Wiley & Sons, 1999, the entirety of each of which is hereby incorporated herein by reference.

As used herein, the phrase "leaving group" (LG) includes, but is not limited to, halogens (e.g. fluoride, chloride, bromide, iodide), sulfonates (e.g. mesylate, tosylate, benzenesulfonate, brosylate, nosylate, triflate), diazonium, and the like.

As used herein, the phrase "oxygen protecting group" includes, for example, carbonyl protecting groups, hydroxyl protecting groups, etc. Hydroxyl protecting groups are well known in the art and include those described in detail in *Protecting Groups in Organic Synthesis*, T. W. Greene and P. G. M. Wuts, 3$^{rd}$ edition, John Wiley & Sons, 1999, the entirety of which is incorporated herein by reference. Examples of suitable hydroxyl protecting groups include, but are not limited to, esters, allyl ethers, ethers, silyl ethers, alkyl ethers, arylalkyl ethers, and alkoxyalkyl ethers. Examples of such esters include formates, acetates, carbonates, and sulfonates. Specific examples include formate, benzoyl formate, chloroacetate, trifluoroacetate, methoxyacetate, triphenylmethoxyacetate, p-chlorophenoxyacetate, 3-phenylpropionate, 4-oxopentanoate, 4,4-(ethylenedithio) pentanoate, pivaloate (trimethylacetyl), crotonate, 4-methoxy-crotonate, benzoate, p-benzylbenzoate, 2,4,6-trimethylbenzoate, carbonates such as methyl, 9-fluorenylmethyl, ethyl, 2,2,2-trichloroethyl, 2-(trimethylsilyl)ethyl, 2-(phenylsulfonyl)ethyl, vinyl, allyl, and p-nitrobenzyl. Examples of such silyl ethers include trimethylsilyl, triethylsilyl, t-butyldimethylsilyl, t-butyldiphenylsilyl, triisopropylsilyl, and other trialkylsilyl ethers. Alkyl ethers include methyl, benzyl, p-methoxybenzyl, 3,4-dimethoxybenzyl, trityl, t-butyl, allyl, and allyloxycarbonyl ethers or derivatives. Alkoxyalkyl ethers include acetals such as methoxymethyl, methylthiomethyl, (2-methoxyethoxy)methyl, benzyloxymethyl, beta-(trimethylsilyl)ethoxymethyl, and tetrahydropyranyl ethers. Examples of arylalkyl ethers include benzyl, p-methoxybenzyl (MPM), 3,4-dimethoxybenzyl, O-nitrobenzyl, p-nitrobenzyl, p-halobenzyl, 2,6-dichlorobenzyl, p-cyanobenzyl, and 2- and 4-picolyl.

Amino protecting groups are well known in the art and include those described in detail in *Protecting Groups in Organic Synthesis*, T. W. Greene and P. G. M. Wuts, 3$^{rd}$ edition, John Wiley & Sons, 1999, the entirety of which is incorporated herein by reference. Suitable amino protecting groups include, but are not limited to, aralkylamines, carbamates, cyclic imides, allyl amines, amides, and the like. Examples of such groups include t-butyloxycarbonyl (BOC), ethyloxycarbonyl, methyloxycarbonyl, trichloroethyloxycarbonyl, allyloxycarbonyl (Alloc), benzyloxocarbonyl (CBZ), allyl, phthalimide, benzyl (Bn), fluorenylmethylcarbonyl (Fmoc), formyl, acetyl, chloroacetyl, dichloroacetyl, trichloroacetyl, phenylacetyl, trifluoroacetyl, benzoyl, and the like.

In certain embodiments, compounds of the present invention of formula I wherein Q is N, $R^z$ is hydrogen, X is N, and Y is C—$R^x$ are generally prepared according to Scheme I set forth below:

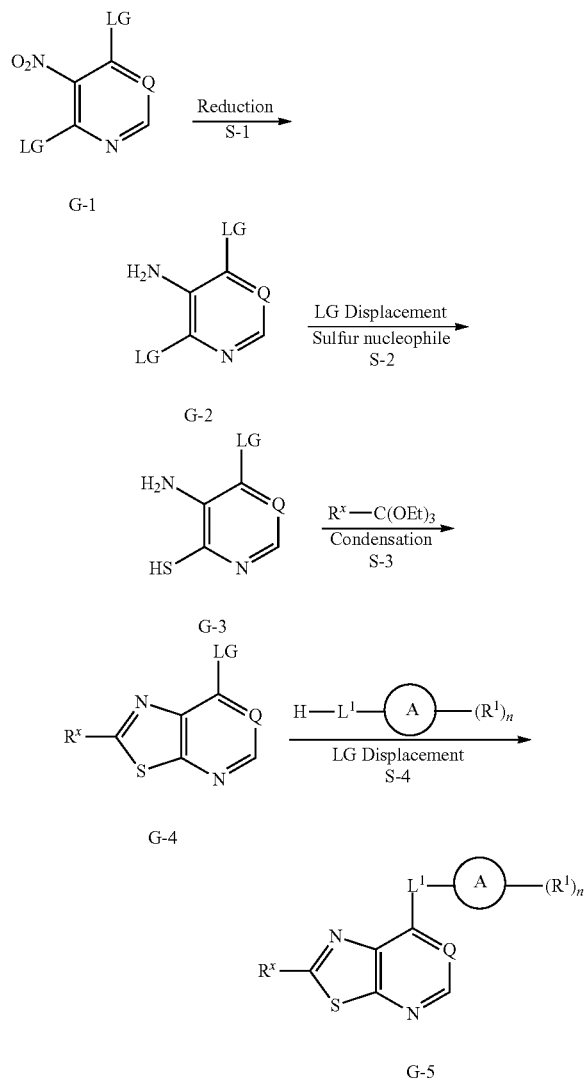

In Scheme I above, each of n, Q, LG, $R^1$, $R^x$, $L^1$, and Ring A is as defined above and below and in classes and subclasses as described herein.

In one aspect, the present invention provides methods for preparing compounds of formula G-5 according to the steps depicted in Scheme I, above. In some embodiments, at step S-1, a nitro substituted pyridine or pyrimidine of formula G-1 containing two leaving groups, LG, is treated with a reducing agent to effect a reduction of the nitro group to form an amino substituted pyridine or pyrimidine of formula G-2. In certain embodiments, the reducing agent is hydrogen with a catalyst. In some embodiments, the reducing agent is a metal or metal salt. In some embodiments, the reducing agent is a hydride. In some embodiments, each LG is a halide. In some embodiments, each LG is chloride.

In some embodiments, step S-2 comprises contacting a compound of formula G-2 with a sulfur nucleophile to form a compound of formula G-3. In some embodiments the sulfur nucleophile is disodium sulfide.

In some embodiments, step S-3 comprises contacting the intermediate of formula G-3 with an orthoester of the carboxylic acid of $R^x$—C(O)OH to form a thiazolopyridine or thiazolopyrimidine compound of formula G-4. In some embodiments the orthoester is a trialkyl orthoester. In some embodiments, the orthoester is the triethyl orthoester.

In some embodiments, step S-4 comprises contacting the compound of formula G-4 with a group of the formula HL$^1$-[Ring A]-($R^1$)$_n$ to displace the leaving group LG, thereby forming a compound of formula G-5. In some embodiments LG is a halogen. In some embodiments LG is chlorine. In some embodiments LG is a sulfonate. In some embodiments a base is added to promote the displacement. In some embodiments, the base is sodium hydride. In some embodiments, the base is an amine.

In certain embodiments, step S-4 comprises contacting a compound of formula G-4 with a compound of the formula

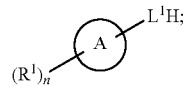

wherein
$L^1$, $R^1$, Ring A, and n are defined above and below and in classes and subclasses as described herein.

In some embodiments $L^1$ is selected from O— and —NH—, such that together with the hydrogen filling the open valence, $L^1$H denotes an —OH or —NH$_2$ group. In some embodiments $L^1$H is —OH. In some embodiments $L^1$H is —NH$_2$.

In some embodiments n is 0-4. In some embodiments n is 1-4. In some embodiments n is 1.

In some embodiments $R^1$ is —NR$_2$. In some embodiments $R^1$ is dimethylamino. In some embodiments $R^1$ is morpholino. In some embodiments, Ring A is piperidino or 4,4-difluoropiperidino. In some embodiments Ring A is cyclohexyl.

In some embodiments step S-4 further comprises contacting the reaction mixture with a base. In some embodiments the base is sodium bis(trimethylsilyl)amide. In some embodiments the reaction further comprises a solvent. In some embodiments the solvent is THF.

One of skill in the art will appreciate that compounds of formula G-5 may contain one or more stereocenters, and may be present as an racemic or diastereomeric mixture. One of skill in the art will also appreciate that there are many methods known in the art for the separation of isomers to obtain stereoenriched or stereopure isomers of those compounds, including but not limited to HPLC, chiral HPLC, fractional crystallization of diastereomeric salts, kinetic enzymatic resolution (e.g. by fungal-, bacterial-, or animal-derived lipases or esterases), and formation of covalent diastereomeric derivatives using an enantioenriched reagent. In some embodiments, the enantiomers of a compound of formula G-5 are resolved by the action of lipase enzymes.

In certain embodiments, compounds of the present invention wherein X is N, Y is C—$R^x$, and $R^z$ is —NH[Ar] are generally prepared according to Scheme II set forth below:

Scheme II

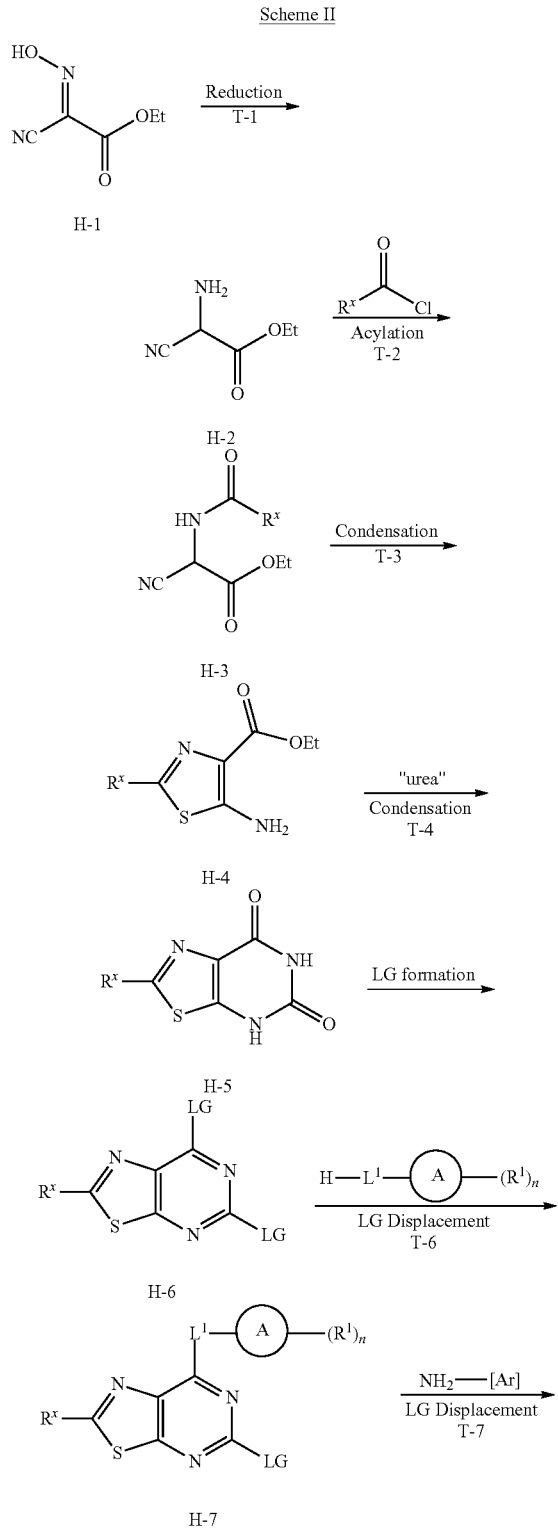

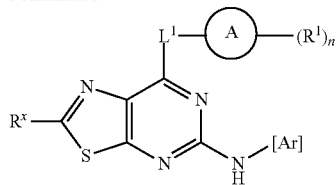

H-8

In Scheme II above, each of n, [Ar], LG, $R^1$, $R^x$, $L^1$, and Ring A is as defined above and below and in classes and subclasses as described herein.

In one aspect, the present invention provides methods for preparing compounds of formula H-8 according to the steps depicted in Scheme 1, above. In some embodiments, at step T-1, a cyanooxime of formula H-1 is reacted with a reducing agent, to effect a reduction of the oxime moiety to form an alpha-aminonitrile of formula H-2. In certain embodiments, the reducing agent is sodium dithionite. In some embodiments the reduction is performed in aqueous bicarbonate solution.

In some embodiments, step T-2 comprises contacting a compound of formula H-2 with an acylating reagent of formula $R^x$—C(O)LG to form an amide of formula H-3. In some embodiments, the acylating reagent is propionyl chloride. In some embodiments a base is added. In some embodiments, the base is an amine. In some embodiments, the base is triethylamine.

In some embodiments, step T-3 comprises contacting an intermediate of formula H-3 with a thionating reagent to form a thiazole compound of formula H-4. In some embodiments the thionating reagent is Lawesson's reagent. In some embodiments, the reaction further comprises contacting the reaction mixture with a base. In some embodiments the base is pyridine.

In some embodiments, step T-4 comprises contacting a compound of formula H-4 with a urea synthon to form a cyclocondensation product of formula H-5. In some embodiments the urea synthon is urea. In some embodiments, the urea synthon is chlorosulfonylisocyanate (ClS(O)$_2$NCO). In some embodiments step T-4 is performed with an additional substep of hydrolyzing the condensation intermediate in situ. In some embodiments, the hydrolysis is promoted by aqueous sodium hydroxide. In some embodiments the reaction mixture is reacidified with acid. In some embodiments the acid is hydrochloric acid.

In some embodiments, step T-5 comprises contacting a compound of formula H-5 with a reagent to generate leaving groups LG from oxo substituents, thereby forming a compound of formula H-6. In some embodiments, the reagent is phosphorus oxychloride, and each LG is chloride.

In some embodiments, step T-6 comprises contacting a compound of LG of compound H-6 with a compound of the formula

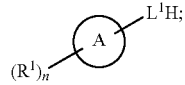

wherein
$L^1$, $R^1$, Ring A, and n are defined above and below and in classes and subclasses as described herein; thereby forming a compound of formula H-7.

In some embodiments $L^1$ is selected from O— and —NH—, such that together with the hydrogen filling the open valence, $L^1$H denotes an —OH or —NH$_2$ group. In some embodiments $L^1$H is —OH. In some embodiments $L^1$H is —NH$_2$.

In some embodiments n is 0-4. In some embodiments n is 1-4. In some embodiments n is 1.

In some embodiments $R^1$ is —$NR_2$. In some embodiments $R^1$ is dimethylamino. In some embodiments $R^1$ is morpholino. In some embodiments, Ring A is piperidine. In some embodiments Ring A is cyclohexyl.

In some embodiments step S-5 further comprises contacting the reaction mixture with a base. In some embodiments the base is sodium bis(trimethylsilyl)amide. In some embodiments the reaction further comprises a solvent. In some embodiments the solvent is THF.

In some embodiments step T-7 comprises contacting a compound of formula H-7 with a compound of formula [Ar]—$NH_2$, thereby forming a compound of formula H-8. In some embodiments step T-7 further comprises contacting the reaction mixture with a base. In some embodiments step T-7 further comprises contacting the reaction mixture with a palladium catalyst. In some embodiments [Ar] is an optionally substituted phenyl or heteroaromatic ring. In some embodiments [Ar] is an optionally substituted phenyl ring. In some embodiments [Ar] is an optionally substituted heteroaromatic ring. In some embodiments [Ar] is an optionally substituted 5-6 membered heteroaromatic ring containing 1-2 heteroatoms independently selected from nitrogen, oxygen and sulfur.

In certain embodiments, compounds of the present invention wherein X is C-$L^2(R^4)_p$—$R^x$, Y is N, $L^1$ is NH, and $R^z$ is hydrogen are generally prepared according to Scheme III set forth below:

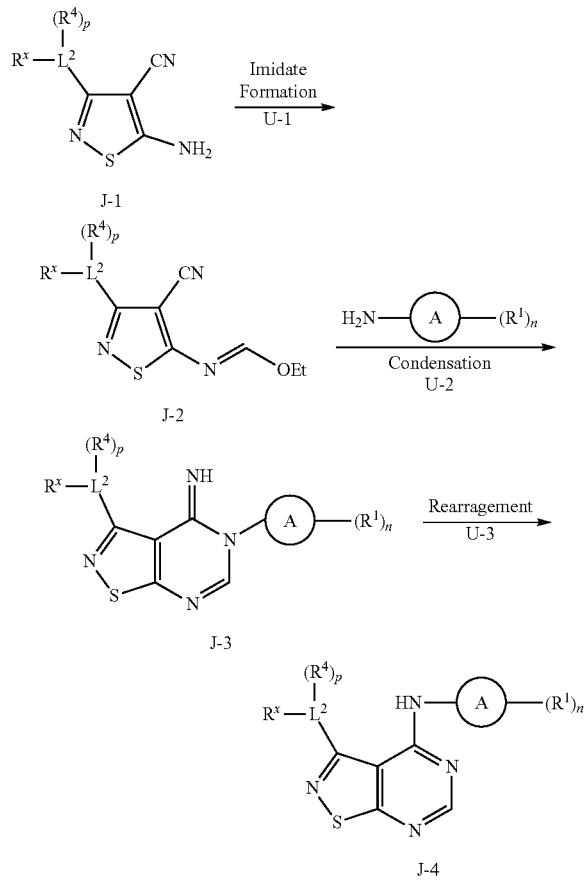

In Scheme III above, each of n, p, LG, $R^1$, $R^4$, $R^x$, and Ring A is as defined above and below and in classes and subclasses as described herein.

In some embodiments step U-1 comprises contacting an aminoisothiazole compound of formula J-1 with an orthoester to form an imidate of formula J-2. In some embodiments the orthoester is triethylorthoformate.

In some embodiments step U-2 comprises contacting an imidate compound of formula J-2 with a compound of formula $H_2N$—[Ring A]-$(R^1)_n$ in a cyclocondensation reaction, thereby forming a compound of formula J-3.

In some embodiments step U-3 comprises the rearrangement of a compound of formula J-3 to form a compound of formula J-4. In some embodiments, the rearrangement is a thermal rearrangement according to the procedure of Anderson, R C et al. (*J. Heterocyclic Chem.* (1975) 12(5), p. 883). In some embodiment, the rearrangement is performed in ethanol.

In certain embodiments, compounds of the present invention of formula I, wherein X is C-$L^2(R^4)_p$—$R^x$, Y is N, and $R^z$ is —NH-[Ar], are generally prepared according to Scheme IV set forth below:

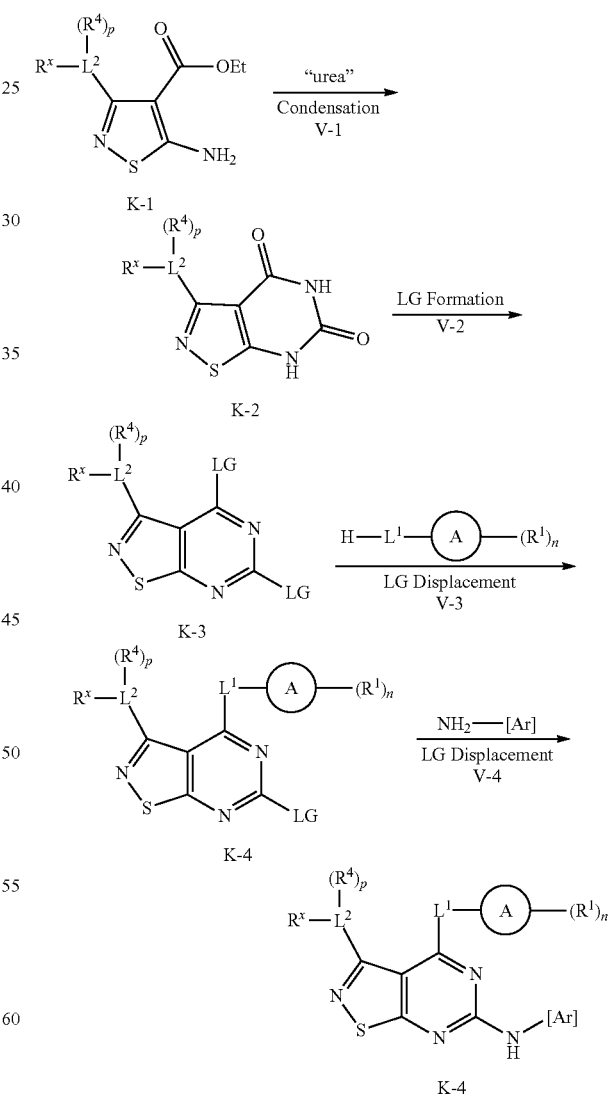

In Scheme IV above, each of n, p, LG, $R^1$, $R^4$, $R^x$, [Ar], $L^1$, and Ring A is as defined above and below and in classes and subclasses as described herein.

In some embodiments step V-1 comprises contacting an aminothiazole ester compound of formula K-1 with a urea synthon, thereby forming a bicyclic compound of formula K-2. In some embodiments, the urea synthon is urea. In some embodiments, the urea synthon is chlorosulfonylisocyanate (ClS(O)$_2$NCO).

In some embodiments step V-2 comprises contacting a compound of formula K-2 with a reagent to convert the oxo substitutents into leaving groups (LG), thereby forming a compound of formula K-3. In some embodiments, each LG is a halogen. In some embodiments, each LG is chloride. In some embodiments the reagent used is phosphorus oxychloride.

In some embodiments step V-3 comprises contacting a compound of formula K-3 with a compound of formula:

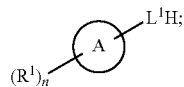

wherein
L$^1$, R$^1$, Ring A, and n are defined above and below and in classes and subclasses as described herein; thereby forming a compound of formula K-4.

In some embodiments L$^1$ is selected from O— and —NH—, such that together with the hydrogen filling the open valence, L$^1$H denotes an —OH or —NH$_2$ group. In some embodiments L$^1$H is —OH. In some embodiments L$^1$H is —NH$_2$.

In some embodiments n is 0-4. In some embodiments n is 1-4. In some embodiments n is 1.

In some embodiments R$^1$ is —NR$_2$. In some embodiments R$^1$ is dimethylamino. In some embodiments R$^1$ is morpholino. In some embodiments, Ring A is piperidine. In some embodiments Ring A is cyclohexyl.

In some embodiments step S-5 further comprises contacting the reaction mixture with a base. In some embodiments the base is sodium bis(trimethylsilyl)amide. In some embodiments the reaction further comprises a solvent. In some embodiments the solvent is THF.

In some embodiments step V-4 comprises contacting a compound of formula K-4 with a compound of formula [Ar]—NH$_2$, thereby forming a compound of formula K-5. In some embodiments step V-4 further comprises contacting the reaction mixture with a base. In some embodiments step V-4 further comprises contacting the reaction mixture with a palladium catalyst. In some embodiments [Ar] is an optionally substituted phenyl or heteroaromatic ring. In some embodiments [Ar] is an phenyl or heteroaromatic ring substituted with m instances of R$^{1'}$, wherein each of m and R$^{1'}$ is as defined above and below described in embodiments herein, both singly and in combination. In some embodiments [Ar] is an optionally substituted phenyl ring. In some embodiments [Ar] is an optionally substituted heteroaromatic ring. In some embodiments [Ar] is an optionally substituted 5-6 membered heteroaromatic ring containing 1-2 heteroatoms independently selected from nitrogen, oxygen and sulfur.

One of skill in the art will appreciate that various functional groups present in compounds of the invention such as aliphatic groups, alcohols, carboxylic acids, esters, amides, aldehydes, halogens and nitriles can be interconverted by techniques well known in the art including, but not limited to reduction, oxidation, esterification, hydrolysis, partial oxidation, partial reduction, halogenation, dehydration, partial hydration, and hydration. "March's Advanced Organic Chemistry", 5$^{th}$ Ed., Ed.: Smith, M. B. and March, J., John Wiley & Sons, New York: 2001, the entirety of which is incorporated herein by reference. Such interconversions may require one or more of the aforementioned techniques, and certain methods for synthesizing compounds of the invention are described below in the Exemplification.

5. Uses, Formulation and Administration

Pharmaceutically Acceptable Compositions

According to another embodiment, the invention provides a composition comprising a compound of this invention or a pharmaceutically acceptable derivative thereof and a pharmaceutically acceptable carrier, adjuvant, or vehicle. The amount of compound in compositions of this invention is such that is effective to measurably inhibit an IRAK protein kinase, or a mutant thereof, in a biological sample or in a patient. In certain embodiments, the amount of compound in compositions of this invention is such that is effective to measurably inhibit an IRAK protein kinase, or a mutant thereof, in a biological sample or in a patient. In certain embodiments, a composition of this invention is formulated for administration to a patient in need of such composition. In some embodiments, a composition of this invention is formulated for oral administration to a patient.

The term "patient," as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A "pharmaceutically acceptable derivative" means any non-toxic salt, ester, salt of an ester or other derivative of a compound of this invention that, upon administration to a recipient, is capable of providing, either directly or indirectly, a compound of this invention or an inhibitorily active metabolite or residue thereof.

As used herein, the term "inhibitorily active metabolite or residue thereof" means that a metabolite or residue thereof is also an inhibitor of an IRAK protein kinase, or a mutant thereof.

Compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, provided pharmaceutically acceptable compositions may be formulated in a suitable ointment containing the active component suspended or dissolved in one or more carriers. Carriers for topical administration of compounds of this invention include, but are not limited to, mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, provided pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

Pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, pharmaceutically acceptable compositions of this invention are formulated for oral administration. Such formulations may be administered with or without food. In some embodiments, pharmaceutically acceptable compositions of this invention are administered without food. In other embodiments, pharmaceutically acceptable compositions of this invention are administered with food.

The amount of compounds of the present invention that may be combined with the carrier materials to produce a composition in a single dosage form will vary depending upon the host treated, the particular mode of administration. Preferably, provided compositions should be formulated so that a dosage of between 0.01-100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Uses of Compounds and Pharmaceutically Acceptable Compositions

Compounds and compositions described herein are generally useful for the inhibition of kinase activity of one or more enzymes.

Examples of kinases that are inhibited by the compounds and compositions described herein and against which the methods described herein are useful include those of the interleukin-1 receptor-associated kinase (IRAK) family of kinases, the members of which include IRAK-1, IRAK-2, and IRAK-4, or a mutant thereof. Li et al., "IRAK-4: A novel member of the IRAK family with the properties of an IRAK-kinase," *PNAS* 2002, 99(8), 5567-5572, Flannery et al., "The interleukin-1 receptor-associated kinases: Critical regulators of innate immune signaling" Biochem Pharm 2010, 80(12), 1981-1991 incorporated by reference in its entirety.

The activity of a compound utilized in this invention as an inhibitor of IRAK-1, IRAK-2, and/or IRAK-4, or a mutant thereof, may be assayed in vitro, in vivo or in a cell line. In vitro assays include assays that determine inhibition of either the phosphorylation activity and/or the subsequent functional consequences, or ATPase activity of activated IRAK-1, IRAK-2, and/or IRAK-4, or a mutant thereof. Alternate in vitro assays quantitate the ability of the inhibitor to bind to IRAK-1, IRAK-2 and/or IRAK-4. Inhibitor binding may be measured by radiolabeling the inhibitor prior to binding, isolating the inhibitor/IRAK-1, inhibitor/IRAK-2, or inhibitor/IRAK-4 complex and determining the amount of radiolabel bound. Alternatively, inhibitor binding may be determined by running a competition experiment where new inhibitors are incubated with IRAK-1, IRAK-2, and/or IRAK-4 bound to known radioligands. Representative in vitro and in vivo assays useful in assaying an IRAK-4 inhibitor include those described and disclosed in, e.g., Kim et al., "A critical role for IRAK4 kinase activity in Toll-like receptor-mediated innate immunity," *J. Exp. Med.* 2007 204(5), 1025-1036; Lebakken et al., "A Fluorescence Lifetime Based Binding Assay to Characterize Kinase Inhibitors," *J. Biomol. Screen.* 2007, 12(6), 828-841; Maschera et al., "Overexpression of an enzymatically inactive interleukin-1-receptor-associated kinase activates nuclear factor-κB," *Biochem. J.* 1999, 339, 227-231; Song et al., "The kinase activities of interleukin-e receptor associated kinase (IRAK)-1 and 4 are redundant in the control of inflammatory cytokine expression in human cells," *Mol. Immunol.* 2009, 46, 1458-1466, each of which is herein incorporated by reference in its entirety. Detailed conditions for assaying a compound utilized in this invention as an inhibitor of IRAK-1, IRAK-2, and/or IRAK-4, or a mutant thereof, are set forth in the Examples below.

The best characterized member of the IRAK family is the serine/threonine kinase IRAK-4. IRAK-4 is implicated in signaling innate immune responses from Toll-like receptors (TLRs) and Toll/IL-1 receptors (TIRs).

Innate immunity detects pathogens through the recognition of pathogen-associated molecular patterns by TLRs, when then links to the adaptive immune response. TLRs recognize conserved structures of both microbes and endogenous molecules. TLRs which recognize bacterial and fungal components are located on the cell surface, whereas TLRs which recognize viral or microbial nucleic acids are localized to intracellular membranes such as endosomes and phagosomes. Cell surface TLRs can be targeted by small molecules and antibodies, whereas intracellular TLRs require targeting with oligonucleotides.

TLRs mediate the innate immune response by upregulating the expression of inflammatory genes in multiple target cells. See, e.g., Sen et al., "Transcriptional signaling by double-stranded RNA: role of TLR3," *Cytokine & Growth Factor Rev.* 2005, 16, 1-14, incorporated by reference in its entirety. While TLR-mediated inflammatory response is critical for innate immunity and host defense against infections, uncontrolled inflammation is detrimental to the host leading to sepsis and chronic inflammatory diseases, such as chronic arthritis, atherosclerosis, multiple sclerosis, cancers, autoimmune disorders such as rheumatoid arthritis, lupus, asthma, psoriasis, and inflammatory bowel diseases.

Upon binding of a ligand, most TLRs recruit the adaptor molecule MyD88 through the TIR domain, mediating the MyD88-dependent pathway. MyD88 then recruits IRAK-4, which engages with the nuclear factor-κB (NF-κB), mitogen-activated protein (MAP) kinase and interferon-regulatory factor cascades and leads to the induction of pro-inflammatory cytokines. The activation of NF-κB results in the induction of inflammatory cytokines and chemokines, such as TNF-α, IL-1α, IL-6 and IL-8. The kinase activity of IRAK-4 has been shown to play a critical role in the TLR-mediated immune and inflammatory responses. IRAK4 is a key mediator of the innate immune response orchestrated by interleukin-1 receptor (IL-1R), interleukin-18 receptor (IL-18R), IL-33 receptor (IL-33R), and Toll-like receptors (TLRs). Inactivation of IRAK-1 and/or IRAK-4 activity has been shown to result in diminished production of cytokines and chemokines in response to stimulation of IL-1 and TLR ligands. See, e.g., Picard et al., "Clinical features and outcome of patients with IRAK-4 and MyD88 deficiency," *Medicine (Baltimore)*, 2010, 89(6), 043-25; Li, "IRAK4 in TLR/IL-1R signaling: Possible clinical applications," *Eur. J. Immunology* 2008, 38:614-618; Cohen et al., "Targeting protein kinases for the development of anti-inflammatory drugs," *Curr. Opin. Cell Bio.* 2009, 21:317-324; Flannery et al., "The interleukin-1 receptor-associated kinases: Critical regulators of innate immune signalling," *Biochem. Pharm.* 2010, 80(12), 1981-1991; Gottipati et al., "IRAK1: A critical signaling mediator of innate immunity," *Cellular Signaling* 2008, 20, 269-276; Kim et al., "A critical role for IRAK4 kinase activity in Toll-like receptor-mediated innate immunity," *J. Exp. Med.* 2007 204(5), 1025-1036; Koziczak-Holbro et al., "IRAK-4 Kinase Activity Is Required for Interleukin-1 (IL-1) Receptor- and Toll-like Receptor 7-mediated Signaling and Gene Expression," *J. Biol. Chem.* 2007, 282(18), 13552-13560; Kubo-Murai et al., "IRAK-4-dependent Degradation of IRAK-1 is a Negative Feedback Signal for TLR-mediated NF-κB Activation," *J. Biochem.* 2008, 143, 295-302; Maschera et al., "Overexpression of an enzymatically inactive interleukin-1-receptor-associated kinase activates nuclear factor-κB," *Biochem. J.* 1999, 339, 227-231; Lin et al., "Helical assembly in the MyD88-IRAK4-IRAK2 complex in TLR/IL-1R signalling," *Nature* 2010, 465(17), 885-891; Suzuki et al., "IRAK-4 as the central TIR signaling mediator in innate immunity," *TRENDS in Immunol.* 2002, 23(10), 503-506; Suzuki et al., "Severe impairment of interleukin-1 and Toll-like receptor signalling in mice lacking IRAK-4," *Nature* 2002, 416, 750-754; Swantek et al., "IL-1 Receptor-Associated Kinase Modulates Host Responsiveness to Endotoxin," *J. Immunol.* 2000, 164, 4301-4306; Hennessy, E., et al., "Targeting Toll-like receptors: emerging therapeutics?" *Nature Reviews*, vol. 9, pp: 293-307 (2010); Dinarello, C. "Interleukin-18 and the Pathogenesis of Inflammatory Diseases," *Seminars in Nephrology*, vol. 27, no. 1, pp: 98-114 (2007), each of which is herein incorporated by reference in its entirety. In fact, knockdown mice that express a catalytically inactive mutant IRAK-4 protein are completely resistant to septic shock and show impaired IL-1 activity. Moreover, these mice are resistant to joint and bone inflammation/destruction in an arthritis model, suggesting that IRAK-4 may be targeted to treat chronic inflammation. Further, while IRAK-4 appears to be vital for childhood immunity against some pyogenic bacteria, it has been shown to play a redundant role in protective immunity to most infections in adults, as demonstrated by one study in which patients older than 14 lacking IRAK-4 activity exhibited no invasive infections. Cohen et al., "Targeting protein kinases for the development of anti-inflammatory drugs," *Curr. Opin. Cell Bio.* 2009, 21:317-324; Ku et al., "Selective predisposition to bacterial infections in IRAK-4-deficient children: IRAK-4-dependent TLRs are otherwise redundant in protective immunity," *J. Exp. Med.* 2007, 204(10), 2407-2422; Picard et al., "Inherited human IRAK-4 deficiency: an update," *Immunol. Res.* 2007, 38, 347-352; Song et al., "The kinase activities of interleukin-e receptor associated kinase (IRAK)-1 and 4 are redundant in the control of inflammatory cytokine expression in human cells," *Mol. Immunol.* 2009, 46, 1458-1466; Rokosz, L. et al., "Kinase inhibitors as drugs for chronic inflammatory and immunological diseases: progress and challenges," *Expert Opinions on Therapeutic Targets*, 12(7), pp: 883-903 (2008); Gearing, A. "Targeting toll-like receptors for drug development: a summary of commercial approaches," *Immunology and Cell Biology*, 85, pp: 490-494 (2007); Dinarello, C. "IL-1: Discoveries, controversies and future directions," *European Journal of Immunology*, 40, pp: 595-653 (2010), each of which is herein incorporated by reference in its entirety. Because TLR activation triggers IRAK-4 kinase activity, IRAK-4 inhibition presents an attractive target for treating the underlying causes of inflammation in countless diseases.

Representative IRAK-4 inhibitors include those described and disclosed in e.g., Buckley et al., *Bioorg. Med. Chem. Lett.* 2008, 18, 3211-3214; Buckley et al., *Bioorg. Med. Chem. Lett.* 2008, 18, 3291-3295; Buckley et al., *Bioorg. Med. Chem. Lett.* 2008, 18, 3656-3660; Powers et al., "Discovery and initial SAR of inhibitors of interleukin-1 receptor-associated kinase-4," *Bioorg. Med. Chem. Lett.* 2006, 16, 2842-2845; Wng et al., "IRAK-4 Inhibitors for Inflammation," *Curr. Topics in Med. Chem.* 2009, 9, 724-737, each of which is herein incorporated by reference in its entirety.

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

Provided compounds are inhibitors of one of more of IRAK-1, IRAK-2, and/or IRAK-4 and are therefore useful for treating one or more disorders associated with activity of one or more of IRAK-1, IRAK-2, and/or IRAK-4. Thus, in certain embodiments, the present invention provides a method for treating a IRAK-1-mediated, a IRAK-2-mediated, and/or a IRAK-4-mediated disorder comprising the step of administering to a patient in need thereof a compound of the present invention, or pharmaceutically acceptable composition thereof.

As used herein, the terms "IRAK-1-mediated", "IRAK-2-mediated", and/or "IRAK-4-mediated" disorders, diseases, and/or conditions as used herein means any disease or other deleterious condition in which one or more of IRAK-1, IRAK-2, and/or IRAK-4, or a mutant thereof, are known to play a role. Accordingly, another embodiment of the present invention relates to treating or lessening the severity of one or more diseases in which one or more of IRAK-1, IRAK-2, and/or IRAK-4, or a mutant thereof, are known to play a role.

In some embodiments, the present invention provides a method for treating one or more disorders, diseases, and/or conditions wherein the disorder, disease, or condition is a cancer, a neurodegenerative disorder, a viral disease, an autoimmune disease, an inflammatory disorder, a hereditary disorder, a hormone-related disease, a metabolic disorder, conditions associated with organ transplantation, immunodeficiency disorders, a destructive bone disorder, a proliferative disorder, an infectious disease, a condition associated with cell death, thrombin-induced platelet aggregation, liver disease, pathologic immune conditions involving T cell activation, a cardiovascular disorder, or a CNS disorder.

Diseases and conditions treatable according to the methods of this invention include, but are not limited to, cancer (see, e.g., Ngo, V. et al., "Oncogenically active MYD88 mutations in human lymphoma," *Nature*, vol. 000, pp: 1-7 (2010); Lust, J. et al., "Induction of a Chronic Disease State in patients With Smoldering of Indolent Multiple Myeloma by Targeting Interleukin 1β-Induced Interleukin 6 Production and the Myeloma Proliferative Component," *Mayo Clinic Proceedings*, 84(2), pp: 114-122 (2009)), diabetes, cardiovascular disease, viral disease, autoimmune diseases such as lupus (see, e.g., Dinarello, C. "Interleukin-18 and the Pathogenesis of Inflammatory Diseases," *Seminars in Nephrology*, vol. 27, no. 1, pp: 98-114 (2007); Cohen et al., "Targeting protein kinases for the development of anti-inflammatory drugs," *Curr. Opin. Cell Bio.* 2009, 21:317-324) and rheumatoid arthritis (see, e.g., Geyer, M. et al., "Actual status of antiinterleukin-1 therapies in rheumatic diseases," *Current Opinion in Rheumatology*, 22, pp: 246-251 (2010)), autoinflammatory syndromes (see, e.g., Hoffman, H. et al., "Efficacy and Safety of Rilonacept (Interleukin-1 Trap) in Patients with Cryopyrin-Associated Periodic Syndromes," *Arthritis & Rheumatism*, vol. 58, no. 8, pp: 2443-2452 (2008)), atherosclerosis, psoriasis, allergic disorders, inflammatory bowel disease (see, e.g., Cario, E. "Therapeutic Impact of Toll-like Receptors on Inflammatory Bowel Diseases: A Multiple-edged Sword," *Inflamm. Bowel Dis.*, 14, pp: 411-421 (2008)), inflammation (see, e.g., Dinarello, C. "Interleukin 1 and interleukin 18 as mediators of inflammation and the aging process," *The American Journal of Clinical Nutrition*, 83, pp: 447S-455S (2006)), acute and chronic gout and gouty arthritis (see, e.g., Terkeltaub, R. "Update on gout: new therapeutic strategies and options," *Nature*, vol. 6, pp: 30-38 (2010); Weaver, A. "Epidemiology of gout," *Cleveland Clinic Journal of Medicine*, vol. 75, suppl. 5, pp: S9-512 (2008); Dalbeth, N. et al., "Hyperuricaemia and gout: state of the art and future perspectives," *Annals of Rheumatic Diseases*, 69, pp: 1738-1743 (2010); Martinon, F. et al., "Gout-associated uric acid crystals activate the NALP3 inflammasome," *Nature*, vol. 440, pp: 237-241 (2006); So, A. et al., "A pilot study of IL-1 inhibition by anakinra in acute gout," *Arthritis Research & Therapy*, vol. 9, no. 2, pp: 1-6 (2007); Terkeltaub, R. et al., "The interleukin 1 inhibitor rilonacept in treatment of chronic gouty arthritis: results of a placebo-controlled, monosequence crossover, non-randomised, single-blind pilot study," *Annals of Rheumatic Diseases*, 68, pp: 1613-1617 (2009); Torres, R. et al., "Hyperalgesia, synovitis and multiple biomarkers of inflammation are suppressed by interleukin 1 inhibition in a novel animal model of gouty arthritis," *Annals of Rheumatic Diseases*, 68, pp: 1602-1608 (2009)), neurological disorders, metabolic syndrome (see, e.g., Troseid, M. "The role of interleukin-18 in the metabolic syndrome," *Cardiovascular Diabetology*, 9:11, pp: 1-8 (2010)), immunodeficiency disorders such as AIDS and HIV (see, e.g., Iannello, A. et al., "Role of Interleukin-18 in the Development and Pathogenesis of AIDS," *AIDS Reviews*, 11, pp: 115-125 (2009)), destructive bone disorders (see, e.g., Hennessy, E., et al., "Targeting Toll-like receptors: emerging therapeutics?" *Nature Reviews*, vol. 9, pp: 293-307 (2010)), osteoarthritis, proliferative disorders, Waldenström's Macroglobulinemia (see, e.g., Treon, et al., "Whole genome sequencing reveals a widely expressed mutation (MYD88 L265P) with oncogenic activity in Waldenström's Macroglobulinemia" 53$^{rd}$ ASH Annual Meeting; Xu, et al., "A somatic variant in MYD88 (L265P) revealed by whole genome sequencing differentiates lymphoplasmacytic lymphoma from marginal zone lymphomas" 53rd ASH Annual Meeting; Yang et al., "Disruption of MYD88 pathway signaling leads to loss of constitutive IRAK1, NK-kB and JAK/STAT signaling and induces apoptosis of cells expressing the MYD88 $L^{265}P$ mutation in Waldenström's Macroglobulinemia" 53rd ASH Annual Meeting; Iriyama et al., "Clinical significance of genetic mutations of CD79B, CARD11, MYD88, and EZH2 genes in diffuse large B-cell lymphoma patients" 53rd ASH Annual Meeting; infectious diseases, conditions associated with cell death, pathologic immune conditions involving T cell activation, and CNS disorders in a patient. In one embodiment, a human patient is treated with a compound of the current invention and a pharmaceutically acceptable carrier, adjuvant, or vehicle, wherein said compound is present in an amount to measurably inhibit IRAK-1 only, IRAK-2-only, IRAK-4-only and/ or IRAK1- and IRAK4 kinase activity.

Compounds of the current invention are useful in the treatment of a proliferative disease selected from a benign or malignant tumor, solid tumor, carcinoma of the brain, kidney, liver, adrenal gland, bladder, breast, stomach, gastric tumors, ovaries, colon, rectum, prostate, pancreas, lung, vagina, cervix, testis, genitourinary tract, esophagus, larynx, skin, bone or thyroid, sarcoma, glioblastomas, neuroblastomas, multiple myeloma, gastrointestinal cancer, especially colon carcinoma or colorectal adenoma, a tumor of the neck and head, an epidermal hyperproliferation, psoriasis, prostate hyperplasia, a neoplasia, a neoplasia of epithelial character, adenoma, adenocarcinoma, keratoacanthoma, epidermoid carcinoma, large cell carcinoma, non-small-cell lung carcinoma, lymphomas, Hodgkins and Non-Hodgkins, a mammary carcinoma, follicular carcinoma, undifferentiated carcinoma, papillary carcinoma, seminoma, melanoma, an IL-1 driven disorder, an MyD88 driven disorder, Smoldering of indolent multiple myeloma, or hematological malignancies (including leukemia, diffuse large B-cell lymphoma (DLBCL), ABC DLBCL, chronic lymphocytic leukemia (CLL), chronic lymphocytic lymphoma, primary effusion lymphoma, Burkitt lymphoma/leukemia, acute lymphocytic leukemia, B-cell prolymphocytic leukemia, lymphoplasmacytic lymphoma, Waldenström's macroglobulinemia (WM), splenic marginal zone lymphoma, multiple myeloma, plasmacytoma, intravascular large B-cell lymphoma).

In some embodiments the proliferative disease which can be treated according to the methods of this invention is an MyD88 driven disorder. In some embodiments, the MyD88 driven disorder which can be treated according to the methods of this invention is selected from ABC DLBCL, Waldenström's macroglobulinemia, Hodgkin's lymphoma, primary cutaneous T-cell lymphoma and chronic lymphocytic leukemia.

In some embodiments the proliferative disease which can be treated according to the methods of this invention is an IL-1 driven disorder. In some embodiments the IL-1 driven disorder is Smoldering of indolent multiple myeloma.

Compounds according to the invention are useful in the treatment of inflammatory or obstructive airways diseases, resulting, for example, in reduction of tissue damage, airways inflammation, bronchial hyperreactivity, remodeling or disease progression. Inflammatory or obstructive airways diseases to which the present invention is applicable include asthma of whatever type or genesis including both intrinsic (non-allergic) asthma and extrinsic (allergic) asthma, mild asthma, moderate asthma, severe asthma, bronchitic asthma, exercise-induced asthma, occupational asthma and asthma induced following bacterial infection. Treatment of asthma is also to be understood as embracing treatment of subjects, e.g. of less than 4 or 5 years of age, exhibiting wheezing symptoms and diagnosed or diagnosable as "wheezy infants", an established patient category of major medical concern and now often identified as incipient or early-phase asthmatics.

Compounds according to the invention are useful in the treatment of heteroimmune diseases. Examples of such heteroimmune diseases include, but are not limited to, graft versus host disease, transplantation, transfusion, anaphylaxis, allergies (e.g., allergies to plant pollens, latex, drugs, foods, insect poisons, animal hair, animal dander, dust mites, or cockroach calyx), type I hypersensitivity, allergic conjunctivitis, allergic rhinitis, and atopic dermatitis.

Prophylactic efficacy in the treatment of asthma will be evidenced by reduced frequency or severity of symptomatic attack, e.g. of acute asthmatic or bronchoconstrictor attack, improvement in lung function or improved airways hyperreactivity. It may further be evidenced by reduced requirement for other, symptomatic therapy, such as therapy for or intended to restrict or abort symptomatic attack when it occurs, for example antiinflammatory or bronchodilatory. Prophylactic benefit in asthma may in particular be apparent in subjects prone to "morning dipping". "Morning dipping" is a recognized asthmatic syndrome, common to a substantial percentage of asthmatics and characterised by asthma attack, e.g. between the hours of about 4 to 6 am, i.e. at a time normally substantially distant form any previously administered symptomatic asthma therapy.

Compounds of the current invention can be used for other inflammatory or obstructive airways diseases and conditions to which the present invention is applicable and include acute lung injury (ALI), adult/acute respiratory distress syndrome (ARDS), chronic obstructive pulmonary, airways or lung disease (COPD, COAD or COLD), including chronic bronchitis or dyspnea associated therewith, emphysema, as well as exacerbation of airways hyperreactivity consequent to other drug therapy, in particular other inhaled drug therapy. The invention is also applicable to the treatment of bronchitis of whatever type or genesis including, but not limited to, acute, arachidic, catarrhal, croupus, chronic or phthinoid bronchitis. Further inflammatory or obstructive airways diseases to which the present invention is applicable include pneumoconiosis (an inflammatory, commonly occupational, disease of the lungs, frequently accompanied by airways obstruction, whether chronic or acute, and occasioned by repeated inhalation of dusts) of whatever type or genesis, including, for example, aluminosis, anthracosis, asbestosis, chalicosis, ptilosis, siderosis, silicosis, tabacosis and byssinosis.

With regard to their anti-inflammatory activity, in particular in relation to inhibition of eosinophil activation, compounds of the invention are also useful in the treatment of eosinophil related disorders, e.g. eosinophilia, in particular eosinophil related disorders of the airways (e.g. involving morbid eosinophilic infiltration of pulmonary tissues) including hypereosinophilia as it effects the airways and/or lungs as well as, for example, eosinophil-related disorders of the airways consequential or concomitant to Loffler's syndrome, eosinophilic pneumonia, parasitic (in particular metazoan) infestation (including tropical eosinophilia), bronchopulmonary aspergillosis, polyarteritis nodosa (including Churg-Strauss syndrome), eosinophilic granuloma and eosinophil-related disorders affecting the airways occasioned by drug-reaction.

Compounds of the invention are also useful in the treatment of inflammatory or allergic conditions of the skin, for example psoriasis, contact dermatitis, atopic dermatitis, alopecia greata, erythema multiforma, dermatitis herpetiformis, scleroderma, vitiligo, hypersensitivity angiitis, urticaria, bullous pemphigoid, lupus erythematosus, systemic lupus erythematosus, pemphigus vulgaris, pemphigus foliaceus, paraneoplastic pemphigus, epidermolysis bullosa acquisita, acne vulgaris, and other inflammatory or allergic conditions of the skin.

Compounds of the invention may also be used for the treatment of other diseases or conditions, such as diseases or conditions having an inflammatory component, for example, treatment of diseases and conditions of the eye such as ocular allergy, conjunctivitis, keratoconjunctivitis sicca, and vernal conjunctivitis, diseases affecting the nose including allergic rhinitis, and inflammatory disease in which autoimmune reactions are implicated or having an autoimmune component or etiology, including autoimmune hematological disorders (e.g. hemolytic anemia, aplastic anemia, pure red cell anemia and idiopathic thrombocytopenia), systemic lupus erythematosus, rheumatoid arthritis, polychondritis, scleroderma, Wegener granulamatosis, dermatomyositis, chronic active hepatitis, myasthenia gravis, Steven-Johnson syndrome, idiopathic sprue, autoimmune inflammatory bowel disease (e.g. ulcerative colitis and Crohn's disease), irritable bowel syndrome, celiac disease, periodontitis, hyaline membrane disease, kidney disease, glomerular disease, alcoholic liver disease, multiple sclerosis, endocrine opthalmopathy, Grave's disease, sarcoidosis, alveolitis, chronic hypersensitivity pneumonitis, multiple sclerosis, primary biliary cirrhosis, uveitis (anterior and posterior), Sjogren's syndrome, keratoconjunctivitis sicca and vernal keratoconjunctivitis, interstitial lung fibrosis, psoriatic arthritis, systemic juvenile idiopathic arthritis, cryopyrin-associated periodic syndrome, Muckle-Wells syndrome, nephritis, vasculitis, diverticulitis, interstitial cystitis, glomerulonephritis (with and without nephrotic syndrome, e.g. including idiopathic nephrotic syndrome or minal change nephropathy), chronic granulomatous disease, endometriosis, leptospirosis renal disease, glaucoma, retinal disease, ageing, headache, pain, complex regional pain syndrome, cardiac hypertrophy, musclewasting, catabolic disorders, obesity, fetal growth retardation, hyperchlolesterolemia, heart disease, chronic heart failure, mesothelioma, anhidrotic ecodermal dysplasia, Behcet's disease, incontinentia pigmenti, Paget's disease, pancreatitis, hereditary periodic fever syndrome, asthma (allergic and non-allergic, mild, moderate, severe, bronchitic, and exercise-induced), acute lung injury, acute respiratory distress syndrome, eosinophilia, hypersensitivities, anaphylaxis, nasal sinusitis, ocular allergy, silica induced diseases, COPD (reduction of damage, airways inflammation, bronchial hyperreactivity, remodeling or disease progression), pulmonary disease, cystic fibrosis, acid-induced lung injury, pulmonary hypertension, polyneuropathy, cataracts, muscle inflammation in conjunction with systemic sclerosis, inclusion body myositis, myasthenia gravis, thyroiditis, Addison's disease, lichen planus, Type 1 diabetes, or Type 2 diabetes, appendicitis, atopic dermatitis, asthma, allergy, blepharitis, bronchiolitis, bronchitis, bursitis, cervicitis, cholangitis, cholecystitis, chronic graft rejection, colitis, conjunctivitis, Crohn's disease, cystitis, dacryoadenitis, dermatitis, dermatomyositis, encephalitis, endocarditis, endometritis, enteritis, enterocolitis, epicondylitis, epididymitis, fasciitis, fibrositis, gastritis, gastroenteritis, Henoch-Schonlein purpura, hepatitis, hidradenitis suppurativa, immunoglobulin A nephropathy, interstitial lung disease, laryngitis, mastitis, meningitis, myelitis myocarditis, myositis, nephritis, oophoritis, orchitis, osteitis, otitis, pancreatitis, parotitis, pericarditis, peritonitis, pharyngitis, pleuritis, phlebitis, pneumonitis, pneumonia, polymyositis, proctitis, prostatitis, pyelonephritis, rhinitis, salpingitis, sinusitis, stomatitis, synovitis, tendonitis, tonsillitis, ulcerative colitis, uveitis, vaginitis, vasculitis, or vulvitis.

In some embodiments the inflammatory disease which can be treated according to the methods of this invention is an disease of the skin. In some embodiments, the inflammatory disease of the skin is selected from contact dermatitis, atompic dermatitis, alopecia greata, erythema multiforma, dermatitis herpetiformis, scleroderma, vitiligo, hypersensitivity angiitis, urticaria, bullous pemphigoid, pemphigus vulgaris, pemphigus foliaceus, paraneoplastic pemphigus, epidermolysis bullosa acquisita, and other inflammatory or allergic conditions of the skin.

In some embodiments the inflammatory disease which can be treated according to the methods of this invention is selected from acute and chronic gout, chronic gouty arthritis, psoriasis, psoriatic arthritis, rheumatoid arthritis, Juvenile rheumatoid arthritis, Systemic jubenile idiopathic arthritis (SJIA), Cryopyrin Associated Periodic Syndrome (CAPS), Muckle-Wells syndrome, and osteoarthritis.

In some embodiments the inflammatory disease which can be treated according to the methods of this invention is a TH17 mediated disease. In some embodiments the TH17 mediated disease is selected from Systemic lupus erythematosus, Multiple sclerosis, and inflammatory bowel disease (including Crohn's disease or ulcerative colitis).

In some embodiments the inflammatory disease which can be treated according to the methods of this invention is selected from Sjogren's syndrome, allergic disorders, osteoarthritis, conditions of the eye such as ocular allergy, conjunctivitis, keratoconjunctivitis sicca and vernal conjunctivitis, and diseases affecting the nose such as allergic rhinitis.

Cardiovascular diseases which can be treated according to the methods of this invention include, but are not limited to, restenosis, cardiomegaly, atherosclerosis, myocardial infarction, ischemic stroke, congestive heart failure, angina pectoris, reocclusion after angioplasty, restenosis after angioplasty, reocclusion after aortocoronary bypass, restenosis after aortocoronary bypass, stroke, transitory ischemia, a peripheral arterial occlusive disorder, pulmonary embolism, and deep venous thrombosis.

In some embodiments, the neurodegenerative disease which can be treated according to the methods of this invention include, but are not limited to, Alzheimer's disease, Parkinson's disease, amyotrophic lateral sclerosis, Huntington's disease, cerebral ischemia, and neurodegenerative disease caused by traumatic injury, glutamate neurotoxicity, hypoxia, epilepsy, treatment of diabetes, metabolic syndrome, obesity, organ transplantation and graft versus host disease.

The loss of IRAK4 function results in decreased Aβ levels in an in vivo murine model of Alzheimer's disease and was associated with diminished microgliosis and astrogliosis in aged mice. Analysis of microglia isolated from the adult mouse brain revealed an altered pattern of gene expression associated with changes in microglial phenotype that were associated with expression of IRF transcription factors that govern microglial phenotype. Further, loss of IRAK4 function also promoted amyloid clearance mechanisms, including elevated expression of insulin-degrading enzyme. Finally, blocking IRAK function restored olfactory behavior (Cameron et al. "Loss of Interleukin Receptor-Associated Kinase 4 Signaling Suppresses Amyloid Pathology and Alters Microglial Phenotype in a Mouse Model of Alzheimer's Disease" Journal of Neuroscience (2012) 32(43), 15112-15123.

In some embodiments the invention provides a method of treating, preventing or lessening the severity of Alzheimer's disease comprising administering to a patient in need thereof a compound of formula I or a pharmaceutically acceptable salt or composition thereof.

In some embodiments the invention provides a method of treating a disease or condition commonly occurring in connection with transplantation. In some embodiments, the disease or condition commonly occurring in connection with transplantation is selected from organ transplantation, organ transplant rejection, and graft versus host disease.

In some embodiments the invention provides a method of treating a metabolic disease. In some embodiments the metabolic disease is selected from Type 1 diabetes, Type 2 diabetes, metabolic syndrome, and obesity.

In some embodiments the invention provides a method of treating a viral disease. In some embodiments, the viral infection is HIV infection.

Furthermore, the invention provides the use of a compound according to the definitions herein, or a pharmaceutically acceptable salt, or a hydrate or solvate thereof for the preparation of a medicament for the treatment of a proliferative disease, an inflammatory disease, an obstructive respiratory disease, a cardiovascular disease, a metabolic disease, a neurological disease, a neurodegenerative disease, a viral disease, or a disorder commonly occurring in connection with transplantation.

Combination Therapies

Depending upon the particular condition, or disease, to be treated, additional therapeutic agents, which are normally administered to treat that condition, may be administered in combination with compounds and compositions of this invention. As used herein, additional therapeutic agents that are normally administered to treat a particular disease, or condition, are known as "appropriate for the disease, or condition, being treated."

In certain embodiments, a provided combination, or composition thereof, is administered in combination with another therapeutic agent.

Examples of agents the combinations of this invention may also be combined with include, without limitation: treatments for Alzheimer's Disease such as Aricept® and Excelon®; treatments for HIV such as ritonavir; treatments for Parkinson's Disease such as L-DOPA/carbidopa, entacapone, ropinrole, pramipexole, bromocriptine, pergolide, trihexephendyl, and amantadine; agents for treating Multiple Sclerosis (MS) such as beta interferon (e.g., Avonex® and Rebif®), Copaxone®, and mitoxantrone; treatments for asthma such as albuterol and Singulair®; agents for treating schizophrenia such as zyprexa, risperdal, seroquel, and haloperidol; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophophamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; agents that prolong or improve pharmacokinetics such as cytochrome P450 inhibitors (i.e., inhibitors of metabolic breakdown) and CYP3A4 inhibitors (e.g., ketokenozole and ritonavir), and agents for treating immunodeficiency disorders such as gamma globulin.

In certain embodiments, combination therapies of the present invention, or a pharmaceutically acceptable composition thereof, are administered in combination with a monoclonal antibody or an siRNA therapeutic.

Those additional agents may be administered separately from a provided combination therapy, as part of a multiple dosage regimen. Alternatively, those agents may be part of a single dosage form, mixed together with a compound of this invention in a single composition. If administered as part of a multiple dosage regime, the two active agents may be submitted simultaneously, sequentially or within a period of time from one another normally within five hours from one another.

As used herein, the term "combination," "combined," and related terms refers to the simultaneous or sequential administration of therapeutic agents in accordance with this invention. For example, a combination of the present invention may be administered with another therapeutic agent simultaneously or sequentially in separate unit dosage forms or together in a single unit dosage form.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

In one embodiment, the present invention provides a composition comprising a compound of formula I and one or more additional therapeutic agents. The therapeutic agent may be administered together with a compound of formula I, or may be administered prior to or following administration of a compound of formula I. Suitable therapeutic agents are described in further detail below. In certain embodiments, a compound of formula I may be administered up to 5 minutes, 10 minutes, 15 minutes, 30 minutes, 1 hour, 2 hours, 3 hours, 4 hours, 5, hours, 6 hours, 7 hours, 8 hours, 9 hours, 10 hours, 11 hours, 12 hours, 13 hours, 14 hours, 15 hours, 16 hours, 17 hours, or 18 hours before the therapeutic agent. In other embodiments, a compound of formula I may be administered up to 5 minutes, 10 minutes, 15 minutes, 30 minutes, 1 hour, 2 hours, 3 hours, 4 hours, 5, hours, 6 hours, 7 hours, 8 hours, 9 hours, 10 hours, 11 hours, 12 hours, 13 hours, 14 hours, 15 hours, 16 hours, 17 hours, or 18 hours following the therapeutic agent.

In another embodiment, the present invention provides a method of treating an inflammatory disease, disorder or condition by administering to a patient in need thereof a compound of formula I and one or more additional therapeutic agents. Such additional therapeutic agents may be small molecules or recombinant biologic agents and include, for example, acetaminophen, non-steroidal anti-inflammatory drugs (NSAIDS) such as aspirin, ibuprofen, naproxen, etodolac (Lodine®) and celecoxib, colchicine (Colcrys®), corticosteroids such as prednisone, prednisolone, methylprednisolone, hydrocortisone, and the like, probenecid, allopurinol, febuxostat (Uloric®), sulfasalazine (Azulfidine®), antimalarials such as hydroxychloroquine (Plaquenil®) and chloroquine (Aralen®), methotrexate (Rheumatrex®), gold salts such as gold thioglucose (Solganal®), gold thiomalate (Myochrysine®) and auranofin (Ridaura®), D-penicillamine (Depen® or Cuprimine®), azathioprine (Imuran®), cyclophosphamide (Cytoxan®), chlorambucil (Leukeran®), cyclosporine (Sandimmune®), leflunomide (Arava®) and "anti-TNF" agents such as etanercept (Enbrel®), infliximab (Remicade®), golimumab (Simponi®), certolizumab pegol (Cimzia®) and adalimumab (Humira®), "anti-IL-1" agents such as anakinra (Kineret®) and rilonacept (Arcalyst®), canakinumab (Ilaris®), anti-Jak inhibitors such as tofacitinib, antibodies such as rituximab (Rituxan®), "anti-T-cell" agents such as abatacept (Orencia®), "anti-IL-6" agents such as tocilizumab (Actemra®), diclofenac, cortisone, hyaluronic acid (Synvisc® or Hyalgan®), monoclonal antibodies such as tanezumab, anticoagulants such as heparin (Calcinparine® or Liquaemin®) and warfarin (Coumadin®), antidiarrheals such as diphenoxylate (Lomotil®) and loperamide (Imodium®), bile acid binding agents such as cholestyramine, alosetron (Lotronex®), lubiprostone (Amitiza®), laxatives such as Milk of Magnesia, polyethylene glycol (MiraLax®), Dulcolax®, Correctol® and Senokot®, anticholinergics or antispasmodics such as dicyclomine (Bentyl®), Singulair®, beta-2 agonists such as albuterol (Ventolin® HFA, Proventil® HFA), levalbuterol (Xopenex®), metaproterenol (Alupent®), pirbuterol acetate (Maxair®), terbutaline sulfate (Brethaire®), salmeterol xinafoate (Serevent®) and formoterol (Foradil®), anticholinergic agents such as ipratropium bromide (Atrovent®) and tiotropium (Spiriva®), inhaled corticosteroids such as beclomethasone dipropionate (Beclovent®, Qvar®, and Vanceril®), triamcinolone acetonide (Azmacort®), mometasone (Asthmanex®), budesonide (Pulmocort®), and flunisolide (Aerobid®), Afviar®, Symbicort®, Dulera®, cromolyn sodium (Intal®), methylxanthines such as theophylline (Theo-Dur®, Theolair®, Slo-bidt, Uniphyl®, Theo-24®) and aminophylline, IgE antibodies such as omalizumab (Xolair®), nucleoside reverse transcriptase inhibitors such as zidovudine (Retrovir®), abacavir (Ziagen®), abacavir/lamivudine (Epzicom®), abacavir/lamivudine/zidovudine (Trizivir®), didanosine (Videx®), emtricitabine (Emtriva®), lamivudine (Epivir®), lamivudine/zidovudine (Combivir®), stavudine (Zerit®), and zalcitabine (Hivid®), non-nucleoside reverse transcriptase inhibitors such as delavirdine (Rescriptor®), efavirenz (Sustiva®), nevairapine (Viramune®) and etravirine (Intelence®), nucleotide reverse transcriptase inhibitors such as tenofovir (Viread®), protease inhibitors such as amprenavir (Agenerase®), atazanavir (Reyataz®), darunavir (Prezista®), fosamprenavir (Lexiva®), indinavir (Crixivan®), lopinavir and ritonavir (Kaletra®), nelfinavir (Viracept®), ritonavir (Norvir®), saquinavir (Fortovase® or Invirase®), and tipranavir (Aptivus®), entry inhibitors such as enfuvirtide (Fuzeon®) and maraviroc (Selzentry®), integrase inhibitors such as raltegravir (Isentress®), doxorubicin (Hydrodaunorubicin®), vincristine (Oncovin®), bortezomib (Velcade®), and dexamethasone (Decadron®) in combination with lenalidomide (Revlimid®), or any combination(s) thereof.

In another embodiment, the present invention provides a method of treating gout comprising administering to a patient in need thereof a compound of formula I and one or more additional therapeutic agents selected from non-steroidal anti-inflammatory drugs (NSAIDS) such as aspirin, ibuprofen, naproxen, etodolac (Lodine®) and celecoxib, colchicine (Colcrys®), corticosteroids such as prednisone, prednisolone, methylprednisolone, hydrocortisone, and the like, probenecid, allopurinol and febuxostat (Uloric®).

In another embodiment, the present invention provides a method of treating rheumatoid arthritis comprising administering to a patient in need thereof a compound of formula I and one or more additional therapeutic agents selected from non-steroidal anti-inflammatory drugs (NSAIDS) such as aspirin, ibuprofen, naproxen, etodolac (Lodine®) and celecoxib, corticosteroids such as prednisone, prednisolone, methylprednisolone, hydrocortisone, and the like, sulfasalazine (Azulfidine®), antimalarials such as hydroxychloroquine (Plaquenil®) and chloroquine (Aralen®), methotrexate (Rheumatrex®), gold salts such as gold thioglucose (Solganal®), gold thiomalate (Myochrysine®) and auranofin (Ridaura®), D-penicillamine (Depen® or Cuprimine®), azathioprine (Imuran®), cyclophosphamide (Cytoxan®), chlorambucil (Leukeran®), cyclosporine (Sandimmune®), leflunomide (Arava®) and "anti-TNF" agents such as etanercept (Enbrel®), infliximab (Remicade®), golimumab (Simponi®), certolizumab pegol (Cimzia®) and adalimumab (Humira®), "anti-IL-1" agents such as anakinra (Kineret®) and rilonacept (Arcalyst®), antibodies such as rituximab (Rituxan®), "anti-T-cell" agents such as abatacept (Orencia®) and "anti-IL-6" agents such as tocilizumab (Actemra®).

In some embodiments, the present invention provides a method of treating osteoarthritis comprising administering to a patient in need thereof a compound of formula I and one or more additional therapeutic agents selected from acetaminophen, non-steroidal anti-inflammatory drugs (NSAIDS) such as aspirin, ibuprofen, naproxen, etodolac (Lodine®) and celecoxib, diclofenac, cortisone, hyaluronic acid (Synvisc® or Hyalgan®) and monoclonal antibodies such as tanezumab.

In some embodiments, the present invention provides a method of treating lupus comprising administering to a patient in need thereof a compound of formula I and one or more additional therapeutic agents selected from acetaminophen, non-steroidal anti-inflammatory drugs (NSAIDS) such as aspirin, ibuprofen, naproxen, etodolac (Lodine®) and celecoxib, corticosteroids such as prednisone, prednisolone, methylprednisolone, hydrocortisone, and the like, antimalarials such as hydroxychloroquine (Plaquenil®) and chloroquine (Aralen®), cyclophosphamide (Cytoxan®), methotrexate (Rheumatrex®), azathioprine (Imuran®) and anticoagulants such as heparin (Calcinparine® or Liquaemin®) and warfarin (Coumadin®).

In some embodiments, the present invention provides a method of treating inflammatory bowel disease comprising administering to a patient in need thereof a compound of formula I and one or more additional therapeutic agents selected from mesalamine (Asacol®) sulfasalazine (Azulfidine®), antidiarrheals such as diphenoxylate (Lomotil®) and loperamide (Imodium®), bile acid binding agents such as cholestyramine, alosetron (Lotronex®), lubiprostone (Amitiza®), laxatives such as Milk of Magnesia, polyethylene glycol (MiraLax®), Dulcolax®, Correctol® and Senokot® and anticholinergics or antispasmodics such as dicyclomine (Bentyl®), anti-TNF therapies, steroids, and antibiotics such as Flagyl or ciprofloxacin.

In some embodiments, the present invention provides a method of treating asthma comprising administering to a patient in need thereof a compound of formula I and one or more additional therapeutic agents selected from Singulair®, beta-2 agonists such as albuterol (Ventolin® HFA, Proventil® HFA), levalbuterol (Xopenex®), metaproterenol (Alupent®), pirbuterol acetate (Maxair®), terbutaline sulfate (Brethaire®), salmeterol xinafoate (Serevent®) and formoterol (Foradil®), anticholinergic agents such as ipratropium bromide (Atrovent®) and tiotropium (Spiriva®), inhaled corticosteroids such as prednisone, prednisolone, beclomethasone dipropionate (Beclovent®, Qvar®, and Vanceril®), triamcinolone acetonide (Azmacort®), mometasone (Asthmanex®), budesonide (Pulmocort®), flunisolide (Aerobid®), Afviar®, Symbicort®, and Dulera®, cromolyn sodium (Intal®), methylxanthines such as theophylline (Theo-Dur®, Theolair®, Slo-bidt, Uniphyl®, Theo-24®) and aminophylline, and IgE antibodies such as omalizumab (Xolair®).

In some embodiments, the present invention provides a method of treating COPD comprising administering to a patient in need thereof a compound of formula I and one or more additional therapeutic agents selected from beta-2 agonists such as albuterol (Ventolin® HFA, Proventil® HFA), levalbuterol (Xopenex®), metaproterenol (Alupent®), pirbuterol acetate (Maxair®), terbutaline sulfate (Brethaire®), salmeterol xinafoate (Serevent®) and formoterol (Foradil®), anticholinergic agents such as ipratropium bromide (Atrovent®) and tiotropium (Spiriva®), methylxanthines such as theophylline (Theo-Dur®, Theolair®, Slo-bid®, Uniphyl®, Theo-24®) and aminophylline, inhaled corticosteroids such as prednisone, prednisolone, beclomethasone dipropionate (Beclovent®, Qvar®, and Vanceril®), triamcinolone acetonide (Azmacort®), mometasone (Asthmanex®), budesonide (Pulmocort®), flunisolide (Aerobid®), Afviar®, Symbicort®, and Dulera®, In some embodiments, the present invention provides a method of treating HIV comprising administering to a patient in need thereof a compound of formula I and one or more additional therapeutic agents selected from nucleoside reverse transcriptase inhibitors such as zidovudine (Retrovir®), abacavir (Ziagen®), abacavir/lamivudine (Epzicom®), abacavir/lamivudine/zidovudine (Trizivir®), didanosine (Videx®), emtricitabine (Emtriva®), lamivudine (Epivir®), lamivudine/zidovudine (Combivir®), stavudine (Zerit®), and zalcitabine (Hivid®), non-nucleoside reverse transcriptase inhibitors such as delavirdine (Rescriptor®), efavirenz (Sustiva®), nevairapine (Viramune®) and etravirine (Intelence®), nucleotide reverse transcriptase inhibitors such as tenofovir (Viread®), protease inhibitors such as amprenavir (Agenerase®), atazanavir (Reyataz®), darunavir (Prezista®), fosamprenavir (Lexiva®), indinavir (Crixivan®), lopinavir and ritonavir (Kaletra®), nelfinavir (Viracept®), ritonavir (Norvir®), saquinavir (Fortovase® or Invirase®), and tipranavir (Aptivus®), entry inhibitors such as enfuvirtide (Fuzeon®) and maraviroc (Selzentry®), integrase inhibitors such as raltegravir (Isentress®), and combinations thereof.

In another embodiment, the present invention provides a method of treating a hematological malignancy comprising administering to a patient in need thereof a compound of formula I and one or more additional therapeutic agents selected from rituximab (Rituxan®), cyclophosphamide (Cytoxan®), doxorubicin (Hydrodaunorubicin®), vincristine (Oncovin®), prednisone, a hedgehog signaling inhibitor, a BTK inhibitor, a JAK/pan-JAK inhibitor, a TYK2 inhibitor, a PI3K inhibitor, a SYK inhibitor, and combinations thereof.

In another embodiment, the present invention provides a method of treating a solid tumor comprising administering to a patient in need thereof a compound of formula I and one or more additional therapeutic agents selected from rituximab (Rituxan®), cyclophosphamide (Cytoxan®), doxorubicin (Hydrodaunorubicin®), vincristine (Oncovin®), prednisone, a hedgehog signaling inhibitor, a BTK inhibitor, a JAK/pan-JAK inhibitor, a TYK2 inhibitor, a PI3K inhibitor, a SYK inhibitor, and combinations thereof.

In another embodiment, the present invention provides a method of treating a hematological malignancy comprising administering to a patient in need thereof a compound of formula I and a Hedgehog (Hh) signaling pathway inhibitor. In some embodiments, the hematological malignancy is DLBCL (Ramirez et at "Defining causative factors contributing in the activation of hedgehog signaling in diffuse large B-cell lymphoma" Leuk. Res. (2012), published online July 17, and incorporated herein by reference in its entirety).

In another embodiment, the present invention provides a method of treating diffuse large B-cell lymphoma (DLBCL) comprising administering to a patient in need thereof a compound of formula I and one or more additional therapeutic agents selected from rituximab (Rituxan®), cyclophosphamide (Cytoxan®), doxorubicin (Hydrodaunorubicin®), vincristine (Oncovin®), prednisone, a hedgehog signaling inhibitor, and combinations thereof.

In another embodiment, the present invention provides a method of treating multiple myeloma comprising administering to a patient in need thereof a compound of formula I and one or more additional therapeutic agents selected from bortezomib (Velcade®), and dexamethasone (Decadron®), a hedgehog signaling inhibitor, a BTK inhibitor, a JAK/pan-JAK inhibitor, a TYK2 inhibitor, a PI3K inhibitor, a SYK inhibitor in combination with lenalidomide (Revlimid®).

In another embodiment, the present invention provides a method of treating Waldenström's macroglobulinemia comprising administering to a patient in need thereof a compound of formula I and one or more additional therapeutic agents selected from chlorambucil (Leukeran®), cyclophosphamide (Cytoxan®, Neosar®), fludarabine (Fludara®), cladribine (Leustatin®), rituximab (Rituxan®), a hedgehog signaling inhibitor, a BTK inhibitor, a JAK/pan-JAK inhibitor, a TYK2 inhibitor, a PI3K inhibitor, and a SYK inhibitor.

In some embodiments, the present invention provides a method of treating Alzheimer's disease comprising administering to a patient in need thereof a compound of formula I and one or more additional therapeutic agents selected from donepezil (Aricept®), rivastigmine (Excelon®), galantamine (Razadyne®), tacrine (Cognex®), and memantine (Namenda®).

In another embodiment, the present invention provides a method of treating organ transplant rejection or graft vs. host disease comprising administering to a patient in need thereof a compound of formula I and one or more additional therapeutic agents selected from a steroid, cyclosporin, FK506, rapamycin, a hedgehog signaling inhibitor, a BTK inhibitor, a JAK/pan-JAK inhibitor, a TYK2 inhibitor, a PI3K inhibitor, and a SYK inhibitor.

In another embodiment, the present invention provides a method of treating or lessening the severity of a disease comprising administering to a patient in need thereof a compound of formula I and a BTK inhibitor, wherein the disease is selected from inflammatory bowel disease, arthritis, systemic lupus erythematosus (SLE), vasculitis, idiopathic thrombocytopenic purpura (ITP), rheumatoid arthritis, psoriatic arthritis, osteoarthritis, Still's disease, juvenile arthritis, diabetes, myasthenia gravis, Hashimoto's thyroiditis, Ord's thyroiditis, Graves' disease, autoimmune thyroiditis, Sjogren's syndrome, multiple sclerosis, systemic sclerosis, Lyme neuroborreliosis, Guillain-Barre syndrome, acute disseminated encephalomyelitis, Addison's disease, opsoclonus-myoclonus syndrome, ankylosing spondylosis, antiphospholipid antibody syndrome, aplastic anemia, autoimmune hepatitis, autoimmune gastritis, pernicious anemia, celiac disease, Goodpasture's syndrome, idiopathic thrombocytopenic purpura, optic neuritis, scleroderma, primary biliary cirrhosis, Reiter's syndrome, Takayasu's arteritis, temporal arteritis, warm autoimmune hemolytic anemia, Wegener's granulomatosis, psoriasis, alopecia universalis, Behcet's disease, chronic fatigue, dysautonomia, membranous glomerulonephropathy, endometriosis, interstitial cystitis, pemphigus vulgaris, bullous pemphigoid, neuromyotonia, scleroderma, vulvodynia, a hyperproliferative disease, rejection of transplanted organs or tissues, Acquired Immunodeficiency Syndrome (AIDS, also known as HIV), type 1 diabetes, graft versus host disease, transplantation, transfusion, anaphylaxis, allergies (e.g., allergies to plant pollens, latex, drugs, foods, insect poisons, animal hair, animal dander, dust mites, or cockroach calyx), type I hypersensitivity, allergic conjunctivitis, allergic rhinitis, and atopic dermatitis, asthma, appendicitis, atopic dermatitis, asthma, allergy, blepharitis, bronchiolitis, bronchitis, bursitis, cervicitis, cholangitis, cholecystitis, chronic graft rejection, colitis, conjunctivitis, Crohn's disease, cystitis, dacryoadenitis, dermatitis, dermatomyositis, encephalitis, endocarditis, endometritis, enteritis, enterocolitis, epicondylitis, epididymitis, fasciitis, fibrositis, gastritis, gastroenteritis, Henoch-Schonlein purpura, hepatitis, hidradenitis suppurativa, immunoglobulin A nephropathy, interstitial lung disease, laryngitis, mastitis, meningitis, myelitis myocarditis, myositis, nephritis, oophoritis, orchitis, osteitis, otitis, pancreatitis, parotitis, pericarditis, peritonitis, pharyngitis, pleuritis, phlebitis, pneumonitis, pneumonia, polymyositis, proctitis, prostatitis, pyelonephritis, rhinitis, salpingitis, sinusitis, stomatitis, synovitis, tendonitis, tonsillitis, ulcerative colitis, uveitis, vaginitis, vasculitis, or vulvitis, B-cell proliferative disorder, e.g., diffuse large B cell lymphoma, follicular lymphoma, chronic lymphocytic lymphoma, chronic lymphocytic leukemia, acute lymphocytic leukemia, B-cell prolymphocytic leukemia, lymphoplasmacytic lymphoma/Waldenstrom macroglobulinemia, splenic marginal zone lymphoma, multiple myeloma (also known as plasma cell myeloma), non-Hodgkin's lymphoma, Hodgkin's lymphoma, plasmacytoma, extranodal marginal zone B cell lymphoma, nodal marginal zone B cell lymphoma, mantle cell lymphoma, mediastinal (thymic) large B cell lymphoma, intravascular large B cell lymphoma, primary effusion lymphoma, Burkitt lymphoma/leukemia, or lymphomatoid granulomatosis, breast cancer, prostate cancer, or cancer of the mast cells (e.g., mastocytoma, mast cell leukemia, mast cell sarcoma, systemic mastocytosis), bone cancer, colorectal cancer, pancreatic cancer, diseases of the bone and joints including, without limitation, rheumatoid arthritis, seronegative spondyloarthropathies (including ankylosing spondylitis, psoriatic arthritis and Reiter's disease), Behcet's disease, Sjogren's syndrome, systemic sclerosis, osteoporosis, bone cancer, bone metastasis, a thromboembolic disorder, (e.g., myocardial infarct, angina pectoris, reocclusion after angioplasty, restenosis after angioplasty, reocclusion after aortocoronary bypass, restenosis after aortocoronary bypass, stroke, transitory ischemia, a peripheral arterial occlusive disorder, pulmonary embolism, deep venous thrombosis), inflammatory pelvic disease, urethritis, skin sunburn, sinusitis, pneumonitis, encephalitis, meningitis, myocarditis, nephritis, osteomyelitis, myositis, hepatitis, gastritis, enteritis, dermatitis, gingivitis, appendicitis, pancreatitis, cholocystitus, agammaglobulinemia, psoriasis, allergy, Crohn's disease, irritable bowel syndrome, ulcerative colitis, Sjogren's disease, tissue graft rejection, hyper-acute rejection of transplanted organs, asthma, allergic rhinitis, chronic obstructive pulmonary disease (COPD), autoimmune polyglandular disease (also known as autoimmune polyglandular syndrome), autoimmune alopecia, pernicious anemia, glomerulonephritis, dermatomyositis, multiple sclerosis, scleroderma, vasculitis, autoimmune hemolytic and thrombocytopenic states, Goodpasture's syndrome, atherosclerosis, Addison's disease, Parkinson's disease, Alzheimer's disease, diabetes, septic shock, systemic lupus erythematosus (SLE), rheumatoid arthritis, psoriatic arthritis, juvenile arthritis, osteoarthritis, chronic idiopathic thrombocytopenic purpura, Waldenstrom macroglobulinemia, myasthenia gravis, Hashimoto's thyroiditis, atopic dermatitis, degenerative joint disease, vitiligo, autoimmune hypopituitarism, Guillain-Barre syndrome, Behcet's disease, scleraderma, mycosis fungoides, acute inflammatory responses (such as acute respiratory distress syndrome and ischemia/reperfusion injury), and Graves' disease.

In another embodiment, the present invention provides a method of treating or lessening the severity of a disease comprising administering to a patient in need thereof a compound of formula I and a PI3K inhibitor, wherein the disease is selected from a cancer, a neurodegenerative disorder, an angiogenic disorder, a viral disease, an autoimmune disease, an inflammatory disorder, a hormone-related disease, conditions associated with organ transplantation, immunodeficiency disorders, a destructive bone disorder, a proliferative disorder, an infectious disease, a condition associated with cell death, thrombin-induced platelet aggregation, chronic myelogenous leukemia (CML), chronic lymphocytic leukemia (CLL), liver disease, pathologic immune conditions involving T cell activation, a cardiovascular disorder, and a CNS disorder.

In another embodiment, the present invention provides a method of treating or lessening the severity of a disease comprising administering to a patient in need thereof a compound of formula I and a PI3K inhibitor, wherein the disease is selected from benign or malignant tumor, carcinoma or solid tumor of the brain, kidney (e.g., renal cell carcinoma (RCC)), liver, adrenal gland, bladder, breast, stomach, gastric tumors, ovaries, colon, rectum, prostate, pancreas, lung, vagina, endometrium, cervix, testis, genitourinary tract, esophagus, larynx, skin, bone or thyroid, sarcoma, glioblastomas, neuroblastomas, multiple myeloma or gastrointestinal cancer, especially colon carcinoma or colorectal adenoma or a tumor of the neck and head, an epidermal hyperproliferation, psoriasis, prostate hyperplasia, a neoplasia, a neoplasia of epithelial character, adenoma, adenocarcinoma, keratoacanthoma, epidermoid carcinoma, large cell carcinoma, non-small-cell lung carcinoma, lymphomas, (including, for example, non-Hodgkin's Lymphoma (NHL) and Hodgkin's lymphoma (also termed Hodgkin's or Hodgkin's disease)), a mammary carcinoma, follicular carcinoma, undifferentiated carcinoma, papillary carcinoma, seminoma, melanoma, or a leukemia, diseases include Cowden syndrome, Lhermitte-Dudos disease and Bannayan-Zonana syndrome, or diseases in which the PI3K/PKB pathway is aberrantly activated, asthma of whatever type or genesis including both intrinsic (non-allergic) asthma and extrinsic (allergic) asthma, mild asthma, moderate asthma, severe asthma, bronchitic asthma, exercise-induced asthma, occupational asthma and asthma induced following bacterial infection, acute lung injury (ALI), adult/acute respiratory distress syndrome (ARDS), chronic obstructive pulmonary, airways or lung disease (COPD, COAD or COLD), including chronic bronchitis or dyspnea associated therewith, emphysema, as well as exacerbation of airways hyperreactivity consequent to other drug therapy, in particular other inhaled drug therapy, bronchitis of whatever type or genesis including, but not limited to, acute, arachidic, catarrhal, croupus, chronic or phthinoid bronchitis, pneumoconiosis (an inflammatory, commonly occupational, disease of the lungs, frequently accompanied by airways obstruction, whether chronic or acute, and occasioned by repeated inhalation of dusts) of whatever type or genesis, including, for example, aluminosis, anthracosis, asbestosis, chalicosis, ptilosis, siderosis, silicosis, tabacosis and byssinosis, Loffler's syndrome, eosinophilic, pneumonia, parasitic (in particular metazoan) infestation (including tropical eosinophilia), bronchopulmonary aspergillosis, polyarteritis nodosa (including Churg-Strauss syndrome), eosinophilic granuloma and eosinophil-related disorders affecting the airways occasioned by drug-reaction, psoriasis, contact dermatitis, atopic dermatitis, alopecia greata, erythema multiforma, dermatitis herpetiformis, scleroderma, vitiligo, hypersensitivity angiitis, urticaria, bullous pemphigoid, lupus erythematosus, pemphisus, epidermolysis bullosa acquisita, conjunctivitis, keratoconjunctivitis sicca, and vernal conjunctivitis, diseases affecting the nose including allergic rhinitis, and inflammatory disease in which autoimmune reactions are implicated or having an autoimmune component or etiology, including autoimmune hematological disorders (e.g. hemolytic anemia, aplastic anemia, pure red cell anemia and idiopathic thrombocytopenia), systemic lupus erythematosus, rheumatoid arthritis, polychondritis, sclerodoma, Wegener granulamatosis, dermatomyositis, chronic active hepatitis, myasthenia gravis, Steven-Johnson syndrome, idiopathic sprue, autoimmune inflammatory bowel disease (e.g. ulcerative colitis and Crohn's disease), endocrine opthalmopathy, Grave's disease, sarcoidosis, alveolitis, chronic hypersensitivity pneumonitis, multiple sclerosis, primary biliary cirrhosis, uveitis (anterior and posterior), keratoconjunctivitis sicca and vernal keratoconjunctivitis, interstitial lung fibrosis, psoriatic arthritis and glomerulonephritis (with and without nephrotic syndrome, e.g. including idiopathic nephrotic syndrome or minal change nephropathy, restenosis, cardiomegaly, atherosclerosis, myocardial infarction, ischemic stroke and congestive heart failure, Alzheimer's disease, Parkinson's disease, amyotrophic lateral sclerosis, Huntington's disease, and cerebral ischemia, and neurodegenerative disease caused by traumatic injury, glutamate neurotoxicity and hypoxia.

The compounds and compositions, according to the method of the present invention, may be administered using any amount and any route of administration effective for treating or lessening the severity of a cancer, an autoimmune disorder, a proliferative disorder, an inflammatory disorder, a neurodegenerative or neurological disorder, schizophrenia, a bone-related disorder, liver disease, or a cardiac disorder. The exact amount required will vary from subject to subject, depending on the species, age, and general condition of the subject, the severity of the infection, the particular agent, its mode of administration, and the like. Compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

Pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to one embodiment, the invention relates to a method of inhibiting protein kinase activity in a biological sample comprising the step of contacting said biological sample with a compound of this invention, or a composition comprising said compound.

According to another embodiment, the invention relates to a method of inhibiting IRAK-1, IRAK-2, and/or IRAK-4, or a mutant thereof, activity in a biological sample comprising the step of contacting said biological sample with a compound of this invention, or a composition comprising said compound. In certain embodiments, the invention relates to a method of irreversibly inhibiting IRAK-1, IRAK-2, and/or IRAK-4, or a mutant thereof, activity in a biological sample comprising the step of contacting said biological sample with a compound of this invention, or a composition comprising said compound.

The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Inhibition of protein kinase, or a protein kinase selected from IRAK-1, IRAK-2, and/or IRAK-4, or a mutant thereof, activity in a biological sample is useful for a variety of purposes that are known to one of skill in the art. Examples of such purposes include, but are not limited to, blood transfusion, organ-transplantation, biological specimen storage, and biological assays.

Another embodiment of the present invention relates to a method of inhibiting protein kinase activity in a patient comprising the step of administering to said patient a compound of the present invention, or a composition comprising said compound.

According to another embodiment, the invention relates to a method of inhibiting one or more of IRAK-1, IRAK-2, and/or IRAK-4, or a mutant thereof, activity in a patient comprising the step of administering to said patient a compound of the present invention, or a composition comprising said compound. According to certain embodiments, the invention relates to a method of irreversibly inhibiting one or more of IRAK-1, IRAK-2, and/or IRAK-4, or a mutant thereof, activity in a patient comprising the step of administering to said patient a compound of the present invention, or a composition comprising said compound. In other embodiments, the present invention provides a method for treating a disorder mediated by one or more of IRAK-1, IRAK-2, and/or IRAK-4, or a mutant thereof, in a patient in need thereof, comprising the step of administering to said patient a compound according to the present invention or pharmaceutically acceptable composition thereof. Such disorders are described in detail herein.

Depending upon the particular condition, or disease, to be treated, additional therapeutic agents that are normally administered to treat that condition, may also be present in the compositions of this invention. As used herein, additional therapeutic agents that are normally administered to treat a particular disease, or condition, are known as "appropriate for the disease, or condition, being treated."

A compound of the current invention may also be used to advantage in combination with other antiproliferative compounds. Such antiproliferative compounds include, but are not limited to aromatase inhibitors; antiestrogens; topoisomerase I inhibitors; topoisomerase II inhibitors; microtubule active compounds; alkylating compounds; histone deacetylase inhibitors; compounds which induce cell differentiation processes; cyclooxygenase inhibitors; MMP inhibitors; mTOR inhibitors; antineoplastic antimetabolites; platin compounds; compounds targeting/decreasing a protein or lipid kinase activity and further anti-angiogenic compounds; compounds which target, decrease or inhibit the activity of a protein or lipid phosphatase; gonadorelin agonists; anti-androgens; methionine aminopeptidase inhibitors; matrix metalloproteinase inhibitors; bisphosphonates; biological response modifiers; antiproliferative antibodies; heparanase inhibitors; inhibitors of Ras oncogenic isoforms; telomerase inhibitors; proteasome inhibitors; compounds used in the treatment of hematologic malignancies; compounds which target, decrease or inhibit the activity of Flt-3; Hsp90 inhibitors such as 17-AAG (17-allylaminogeldanamycin, NSC330507), 17-DMAG (17-dimethylaminoethyl-amino-17-demethoxy-geldanamycin, NSC707545), IPI-504, CNF1010, CNF2024, CNF1010 from Conforma Therapeutics; temozolomide (Temodal); kinesin spindle protein inhibitors, such as SB715992 or SB743921 from GlaxoSmithKline, or pentamidine/chlorpromazine from CombinatoRx; MEK inhibitors such as ARRY142886 from Array BioPharma, AZD6244 from AstraZeneca, PD181461 from Pfizer and leucovorin. The term "aromatase inhibitor" as used herein relates to a compound which inhibits estrogen production, for instance, the conversion of the substrates androstenedione and testosterone to estrone and estradiol, respectively. The term includes, but is not limited to steroids, especially atamestane, exemestane and formestane and, in particular, non-steroids, especially aminoglutethimide, roglethimide, pyridoglutethimide, trilostane, testolactone, ketokonazole, vorozole, fadrozole, anastrozole and letrozole. Exemestane is marketed under the trade name Aromasin™. Formestane is marketed under the trade name Lentaron™. Fadrozole is marketed under the trade name Afema™. Anastrozole is marketed under the trade name Arimidex™. Letrozole is marketed under the trade names Femara™ or Femar™. Aminoglutethimide is marketed under the trade name Orimeten™. A combination of the invention comprising a chemotherapeutic agent which is an aromatase inhibitor is particularly useful for the treatment of hormone receptor positive tumors, such as breast tumors.

The term "antiestrogen" as used herein relates to a compound which antagonizes the effect of estrogens at the estrogen receptor level. The term includes, but is not limited to tamoxifen, fulvestrant, raloxifene and raloxifene hydrochloride. Tamoxifen is marketed under the trade name Nolvadex™. Raloxifene hydrochloride is marketed under the trade name Evista™. Fulvestrant can be administered under the trade name Faslodex™. A combination of the invention comprising a chemotherapeutic agent which is an antiestrogen is particularly useful for the treatment of estrogen receptor positive tumors, such as breast tumors.

The term "anti-androgen" as used herein relates to any substance which is capable of inhibiting the biological effects of androgenic hormones and includes, but is not limited to, bicalutamide (Casodex™). The term "gonadorelin agonist" as used herein includes, but is not limited to abarelix, goserelin and goserelin acetate. Goserelin can be administered under the trade name Zoladex™.

The term "topoisomerase I inhibitor" as used herein includes, but is not limited to topotecan, gimatecan, irinotecan, camptothecian and its analogues, 9-nitrocamptothecin and the macromolecular camptothecin conjugate PNU-166148. Irinotecan can be administered, e.g. in the form as it is marketed, e.g. under the trademark Camptosar™. Topotecan is marketed under the trade name Hycamptin™.

The term "topoisomerase II inhibitor" as used herein includes, but is not limited to the anthracyclines such as doxorubicin (including liposomal formulation, such as Caelyx™), daunorubicin, epirubicin, idarubicin and nemorubicin, the anthraquinones mitoxantrone and losoxantrone, and the podophillotoxines etoposide and teniposide. Etoposide is marketed under the trade name Etopophos™. Teniposide is marketed under the trade name VM 26-Bristol Doxorubicin is marketed under the trade name Acriblastin™ or Adriamycin™. Epirubicin is marketed under the trade name Farmorubicin™. Idarubicin is marketed. under the trade name Zavedos™. Mitoxantrone is marketed under the trade name Novantron.

The term "microtubule active agent" relates to microtubule stabilizing, microtubule destabilizing compounds and microtublin polymerization inhibitors including, but not limited to taxanes, such as paclitaxel and docetaxel; vinca alkaloids, such as vinblastine or vinblastine sulfate, vincristine or vincristine sulfate, and vinorelbine; discodermolides; cochicine and epothilones and derivatives thereof. Paclitaxel is marketed under the trade name Taxol™. Docetaxel is marketed under the trade name Taxotere™. Vinblastine sulfate is marketed under the trade name Vinblastin R.P™. Vincristine sulfate is marketed under the trade name Farmistin™.

The term "alkylating agent" as used herein includes, but is not limited to, cyclophosphamide, ifosfamide, melphalan or nitrosourea (BCNU or Gliadel). Cyclophosphamide is marketed under the trade name Cyclostin™. Ifosfamide is marketed under the trade name Holoxan™.

The term "histone deacetylase inhibitors" or "HDAC inhibitors" relates to compounds which inhibit the histone deacetylase and which possess antiproliferative activity. This includes, but is not limited to, suberoylanilide hydroxamic acid (SAHA).

The term "antineoplastic antimetabolite" includes, but is not limited to, 5-fluorouracil or 5-FU, capecitabine, gemcitabine, DNA demethylating compounds, such as 5-azacytidine and decitabine, methotrexate and edatrexate, and folic acid antagonists such as pemetrexed. Capecitabine is marketed under the trade name Xeloda™. Gemcitabine is marketed under the trade name Gemzar™.

The term "platin compound" as used herein includes, but is not limited to, carboplatin, cis-platin, cisplatinum and oxaliplatin. Carboplatin can be administered, e.g., in the form as it is marketed, e.g. under the trademark Carboplat™.

Oxaliplatin can be administered, e.g., in the form as it is marketed, e.g. under the trademark Eloxatin™.

The term "compounds targeting/decreasing a protein or lipid kinase activity; or a protein or lipid phosphatase activity; or further anti-angiogenic compounds" as used herein includes, but is not limited to, protein tyrosine kinase and/or serine and/or threonine kinase inhibitors or lipid kinase inhibitors, such as a) compounds targeting, decreasing or inhibiting the activity of the platelet-derived growth factor-receptors (PDGFR), such as compounds which target, decrease or inhibit the activity of PDGFR, especially compounds which inhibit the PDGF receptor, such as an N-phenyl-2-pyrimidine-amine derivative, such as imatinib, SU101, SU6668 and GFB-111; b) compounds targeting, decreasing or inhibiting the activity of the fibroblast growth factor-receptors (FGFR); c) compounds targeting, decreasing or inhibiting the activity of the insulin-like growth factor receptor I (IGF-IR), such as compounds which target, decrease or inhibit the activity of IGF-IR, especially compounds which inhibit the kinase activity of IGF-I receptor, or antibodies that target the extracellular domain of IGF-I receptor or its growth factors; d) compounds targeting, decreasing or inhibiting the activity of the Trk receptor tyrosine kinase family, or ephrin B4 inhibitors; e) compounds targeting, decreasing or inhibiting the activity of the AxI receptor tyrosine kinase family; f) compounds targeting, decreasing or inhibiting the activity of the Ret receptor tyrosine kinase; g) compounds targeting, decreasing or inhibiting the activity of the Kit/SCFR receptor tyrosine kinase, such as imatinib; h) compounds targeting, decreasing or inhibiting the activity of the C-kit receptor tyrosine kinases, which are part of the PDGFR family, such as compounds which target, decrease or inhibit the activity of the c-Kit receptor tyrosine kinase family, especially compounds which inhibit the c-Kit receptor, such as imatinib; i) compounds targeting, decreasing or inhibiting the activity of members of the c-Abl family, their gene-fusion products (e.g. BCR-Abl kinase) and mutants, such as compounds which target decrease or inhibit the activity of c-Abl family members and their gene fusion products, such as an N-phenyl-2-pyrimidine-amine derivative, such as imatinib or nilotinib (AMN107); PD180970; AG957; NSC 680410; PD173955 from ParkeDavis; or dasatinib (BMS-354825); j) compounds targeting, decreasing or inhibiting the activity of members of the protein kinase C (PKC) and Raf family of serine/threonine kinases, members of the MEK, SRC, JAK/pan-JAK, FAK, PDK1, PKB/Akt, Ras/MAPK, PI3K, SYK, TYK2, BTK and TEC family, and/or members of the cyclin-dependent kinase family (CDK) including staurosporine derivatives, such as midostaurin; examples of further compounds include UCN-01, safingol, BAY 43-9006, Bryostatin 1, Perifosine; llmofosine; RO 318220 and RO 320432; GO 6976; Isis 3521; LY333531/LY379196; isochinoline compounds; FTIs; PD184352 or QAN697 (a PI3K inhibitor) or AT7519 (CDK inhibitor); k) compounds targeting, decreasing or inhibiting the activity of protein-tyrosine kinase inhibitors, such as compounds which target, decrease or inhibit the activity of protein-tyrosine kinase inhibitors include imatinib mesylate (Gleevec™) or tyrphostin such as Tyrphostin A23/RG-50810; AG 99; Tyrphostin AG 213; Tyrphostin AG 1748; Tyrphostin AG 490; Tyrphostin B44; Tyrphostin B44 (+) enantiomer; Tyrphostin AG 555; AG 494; Tyrphostin AG 556, AG957 and adaphostin (4-{[(2,5-dihydroxyphenyl)methyl]amino}-benzoic acid adamantyl ester; NSC 680410, adaphostin); l) compounds targeting, decreasing or inhibiting the activity of the epidermal growth factor family of receptor tyrosine kinases (EGFR, ErbB2, ErbB3, ErbB4 as homo- or heterodimers) and their mutants, such as compounds which target, decrease or inhibit the activity of the epidermal growth factor receptor family are especially compounds, proteins or antibodies which inhibit members of the EGF receptor tyrosine kinase family, such as EGF receptor, ErbB2, ErbB3 and ErbB4 or bind to EGF or EGF related ligands, CP 358774, ZD 1839, ZM 105180; trastuzumab (Herceptin™), cetuximab (Erbitux™), Iressa, Tarceva, OSI-774, CI-1033, EKB-569, GW-2016, E1.1, E2.4, E2.5, E6.2, E6.4, E2.11, E6.3 or E7.6.3, and 7H-pyrrolo-[2,3-d]pyrimidine derivatives; m) compounds targeting, decreasing or inhibiting the activity of the c-Met receptor, such as compounds which target, decrease or inhibit the activity of c-Met, especially compounds which inhibit the kinase activity of c-Met receptor, or antibodies that target the extracellular domain of c-Met or bind to HGF, n) compounds targeting, decreasing or inhibiting the kinase activity of one or more JAK family members (JAK1/JAK2/JAK3/TYK2 and/or pan-JAK), including but not limited to PRT-062070, SB-1578, baricitinib, pacritinib, momelotinib, VX-509, AZD-1480, TG-101348, tofacitinib, and ruxolitinib; o) compounds targeting, decreasing or inhibiting the kinase activity of PI3 kinase (PI3K) including but not limited to ATU-027, SF-1126, DS-7423, PBI-05204, GSK-2126458, ZSTK-474, buparlisib, pictrelisib, PF-4691502, BYL-719, dactolisib, XL-147, XL-765, and idelalisib; and; and q) compounds targeting, decreasing or inhibiting the signaling effects of hedgehog protein (Hh) or smoothened receptor (SMO) pathways, including but not limited to cyclopamine, vismodegib, itraconazole, erismodegib, and IPI-926 (saridegib).

The term "PI3K inhibitor" as used herein includes, but is not limited to compounds having inhibitory activity against one or more enzymes in the phosphatidylinositol-3-kinase family, including, but not limited to PI3Kα, PI3Kγ, PI3Kδ, PI3Kβ, PI3K-C2α, PI3K-C2β, PI3K-C2γ, Vps34, p110-α, p110-β, p110-γ, p110-δ, p85-α, p85-β, p55-γ, p150, p101, and p87. Examples of PI3K inhibitors useful in this invention include but are not limited to ATU-027, SF-1126, DS-7423, PBI-05204, GSK-2126458, ZSTK-474, buparlisib, pictrelisib, PF-4691502, BYL-719, dactolisib, XL-147, XL-765, and idelalisib.

The term "BTK inhibitor" as used herein includes, but is not limited to compounds having inhibitory activity against Bruton's Tyrosine Kinase (BTK), including, but not limited to AVL-292 and ibrutinib.

The term "SYK inhibitor" as used herein includes, but is not limited to compounds having inhibitory activity against spleen tyrosine kinase (SYK), including but not limited to PRT-062070, R-343, R-333, Excellair, PRT-062607, and fostamatinib Further examples of BTK inhibitory compounds, and conditions treatable by such compounds in combination with compounds of this invention can be found in WO2008039218 and WO2011090760, the entirety of which are incorporated herein by reference.

Further examples of SYK inhibitory compounds, and conditions treatable by such compounds in combination with compounds of this invention can be found in WO2003063794, WO2005007623, and WO2006078846, the entirety of which are incorporated herein by reference.

Further examples of PI3K inhibitory compounds, and conditions treatable by such compounds in combination with compounds of this invention can be found in WO2004019973, WO2004089925, WO2007016176, U.S. Pat. No. 8,138,347, WO2002088112, WO2007084786, WO2007129161, WO2006122806, WO2005113554, and WO2007044729 the entirety of which are incorporated herein by reference.

Further examples of JAK inhibitory compounds, and conditions treatable by such compounds in combination with compounds of this invention can be found in WO2009114512, WO2008109943, WO2007053452, WO2000142246, and WO2007070514, the entirety of which are incorporated herein by reference.

Further anti-angiogenic compounds include compounds having another mechanism for their activity, e.g. unrelated to protein or lipid kinase inhibition e.g. thalidomide (Thalomid™) and TNP-470.

Examples of proteasome inhibitors useful for use in combination with compounds of the invention include, but are not limited to bortezomib, disulfuram, epigallocatechin-3-gallate (EGCG), salinosporamide A, carfilzomib, ONX-0912, CEP-18770, and MLN9708.

Compounds which target, decrease or inhibit the activity of a protein or lipid phosphatase are e.g. inhibitors of phosphatase 1, phosphatase 2A, or CDC25, such as okadaic acid or a derivative thereof.

Compounds which induce cell differentiation processes include, but are not limited to, retinoic acid, α- γ- or δ-tocopherol or α- γ- or δ-tocotrienol.

The term cyclooxygenase inhibitor as used herein includes, but is not limited to, Cox-2 inhibitors, 5-alkyl substituted 2-arylaminophenylacetic acid and derivatives, such as celecoxib (Celebrex™), rofecoxib (Vioxx™), etoricoxib, valdecoxib or a 5-alkyl-2-arylaminophenylacetic acid, such as 5-methyl-2-(2'-chloro-6'-fluoroanilino)phenyl acetic acid, lumiracoxib.

The term "bisphosphonates" as used herein includes, but is not limited to, etridonic, clodronic, tiludronic, pamidronic, alendronic, ibandronic, risedronic and zoledronic acid. Etridonic acid is marketed under the trade name Didronel™. Clodronic acid is marketed under the trade name Bonefos™. Tiludronic acid is marketed under the trade name Skelid™ Pamidronic acid is marketed under the trade name Aredia™. Zolendronic acid is marketed under the trade name Fosamax™. Ibandronic acid is marketed under the trade name Bondranat™ Risedronic acid is marketed under the trade name Actonel™. Zoledronic acid is marketed under the trade name Zometa™. The term "mTOR inhibitors" relates to compounds which inhibit the mammalian target of rapamycin (mTOR) and which possess antiproliferative activity such as sirolimus (Rapamune®), everolimus (Certican™), CCI-779 and ABT578.

The term "heparanase inhibitor" as used herein refers to compounds which target, decrease or inhibit heparin sulfate degradation. The term includes, but is not limited to, PI-88. The term "biological response modifier" as used herein refers to a lymphokine or interferons.

The term "inhibitor of Ras oncogenic isoforms", such as H-Ras, K-Ras, or N-Ras, as used herein refers to compounds which target, decrease or inhibit the oncogenic activity of Ras; for example, a "farnesyl transferase inhibitor" such as L-744832, DK8G557 or R115777 (Zarnestra™). The term "telomerase inhibitor" as used herein refers to compounds which target, decrease or inhibit the activity of telomerase. Compounds which target, decrease or inhibit the activity of telomerase are especially compounds which inhibit the telomerase receptor, such as telomestatin.

The term "methionine aminopeptidase inhibitor" as used herein refers to compounds which target, decrease or inhibit the activity of methionine aminopeptidase. Compounds which target, decrease or inhibit the activity of methionine aminopeptidase include, but are not limited to, bengamide or a derivative thereof.

The term "proteasome inhibitor" as used herein refers to compounds which target, decrease or inhibit the activity of the proteasome. Compounds which target, decrease or inhibit the activity of the proteasome include, but are not limited to, Bortezomib (Velcade™) and MLN 341.

The term "matrix metalloproteinase inhibitor" or ("MMP" inhibitor) as used herein includes, but is not limited to, collagen peptidomimetic and nonpeptidomimetic inhibitors, tetracycline derivatives, e.g. hydroxamate peptidomimetic inhibitor batimastat and its orally bioavailable analogue marimastat (BB-2516), prinomastat (AG3340), metastat (NSC 683551) BMS-279251, BAY 12-9566, TAA211, MMI270B or AAJ996.

The term "compounds used in the treatment of hematologic malignancies" as used herein includes, but is not limited to, FMS-like tyrosine kinase inhibitors, which are compounds targeting, decreasing or inhibiting the activity of FMS-like tyrosine kinase receptors (Flt-3R); interferon, 1-β-D-arabinofuransylcytosine (ara-c) and bisulfan; and ALK inhibitors, which are compounds which target, decrease or inhibit anaplastic lymphoma kinase.

Compounds which target, decrease or inhibit the activity of FMS-like tyrosine kinase receptors (Flt-3R) are especially compounds, proteins or antibodies which inhibit members of the Flt-3R receptor kinase family, such as PKC412, midostaurin, a staurosporine derivative, SU11248 and MLN518.

The term "HSP90 inhibitors" as used herein includes, but is not limited to, compounds targeting, decreasing or inhibiting the intrinsic ATPase activity of HSP90; degrading, targeting, decreasing or inhibiting the HSP90 client proteins via the ubiquitin proteosome pathway. Compounds targeting, decreasing or inhibiting the intrinsic ATPase activity of HSP90 are especially compounds, proteins or antibodies which inhibit the ATPase activity of HSP90, such as 17-allylamino,17-demethoxygeldanamycin (17AAG), a geldanamycin derivative; other geldanamycin related compounds; radicicol and HDAC inhibitors.

The term "antiproliferative antibodies" as used herein includes, but is not limited to, trastuzumab (Herceptin™), Trastuzumab-DM1, erbitux, bevacizumab (Avastin™), rituximab (Rituxan®), PRO64553 (anti-CD40) and 2C4 Antibody. By antibodies is meant intact monoclonal antibodies, polyclonal antibodies, multispecific antibodies formed from at least 2 intact antibodies, and antibodies fragments so long as they exhibit the desired biological activity.

For the treatment of acute myeloid leukemia (AML), compounds of the current invention can be used in combination with standard leukemia therapies, especially in combination with therapies used for the treatment of AML. In particular, compounds of the current invention can be administered in combination with, for example, farnesyl transferase inhibitors and/or other drugs useful for the treatment of AML, such as Daunorubicin, Adriamycin, Ara-C, VP-16, Teniposide, Mitoxantrone, Idarubicin, Carboplatinum and PKC412.

Other anti-leukemic compounds include, for example, Ara-C, a pyrimidine analog, which is the 2'-alpha-hydroxy ribose (arabinoside) derivative of deoxycytidine. Also included is the purine analog of hypoxanthine, 6-mercaptopurine (6-MP) and fludarabine phosphate. Compounds which target, decrease or inhibit activity of histone deacetylase (HDAC) inhibitors such as sodium butyrate and suberoylanilide hydroxamic acid (SAHA) inhibit the activity of the enzymes known as histone deacetylases. Specific HDAC inhibitors include MS275, SAHA, FK228 (formerly FR901228), Trichostatin A and compounds disclosed in U.S. Pat. No. 6,552,065 including, but not limited to, N-hydroxy-3-[4-[[[2-(2-methyl-1H-indol-3-yl)-ethyl]-amino]methyl] phenyl]-2E-2-propenamide, or a pharmaceutically acceptable salt thereof and N-hydroxy-3-[4-[(2-hydroxyethyl){2-(1H-indol-3-yl)ethyl]-amino]methyl]phenyl]-2E-2-propenamide, or a pharmaceutically acceptable salt thereof, especially the lactate salt. Somatostatin receptor antagonists as used herein refer to compounds which target, treat or inhibit the somatostatin receptor such as octreotide, and SOM230. Tumor cell damaging approaches refer to approaches such as ionizing radiation. The term "ionizing radiation" referred to above and hereinafter means ionizing radiation that occurs as either electromagnetic rays (such as X-rays and gamma rays) or particles (such as alpha and beta particles). Ionizing radiation is provided in, but not limited to, radiation therapy and is known in the art. See Hellman, Principles of Radiation Therapy, Cancer, in Principles and Practice of Oncology, Devita et al., Eds., 4$^{th}$ Edition, Vol. 1, pp. 248-275 (1993).

Also included are EDG binders and ribonucleotide reductase inhibitors. The term "EDG binders" as used herein refers to a class of immunosuppressants that modulates lymphocyte recirculation, such as FTY720. The term "ribonucleotide reductase inhibitors" refers to pyrimidine or purine nucleoside analogs including, but not limited to, fludarabine and/or cytosine arabinoside (ara-C), 6-thioguanine, 5-fluorouracil, cladribine, 6-mercaptopurine (especially in combination with ara-C against ALL) and/or pentostatin. Ribonucleotide reductase inhibitors are especially hydroxyurea or 2-hydroxy-1H-isoindole-1,3-dione derivatives.

Also included are in particular those compounds, proteins or monoclonal antibodies of VEGF such as 1-(4-chloroanilino)-4-(4-pyridylmethyl)phthalazine or a pharmaceutically acceptable salt thereof, 1-(4-chloroanilino)-4-(4-pyridylmethyl)phthalazine succinate; Angiostatin™; Endostatin™; anthranilic acid amides; ZD4190; ZD6474; SU5416; SU6668; bevacizumab; or anti-VEGF antibodies or anti-VEGF receptor antibodies, such as rhuMAb and RHUFab, VEGF aptamer such as Macugon; FLT-4 inhibitors, FLT-3 inhibitors, VEGFR-2 IgGI antibody, Angiozyme (RPI 4610) and Bevacizumab (Avastin™).

Photodynamic therapy as used herein refers to therapy which uses certain chemicals known as photosensitizing compounds to treat or prevent cancers. Examples of photodynamic therapy include treatment with compounds, such as Visudyne™ and porfimer sodium.

Angiostatic steroids as used herein refers to compounds which block or inhibit angiogenesis, such as, e.g., anecortave, triamcinolone, hydrocortisone, 11-α-epihydrocotisol, cortexolone, 17α-hydroxyprogesterone, corticosterone, desoxycorticosterone, testosterone, estrone and dexamethasone.

Implants containing corticosteroids refers to compounds, such as fluocinolone and dexamethasone.

Other chemotherapeutic compounds include, but are not limited to, plant alkaloids, hormonal compounds and antagonists; biological response modifiers, preferably lymphokines or interferons; antisense oligonucleotides or oligonucleotide derivatives; shRNA or siRNA; or miscellaneous compounds or compounds with other or unknown mechanism of action.

The compounds of the invention are also useful as co-therapeutic compounds for use in combination with other drug substances such as anti-inflammatory, bronchodilatory or antihistamine drug substances, particularly in the treatment of obstructive or inflammatory airways diseases such as those mentioned hereinbefore, for example as potentiators of therapeutic activity of such drugs or as a means of reducing required dosaging or potential side effects of such drugs. A compound of the invention may be mixed with the other drug substance in a fixed pharmaceutical composition or it may be administered separately, before, simultaneously with or after the other drug substance. Accordingly the invention includes a combination of a compound of the invention as hereinbefore described with an anti-inflammatory, bronchodilatory, antihistamine or anti-tussive drug substance, said compound of the invention and said drug substance being in the same or different pharmaceutical composition.

Suitable anti-inflammatory drugs include steroids, in particular glucocorticosteroids such as budesonide, beclamethasone dipropionate, fluticasone propionate, ciclesonide or mometasone furoate; non-steroidal glucocorticoid receptor agonists; LTB4 antagonists such LY293111, CGS025019C, CP-195543, SC-53228, BIIL 284, ONO 4057, SB 209247; LTD4 antagonists such as montelukast and zafirlukast; PDE4 inhibitors such cilomilast (Ariflo® GlaxoSmithKline), Roflumilast (Byk Gulden), V-11294A (Napp), BAY19-8004 (Bayer), SCH-351591 (Schering-Plough), Arofylline (Almirall Prodesfarma), PD189659/PD168787 (Parke-Davis), AWD-12-281 (Asta Medica), CDC-801 (Celgene), SelCID™ CC-10004 (Celgene), VM554/UM565 (Vernalis), T-440 (Tanabe), KW-4490 (Kyowa Hakko Kogyo); A2a agonists; A2b antagonists; and beta-2 adrenoceptor agonists such as albuterol (salbutamol), metaproterenol, terbutaline, salmeterol fenoterol, procaterol, and especially, formoterol and pharmaceutically acceptable salts thereof. Suitable bronchodilatory drugs include anticholinergic or antimuscarinic compounds, in particular ipratropium bromide, oxitropium bromide, tiotropium salts and CHF 4226 (Chiesi), and glycopyrrolate.

Suitable antihistamine drug substances include cetirizine hydrochloride, acetaminophen, clemastine fumarate, promethazine, loratidine, desloratidine, diphenhydramine and fexofenadine hydrochloride, activastine, astemizole, azelastine, ebastine, epinastine, mizolastine and tefenadine.

Other useful combinations of compounds of the invention with anti-inflammatory drugs are those with antagonists of chemokine receptors, e.g. CCR-1, CCR-2, CCR-3, CCR-4, CCR-5, CCR-6, CCR-7, CCR-8, CCR-9 and CCR10, CXCR1, CXCR2, CXCR3, CXCR4, CXCR5, particularly CCR-5 antagonists such as Schering-Plough antagonists SC-351125, SCH-55700 and SCH-D, and Takeda antagonists such as N-[[4-[[[6,7-dihydro-2-(4-methylphenyl)-5H-b enzo-cyclohepten-8-yl]carbonyl]amino]phenyl]-methyl]tetrahydro-N,N-dimethyl-2H-pyran-4-aminium chloride (TAK-770).

The structure of the active compounds identified by code numbers, generic or trade names may be taken from the actual edition of the standard compendium "The Merck Index" or from databases, e.g. Patents International (e.g. IMS World Publications).

A compound of the current invention may also be used in combination with known therapeutic processes, for example, the administration of hormones or radiation. In certain embodiments, a provided compound is used as a radiosensitizer, especially for the treatment of tumors which exhibit poor sensitivity to radiotherapy.

A compound of the current invention can be administered alone or in combination with one or more other therapeutic compounds, possible combination therapy taking the form of fixed combinations or the administration of a compound of the invention and one or more other therapeutic compounds being staggered or given independently of one another, or the combined administration of fixed combinations and one or more other therapeutic compounds. A compound of the current invention can besides or in addition be administered especially for tumor therapy in combination with chemotherapy, radiotherapy, immunotherapy, phototherapy, surgical intervention, or a combination of these. Long-term therapy is equally possible as is adjuvant therapy in the context of other treatment strategies, as described above. Other possible treatments are therapy to maintain the patient's status after tumor regression, or even chemopreventive therapy, for example in patients at risk.

Those additional agents may be administered separately from an inventive compound-containing composition, as part of a multiple dosage regimen. Alternatively, those agents may be part of a single dosage form, mixed together with a compound of this invention in a single composition. If administered as part of a multiple dosage regime, the two active agents may be submitted simultaneously, sequentially or within a period of time from one another normally within five hours from one another.

As used herein, the term "combination," "combined," and related terms refers to the simultaneous or sequential administration of therapeutic agents in accordance with this invention. For example, a compound of the present invention may be administered with another therapeutic agent simultaneously or sequentially in separate unit dosage forms or together in a single unit dosage form. Accordingly, the present invention provides a single unit dosage form comprising a compound of the current invention, an additional therapeutic agent, and a pharmaceutically acceptable carrier, adjuvant, or vehicle.

The amount of both an inventive compound and additional therapeutic agent (in those compositions which comprise an additional therapeutic agent as described above) that may be combined with the carrier materials to produce a single dosage form will vary depending upon the host treated and the particular mode of administration. Preferably, compositions of this invention should be formulated so that a dosage of between 0.01-100 mg/kg body weight/day of an inventive compound can be administered.

In those compositions which comprise an additional therapeutic agent, that additional therapeutic agent and the compound of this invention may act synergistically. Therefore, the amount of additional therapeutic agent in such compositions will be less than that required in a monotherapy utilizing only that therapeutic agent. In such compositions a dosage of between 0.01-1,000 μg/kg body weight/day of the additional therapeutic agent can be administered.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

The compounds of this invention, or pharmaceutical compositions thereof, may also be incorporated into compositions for coating an implantable medical device, such as prostheses, artificial valves, vascular grafts, stents and catheters. Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a pharmaceutically acceptable composition comprising a kinase inhibitor. Implantable devices coated with a compound of this invention are another embodiment of the present invention.

EXEMPLIFICATION

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein.

Example 1

(1r,4r)-N1-(2-ethylthiazolo[5,4-d]pyrimidin-7-yl)-N4,N4-dimethylcyclohexane-1,4-diamine, I-1

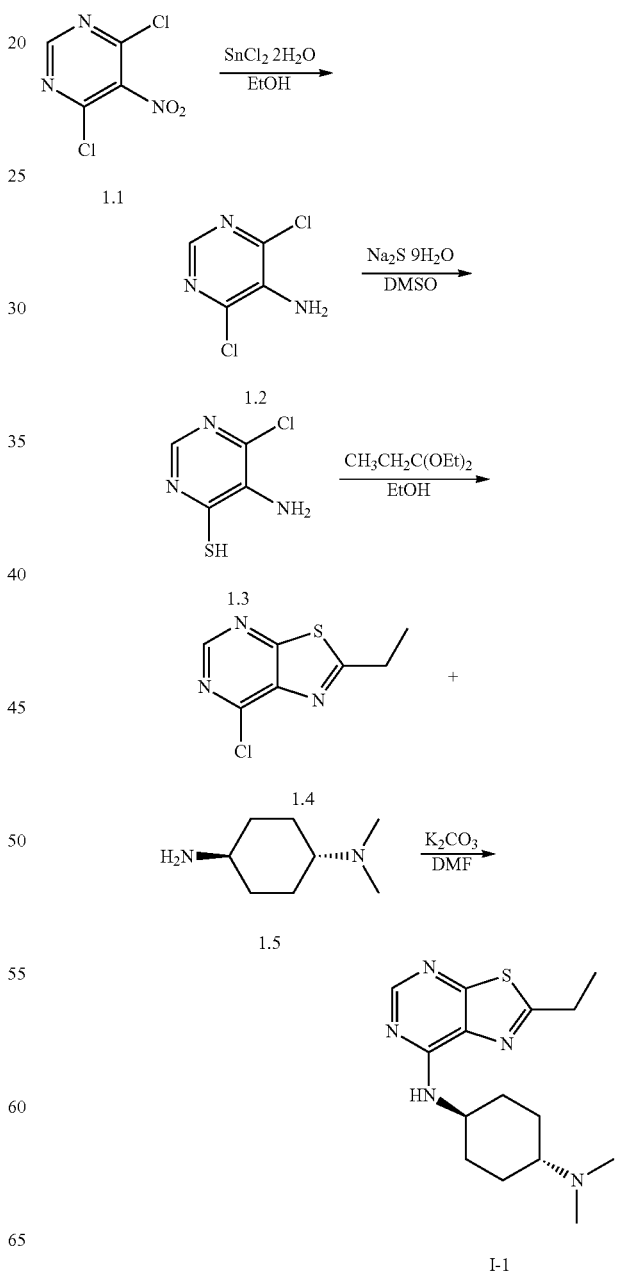

Synthesis of Compound 1.2.

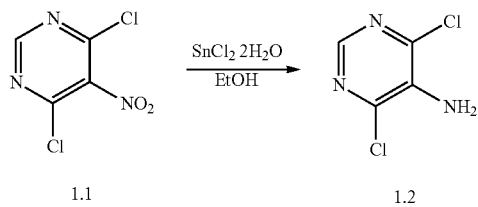

Into a 250 mL round-bottom flask, were placed (4,6-dichloropyrimidin-5-yl)azinic acid, 1.1 (4 g, 20.51 mmol, 1.00 equiv.) and SnCl$_2$-2H$_2$O (23.2 g, 102.65 mmol, 5.00 equiv.) in ethanol (60 mL). The resulting solution was heated to reflux for 6 hours and then cooled. The resulting mixture was concentrated under vacuum. The solution was adjusted to pH 8.0 with sodium bicarbonate (aq.). The resulting solution was extracted with 3×150 mL of ether and the organic layers were combined and dried over anhydrous sodium sulfate and concentrated under vacuum to yield 2.5 g (74%) of 4,6-dichloropyrimidin-5-amine, intermediate 1.2, as a white solid.

Synthesis of Compound 1.3.

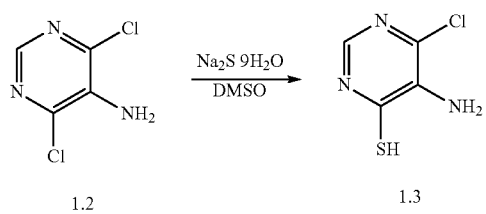

Into a 50 mL round-bottom flask, were placed 4,6-dichloropyrimidin-5-amine, Intermediate 1.2, (500 mg, 3.05 mmol, 1.00 equiv) and disodium sulfide (810 mg, 3.38 mmol, 1.11 equiv) in DMSO (6 mL). The resulting solution was stirred for 2 h at 80° C. The reaction mixture was cooled. The product was precipitated by the addition of 6N HCl (aq). The solids formed were collected by filtration and dried to yield 330 mg (67%) of 5-amino-6-chloropyrimidine-4-thiol, intermediate 1.3 as a yellow solid.

Synthesis of Compound 1.4.

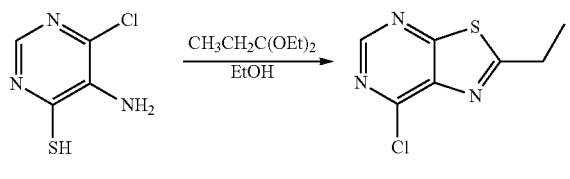

Into a 100 mL round-bottom flask, were placed 5-amino-6-chloropyrimidine-4-thiol, Intermediate 1.3, (300 mg, 1.86 mmol, 1.00 equiv) and 1,1,1-triethoxypropane (5 mL) in ethanol (10 mL). The resulting solution was refluxed for 12 hr. The reaction mixture was cooled and concentrated under vacuum. The residue was purified by flash column chromatograph to yield 290 mg (78%) of 7-chloro-2-ethyl-[1,3]thiazolo[5,4-d]pyrimidine, intermediate 1.4, as a yellow oil.

Synthesis of Compound I-1.

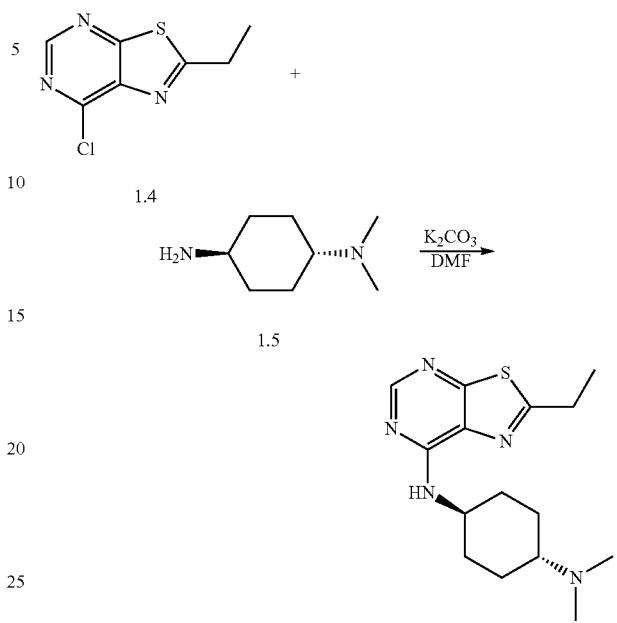

Into a 50 mL round-bottom flask, were placed 7-chloro-2-ethyl-[1,3]thiazolo[5,4-d]pyrimidine, Intermediate 1.4, (200 mg, 1.00 mmol, 1.00 equiv), 1-N,1-N-dimethylcyclohexane-1,4-diamine (170.4 mg, 1.20 mmol, 1.20 equiv) and potassium carbonate (207 mg, 1.50 mmol, 1.50 equiv) in N,N-dimethylformamide (10 mL). The resulting solution was stirred overnight at 40° C. in an oil bath. The resulting solution was diluted with 200 mL of water and extracted with 3×200 mL of ethyl acetate. The organic layers were combined and washed with 3×300 mL of brine. The organic layer was dried over anhydrous sodium sulfate and concentrated under vacuum. The crude material was purified by preparative HPLC to yield 29.1 mg (10%) of 4-N-[2-ethyl-[1,3]thiazolo[5,4-d]pyrimidin-7-yl]-1-N,1-N-dimethylcyclohexane-1,4-diamine as a white solid.

$^1$H-NMR: (400 MHz, CDCl$_3$, ppm) δ8.45 (1H, s), 5.83-5.80 (1H, d), 4.14-4.11 (1H, m), 3.13-3.06 (2H, q), 2.39 (6H, s), 2.30-2.26 (2H, d), 2.07-2.03 (2H, d), 1.59-1.24 (7H, m). (ES, m/z): 306 [M+H]$^+$.

Example 2

(1r,4r)-N-1-(2-isopropylthiazolo[5,4-d]pyrimidin-7-yl)-N4,N4-dimethylcyclohexane-1,4-diamine, I-2

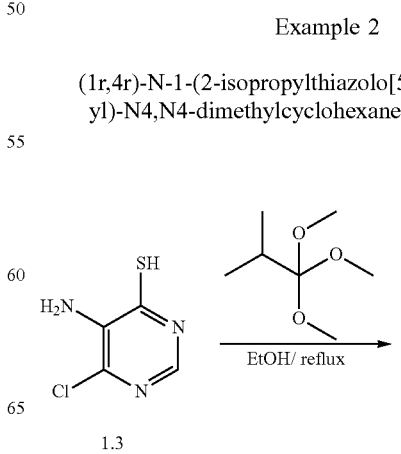

-continued

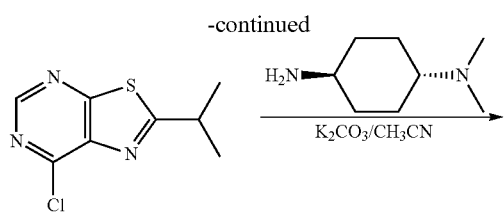

Synthesis of Intermediate 2.1

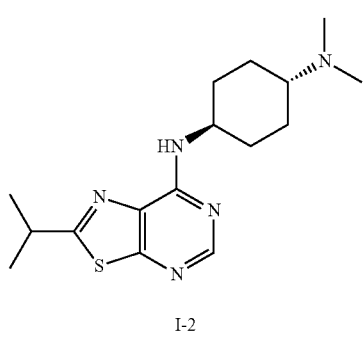

Under inert atmosphere, to a 100 mL round-bottom flask, were added a solution of intermediate 1.3, 5-amino-6-chloropyrimidine-4-thiol (600 mg, 3.71 mmol, 1.00 equiv) in ethanol (mL), followed by 1,1,1-trimethoxy-2-methylpropane (2 mL). The resulting solution was heated to reflux overnight. Solvents were removed under vacuum, and the resulting residue was purified via flash column chromatography to provide 120 mg (15%) of 7-chloro-2-(propan-2-yl)-[1,3]thiazolo[5,4-d]pyrimidine, intermediate 2.1 as colorless oil. (ES, m/z): 255 [M+H+ CH$_3$CN]$^+$.

Synthesis of I-2

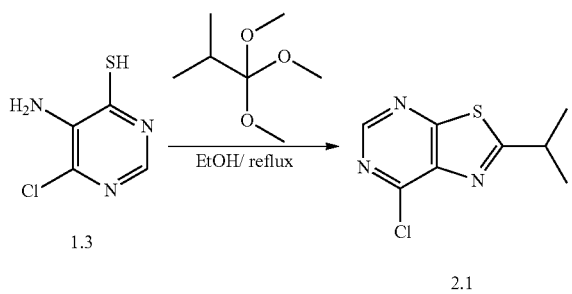

To a solution of 7-chloro-2-(propan-2-yl)-[1,3]thiazolo[5,4-d]pyrimidine (120 mg, 0.56 mmol, 1.00 equiv) in CH$_3$CN (20 mL) were added trans-dimethylcyclohexane-1,4-diamine (400 mg, 2.81 mmol, 5.00 equiv), potassium carbonate (773 mg, 5.60 mmol, 10.00 equiv) and triethylamine (170 mg, 1.68 mmol, 3.00 equiv) successively at room temperature. The resulting solution was stirred overnight at 80° C. The reaction was cooled to room temperature, filtered and solvents were removed under vacuum. The crude material (500 mg) was purified by preparative HPLC to provide the desired compound I-2 (56.6 mg) as a white solid. $^1$H-NMR (300 MHz, CD$_3$OD): δ 8.26 (1H, m), 4.14-4.03 (1H, m), 3.43-3.31 (1H, m), 2.54-2.42 (1H, m), 2.368 (6H, s), 2.15-2.13 (2H, m), 2.09-2.01 (2H, m), 1.55-1.41 (10H, m). (ES, m/z): 307 [M+H]$^+$, 348 [M+H+CH$_3$CN]$^+$.

Example 3

(1r,4r)-4-((2-ethylthiazolo[5,4-d]pyrimidin-7-yl)oxy)-N,N-dimethylcyclo-hexanamine, I-3

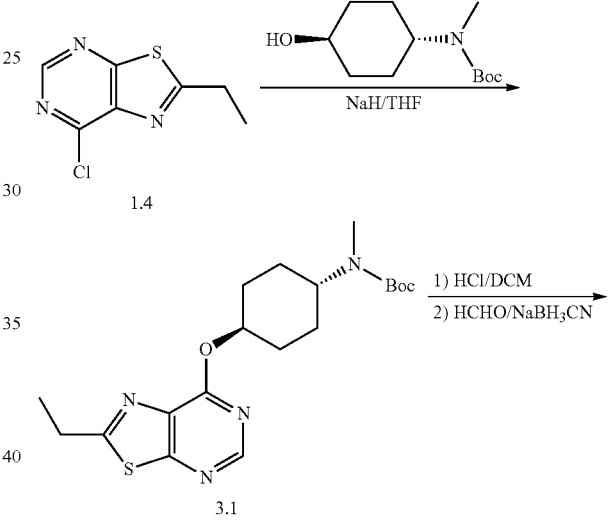

Synthesis of Compound 3.1.

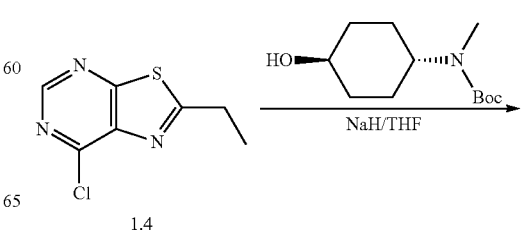

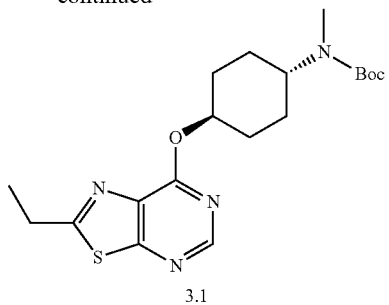

3.1

To a solution of tert-butyl N-(4-hydroxycyclohexyl)-N-methylcarbamate and Intermediate 1.4 (387 mg, 1.69 mmol, 1.70 equiv) in 10 mL of dry THF was added sodium hydride (60% dispersion in mineral oil, 260 mg, 5.00 equiv.) slowly at 0° C. under nitrogen. The resulting solution was stirred for 30 min at room temperature. Then a solution of 7-chloro-2-ethyl-[1,3]thiazolo[5,4-d]pyrimidine (260 mg, 1.30 mmol, 1.00 equiv) in 5 mL of THF was added and the resulting solution was stirred for an additional 6 h at ambient temperature. The reaction was quenched with NH$_4$Cl (sat), and extracted with EtOAc. The organic layer was dried over anhydrous sodium sulfate. After filtration and concentration under reduced pressure, the residue was purified by flash column chromatography with to provide tert-butyl N-[4-([2-ethyl-[1,3]thiazolo[5,4-d]pyrimidin-7-yl]oxy)cyclohexyl]-N-methylcarbamate, Intermediate 3.1 (300 mg, 59%) as light yellow oil. (ES, m/z): 393 [M+H]$^+$.

Synthesis of I-3

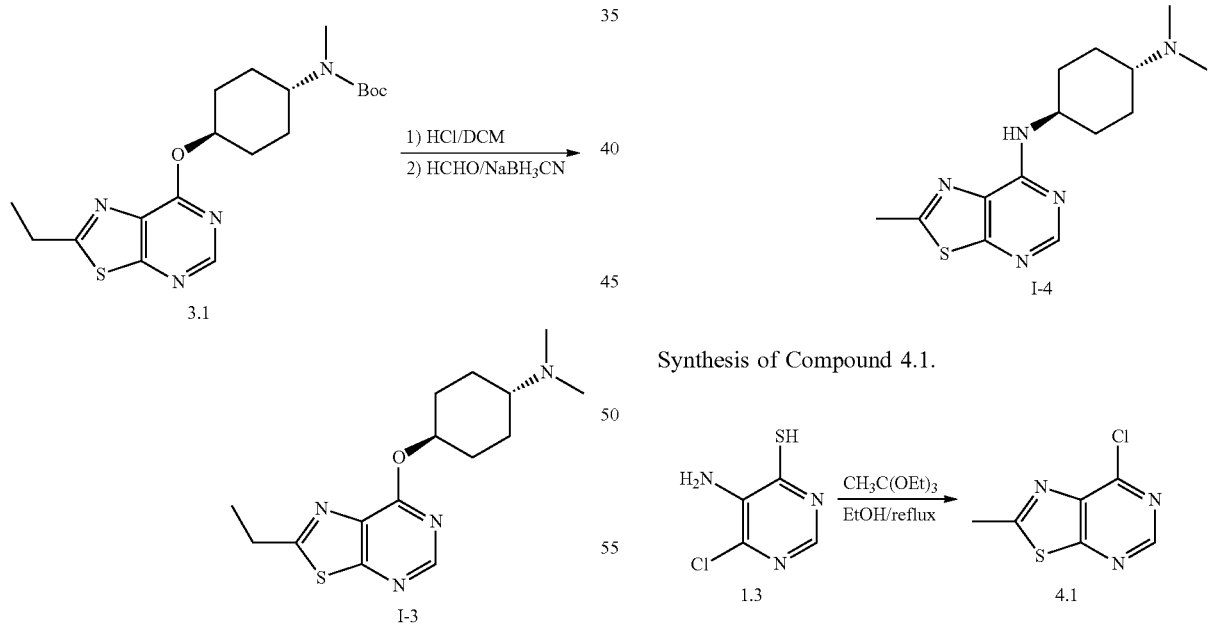

To a solution of tert-butyl N-[4-([2-ethyl-[1,3]thiazolo[5,4-d]pyrimidin-7-yl]oxy)cyclohexyl]-N-methylcarbamate (300 mg, 0.76 mmol, 1.00 equiv) in dichloromethane (30 mL) was added hydrochloric acid (12 M, 0.5 mL) at 0° C. and the resulting solution was stirred for 2 h at room temperature. After concentration in vacuo, the residue was dissolved in methanol (10 mL) and HCHO (375, 0.5 mL) and acetic acid (0.5 mL) were added. The solution was stirred for 20 min. NaBH$_3$CN (200 mg) was added and the resulting solution was stirred for 2 h at room temperature. After filtration and concentration in vacuo, crude product (250 mg) was purified by preparative HPLC to give the desired 4-([2-ethyl-[1,3]thiazolo[5,4-d]pyrimidin-7-yl]oxy)-N,N-dimethylcyclohexan-1-amine (83 mg) as a light yellow semi-solid. $^1$H-NMR (300 MHz, CD$_3$OD): δ 8.57 (1H, m), 5.38-5.28 (1H, m), 3.15 (2H, d), 2.53-2.42 (1H, m), 2.37 (6H, s), 2.32-2.25 (2H), 1.68-1.41 (7H, m). LC-MS (ES, m/z): 307 [M+H]$^+$, 348 [M+H+CH$_3$CN]$^+$.

Example 4

(1r,4r)-N1,N1-dimethyl-N4-(2-methylthiazolo[5,4-d]pyrimidin-7-yl)cyclo-hexane-1,4-diamine

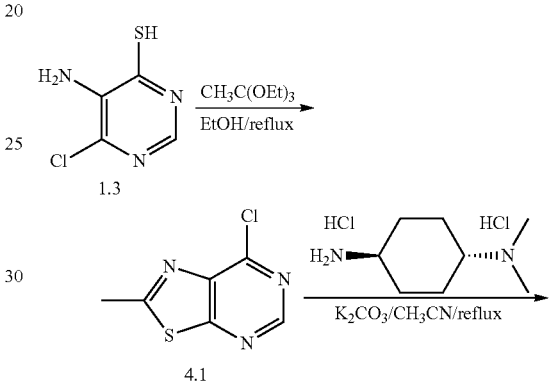

Synthesis of Compound 4.1.

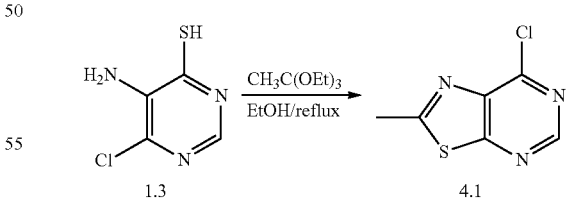

To a solution of 5-amino-6-chloropyrimidine-4-thiol, Intermediate 1.3 (810 mg, 5.01 mmol, 1.00 equiv) in ethanol (30 mL) was added CH(OEt)$_3$ (4.5 mL). The reaction was stirred overnight at 90° C. under nitrogen. The resulting mixture was concentrated under vacuum and the residue was purified via flash column chromatography to yield 0.7 g (75%) of Intermediate 4.1 as a white solid. LCMS (ES, m/z): 185 and 187 (M+H$^+$).

Synthesis of Compound I-4.

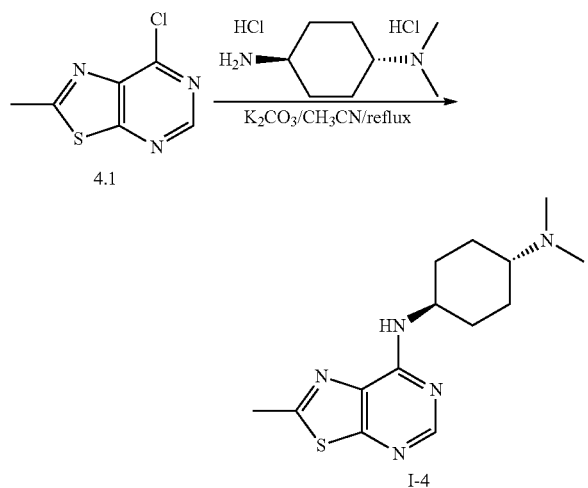

To a 50 mL round-bottom flask containing a solution of 7-chloro-2-methyl-[1,3]thiazolo[5,4-d]pyrimidine (100 mg, 0.54 mmol, 1.00 equiv) in CH$_3$CN (20 mL) were added trans-1-N,1-N-dimethylcyclohexane-1,4-diamine dichloride (173 mg, 0.80 mmol, 1.50 equiv) and K$_2$CO$_3$ (223 mg, 1.62 mmol, 3.00 equiv) at room temperature. The resulting mixture was stirred overnight at 80° C. in an oil bath under nitrogen. The resulting mixture was concentrated under vacuum and the residue was diluted with water, extracted with 3×30 mL of dichloromethane. The combined organic layers were dried over anhydrous sodium sulfate and concentrated under vacuum. The residue was purified via flash column chromatography to yield 102 mg (65%) of the desired (1r,4r)-N1,N1-dimethyl-N4-(2-methylthiazolo[5,4-d]pyrimidin-7-yl)cyclo-hexane-1,4-diamine as a light yellow solid. $^1$H NMR (300 MHz, CDCl$_3$) δ 8.46 (s, 1H), 5.81 (d, 1H), 4.21-4.02 (m, 1H), 2.80 (s, 3H), 2.51-2.45 (brs, 7H), 2.28 (d, 2H), 2.06 (d, 2H), 1.57-1.49 (m, 2H), 1.42-1.33 (m, 2H). LCMS (ES, m/z): 292 (M+H$^+$).

Example 5

Synthesis of I-5,2-ethyl-N-((1r,4r)-4-morpholinocyclohexyl)thiazolo[5,4-d]pyrimidin-7-amine, I-5

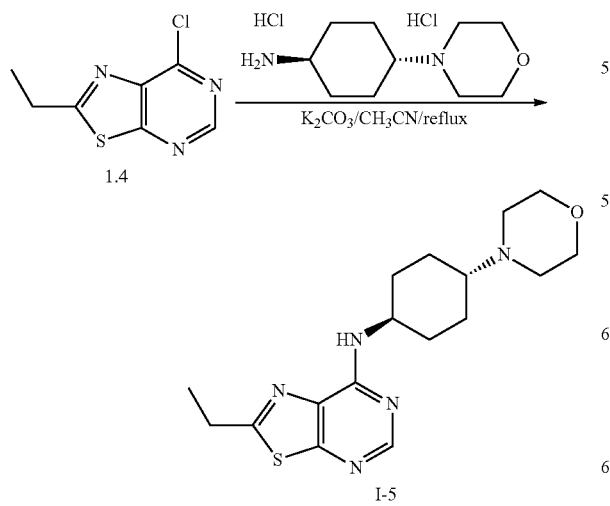

To a solution of trans-4-(morpholin-4-yl)cyclohexan-1-amine dichloride, Intermediate 1.4 (193 mg, 0.75 mmol, 1.50 equiv.) in anhydrous CH$_3$CN (20 mL) were added 7-chloro-2-ethyl-[1,3]thiazolo[5,4-d]pyrimidine (100 mg, 0.50 mmol, 1.00 equiv) and potassium carbonate (207 mg, 1.50 mmol, 3.00 equiv). The resulting mixture was heated to reflux overnight in an oil bath. The resulting mixture was concentrated under vacuum and the residue was purified via flash column chromatography to yield 103.8 mg (60%) of 2-ethyl-N-[trans-4-(morpholin-4-yl)cyclohexyl]-[1,3]thiazolo[5,4-d]pyrimidin-7-amine I-5, as a light yellow solid. $^1$H NMR (300 MHz, CDCl$_3$) δ 8.45 (s, 1H), 5.81 (d, 1H), 4.20-4.01 (m, 1H), 3.78 (brs, 4H), 3.09 (t, 2H), 2.62 (brs, 4H), 2.30 (d, 2H), 2.15-1.95 (m, 2H), 1.75-1.20 (m, 7H). LCMS (ES, m/z): 348 (M+H$^+$).

Example 6

Synthesis of N,2-diethyl-N-((1r,4r)-4-morpholinocyclohexyl)thiazolo[5,4-d]pyrimidin-7-amine, I-6

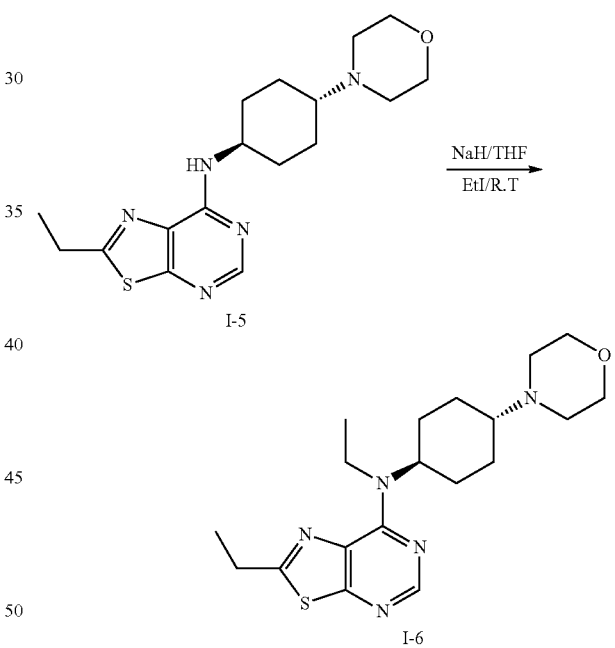

To a solution of 2-ethyl-N-[trans-4-(morpholin-4-yl)cyclohexyl]-[1,3]thiazolo[5,4-d]pyrimidin-7-amine (116 mg, 0.33 mmol, 1.00 equiv) in anhydrous THF (15 mL) was added sodium hydride (26.4 mg, 0.66 mmol, 2.00 equiv, 60%) and stirred for 1 h under nitrogen. Iodoethane (104 mg, 0.67 mmol, 2.00 equiv) was added and the resulting solution was stirred for 2 h at ambient temperature. The reaction was quenched with water, extracted with CH$_2$Cl$_2$, dried over sodium sulfate and concentrated in vacuo. The residue was purified via flash column chromatography to give 50 mg (40%) of N,2-diethyl-N-[(1r,4r)-4-(morpholin-4-yl)cyclohexyl]-[1,3]thiazolo[5,4-d]pyrimidin-7-amine as a yellow solid. LCMS (ES, m/z) 376 (M+H$^+$).

Example 7

2-ethyl-N5-(1-methyl-1H-pyrazol-4-yl)-N7-((1r,4r)-4-morpholinocyclohexyl)-thiazolo[5,4-d]pyrimidine-5,7-diamine, I-7

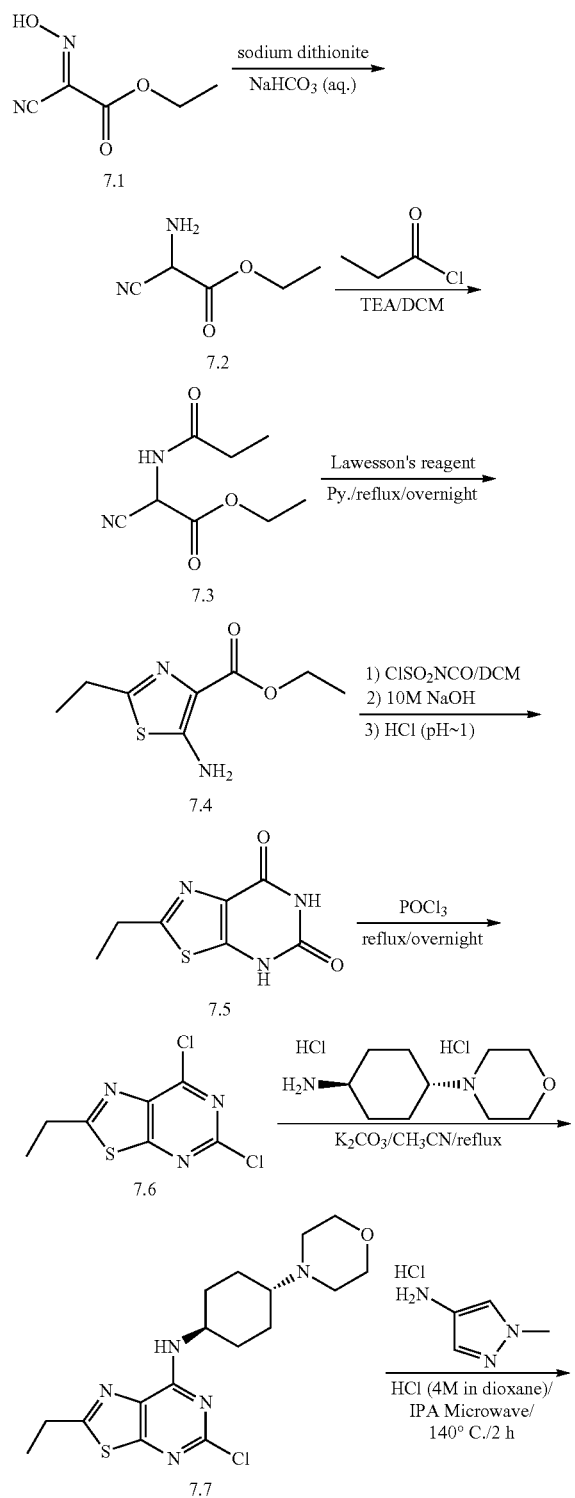

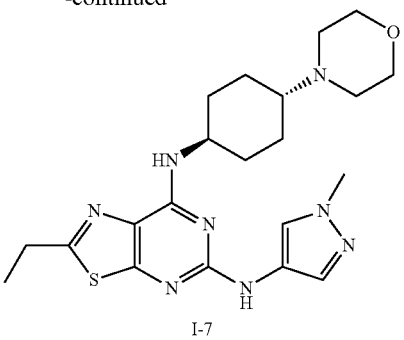

Synthesis of Intermediate 7.2

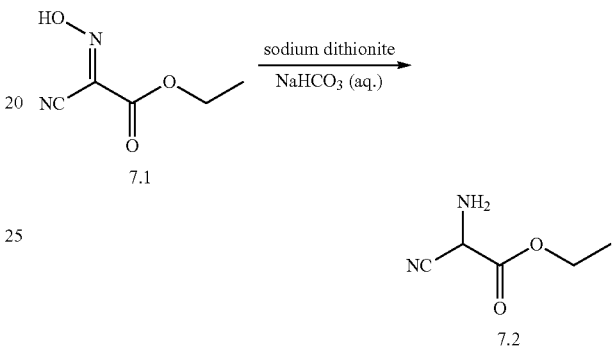

Into a 500-mL round-bottom flask containing a solution of (E)-ethyl 2-cyano-2-(hydroxyimino)acetate (10.0 g, 70.37 mmol, 1.00 equiv) in water (120 mL) was added saturated aqueous sodium bicarbonate (80 mL), followed by addition of sodium dithionite (34.0 g, 3.00 equiv) at room temperature. The resulting solution was stirred for 2 h at this temperature and extracted with 3×100 mL of dichloromethane. The combined organic layers was dried over anhydrous sodium sulfate and concentrated under vacuum to give 2 g (crude) of ethyl 2-amino-2-cyanoacetate as a light yellow solid. LCMS (ES, m/z): 129 (M+H$^+$).

Synthesis of Intermediate 7.3

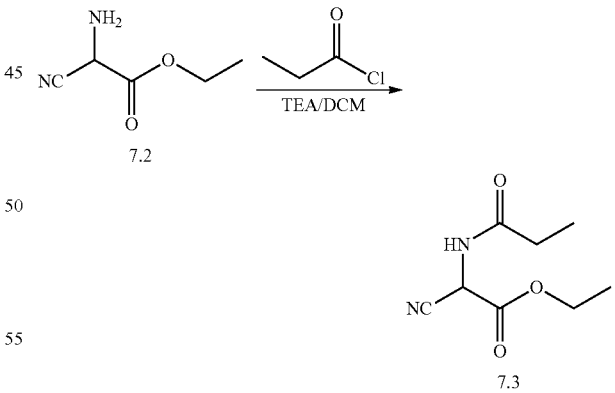

To a solution of ethyl 2-amino-2-cyanoacetate (2.0 g, 15.61 mmol, 1.00 equiv) and TEA (1.59 g, 15.68 mmol, 1.00 equiv) in dichloromethane (20 mL) at 0° C. was added dropwise propanoyl chloride (1.44 g, 15.61 mmol, 1.00 equiv) under nitrogen. The resulting solution was stirred for 10 min at 0° C. and stirred for an additional 6 h at room temperature. The reaction was then quenched with water, extracted with 3×40 mL of dichloromethane. The combined organic layers were washed with brine and dried over anhydrous sodium sulfate. After concentration in vacuo, was purified via flash column chromatography to yield 2.1 g (73%) of intermediate 7.3 as a light yellow solid. $^1$H NMR (400 MHz, CDCl$_3$) δ 6.59 (d, J=6.8 Hz, 1H), 5.56 (d, J=7.6 Hz, 1H), 4.36 (q, J=7.4 Hz, 2H), 2.37 (q, J=7.6 Hz, 2H), 1.38 (t, J=7.4 Hz, 3H), 1.19 (t, J=7.6 Hz, 3H). LCMS (ES, m/z): 185 (M+H$^+$).

Synthesis of Intermediate 7.4

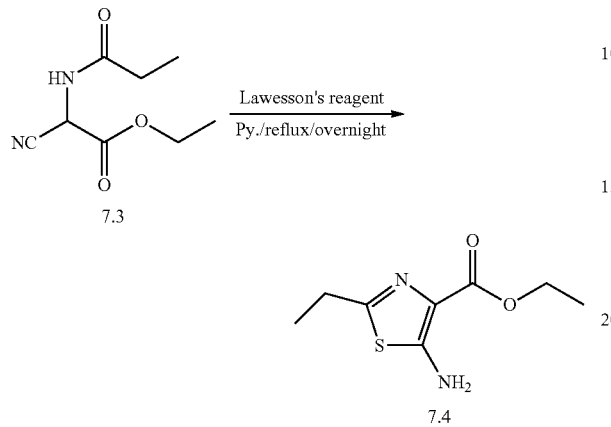

7.3

7.4

To a solution of ethyl 2-cyano-2-propanamidoacetate (2.0 g, 10.86 mmol, 1.00 equiv) in pyridine (30 mL) was added Lawesson's reagent (2.48 g, 6.13 mmol, 0.60 equiv) at room temperature. The reaction was stirred at 110° C. overnight in an oil bath under nitrogen. The resulting mixture was concentrated under vacuum and diluted with 50 mL of H$_2$O, extracted with 3×80 mL of ethyl acetate. The organic phase was washed with 1M HCl, and brine then dried over anhydrous sodium sulfate and concentrated under vacuum. The residue was purified via flash column chromatography to afford 700 mg (32%) of ethyl 5-amino-2-ethyl-1,3-thiazole-4-carboxylate as a light yellow solid. $^1$H NMR (300 MHz, CDCl$_3$) δ 5.92 (br s, 2H), 4.38 (q, J=7.2 Hz, 2H), 2.89 (q, J=7.5 Hz, 2H), 1.40 (t, J=7.2 Hz, 3H), 1.30 (t, J=7.5 Hz, 3H). LCMS (ES, m/z): 201 (M+H$^+$).

Synthesis of Intermediate 7.5

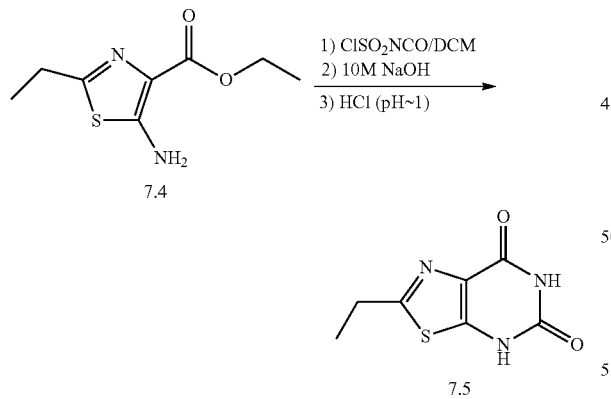

7.4

7.5

To a solution of ethyl 5-amino-2-ethyl-1,3-thiazole-4-carboxylate (500 mg, 2.50 mmol, 1.00 equiv) in dichloromethane (10 mL) cooled to −60° C. under nitrogen was added ClSO$_2$NCO (529 mg, 1.50 equiv) dropwise and the resulting mixture was stirred for 1 h. After the starting material was consumed, the reaction mixture was concentrated to dryness under reduced pressure. The solid residue transferred back to the 100 mL reaction flask as suspension in water (10 mL). This mixture was heated at 75° C. for 1 h, and then cooled to 30° C. Next, 10M aqueous NaOH (10 mL) was added and this mixture was heated at 85° C. for 20 min and then cooled to ambient temperature. The mixture was then acidified to pH 1 by the addition of concentrated HCl. The resulting solution was extracted with 3×50 mL of i-propanol/CHCl$_3$ (1:3) and the combined organic layers were dried over anhydrous sodium sulfate and concentrated under vacuum to give 293 mg (crude) of 2-ethyl-4H,5H,6H,7H-[1,3]thiazolo[5,4-d]pyrimidine-5,7-dione as a light yellow solid.

Synthesis of Intermediate 7.6

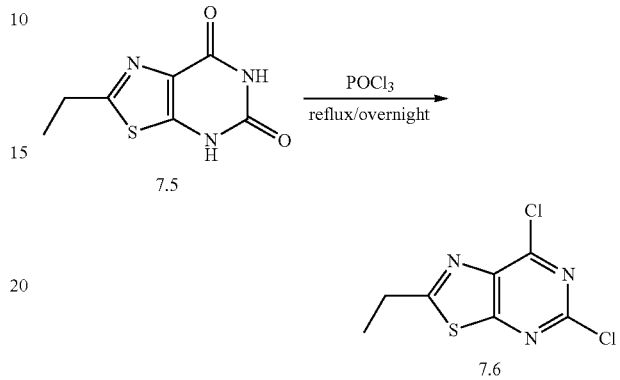

7.5

7.6

Into a 25 mL round-bottom flask, was placed intermediate 7.5 (200 mg, 1.01 mmol, 1.00 equiv) at room temperature. Phosphoroyl trichloride (4 mL) and N,N-diethylaniline (2.5 equiv) were added and the resulting mixture was stirred for 8 h at 100° C. under nitrogen. The resulting mixture was concentrated under vacuum and the residue was poured into 10 mL of water/ice, extracted with 3×10 mL of ethyl acetate. The combined organic layers were washed with brine, dried over sodium sulfate and concentrated under vacuum. The residue was purified via flash column chromatography to give 172 mg (73%) of 5,7-dichloro-2-ethyl-[1,3]thiazolo[5,4-d]pyrimidine, intermediate 7.6 as a white solid. $^1$H NMR (300 MHz, CDCl$_3$) δ 3.22 (q, J=7.5 Hz, 2H), 1.51 (t, J=7.5 Hz, 3H). LCMS (ES, m/z): 234 and 236 (M+H$^+$).

Synthesis of Intermediate 7.7

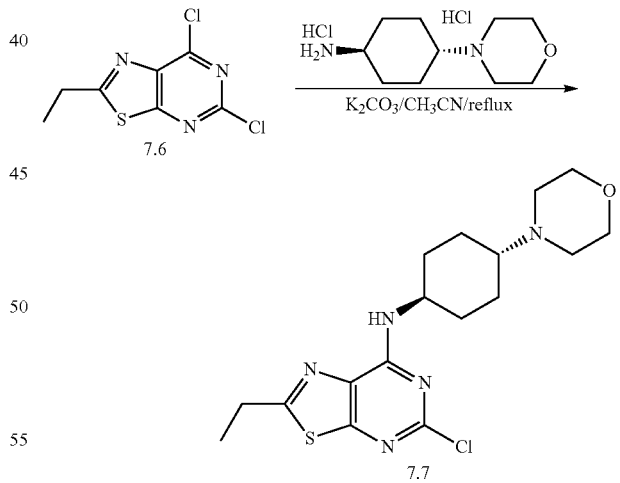

7.6

7.7

A solution of intermediate 7.6 (54 mg, 0.23 mmol, 1.00 equiv) in CH$_3$CN (5 mL) was added trans-4-(morpholin-4-yl)cyclohexan-1-amine (90 mg, 0.49 mmol, 1.50 equiv) and potassium carbonate (127 mg, 4.00 equiv). Resulting mixture was stirred for 14 h at 80° C. under nitrogen. The resulting mixture was concentrated under vacuum and the residue was purified via flash column chromatography to afford 85 mg (96%) of 5-chloro-2-ethyl-N-[4-(morpholin-4-yl)cyclohexyl]-[1,3]thiazolo[5,4-d]pyrimidin-7-amine, intermediate 7.7 as a white solid. LCMS (ES, m/z): 382 and 384 (M+H$^+$).

Synthesis of I-7

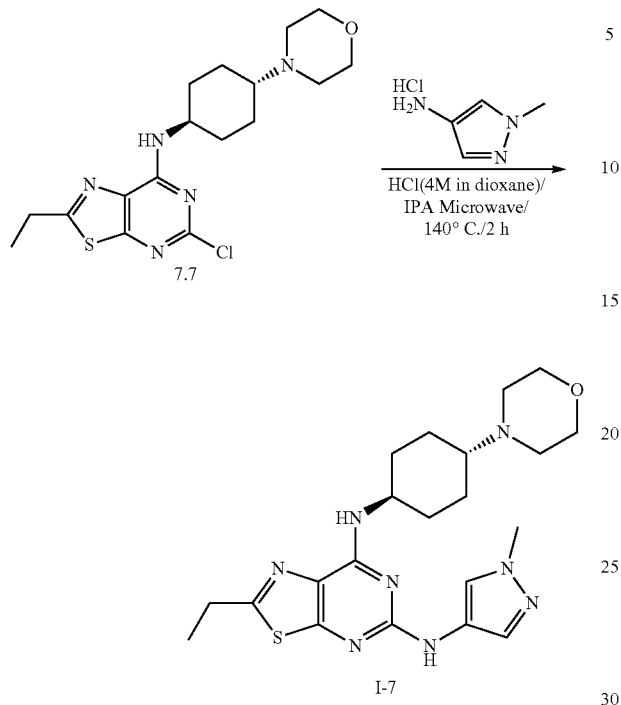

Example 8

Synthesis of 2-ethyl-N5-(1-isopropyl-1H-pyrazol-4-yl)-N7-((1r,4r)-4-morpholinocyclohexyl)thiazolo[5,4-d]pyrimidine-5,7-diamine I-8

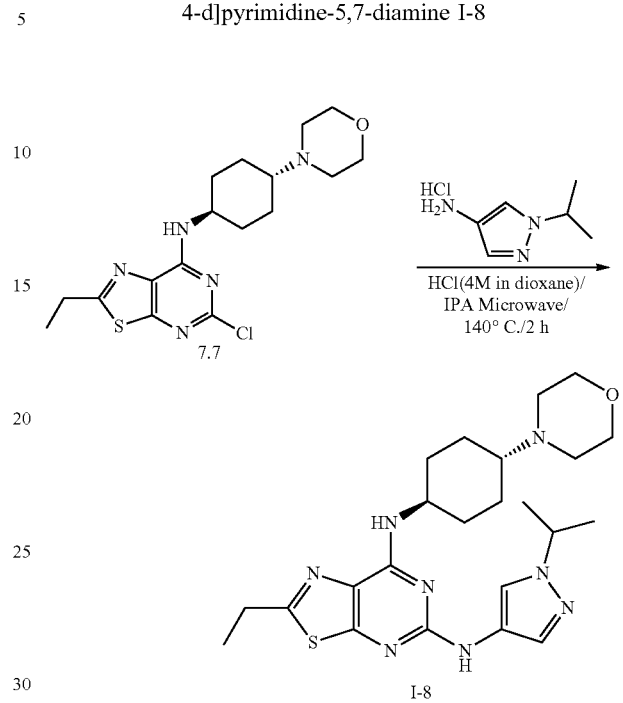

A sealed tube (10 mL) containing a solution of 5-chloro-2-ethyl-N-[4-(morpholin-4-yl)cyclohexyl]-[1,3]thiazolo[5,4-d]pyrimidin-7-amine (85 mg, 0.22 mmol, 1.00 equiv), 1-methyl-1H-pyrazol-4-amine (47 mg, 0.48 mmol, 1.50 equiv) and 0.5 mL of hydrochloric acid (4 M in dioxane) in isopropanol was heated in a microwave reactor for 2 h at 140° C. After cooling, the resulting mixture was diluted with H$_2$O, and extracted with 3×30 mL of dichloromethane. The combined organic layers were dried over anhydrous sodium sulfate and concentrated under vacuum. The residue was purified via flash column chromatography to afford 67.3 mg (68%) of 2-ethyl-5-N-(1-methyl-1H-pyrazol-4-yl)-7-N-[trans-4-(morpholin-4-yl)cyclohexyl]-[1,3]thiazolo[5,4-d]pyrimidine-5,7-diamine, I-7 as a light yellow solid. $^1$H NMR (300 MHz, CDCl$_3$) δ 7.82 (s, 1H), 7.47 (s, 1H), 6.71 (s, 1H), 5.67 (d, J=7.8 Hz, 1H), 4.10-3.90 (m, 1H), 3.89 (s, 3H), 3.75 (br s, 4H), 2.99 (q, J=7.8 Hz, 2H), 2.60 (br s, 4H), 2.28 (d, J=11.4 Hz, 3H), 2.04 (d, J=12.0 Hz, 2H), 1.50-1.25 (m, 7H). LC-MS (ES, m/z): 443 (M+H$^+$).

To a 10 mL sealed tube containing solution of 5-chloro-2-ethyl-N-[trans-4-(morpholin-4-yl)cyclohexyl]-[1,3]thiazolo[5,4-d]pyrimidin-7-amine (90 mg, 0.24 mmol, 1.00 equiv) and 1-(propan-2-yl)-1H-pyrazol-4-amine hydrochloride (45 mg, 0.28 mmol, 4.50 equiv) in isopropanol (4 mL) was added 0.1 mL of hydrochloric acid (4 M in dioxane) and the resulting mixture was irradiated in a microwave reactor for 2 h at 140° C. Suspension was filtered and crude solid was purified via flash column chromatography to yield 46.7 mg (42%) of 2-ethyl-5-N-[1-(propan-2-yl)-1H-pyrazol-4-yl]-7-N-[trans-4-(morpholin-4-yl)cyclohexyl]-[1,3]thiazolo[5,4-d]pyrimidine-5,7-diamine, I-8 as a light yellow solid. $^1$H-NMR (400 MHz, CDCl$_3$) δ 7.86 (s, 1H), 7.55 (s, 1H), 6.74 (s, 1H), 5.69 (d, 1H), 4.50 (quintet, 1H), 4.15-3.98 (m, 1H), 3.85 (brs, 3H), 3.00 (q, 2H), 2.75 (br s, 4H), 2.45-2.25 (m, 3H), 2.18-1.98 (m, 2H), 1.55 (d, 6H), 1.55-1.35 (m, 7H). LCMS (ES, m/z): 471 (M+H$^+$).

Example 9

Synthesis 2-ethyl-5-N-[1-(oxan-4-yl)-1H-pyrazol-4-yl]-7-N—[trans-4-(morpholin-4-yl)cyclohexyl]-[1,3]thiazolo[5,4-d]pyrimidine-5,7-diamine I-9

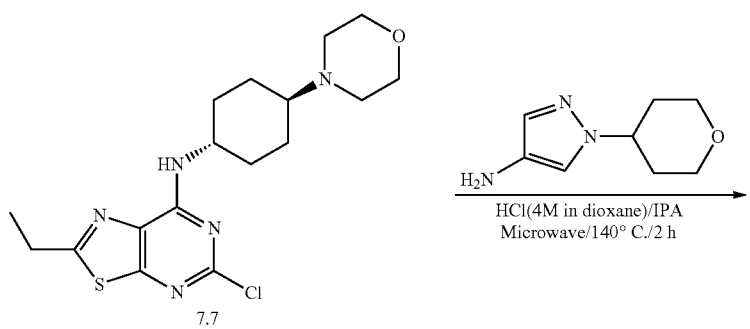

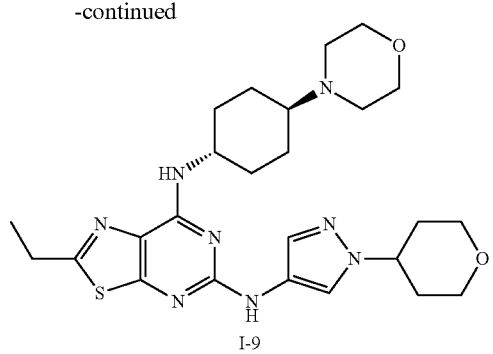

I-9

To a 20 mL vial containing 5-chloro-2-ethyl-N-[trans-4-(morpholin-4-yl)cyclohexyl]-[1,3]thiazolo[5,4-d]pyrimidin-7-amine (600 mg, 1.57 mmol, 1.00 equiv) and 1-(oxan-4-yl)-1H-pyrazol-4-amine (480 mg, 2.87 mmol, 1.83 equiv) in isopropanol (15 mL) was added 0.1 mL of HCl (4 m in dioxane) at room temperature. The final reaction mixture was irradiated in a microwave reactor for 3 h at 140° C. After cooling, the solids were collected by filtration purified by flash column chromatography to yield 636.7 mg (79%) of 2-ethyl-5-N-[1-(oxan-4-yl)-1H-pyrazol-4-yl]-7-N-[trans-4-(morpholin-4-yl)cyclohexyl]-[1,3]thiazolo[5,4-d]pyrimidine-5,7-diamine as a light yellow solid. $^1$H-NMR (300 MHz, DMSO) δ 9.04 (s, 1H), 7.91 (s, 1H), 7.46 (s, 1H), 7.43 (br s, 1H), 4.42-4.25 (m, 1H), 4.12-3.85 (m, 3H), 3.57 (s, 4H), 3.43 (td, 2H), 2.97 (q, 2H), 2.49 (s, 4H), 2.30-2.15 (m, 1H), 2.08-1.82 (m, 8H), 1.58-1.40 (m, 2H), 1.39-1.22 (m, 5H). LCMS (ES, m/z): 513 (M+H$^+$).

Example 10

Synthesis of 4-(4-((2-ethyl-7-(((1r,4r)-4-morpholino-cyclohexyl)amino)-thiazolo[5,4-d]pyrimidin-5-yl)amino)-1H-pyrazol-1-yl)tetrahydro-2H-thiopyran 1,1-dioxide I-10

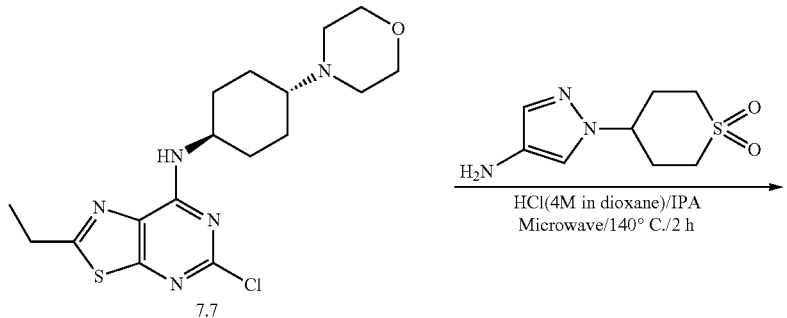

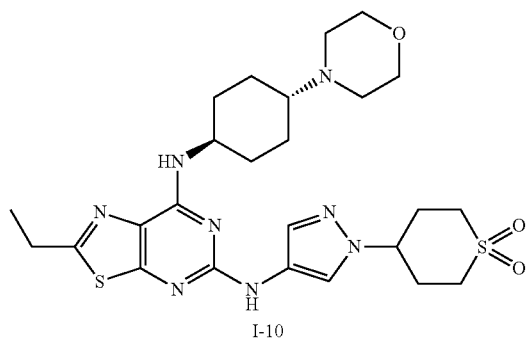

I-10

To a 10 mL microwave vial containing a mixture of 5-chloro-2-ethyl-N-[trans-4-(morpholin-4-yl)cyclohexyl]-[1,3]thiazolo[5,4-d]pyrimidin-7-amine (60 mg, 0.16 mmol, 1.00 equiv) and 4-(4-amino-1H-pyrazol-1-yl)-1^6-thiane-1,1-dione hydrochloride (67.8 mg, 0.27 mmol, 1.50 equiv) in isopropanol (4 mL) was added 0.1 mL of HCl (4 m in dioxane) at room temperature. Reaction mixture was irradiated in a microwave reactor for 2 h at 140° C. After cooling, the solids were collected by filtration and purified via flash column chromatography to afford 34.9 mg (40%) 4-(4-((2-ethyl-7-4(1r,4r)-4-morpholinocyclohexyl)amino)thiazolo[5,4-d]pyrimidin-5-yl)amino)-1H-pyrazol-1-yl)tetrahydro-2H-thiopyran 1,1-dioxide, I-10 as a light yellow solid. $^1$H-NMR (300 MHz, DMSO) δ 9.04 (s, 1H), 7.87 (s, 1H), 7.54 (s, 1H), 7.40 (br s, 1H), 4.62-4.43 (m, 1H), 4.10-3.85 (m, 1H), 3.56 (s, 4H), 3.45-3.35 (m, 2H), 3.25-3.15 (m, 2H), 2.97 (q, 2H), 2.49 (s, 4H), 2.48-2.26 (m, 4H), 2.25-2.09 (m, 1H), 2.05-1.82 (m, 4H), 1.58-1.40 (m, 2H), 1.39-1.18 (m, 5H). LCMS (ES, m/z): 561 (M+H$^+$).

Example 11

N7-((1r,4r)-4-(4,4-difluoropiperidin-1-yl)cyclohexyl)-2-ethyl-N5-(1-methyl-1H-pyrazol-4-yl)thiazolo[5,4-d]pyrimidine-5,7-diamine, I-11

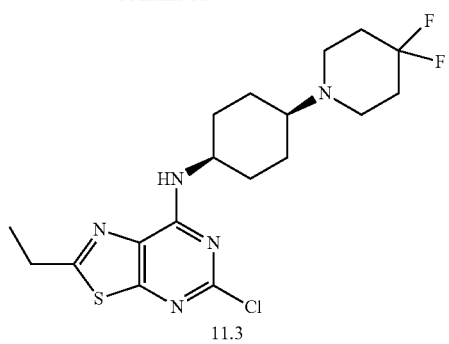

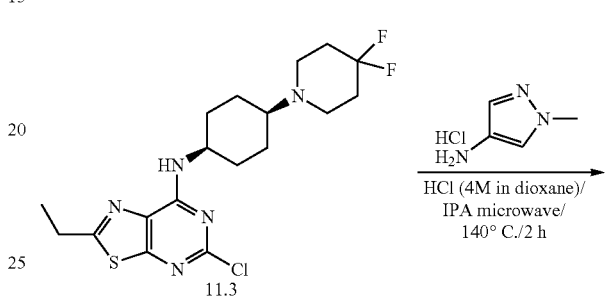

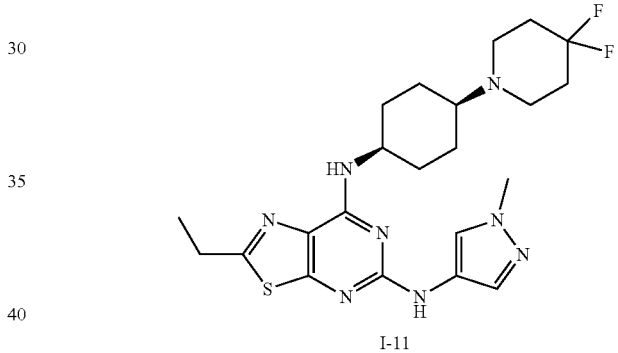

Synthesis of Compounds 11.2 and 11.3.

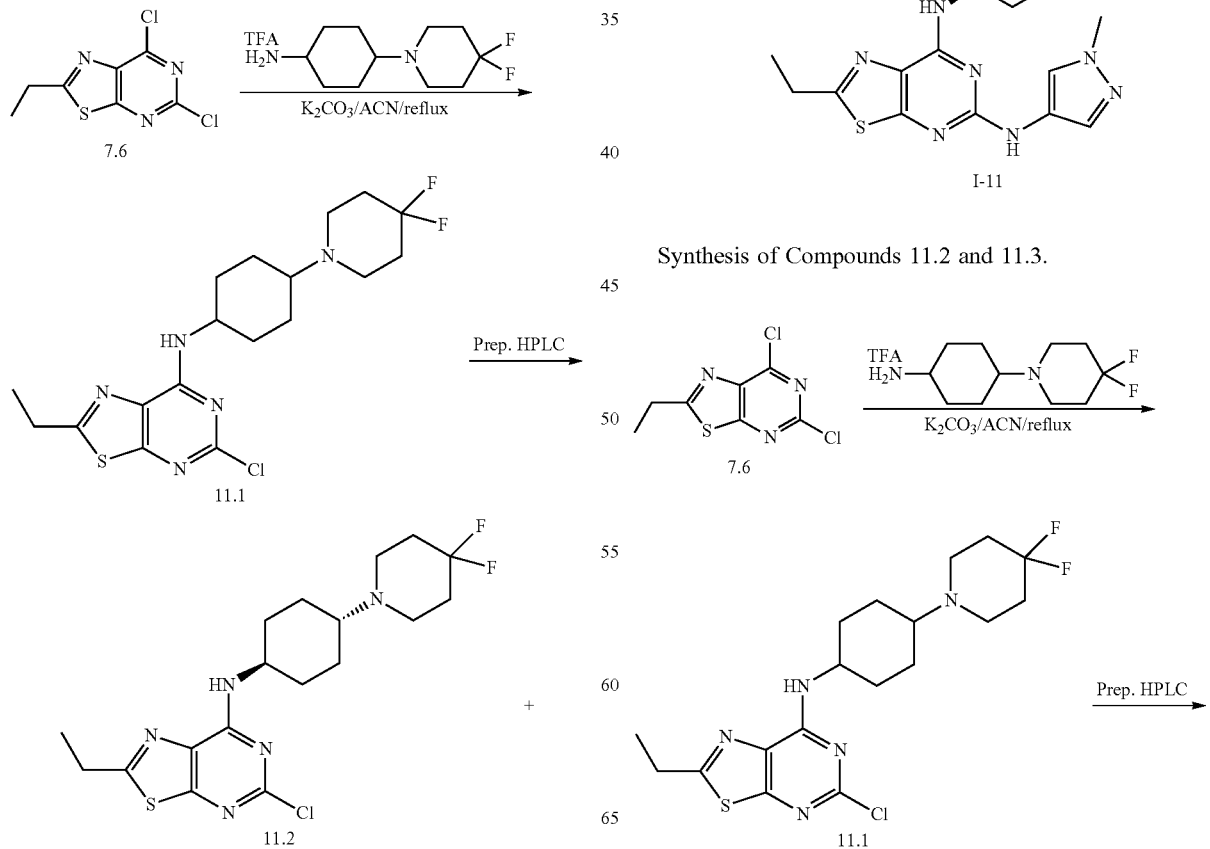

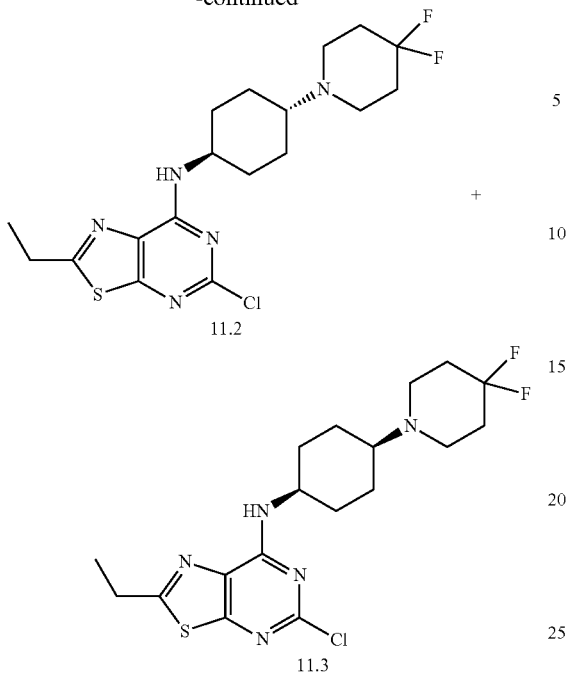

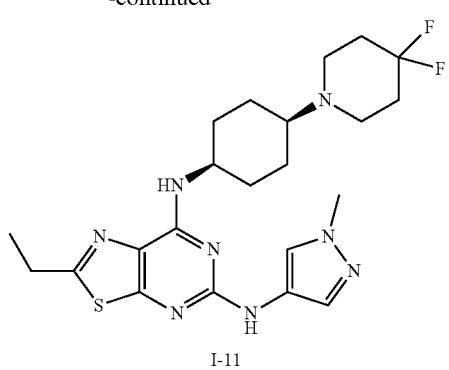

To a solution of 5,7-dichloro-2-ethyl-[1,3]thiazolo[5,4-d]pyrimidine, intermediate 7.6 (150 mg, 0.64 mmol, 1.00 equiv) in dry $CH_3CN$ (5 mL) was added potassium carbonate (353 mg, 4.00 equiv), followed by 4-(4,4-difluoropiperidin-1-yl)cyclohexan-1-amine (303 mg, 0.96 mmol, 1.50 equiv). Reaction mixture was stirred for 14 h at 80° C. in an oil bath. After cooling, the resulting mixture was concentrated under vacuum and the residue was purified by flash column chromatography to yield 120 mg (45%) of intermediate 11.1 as a light yellow solid. Cis/trans isomers were separated using preparative HPLC to yield 20 mg of trans-5-chloro-2-ethyl-N-[4-(4,4-difluoropiperidin-1-yl)cyclohexyl]-[1,3]thiazolo[5,4-d]pyrimidin-7-amine, intermediate 11.2 and 80 mg (67%) of cis-5-chloro-2-ethyl-N-[4-(4,4-difluoropiperidin-1-yl)cyclohexyl]-[1,3]thiazolo[5,4-d]pyrimidin-7-amine, intermediate 11.3 as a light yellow solid.

Intermediate 11.2:
$^1$H-NMR (400 MHz, $CDCl_3$) δ 5.96 (d, 1H), 4.21-4.05 (m, 1H), 3.07 (q, 2H), 2.75 (br s, 4H), 2.56 (brs, 1H), 2.28 (d, 2H), 2.20-1.88 (m, 6H), 1.60-1.48 (m, 2H), 1.47 (t, 3H), 1.48-1.35 (m, 2H). LCMS (ES, m/z): 416 and 418 (M+H$^+$).

Intermediate 11.3:
$^1$H-NMR (400 MHz, $CDCl_3$) δ 6.24 (brs, 1H), 4.43 (brs, 1H), 3.09 (q, 2H), 2.72 (brs, 4H), 2.43 (brs, 1H), 2.03 (brs, 6H), 1.90-1.60 (m, 8H), 1.48 (t, 3H). LCMS (ES, m/z): 416 and 418 (M+H$^+$).

Synthesis of I-11.

To an isopropanol solution (3 mL) of 5-chloro-2-ethyl-N-[trans-4-(4,4-difluoropiperidin-1-yl)cyclohexyl]-[1,3]thiazolo[5,4-d]pyrimidin-7-amine, intermediate 11.2 (20 mg, 0.05 mmol, 1.00 equiv) and 1-methyl-1H-pyrazol-4-amine hydrochloride (10.7 mg, 0.08 mmol, 1.6 equiv) in a 5 mL microwave vial was added 0.05 mL of hydrochloric acid (4 M in dioxane). Reaction mixture was irradiated in a microwave reactor for 2 h at 140° C. The resulting mixture was concentrated under vacuum and purified by preparative HPLC to afford 8.9 mg of N7-((1r,4r)-4-(4,4-difluoropiperidin-1-yl)cyclohexyl)-2-ethyl-N5-(1-methyl-1H-pyrazol-4-yl)thiazolo[5,4-d]pyrimidine-5,7-diamine, I-11 as a white solid. $^1$H-NMR (300 MHz, $CDCl_3$) δ 7.80 (s, 1H), 7.49 (s, 1H), 6.59 (s, 1H), 5.68 (d, 1H), 4.11-3.90 (m, 1H), 3.89 (s, 3H), 2.96 (q, 2H), 2.74 (brs, 4H), 2.68-2.45 (m, 1H), 2.28 (d, 2H), 2.28-1.92 (m, 6H), 1.50-1.28 (m, 7H). LC-MS (ES, m/z): 477 (M+H$^+$).

Example 12

N7-((1s,4s)-4-(4,4-difluoropiperidin-1-yl)cyclohexyl)-2-ethyl-N5-(1-methyl-4H-pyrazol-4-yl)thiazolo[5,4-d]pyrimidine-5,7-diamine, I-12

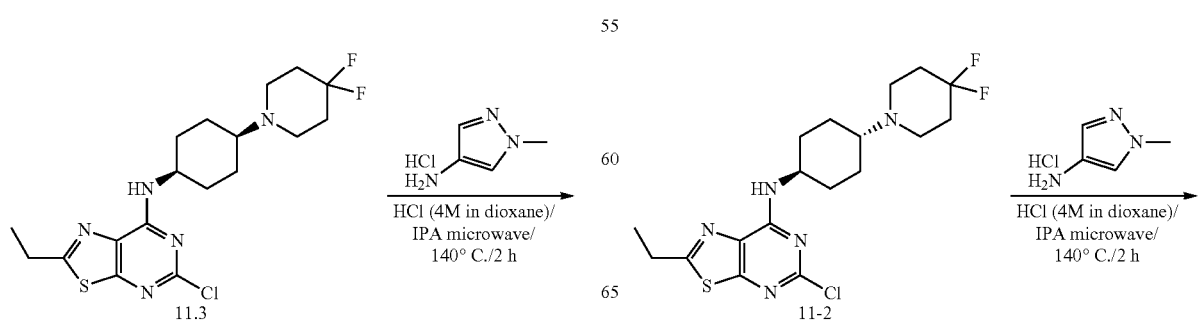

-continued

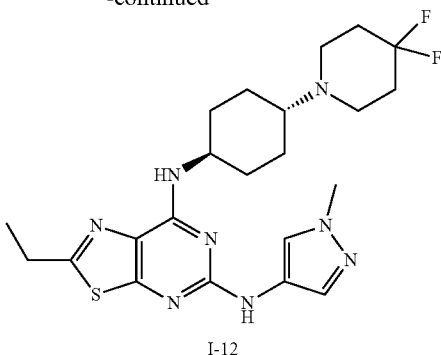

I-12

Into a 10 mL microwave vial, was placed a solution of cis-5-chloro-2-ethyl-N-[(1s,4s)-4-(4,4-difluoropiperidin-1-yl)cyclohexyl]-[1,3]thiazolo[5,4-d]pyrimidin-7-amine (80 mg, 0.19 mmol, 1.00 equiv) in i-propanol (4 mL), followed by hydrogen chloride (4 M in dioxane) (0.1 mL) and 1-methyl-1H-pyrazol-4-amine (29 mg, 0.30 mmol, 1.50 equiv). Reaction mixture was irradiated in a microwave reactor for 2 h at 140° C. Resulting solids were collected by filtration and purified by flash column chromatography to 37.2 mg (41%) of N7-((1 s,4s)-4-(4,4-difluoropiperidin-1-yl)cyclo-hexyl)-2-ethyl-N5-(1-methyl-1H-pyrazol-4-yl)thiazolo[5,4-d]pyrimidine-5,7-diamine, I-12 as a light yellow solid. $^1$H-NMR (300 MHz, CDCl$_3$) δ 7.80 (s, 1H), 7.48 (s, 1H), 6.63 (s, 1H), 5.95 (d, 1H), 4.30 (brs, 1H), 3.88 (s, 3H), 3.00 (q, 2H), 2.70 (brs, 4H), 2.42 (brs, 1H), 2.15-1.92 (m, 6H), 1.85-1.58 (m, 6H), 1.40 (t, 3H). LCMS (ES, m/z): 477 (M+H$^+$).

Example 13

2-ethyl-5-N-[1-(oxan-4-yl)-1H-pyrazol-4-yl]-7-N-[trans-4-(4,4-difluoropiperidin-1-yl)cyclohexyl]-[1,3]thiazolo[5,4-d]pyrimidine-5,7-diamine, I-19

Into a 10 mL vial placed a mixture of 11.2 (100 mg, 0.24 mmol, 1.00 equiv) and 1-(oxan-4-yl)-1H-pyrazol-4-amine hydrochloride (86.5 mg, 0.36 mmol, 1.50 equiv) in 5 mL of isopropanol was added 0.05 mL of hydrochloric acid (4 M in dioxane) at room temperature. The final reaction mixture was irradiated with microwave radiation for 2 h at 140° C. The resulting solution was cooled and diluted with sodium dicarbonate (aq.), and extracted with 3×30 mL of ethyl acetate. The combined organic layers were dried over anhydrous sodium sulfate and concentrated under vacuum. The residue was applied onto a silica gel column with dichloromethane/methanol (50/1) to give 49.3 mg (38%) of I-19 as a light yellow solid. LCMS (ES, m/z): 547 [M+H]+; $^1$H-NMR (300 MHz, CDCl$_3$, ppm): δ 7.90 (1H, s), 7.53 (1H, s), 6.65 (1H, s), 5.71 (1H, d), 4.32 (1H, quintet), 4.18-4.08 (2H, m), 4.06-3.92 (1H, m), 3.62-3.45 (2H, m), 3.00 (2H, q), 2.74 (4H, d), 2.65-2.45 (1H, m), 2.29 (2H, d), 2.20-1.89 (10H, m), 1.62-1.25 (7H, m).

Example 14

Synthesis of N7-((1r,4r)-4-(2-oxa-7-azaspiro[3.5]nonan-7-yl)cyclohexyl)-2-ethyl-N5-(1-methyl-1H-pyrazol-4-yl)thiazolo[5,4-d]pyrimidine-5,7-diamine, I-13

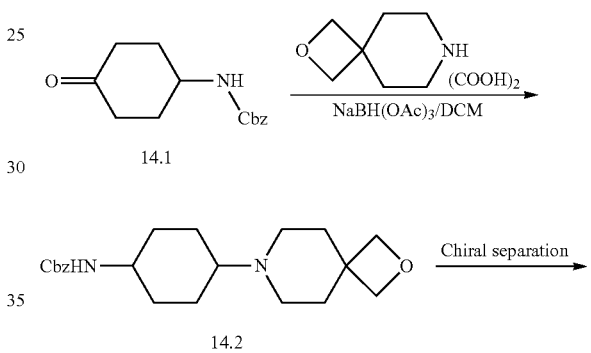

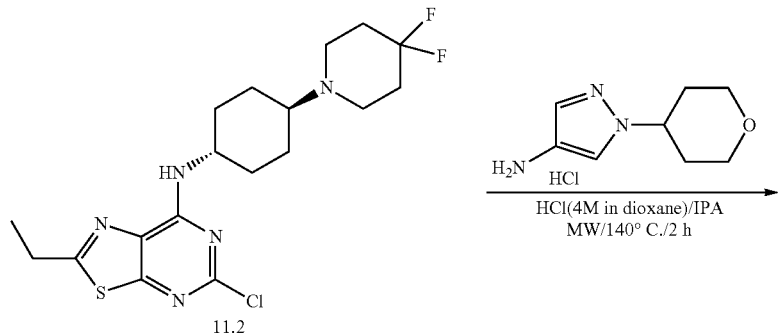

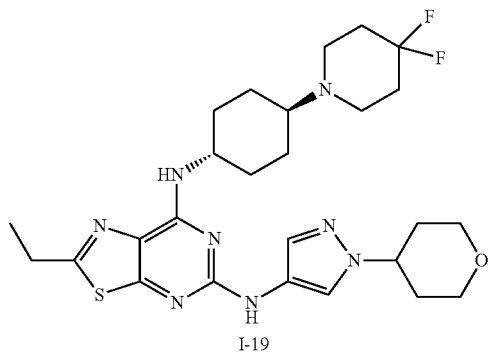

I-19

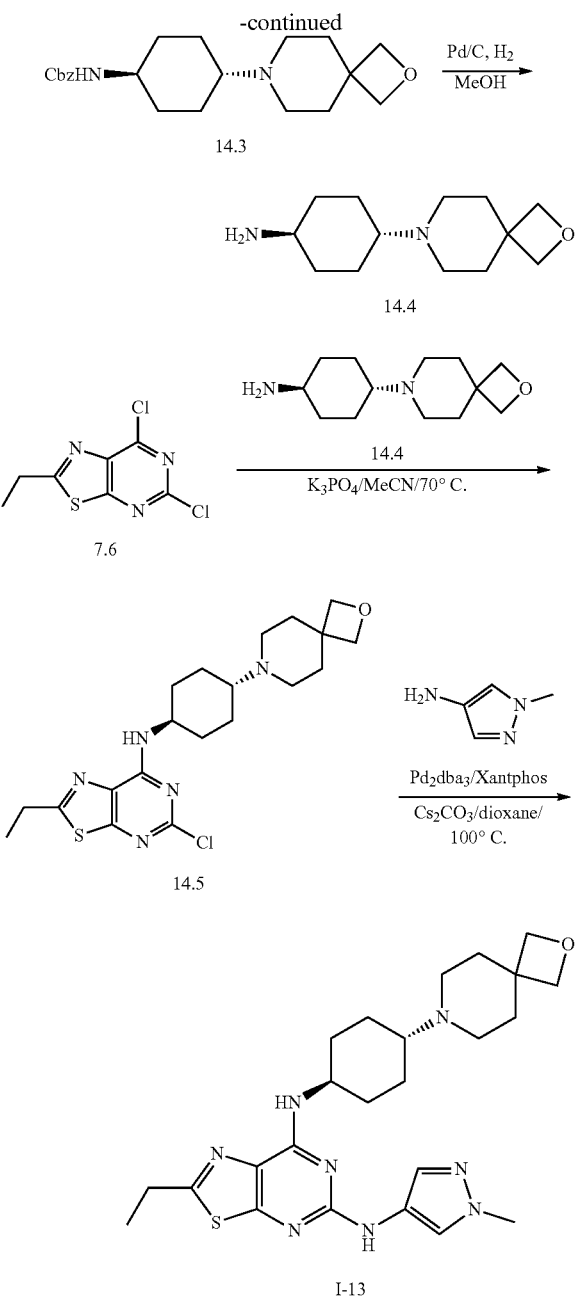

to 40:1) to give 1.40 g of intermediate 14.2 as a white solid. LCMS (ES, m/z): 359 [M+H]+;

Synthesis of Intermediate 14.3.

Racemic intermediate 14.2 (1.35 g) was resolved by preparative chiral chromatography to provide 360 mg of intermediate 14.3 as a white solid. LCMS (ES, m/z): 359 [M+H]+; $^1$H NMR (300 MHz, CDCl$_3$) δ 7.38-7.27 (m, 5H), 5.07 (s, 2H), 4.56 (d, 1H), 4.38 (s, 4H), 3.50-3.30 (m, 1H), 2.41 (brs, 4H), 2.32-2.18 (m, 1H), 2.07 (d, 2H), 1.85 (m, 6H), 1.52-1.32 (m, 2H), 1.18-1.02 (m, 2H).

Synthesis of Intermediate 14.4.

To a solution of intermediate 14.3 (0.5 g) in 10 mL of methanol was added 10% palladium on carbon (100 mg) under nitrogen at room temperature. Then hydrogen (~2 atm) was introduced and the reaction mixture was degassed three times and stirred for 3 hours at ambient temperature. Upon completion of the reaction solids were filtered out and the filtrate was concentrated under vacuum to give 300 mg (crude) of intermediate 14.4 as a light yellow solid. LCMS (ES, m/z): 225 [M+H]+.

Synthesis of Intermediate 14.5.

A 50 mL round-bottom flask was charged with intermediate 7.6 (150 mg, 0.64 mmol, 1.00 equiv) and intermediate 14.4 (150 mg, 0.64 mmol, 1.00 equiv) in 15 mL of CH$_3$CN at room temperature. Then K$_3$PO$_4$ (410 mg, 1.92 mmol, 3.00 equiv) was added and the resulting mixture was stirred overnight under nitrogen. The solids were filtered and washed three times with Ethyl acetate. organic layers were combined and solvents were removed under reduced pressure. The crude was purified by chromatography on silica gel with CH$_2$Cl$_2$/MeOH (60:1 to 30:1) to furnish 225 mg (83%) of intermediate 14.5 as a light yellow solid. LCMS (ES, m/z): 422 and 424 [M+H]+.

Synthesis of I-13.

To a solution of intermediate 14.5 (100 mg, 0.24 mmol, 1.00 equiv) and 1-methyl-1H-pyrazol-4-amine (28 mg, 0.29 mmol, 1.20 equiv) in dioxane (5 mL) were added Cs$_2$CO$_3$ (231 mg, 0.71 mmol, 3.00 equiv), Pd$_2$(dba)$_3$ (12 mg, 0.05 equiv) and Xantphos (14 mg, 0.02 mmol, 0.10 equiv) at room temperature under nitrogen. The resulting mixture was stirred for 5 h at 100° C. in an oil bath. After completion the reaction was quenched water and extracted with 3×30 mL of ethyl acetate. Organic layers were combined and dried over sodium sulfate and concentrated in vacuo. The crude product (150 mg) was purified using preparative HPLC to furnish 33.1 mg (29%) of compound I-13 as a white solid. LCMS (ES, m/z): 483 [M+H]+; $^1$H NMR (300 MHz, CD$_3$OD) δ 7.85 (s, 1H), 7.58 (s, 1H), 4.44 (s, 4H), 4.04-4.01 (m, 1H), 3.88 (s, 1H), 3.05-2.97 (q, 2H), 2.57 (m, 4H), 2.47-2.43 (m, 1H), 2.26-2.22 (m, 2H), 2.04-2.01 (m, 2H), 1.94-1.92 (m, 4H), 1.56-1.37 (m, 7H).

Synthesis of Intermediate 14.2.

A solution of 2-oxa-7-azaspiro[3.5]nonane; oxalic acid (4.10 g, 18.87 mmol, 1.0 equiv) and compound 14.1 (5.6 g, 22.64 mmol, 1.2 equiv) in 100 mL of dry methylene chloride was added NaBH(OAc)$_3$ (8.0 g, 37.74 mmol, 2.0 equiv) and the resulting mixture was stirred overnight at room temperature. Additional compound 14.1 (2.8 g, 11.32 mmol, 0.6 equiv) and NaBH(OAc)$_3$ (4.0 g, 18.87 mmol, 1.0 equiv) was added and stirred for 24 h. Then the reaction was quenched with saturated NaHCO$_3$ solution and extracted with CH$_2$Cl$_2$. The organic phase was separated and dried over sodium sulfate and concentrated in vacuo. The residue was purified by chromatography on silica gel with CH$_2$Cl$_2$/MeOH (100:1

Example 15

Synthesis of N7-((1r,4r)-4-(2-oxa-7-azaspiro[3.5]nonan-7-yl)cyclohexyl)-2-ethyl-N5-(1-(tetrahydro-2H-pyran-4-yl)-1H-pyrazol-4-yl)thiazolo[5,4-d]pyrimidine-5,7-diamine, I-14

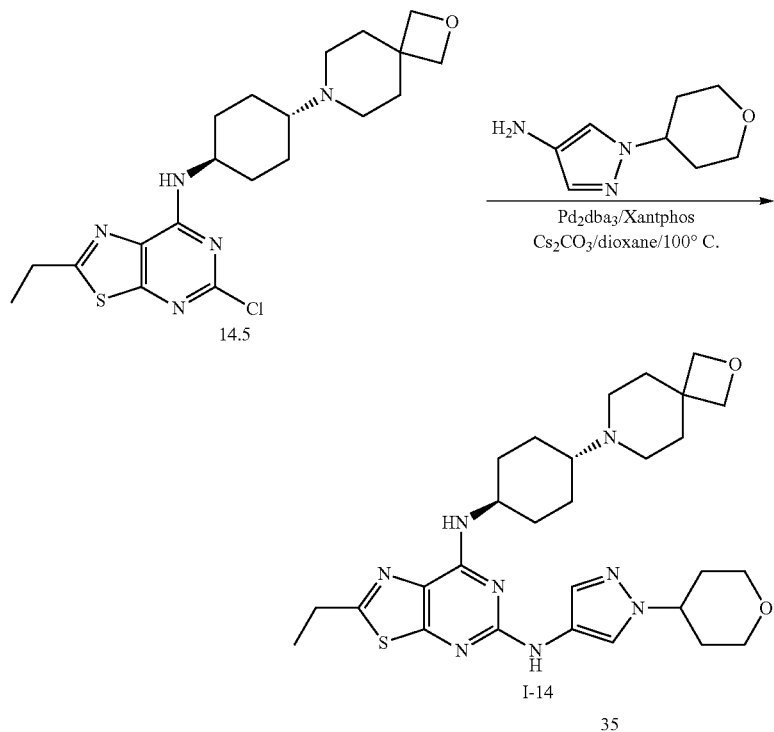

A 50 mL round-bottom under nitrogen was charged with a solution of intermediate 7.6 (100 mg, 0.24 mmol, 1.00 equiv) in 1,4-dioxane (15 mL), 1-(oxan-4-yl)-1H-pyrazol-4-amine (66 mg, 0.39 mmol, 2.00 equiv), Cs$_2$CO$_3$ (154 mg, 0.47 mmol, 2.00 equiv), xantphos (14 mg, 0.02 mmol, 0.10 equiv) and Pd$_2$(dba)$_3$ (14 mg, 0.02 mmol, 0.05 equiv). Reaction was stirred for 3 h at 90° C. in an oil bath. Upon completion reaction was diluted with 30 mL of water and extracted with 3×30 mL of ethyl acetate. Organic layers were combined and dried over anhydrous sodium sulfate. Solvents were removed under vacuum and crude was purified using flash column chromatography to furnish 43.9 mg (34%) of compound I-14 as a white solid. LCMS (ES, m/z): 553.4 [M+H]$^+$; $^1$H-NMR (DMSO, 300 MHz): δ 9.051 (1H, s), 7.920 (1H, s), 7.432 (2H, s), 4.362-4.259 (5H, m), 3.952-3.945 (3H, d). 3.485-3.399 (2H, m), 3.007-2.932 (2H, m), 2.399-2.272 (5H, m), 1.960-1.863 (6H, m), 1.815-1.742 (6H, m), 1.548-1.463 (4H, m), 1.463-1.277 (3H, m).

Example 16

Synthesis of 2-(((1r,4r)-4-((2-ethyl-5-((1-methyl-1H-pyrazol-4-yl)amino)-thiazolo[5,4-d]pyrimidin-7-yl)amino)cyclohexyl)(methyl)amino)-1-(pyrrolidin-1-yl)ethan-1-one I-15

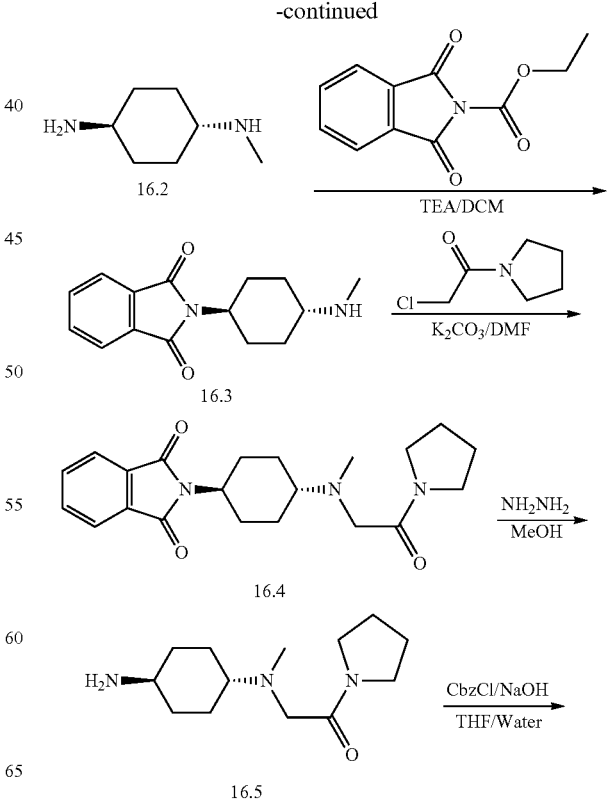

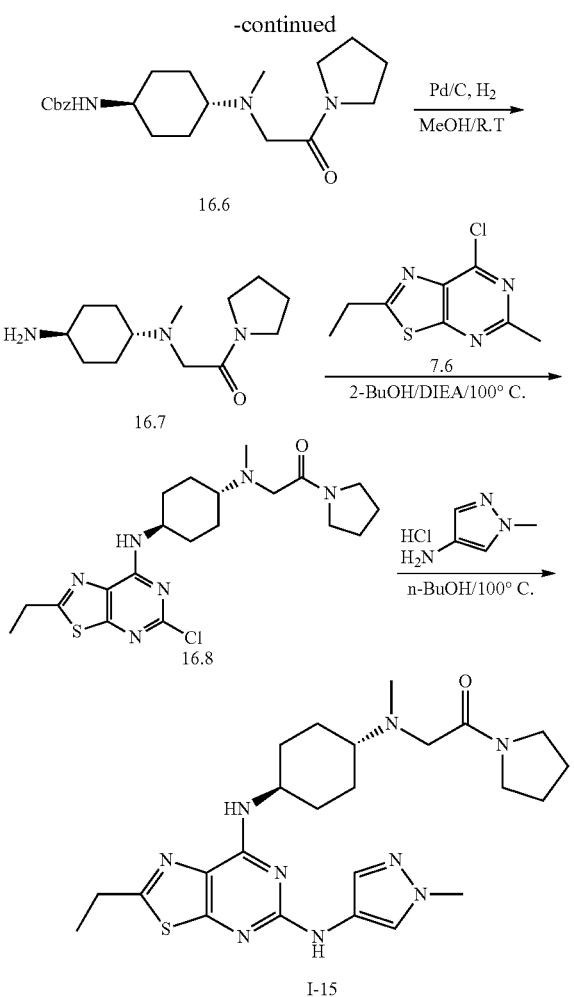

Synthesis of Intermediate 16.2.

To a solution of tert-butyl N-[trans-4-aminocyclohexyl]-carbamate (6.43 g, 30.00 mmol, 1.00 equiv) in 80 mL of distilled THF was added LiAlH$_4$ (5.7 g, 168.03 mmol, 5.00 equiv) portionwise at 0° C. under nitrogen. Reaction was stirred for 4 h at 80° C. in an oil bath. The reaction was then quenched with Na$_2$SO$_4$.10H$_2$O and the solids were filtered out and washed with 100 mL of THF. The filtrate was concentrated under vacuum to give 3.5 g (crude) of intermediate 16.2 as a white solid.

Synthesis of Intermediate 16.3.

A solution of intermediate 16.2 (2.41 g, 18.80 mmol, 1.00 equiv) in dichloromethane (20 mL) was added ethyl 1,3-dioxo-2,3-dihydro-1H-isoindole-2-carboxylate (3.74 g, 17.06 mmol, 2.00 equiv) and triethylamine (3.79 g, 37.45 mmol, 0.91 equiv). The reaction was stirred for 4 h at ambient temperature. The reaction was then quenched with saturated aqueous NH$_4$Cl, extracted with 3×60 mL of dichloromethane. The combined organic layers were washed with brine, dried over sodium sulfate and concentrated under vacuum to give 5.6 g (crude) of intermediate 16.3 as a off-white solid.

Synthesis of Intermediate 16.4.

To a solution of intermediate 16.3 (4.6 g, 17.81 mmol, 1.00 equiv) in distilled DMF (20 mL) was added 2-chloro-1-(pyrrolidin-1-yl)ethan-1-one (3.14 g, 21.27 mmol, 1.20 equiv) and K$_2$CO$_3$ (4.9 g, 35.20 mmol, 2.00 equiv). The reaction was stirred overnight at 25° C., quenched with water and extracted with 3×60 mL of ethyl acetate. The organic layers were combined, dried over sodium sulfate and concentrated under vacuum. The crude product was purified via flash column chromatography to give 4.5 g (68%) of intermediate 16.4 as a yellow solid.

Synthesis of Intermediate 16.5.

Into a 50 mL round-bottom flask containing a solution of intermediate 16.4 (4.5 g, 12.18 mmol, 1.00 equiv) in MeOH (15 mL) was added hydrazine hydrate (3.1 g, 61.26 mmol, 5.00 equiv). The reaction was stirred for 1.5 h at 65° C. in an oil bath. The solids were filtered out and the filtrate was concentrated under vacuum to afford 3.1 g (crude) of the desired intermediate 16.5 as a yellow oil.

Synthesis of Intermediate 16.6.

To a solution of intermediate 16.5 (4.0 g, 16.71 mmol, 1.0 equiv) in THF/H$_2$O (20/20 mL) was added benzyl chloroformate (5.69 g, 33.35 mmol, 2.0 equiv) dropwise with stirring at 0° C., followed by addition of sodium hydroxide (1.32 g, 33.0 mmol, 2.00 equiv). The reaction was stirred for 4 h. Upon completion solvents were removed under vacuum. The residue was diluted with 150 mL of EtOAc, washed with brine, and the organic layer was dried over sodium sulfate and concentrated under reduced pressure. The crude was purified using flash column chromatography to give 4.0 g (64%) of intermediate 16.6 as colorless oil.

Synthesis of Intermediate 16.7.

To a solution of intermediate 16.6 (4.0 g, 10.71 mmol, 1.00 equiv) in methanol (30 mL) was added 10% palladium on activated carbon (0.4 g, 0.10 equiv) under reduced pressure. Then H$_2$ (g) was introduced and the resulting mixture was stirred for 4 h at 25° C. The solids were filtered out and the filtrate was concentrated under vacuum to give 2.6 g (crude) of intermediate 16.7 as yellow oil.

Synthesis of Intermediate 16.8.

A 100 mL round-bottom flask was charged with a solution of intermediate 16.7 (99 mg, 0.41 mmol, 1.00 equiv) in 2-BuOH (15 mL), intermediate 7.6 (108 mg, 0.46 mmol, 1.10 equiv) and DIEA (106.8 mg, 0.83 mmol, 2.00 equiv). The resulting solution was stirred for 4 h at 100° C. in an oil bath, then concentrated under vacuum. The crude product was purified using flash column chromatography to give 170 mg (78%) of intermediate 16.8 as a yellow solid. LCMS (ES, m/z): 437 and 439 [M+H]$^+$.

Synthesis of Intermediate I-15.

A solution of intermediate 16.8 (70 mg, 0.16 mmol, 1.00 equiv) and 1-methyl-1H-pyrazol-4-amine dihydrochloride (43 mg, 0.32 mmol, 2.0 equiv) in n-BuOH (10 mL) was stirred overnight at 100° C. in an oil bath. The resulting mixture was concentrated under vacuum. The crude product was purified by flash column chromatography to give 47.5 mg (60%) of I-15 as a yellow solid. LCMS (ES, m/z): 498 [M+H]$^+$; $^1$H NMR (300 MHz, DMSO) δ 9.02 (1H, br s), 7.84 (1H, s), 7.43 (1H, s), 4.08-3.95 (1H, m), 3.79 (3H, s), 3.49 (2H, t), 3.28 (2H, t), 3.18 (2H, s), 2.96 (2H, q), 2.50-2.40 (1H, m), 2.23 (3H, s), 2.05-1.92 (2H, m), 1.89-1.68 (6H, m), 1.58-1.25 (4H, m), 1.31 (3H, t).

Example 17

Synthesis of 1-((1r,4r)-4-((2-ethyl-5-β1-(tetrahydro-2H-pyran-4-yl)-1H-pyrazol-4-yl)amino)thiazolo[5,4-d]pyrimidin-7-yl)amino)cyclohexyl)piperidin-4-ol I-16

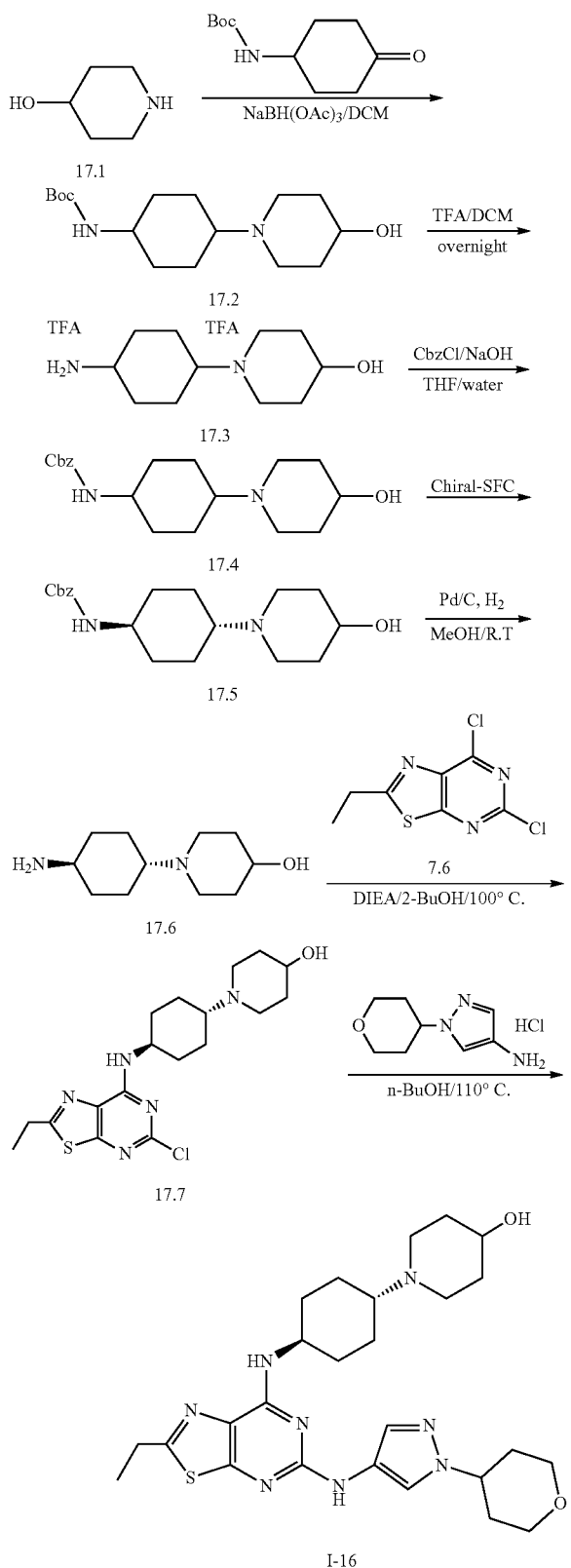

Synthesis of Intermediate 17.2.

Into a 500-mL round-bottom flask, were placed tert-butyl 4-oxopiperidine-1-carboxylate (11.8 g, 59.22 mmol, 1.20 equiv), dichloromethane (100 mL), compound 17.1 (5 g, 49.43 mmol, 1.00 equiv) and acetic acid (5 drops). The resulting solution was stirred overnight at room temperature. Afterwards NaBH(CH3COO)$_3$ (30 g, 3.00 equiv) was added. Reaction was stirred for an additional 1 hour at room temperature. Upon completion reaction was diluted with saturated sodium bicarbonate solution. The resulting solution was extracted with 3×50 mL of chloroform:isopropanol (4:1), organic layers were combined, dried over anhydrous sodium sulfate and concentrated under vacuum. The crude product was purified using flash column chromatography to afford 3.5 g (24%) of intermediate 17.2 as an off-white solid.

Synthesis of Intermediate 17.3.

Into a 100 mL round-bottom flask, was placed intermediate 17.2 (3 g, 10.05 mmol, 1.00 equiv), dichloromethane (20 mL) and trifluoroacetic acid (11.4 g, 100.85 mmol, 10.0 equiv). Reaction was stirred for 3 h at room temperature. The resulting mixture was concentrated under vacuum to give 6.5 g (crude) of intermediate 17.3 as a white syrup.

Synthesis of Intermediate 17.4.

To a solution of Intermediate 17.3 (5.8 g, crude) in THF/H$_2$O (30 mL/30 mL) was added 2 M sodium hydroxide to bring pH ~10 at 0° C. To the solution was added benzyl chloroformate (2.29 g) dropwise via syringe. The reaction was stirred for 1.5 h at room temperature and extracted with 4×80 mL of chloroform:isopropanol (4:1). Combined organic layers were dried over anhydrous sodium sulfate and concentrated under vacuum. Resulting crude product was purified using flash column chromatography to provide 2.0 g of intermediate 17.4 as a white solid.

Synthesis of Intermediate 17.5.

Intermediate 17.4 (2.0 g) was resolved using preparative chiral HPLC to give (450) mg of intermediate 17.5 as off-white solid. LCMS (ES, m/z): 333 [M+H]$^+$; $^1$H NMR (400 MHz, CDCl$_3$) δ 7.45-7.30 (m, 5H), 5.10 (s, 2H), 4.59 (d, 1H), 3.69 (brs, 1H), 3.45 (brs, 1H), 2.82 (brs, 2H), 2.34 (brs, 3H), 2.10 (d, 2H), 1.92 (brs, 4H), 1.65-1.50 (m, 2H), 1.45-1.30 (m, 2H), 1.22-1.10 (m, 2H).

Synthesis of Intermediate 17.6.

To a solution of intermediate 17.5 (200 mg, 0.60 mmol, 1.00 equiv) in 10 mL of methanol was added 10% Palladium on carbon (60 mg) under nitrogen. The mixture was degassed with H$_2$ (g) three times and stirred for 2 h at room temperature. The solids were filtered out and the cake was washed with methanol. The filtrate was concentrated under vacuum to give 123 mg (crude) of intermediate 17.6 as a white solid.

Synthesis of Intermediate 17.7.

To intermediate 17.6 (123 mg, 0.62 mmol, 1.03 equiv) and intermediate 7.6 (140 mg, 0.60 mmol, 1.00 equiv) in 2-butanol (5 mL) was added DIEA (155 mg, 1.20 mmol, 2.00 equiv) and the resulting solution was stirred for 4 h at 100° C. under nitrogen. The resulting mixture was concentrated under vacuum and resulting crude was purified using flash column chromatography to give 160 mg of intermediate 17.7 as a white solid. LCMS (ES, m/z): 396 and 398 [M+H]$^+$.

Synthesis of I-16.

To solution of intermediate 17.7 (80 mg, 0.20 mmol, 1.00 equiv) in butanol (5 mL) was added 1-(oxan-4-yl)-1H-pyrazol-4-amine hydrochloride (976.97 mg, 4.80 mmol, 2.00 equiv). The reaction was stirred overnight at 110° C. in an oil bath. Resulting mixture was concentrated under vacuum and the residue was purified using flash column chromatography and preparative HPLC to furnish 48.1 mg (45%) of I-16 as an off-white solid. LCMS (ES, m/z): 527 [M+H$^+$]; $^1$H NMR (300 MHz, CD$_3$OD) δ 7.98 (s, 1H), 7.66

(s, 1H), 4.48-4.35 (m, 1H), 4.37-4.34 (m, 3H), 3.96-3.87 (m, 1H), 3.64-3.56 (m, 2H), 3.07-2.80 (m, 5H), 2.36-2.32 (m, 2H), 2.16-2.06 (m, 6H), 1.89-1.41 (m, 6H), 1.39-1.31 (m, 3H).

Example 18

Synthesis of 1-((1r,4r)-4-((2-ethyl-5-((1-methyl-1H-pyrazol-4-yl)amino)-thiazolo[5,4-d]pyrimidin-7-yl)amino)cyclohexyl)piperidin-4-ol I-17

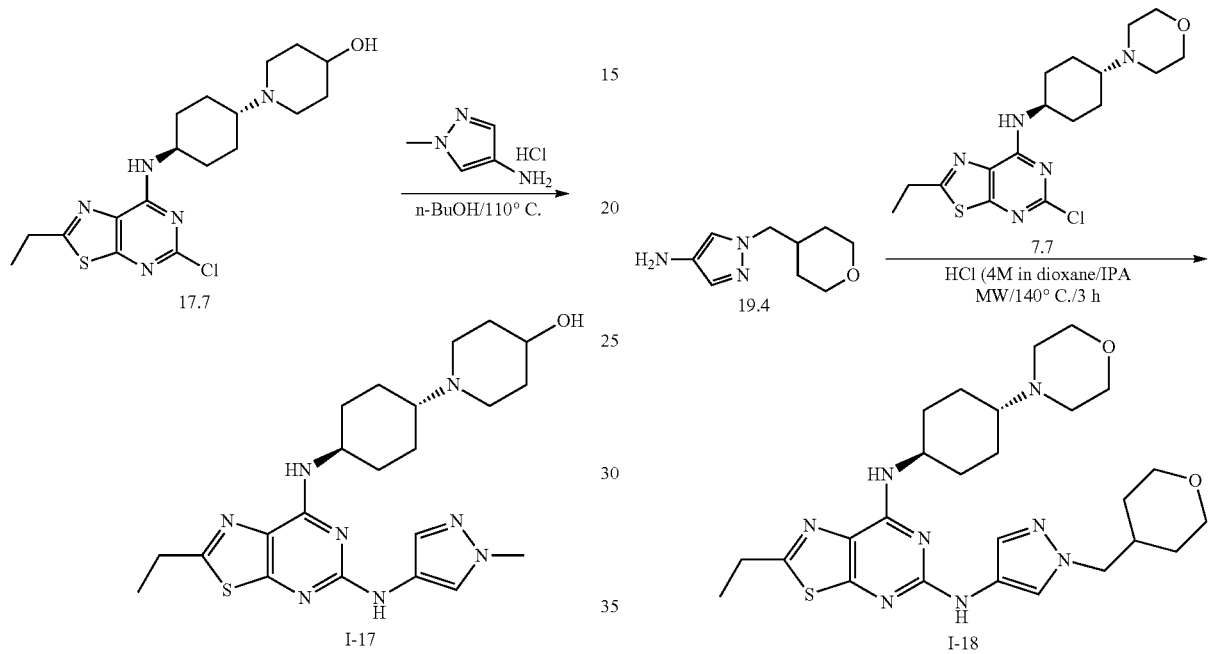

Into a 50 mL round-bottom flask, was placed a solution of intermediate 17.7 (60 mg, 0.15 mmol, 1.00 equiv) in butanol (5 mL), and 1-methyl-1H-pyrrol-3-amine (29.4 mg, 0.31 mmol, 2.00 equiv). Reaction was stirred overnight at 110° C. in an oil bath. The resulting mixture was concentrated under vacuum. The crude product was purified using flash column chromatography to give 29.9 mg (43%) of I-17 as a light yellow solid. LCMS (ES, m/z): 457 [M+H]$^+$; $^1$H NMR (300 MHz, CD$_3$OD) δ 7.86 (s, 1H), 7.58 (s, 1H), 4.08 (br s, 1H), 3.88 (s, 3H), 3.66 (br s, 1H), 3.08-2.96 (m, 4H), 2.51-2.49 (m, 3H), 2.28-2.24 (m, 2H), 2.09-2.06 (m, 2H), 1.94-1.91 (m, 2H), 1.66-1.63 (m, 3H), 1.60-1.56 (m, 2H), 1.51-1.47 (m, 4H).

Example 19

Synthesis of 2-ethyl-N7-((1r,4r)-4-morpholinocyclohexyl)-N5-(1-((tetrahydro-2H-pyran-4-yl)methyl)-1H-pyrazol-4-yl)thiazolo[5,4-d]pyrimidine-5,7-diamine I-18

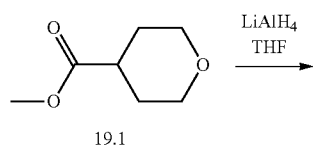

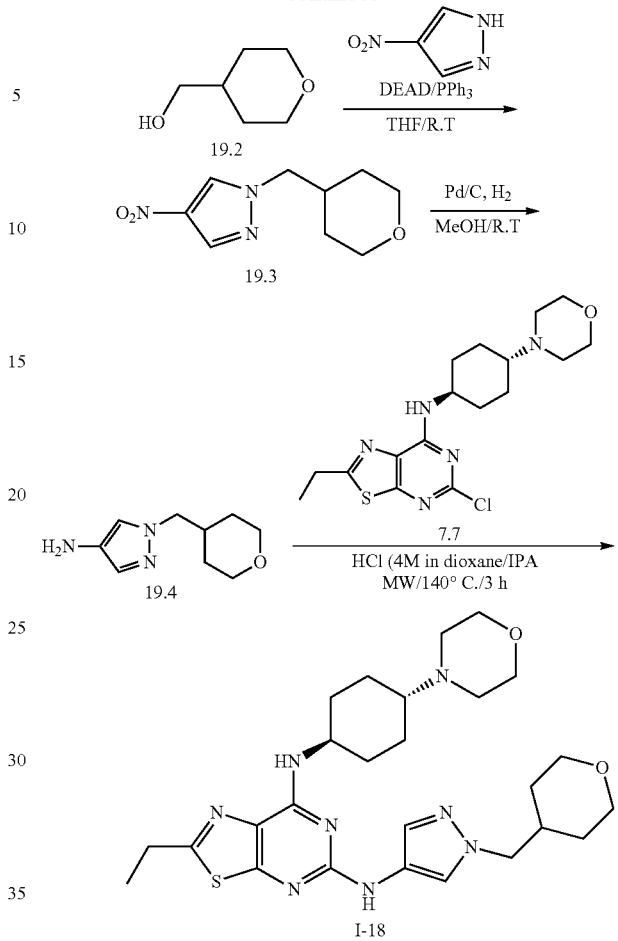

Synthesis of Intermediate 19.2.

Into a 100 mL round-bottom flask, were placed a solution of compound 19.1 (200 mg, 1.39 mmol, 1.00 equiv) in THF (50 mL) and LiAlH$_4$ (63 mg, 1.66 mmol, 1.20 equiv). Reaction was stirred for 3 h at room temperature and then quenched using NaSO$_4$.10H$_2$O. The solids were filtered out. Resulting solution was concentrated under vacuum furnish 150 mg (crude) of oxan-4-ylmethanol as a yellow solid.

Synthesis of Intermediate 19.3.

Into a 100 mL round-bottom flask, was placed a solution of intermediate 19.2 (2 g, 17.22 mmol, 1.00 equiv) in THF (50 mL), 4-nitro-1H-pyrazole (1.95 g, 17.25 mmol, 1.00 equiv), triphenylphosphane (8.9 g, 33.93 mmol, 2.00 equiv) and DEAD (4.4 g, 25.27 mmol, 1.50 equiv). The resulting solution was stirred overnight at room temperature. Upon completion reaction was washed with 100 mL of water. The resulting solution was extracted with 3×30 mL of ethyl acetate and the organic layers were combined and washed with 1×20 mL of sodium chloride (aq.). The mixture was dried over anhydrous sodium sulfate and concentrated under vacuum. The crude was purified using dlash column chromatography to provide 2.1 g (58%) of intermediate 19.3 as a light yellow solid.

Synthesis of Intermediate 19.4.

Into a 50 mL round-bottom flask, were placed a solution of intermediate 19.3 (500 mg, 2.37 mmol, 1.00 equiv) in methanol (15 mL), Palladium on carbon (10 mg). The flask was flushed with H$_2$ gas. Reaction was stirred for 3 h at room temperature. The solids were filtered out solvents removed under vacuum. Crude was applied purified using flash column chromatography to furnish 450 mg (95) of intermediate 19.4 as a yellow solid.

Synthesis of I-18.

Into a 10 mL microwave vial, were placed a solution of intermediate 7.7 (100 mg, 0.26 mmol, 1.00 equiv) in isopropanol (5 mL), hydrogen chloride (4N in dioxane) (0.25 mL), and intermediate 19.4 (71 mg, 0.39 mmol, 1.50 equiv). The final reaction mixture was irradiated in a microwave reactor for 2 h at 140° C. Mixture was concentrated under vacuum and resulting crude product was purified using preparative HPLC to furnish 25.5 mg (18%) of I-18 as a white solid. LCMS (ES, m/z): 527.3 [M+H]−; $^1$H NMR: (300 MHz, MeOD): δ 7.90 (s, 1H), 7.63 (s, 1H), 4.07-3.89 (m, 5H), 3.78 (s, 4H), 3.40 (t, 2H), 3.03 (dd, 2H), 2.80 (s, 4H), 2.55 (s, 1H), 2.30-2.04 (m, 5H), 1.59-1.39 (m, 11H).

Example 20

Synthesis of N7((1r,4r)-4-(6-azaspiro[2.5]octan-6-yl)cyclohexyl)-2-ethyl-N5-(1-methyl-1H-pyrazol-4-yl)thiazolo[5,4-d]pyrimidine-5,7-diamine I-21

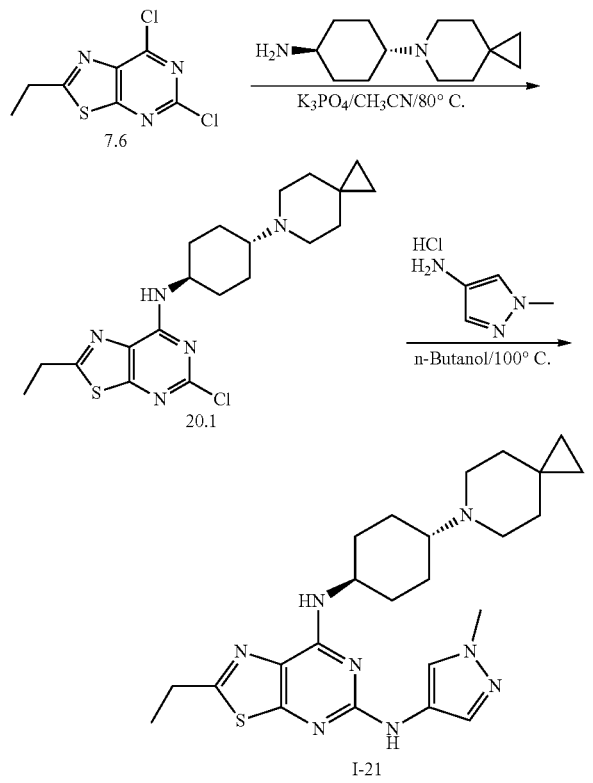

Synthesis of Intermediate 20.1.

A mixture of trans-4-[6-azaspiro[2.5]octan-6-yl]cyclohexan-1-amine (150 mg, 0.72 mmol, 1.00 equiv), intermediate 7.6 (203 mg, 0.87 mmol, 1.20 equiv) and K$_3$PO$_4$ (459 mg, 2.16 mmol, 3.00 equiv) in MeCN (10 mL) was stirred overnight at 80° C. in an oil bath under nitrogen. The resulting mixture was concentrated under vacuum and crude was purified using flash column chromatography to give 260 mg (89%) of intermediate 20.1 as a yellow solid. LCMS (ES, m/z): 406 and 408 [M+H]$^+$.

Synthesis of Compound I-21.

To a 25 mL round-bottom flask containing a solution of intermediate 20.1 (110 mg, 0.27 mmol, 1.00 equiv) in n-Butanol (6 mL) was added 1-methyl-1H-pyrazol-4-amine hydrochloride (103.2 mg, 0.77 mmol, 2.85 equiv) at room temperature under nitrogen. The reaction was stirred overnight at 110° C. in an oil bath. After cooling, the resulting mixture was concentrated under vacuum and resulting crude was purified using flash column chromatography to furnish 120 mg (95%) of compound I-21 as a yellow solid. LCMS (ES, m/z): 467 [M+H]$^+$; $^1$H NMR (400 MHz, CDCl$_3$): δ 9.02 (1H, s), 7.81 (1H, s), 7.46 (1H, s), 7.43 (1H, brs), 4.05-3.93 (1H, m), 3.79 (3H, s), 2.98 (2H, q), 2.53-2.50 (4H, m), 2.39-2.28 (1H, m), 2.05-1.94 (2H, m), 1.85 (2H, d), 1.58-1.30 (8H, m), 1.31 (3H, t), 0.23 (4H, s).

Example 21

Synthesis of 2-ethyl-N5-(1-ethyl-1H-pyrazol-4-yl)-N7-((1r,4r)-4-morpholino-cyclohexyl)thiazolo[5,4-d]pyrimidine-5,7-diamine I-22

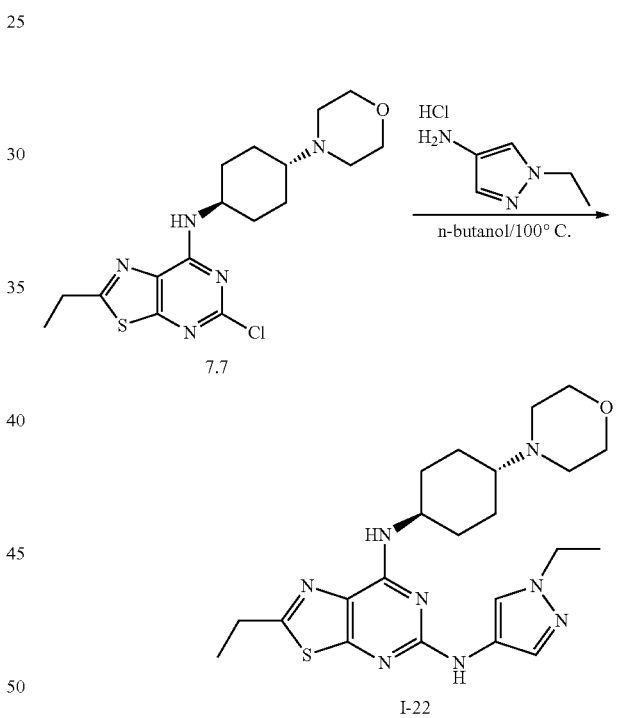

Into a 50 mL round-bottom flask, was placed a solution of intermediate 7.7 (150 mg, 0.39 mmol, 1.00 equiv) in n-butanol (6 mL), and 1-ethyl-1H-pyrazol-4-amine hydrochloride (87 mg, 0.78 mmol, 1.99 equiv). Reaction was stirred overnight at 110° C. in an oil bath. Upon completion of the reaction resulting mixture was concentrated under vacuum, and crude purified using flash column chromatography to furnish 180 mg (98%) of compound I-22 as a yellow solid. LCMS (ES, m/z): 457 [M+H]$^+$; $^1$H NMR (400 MHz, DMSO) δ 9.03 (1H, s), 7.85 (1H, s), 7.46 (1H, s), 7.45 (br s, 1H), 4.07 (2H, q), 4.05-3.95 (1H, m), 3.58 (4H, br s), 2.97 (2H, q), 2.50 (4H, s), 2.25-2.16 (1H, m), 2.02-1.85 (4H, m), 1.52-1.42 (2H, m), 1.40-1.29 (8H, m).

Example 22

Synthesis of N7-((1r,4r)-4-(6-azaspiro[2.5]octan-6-yl)cyclohexyl)-2-ethyl-N5-(1-(tetrahydro-2H-pyran-4-yl)-1H-pyrazol-4-yl)thiazolo[5,4-d]pyrimidine-5,7-diamine, I-23

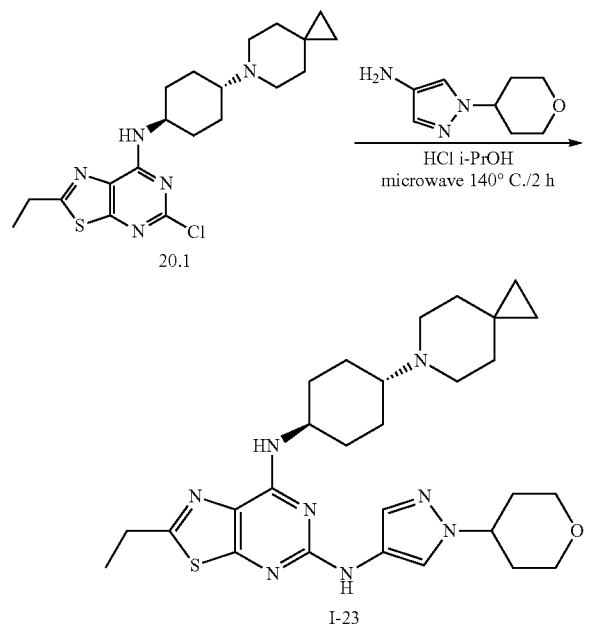

Into a 5 mL microwave vial, was placed a solution of intermediate 20.1 (70 mg, 0.17 mmol, 1.00 equiv) in isopropanol (1.5 mL), 1-(oxan-4-yl)-1H-pyrazol-4-amine (35 mg, 0.21 mmol, 1.21 equiv) and hydrogen chloride (4 M in dioxane, 0.05 mL). The final reaction mixture was irradiated with microwave radiation for 2 h at 140° C. Upon completion reaction mixture was cooled and the solids were collected by filtration. The resulting solution was diluted with 5 mL of H$_2$O and the pH value of the solution was adjusted to 8 with sodium hydroxide (1M). The solids were collected by filtration and dried in an oven under reduced pressure. To furnish 45 mg (49%) of compound I-23 as a yellow solid. LCMS: (ES, m/z): 537 [M+H]$^+$; $^1$H NMR (400 MHz, DMSO, ppm): δ 9.071 (1H, s), 7.938 (1H, s), 7.437 (2H, s), 4.354-4.303 (1H, m), 3.968-3.939 (3H, d), 3.460-3.425 (2H, m), 3.006-2.949 (2H, m), 2.545-2.506 (4H, m), 2.368-2.333 (1H, m), 1.969-1.908 (6H, m), 1.866-1.839 (2H, m), 1.525-1.466 (4H, m), 1.382-1.192 (7H, m), 0.210 (4H, s).

Example 23

Synthesis of 2-methyl-N5-(1-methyl-1H-pyrazol-4-yl)-N7-((1r,4r)-4-morpholinocyclohexyl)thiazolo[5,4-d]pyrimidine-5,7-diamine I-24

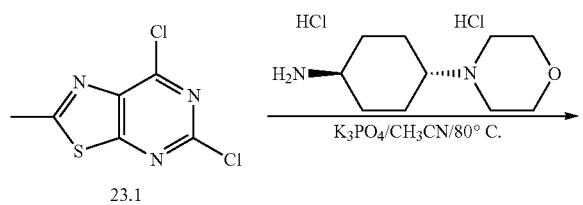

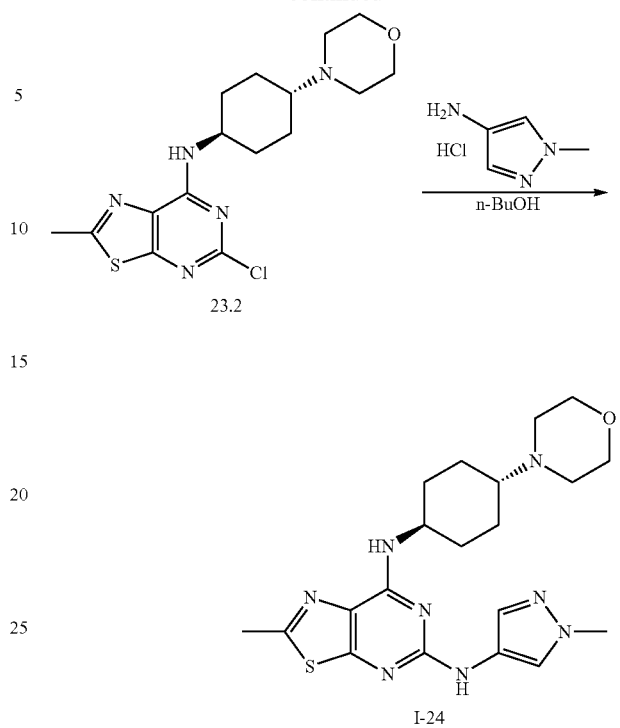

Synthesis of Intermediate 23.2.

Into a 2000-mL 3-necked round-bottom flask, was placed a solution of compound 23.1 (50 g, 227.19 mmol, 1.00 equiv) in MeCN (1500 mL), K$_3$PO$_4$ (145.2 g, 684.03 mmol, 3.01 equiv), and (1r,4r)-4-(morpholin-4-yl)cyclohexan-1-amine (50.4 g, 273.50 mmol, 1.20 equiv). The resulting solution was stirred overnight at 85° C. in an oil bath. The reaction mixture was cooled to room temperature, solids were filtered out and the resulting mixture was concentrated under vacuum. The crude product was re-crystallized to furnish 56 g (67%) of intermediate 23.2 as a yellow solid.

Synthesis of I-24.

Into a 2000-mL 3-necked round-bottom flask, were placed a solution of intermediate 24.3 (56 g, 152.22 mmol, 1.00 equiv) in n-butanol (1000 mL) and 1-methyl-1H-pyrazol-4-amine hydrochloride (40.89 g, 306.11 mmol, 2.01 equiv). The reaction was stirred overnight at 110° C. in an oil bath. Upon completion, the reaction was cooled to room temperature solids were collected by filtration and the resulting solution was diluted with 500 mL of H$_2$O. The pH value of the solution was adjusted to 10 with sodium hydroxide (1 mol/L). The resulting solids were collected by filtration and dried in an oven under reduced pressure to furnish 61.9 g (95%) of compound I-24 as an off-white solid. LCMS: (ES, m/z): 429 [M+H]$^+$; $^1$H NMR: (400 MHz, CD$_3$OD): δ 7.877 (1H, s), 7.568 (1H, s), 4.044 (1H, s), 3.887 (3H, s), 3.751-3.740 (4H, d), 2.692-0.2638 (7H, m), 2.343 (1H, s), 2.264 (2H, s), 2.099 (2H, s), 1.514-1.392 (4H, m).

Example 24

Synthesis of 2-methyl-N7-((1r,4r)-4-morpholinocyclohexyl)-N5-(1-(tetrahydro-2H-pyran-4-yl)-1H-pyrazol-4-yl)thiazolo[5,4-d]pyrimidine-5,7-diamine I-25

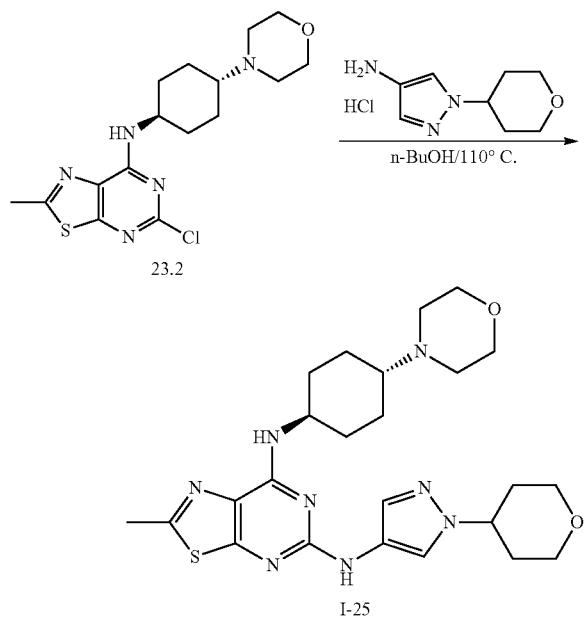

A 250 mL round-bottom flask, was charged with solution of intermediate 23.2 (400 mg, 1.09 mmol, 1.00 equiv) in n-BuOH (100 mL) and 1-(oxan-4-yl)-1H-pyrazol-4-amine (286.4 mg, 1.71 mmol, 2.00 equiv). The reaction was stirred overnight at 100° C. The resulting mixture was concentrated under vacuum and the crude product was purified by preparative HPLC to furnish 252.7 mg (47%) of compound I-25 as a light yellow solid. LCMS (ES, m/z): 499.3[M+H]$^-$; $^1$H NMR (300 MHz, CDCl$_3$): δ 9.02 (s, 1H), 7.91 (s, 1H), 7.46 (s, 2H), 4.38-4.28 (m, 1H), 3.95 (d, 3H), 3.56 (t, 4H), 3.43 (t, 2H), 2.65 (s, 1H), 2.21 (t, 1H), 2.18-1.88 (m, 8H), 1.54-1.23 (m, 7H), 0.92 (t, 1H).

Example 25

Synthesis of 2-ethyl-7-(((1r,4r)-4-morpholinocyclohexyl)oxy)-N-(1-(tetrahydro-2H-pyran-4-yl)-1H-pyrazol-4-yl)thiazolo[5,4-d]pyrimidin-5-amine I-26

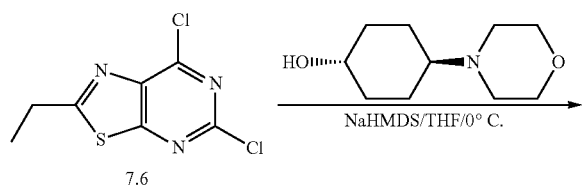

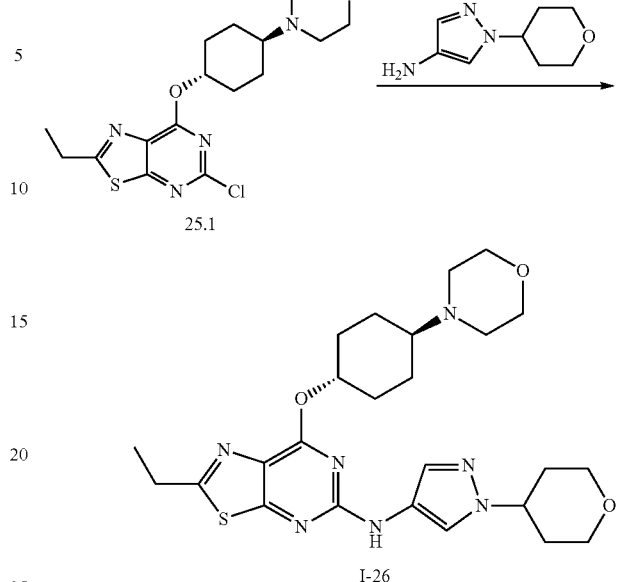

Synthesis of Intermediate 25.1.

Into a 25 mL 3-necked round-bottom flask purged and maintained with an inert atmosphere of nitrogen, was placed a solution of (1r,4r)-4-(morpholin-4-yl)cyclohexan-1-ol (380 mg, 2.05 mmol, 1.20 equiv) in THF (2 mL). This was followed by the addition of NaHMDS (1.28 mL, 1.50 equiv) dropwise with stirring at 0° C. To the reaction was added a solution of intermediate 7.6 (400 mg, 1.71 mmol, 1.00 equiv) in THF (8 mL) dropwise with stirring at 0° C. The reaction was stirred for 10 min at 0° C. then quenched by the addition of NH$_4$Cl (aq.) and extracted with 3×10 mL of ethyl acetate. The organic layers were combined, dried over sodium sulfate and concentrated under vacuum. The crude product was purified using flash column chromatography to furnish 220 mg (34%) of intermediate 25.1 as a light yellow solid.

Synthesis of Compound I-26.

Into a 10 mL round-bottom flask, was placed a solution of intermediate 25.1 (80 mg, 0.21 mmol, 1.00 equiv) in n-BuOH (2 mL), followed by 1-(oxan-4-yl)-1H-pyrazol-4-amine dihydrochloride (69 mg, 0.29 mmol, 2.00 equiv). The reaction was stirred overnight at 110° C. in an oil bath. The resulting solution was diluted with 5 mL of H$_2$O, extracted with 3×5 mL of ethyl acetate. The organic layers were combined, dried over sodium sulfate and concentrated under vacuum. The crude product was purified using flash column chromatography to furnish 20.8 mg (19%) of compound I-26 as a white solid. LCMS (ES, m/z): 514.3 [M+H]$^+$; $^1$H NMR (300 MHz, CDCl$_3$): δ 7.89 (s, 1H), 7.55 (s, 1H), 6.78 (s, 1H), 5.19 (m, 1H), 4.34 (m, 1H), 4.10-4.15 (m, 2H), 3.77 (s, 1H), 3.55 (m, 2H), 3.09 (m, 2H), 2.64 (s, 4H), 2.32 (m, 3H), 2.11 (m, 6H), 1.76 (m, 4H), 1.40 (m, 3H).

Example 26

Synthesis of 2-ethyl-N5-(1-(3-(methylsulfonyl)propyl)-1H-pyrazol-4-yl)-N7-((1r,4r)-4-morpholinocyclohexyl)thiazolo[5,4-d]pyrimidine-5,7-diamine I-27

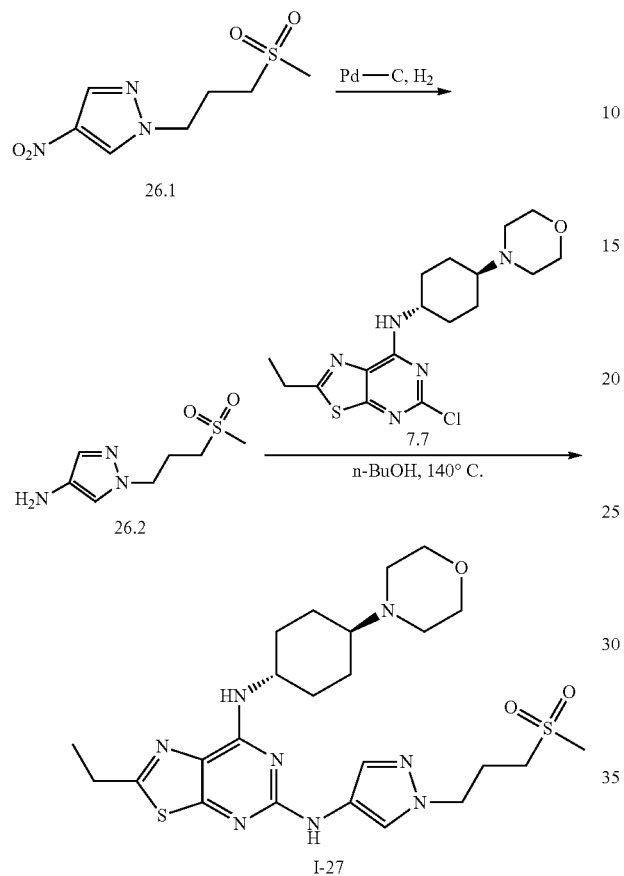

Synthesis of Intermediate 26.2.

Into a 50 mL round-bottom flask, was placed a compound 26.1 (100 mg, 0.43 mmol, 1.00 equiv) in methanol (5 mL), Pd/C (10 mg). Then hydrogen (g) was introduced. The resulting solution was stirred for 3 h at room temperature. The solids were filtered out and resulting mixture was concentrated under vacuum to provide 80 mg (86%) of intermediate 26.2 as a light yellow oil.

Synthesis of Compound I-27.

Into a 20 mL sealed tube, was placed a solution of intermediate 26.2 (138 mg, 0.36 mmol, 1.00 equiv) in n-BuOH (3 mL) and 1-(3-methanesulfonylpropyl)-1H-pyrazol-4-amine (80 mg, 0.39 mmol, 1.09 equiv). The reaction mixture was irradiated in a microwave reactor for 3 h at 140° C. The resulting mixture was concentrated under vacuum. The crude was purified using preparative TLC and HPLC to furnish 21.8 mg (11%) of compound I-27 as a white solid. LCMS (ES, m/z): 499 $[M+H]^+$; $^1$H-NMR: (400 MHz, DMSO): δ 9.07 (s, 1H), 7.87 (s, 1H), 7.54 (s, 1H), 7.42 (s, 2H), 4.25-4.17 (m, 2H), 3.94 (s, 1H), 3.58-3.56 (t, 4H), 3.32-3.29 (m, 2H), 3.09-3.05 (m, 5H), 2.51-2.50 (m, 4H), 2.20-2.16 (m, 3H), 1.98-1.89 (m, 4H), 1.51-1.48 (m, 2H), 1.34-1.32 (t, 5H).

Example 27

Synthesis of 2-(2-(4-((2-ethyl-7-(((1r,4r)-4-morpholinocyclohexyl)amino)thia-zolo[5,4-d]pyrimidin-5-yl)amino)-1H-pyrazol-1-yl)ethoxy)ethan-1-ol I-28

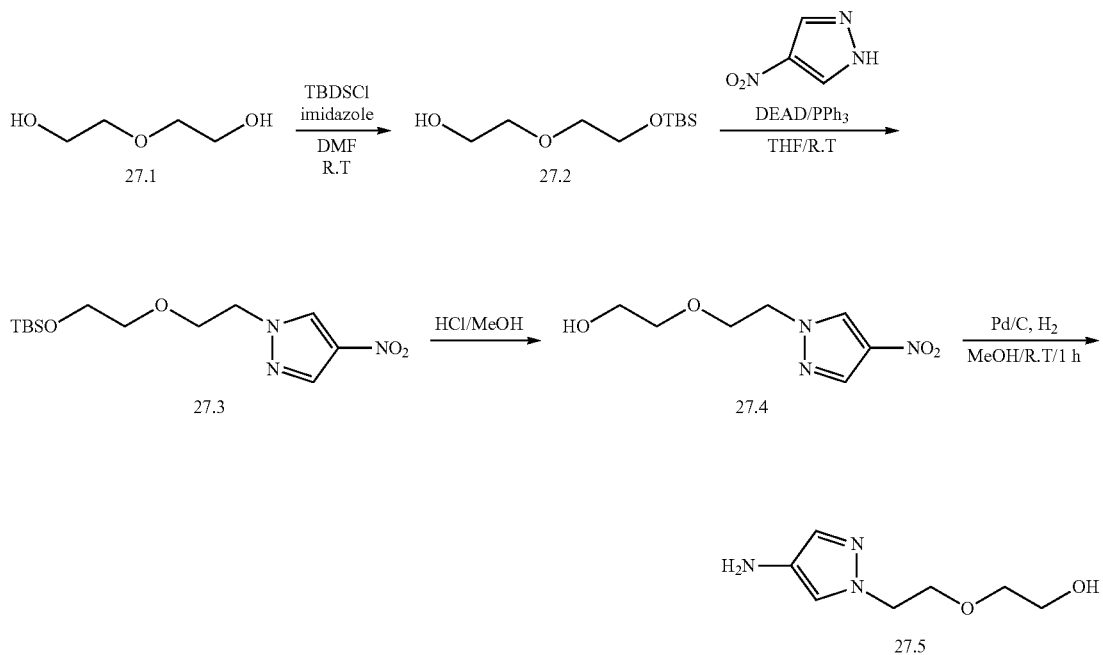

-continued

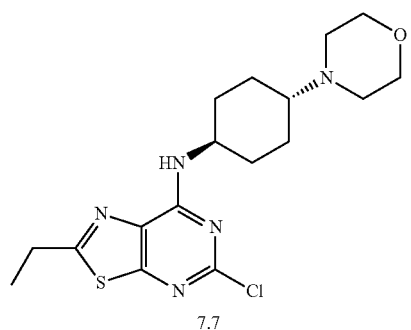 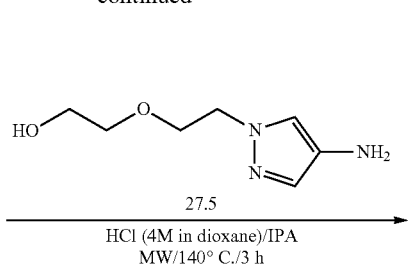

HCl (4M in dioxane)/IPA
MW/140° C./3 h

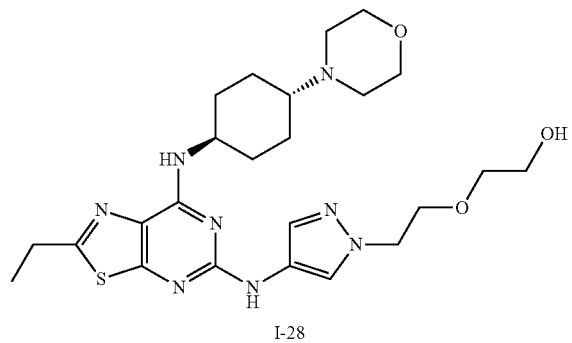

I-28

Synthesis of Intermediate 27.2.

Into a 100 mL 3-necked round-bottom flask, was placed compound 27.1 (5 g, 47.12 mmol, 1.00 equiv), 1H-imidazole (9.6 g, 141.02 mmol, 3.00 equiv), N,N-dimethylformamide (25 mL). This was followed by the addition of tert-butyl(chloro)dimethylsilane (7.8 g, 51.75 mmol, 1.10 equiv) dropwise with stirring at 0° C. The reaction was stirred for 2 h at room temperature. The resulting solution was diluted with 30 mL of water and extracted with 3×50 mL of ethyl acetate. The organic layers were combined washed with 2×30 mL of brine, dried over anhydrous sodium sulfate and concentrated under vacuum to give 11.4 g (crude) of intermediate 27.2 as a colorless oil.

Synthesis of Intermediate 27.3.

Into a 250 mL 3-necked round-bottom flask, was placed intermediate 27.2 (3.9 g, 17.70 mmol, 1.00 equiv), 4-nitro-1H-pyrazole (2 g, 17.69 mmol, 1.00 equiv), PPh$_3$ (9.27 g, 35.34 mmol, 2.00 equiv) and THF (50 mL). This was followed by the addition of DEAD (4.62 g, 26.53 mmol, 1.50 equiv) dropwise with stirring at 0° C. The reaction was stirred for 4 h at room temperature. The resulting solution was diluted with 50 mL of water and extracted with 3×80 mL of ethyl acetate. The organic layers combined and dried over anhydrous sodium sulfate and concentrated under vacuum. The crude product was purified by flash column chromatography to furnish 1.1 g (20%) of intermediate 27.3 as light yellow oil.

Synthesis of Intermediate 27.4.

Into a 100 mL round-bottom flask, was placed intermediate 27.3 (1.1 g, 3.49 mmol, 1.00 equiv), methanol (100 mL). This was followed by the addition of hydrogen chloride (12N, 0.2 mL) dropwise with stirring at 0° C. The reaction was stirred for 10 min at 0° C. in an ice/salt bath. The resulting mixture was concentrated under vacuum. The crude product was purified using flash column chromatography to give 370 mg (53%) of intermediate 27.4 as a colorless oil.

Synthesis of Intermediate 27.5.

To a solution of intermediate 27.4 (370 mg, 1.84 mmol, 1.00 equiv) in 10 mL of methanol (10 mL) was added palladium on carbon (200 mg) under nitrogen. Then H$_2$ (g) was introduced and the reaction was stirred for 1.5 h at room temperature. The solids were filtered out and the filtrate was concentrated under vacuum to afford 300 mg (crude) of intermediate 27.5 as a light red solid. LCMS (ES, m/z): 172 [M+H]$^+$.

Synthesis of Compound I-28.

Into a 10 mL microwave vial, was placed a solution of intermediate 7.7 (100 mg, 0.26 mmol, 1.00 equiv) in isopropanol (5 mL), intermediate 27.5 (54 mg, 0.32 mmol, 1.20 equiv), 4M hydrogen chloride in dioxane (0.1 mL). The reaction was irradiated in a microwave reactor for 2 h at 145° C. The resulting mixture was concentrated under vacuum and crude purified using preparative HPLC to furnish 45 mg (33%) of compound I-28 as a white solid. LCMS (ES, m/z): 517 [M+H]$^+$; $^1$H NMR (300 MHz, CD$_3$OD) δ 7.97 (s, 1H), 7.61 (s, 1H), 4.31-4.27 (t, 1H), 4.07 (br s, 1H), 3.86-3.83 (t, 2H), 3.75-3.72 (m, 4H), 3.68-3.63 (m, 2H), 3.55-3.50 (m, 2H), 3.08-2.87 (m, 4H), 3.08-2.87 (m, 4H), 2.38-2.27 (m, 3H), 2.17-2.12 (m, 2H).

Example 28

Synthesis of 2-(4-((2-ethyl-7-(((1r,4r)-4-morpholinocyclohexyl)-amino)thiazolo[5,4-d]pyrimidin-5-yl)amino)-1H-pyrazol-1-yl)ethan-1-ol I-29

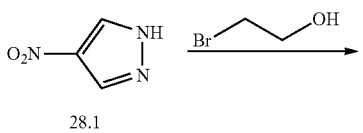

28.1

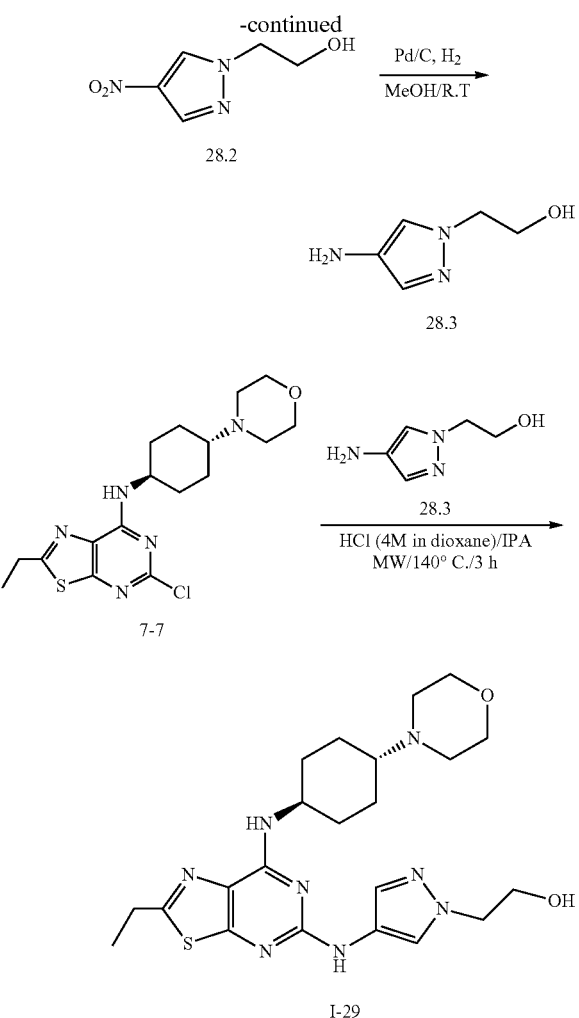

intermediate 28.3 (40 mg, 0.31 mmol, 1.20 equiv) and 4N hydrogen chloride in dioxane (0.5 mL). The reaction mixture was irradiated in a microwave reactor for 2 h at 14 0° C. The resulting mixture was concentrated under vacuum and the crude product purified using preparative HPLC to furnish 37.1 mg (30%) of compound I-29 as a white solid. LCMS (ES, m/z): 473 [M+H]$^+$; $^1$H NMR (400 MHz, CD$_3$OD) δ 7.99 (s, 1H), 7.60 (s, 1H), 4.23-4.20 (t, 2H), 4.09 (m, 1H), 3.91-3.89 (t, 2H), 3.74 (t, 4H), 3.05-3.02 (q, 2H), 2.67-2.65 (t, 4H), 2.35-2.32 (m, 1H), 2.27-2.25 (m, 2H), 2.12-2.06 (m, 2H), 1.54-1.46 (m, 7H).

Example 29

Synthesis of compound 1-((1r,4r)-4-((2-methyl-5-((1-methyl-1H-pyrazol-4-yl)amino)thiazolo[5,4-d]pyrimidin-7-yl)amino)cyclohexyl)piperidin-4-ol, I-30

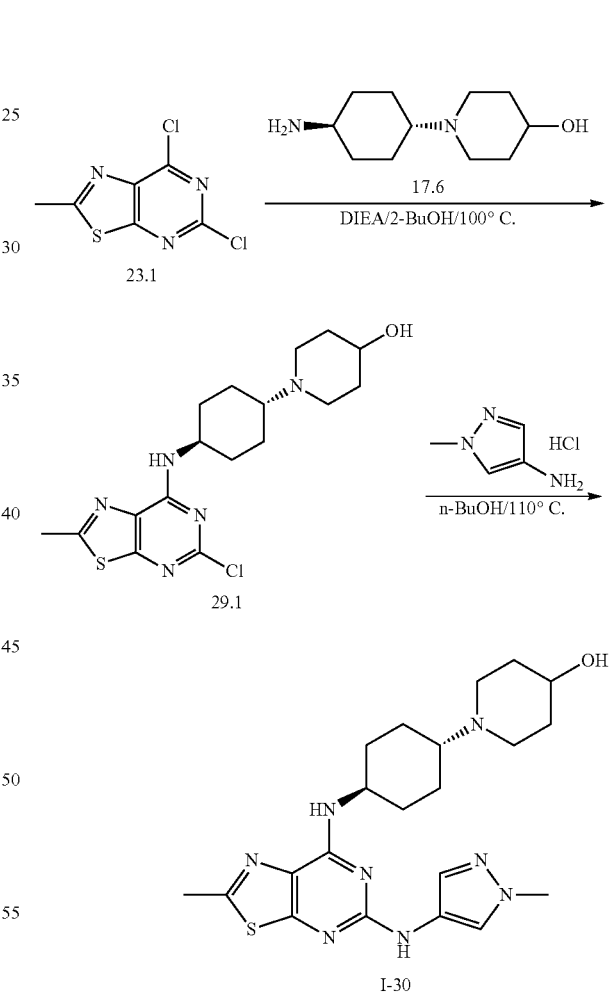

Synthesis of Intermediate 28.2.

Into a 250 mL round-bottom flask, was placed a solution of compound 28.1 (5 g, 44.22 mmol, 1.00 equiv) in CH$_3$CN (100 mL), 2-bromoethan-1-ol (11 g, 88.02 mmol, 2.00 equiv) and potassium carbonate (18.5 g, 133.85 mmol, 3.00 equiv). The resulting solution was stirred overnight at 95° C. in an oil bath. The reaction was then quenched by the addition of water and extracted with 3×100 mL of ethyl acetate. Organic layers were combined and concentrated under vacuum. The product crude was purified using flash column chromatography to furnish 3.5 g (50%) of intermediate 28.2 as yellow oil.

Synthesis of Intermediate 28.3.

A 100 mL round-bottom flask was charged with a solution of intermediate 28.2 (500 mg, 3.18 mmol, 1.00 equiv) in methanol (20 mL) and palladium on carbon (100 mg). To the above hydrogen gas was introduced. The resulting solution was stirred for 2 h at room temperature. The solids were filtered out and mixture was concentrated under vacuum to provide 350 mg (crude) of intermediate 28.3 as yellow oil. LCMS (ES, m/z): 128 [M+H]$^+$.

Synthesis of Compound I-29.

Into a 10 mL vial, was placed a solution of intermediate 7.7 (100 mg, 0.26 mmol, 1.00 equiv) in IPA (5 mL), Synthesis of Intermediate 29.1.

To intermediate 17.6 (123 mg, 0.62 mmol, 1.03 equiv) and compound 23.1 (132 mg, 0.60 mmol, 1.00 equiv) in 2-butanol (5 mL) was added DIEA (155 mg, 1.20 mmol, 2.00 equiv) and the resulting solution was stirred for 4 h at 100° C. under nitrogen. The resulting mixture was concentrated under vacuum and crude was purified using flash column chromatography to furnish 160 mg of intermediate 29.1 as a white solid. LCMS (ES, m/z): 382 and 384 [M+H]+.

Synthesis of Compound I-30.

Into a 50 mL round-bottom flask, was placed intermediate 29.1 (80 mg, 0.21 mmol, 1.00 equiv) and 1-methyl-1H-pyrazol-4-amine (41 mg, 0.42 mmol, 2.00 equiv) in butanol (5 mL). The resulting solution was stirred overnight at 110° C. under nitrogen. After cooling to room temperature, the formed solids were collected by filtration. The solid was dissolved in water and basified with 2 M NaOH to PH ~8. The resulting solution was extracted with 4×40 mL of ethyl acetate and the combined organic layers were dried over anhydrous sodium sulfate and concentrated under vacuum. The crude was recrystallized from ethyl acetate to give 32.6 mg of I-30 as a light brown solid. LCMS (ES, m/z): 443 [M+H]+; $^1$H NMR (400 MHz, CDCl$_3$) δ 7.84 (s, 1H), 7.50 (s, 1H), 6.66 (s, 1H), 5.70-5.68 (m, 1H), 4.01 (br s, 1H), 3.74 (br s, 1H), 2.89-2.70 (m, 2H), 2.68 (s, 3H), 2.54-2.41 (m, 2H), 2.30-2.27 (m, 2H), 2.01 (m, 4H), 1.64-1.49 (m, 6H), 1.39-1.30 (m, 2H).

Example 30

Synthesis of 2-ethyl-N7-((1r,4r)-4-morpholinocyclohexyl)thiazolo[5,4-d]pyrimidine-5,7-diamine I-31

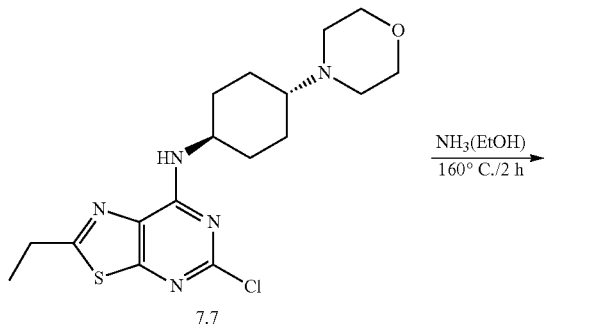

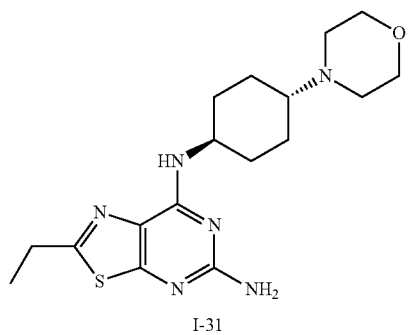

Into a 10 mL microwave vial were placed intermediate 7.7 (100 mg, 0.26 mmol, 1.00 equiv) and NH$_3$ (a solution of EtOH) (5 mL). The final reaction mixture was irradiated in a microwave reactor for 2 h at 160° C. The resulting solution was diluted with 30 mL of water. The resulting solution was extracted with 3×30 mL of ethyl acetate, and the organic layers were combined, dried over anhydrous sodium sulfate and concentrated under vacuum. The residue was purified using flash column chromatography to furnish 21.7 mg (23%) of compound I-31 as a yellow solid. LCMS (ES, m/z): 363.2 [M+H]+; $^1$H NMR (d6-DMSO, 400 MHz, ppm): δ 7.122-7.101 (1H, d), 6.169 (2H, s), 4.084-3.864 (1H, m), 3.570-3.512 (4H, m), 2.964-2.908 (2H, m), 2.505-2.486 (4H, m), 2.149-2.068 (1H, m), 1.900-1.757 (4H, m), 1.496-1.375 (2H, m), 1.354-1.177 (5H, m).

Example 31

Synthesis of 4-(4-((2-ethyl-7-(((1r,4r)-4-morpholinocyclohexyl)-amino)thiazolo[5,4-d]pyrimidin-5-yl)amino)-1H-pyrazol-1-yl)cyclohexan-1-ol I-32

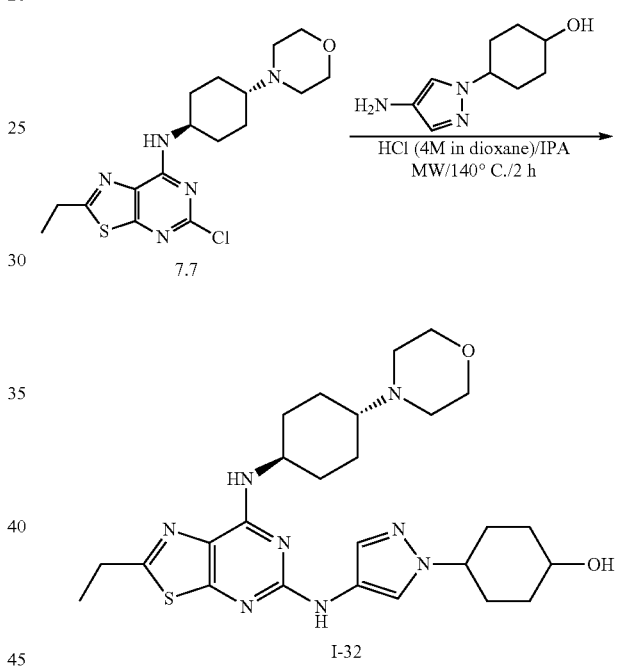

Into a 10 mL microwave vial, was placed a solution of intermediate and 7.7 (100 mg, 0.26 mmol, 1.00 equiv) in isopropanol (10 mL), 4-(4-amino-1H-pyrazol-1-yl)cyclohexan-1-ol (94 mg, 0.52 mmol, 2.00 equiv) and hydrogen chloride in 1,4-dioxane (1 mL). The final reaction mixture was irradiated in a microwave reactor for 2 h at 120° C. The resulting solution was diluted with 30 mL of water and extracted with 3×50 mL of ethyl acetate. The organic layers were combined, dried over anhydrous sodium sulfate and concentrated under vacuum. The crude product was purified using flash column chromatography to furnish 63.4 mg (46%) of compound I-32 as a white solid. LCMS (ES, m/z): 527.3 [M+H]+; $^1$H NMR (DMSO, 400 MHz): δ 9.014 (1H, s), 7.868 (1H, s), 7.454 (2H, s), 4.482 (1H, s), 4.127-3.915 (2H, m), 3.845 (1H, s), 3.582-3.562 (4H, m), 2.982-2.964 (2H, m), 2.505-2.502 (4H, s), 2.237-2.058 (3H, m), 2.056-1.882 (4H, m), 1.753-1.724 (4H, d), 1.600-1.421 (4H, m), 1.400-1.22 (5H, m).

Example 32

Synthesis of 2-(2-(4-((7-(((1r,4r)-4-(6-azaspiro[2.5]octan-6-yl)cyclohexyl)-amino)-2-ethylthiazolo[5,4-d]pyrimidin-5-yl)amino)-1H-pyrazol-1-yl)ethoxy)ethan-1-ol, I-33

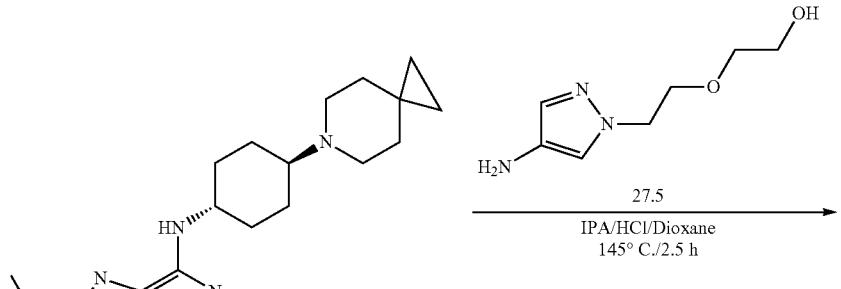

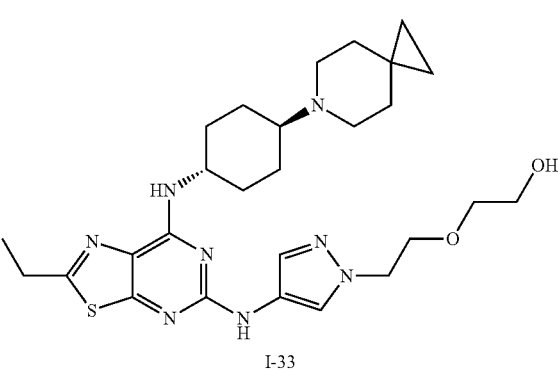

Into a 5 mL microwave vial, was placed intermediate 20.1 (70 mg, 0.17 mmol, 1.00 equiv), intermediate 27.5 (35 mg, 0.20 mmol, 1.19 equiv), IPA (3 mg, 0.05 mmol, 0.29 equiv) and hydrogen chloride in dioxane (0.2 mL). The final reaction mixture was irradiated in a microwave reactor for 2 h at 145° C. The resulting solution was diluted with 30 mL of ethyl acetate and extracted with 3×30 mL of ethyl acetate. The organic layers were combined and washed with 3×30 mL of brine. The mixture was dried over anhydrous sodium sulfate and concentrated under vacuum. The crude was purified using flash column chromatography to furnish 24.2 mg (26%) of compound I-33 as a off-white solid. LCMS (ES, m/z): 541 [M+H]$^+$; $^1$H NMR (300 MHz, CD$_3$OD) δ7.96 (1H, s), 7.61 (1H, s), 4.31 (2H, m), 4.05 (1H, m), 3.85 (2H, m), 3.65 (2H, m), 3.53 (2H, m), 3.09-2.91 (2H, m), 2.91-2.78 (4H, m), 2.78-2.59 (1H, m), 2.33 (2H, m), 2.14 (2H, m), 1.78-1.38 (11H, m), 0.38 (4H, s).

Example 33

Synthesis of 2-ethyl-N5-(1-(2-methoxyethyl)-1H-pyrazol-4-yl)-N7-((1r,4r)-4-morpholinocyclohexyl)thiazolo[5,4-d]pyrimidine-5,7-diamine, I-34

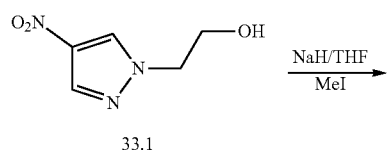

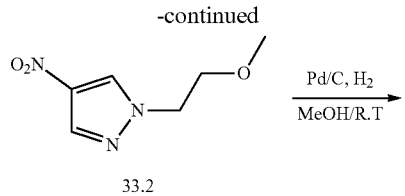

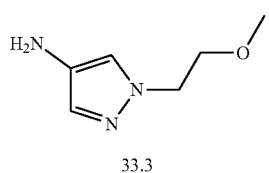

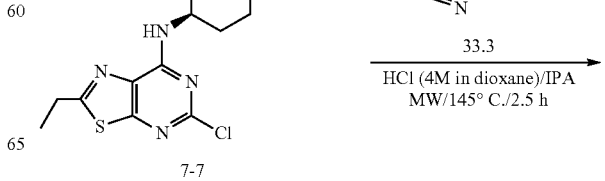

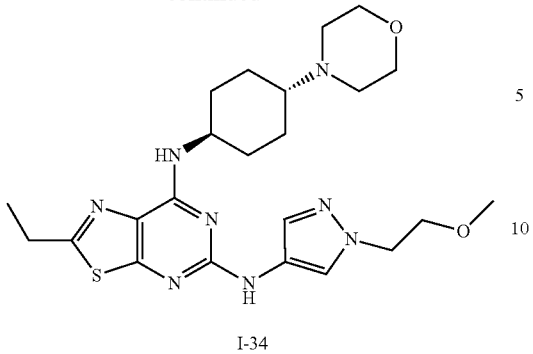

I-34

Synthesis of Compound 33.1.

Into a 100 mL round-bottom flask purged and maintained under inert atmosphere of nitrogen, were placed compound 33.1 (500 mg, 3.18 mmol, 1.00 equiv) in 10 mL of distilled DMF. This was followed by the addition of sodium hydride (191 mg, 7.96 mmol, 1.50 equiv) in portions. After stirring for 30 min, MeI (2.26 g, 15.92 mmol, 5.00 equiv) was added dropwise via syringe and the resulting solution was stirred for 16 h at room temperature. The reaction was then quenched with 50 mL of water, extracted with 3×60 mL of ethyl acetate. The organic layers were combined and washed with brine, dried over anhydrous sodium sulfate, and concentrated under vacuum. The residue was purified using flash column chromatography to furnish 420 mg (77%) of intermediate 33.2 as a yellow solid.

Synthesis of Compound 33.3.

Intermediate 33.2 (90 mg, 0.53 mmol, 1.00 equiv) in methanol (5 mL) was added 10% palladium on carbon (18 mg) under nitrogen. The flask was degassed three times with hydrogen (2 atm) and the mixture was stirred 1 h at room temperature. The solids were filtered out and the filtrate was concentrated under vacuum to give 74 mg (crude) of intermediate 33.2 as a yellow solid. LCMS (ES, m/z): 142 [M+H]$^+$.

Synthesis of Compound I-34.

Into a 10 mL microwave vial purged and maintained with an inert atmosphere of nitrogen, was placed intermediate 7.7 (100 mg, 0.26 mmol, 1.00 equiv), intermediate 33.2 (74 mg, 0.52 mmol, 1.50 equiv), IPA (5 mL) and hydrogen chloride (4 M in dioxane) (2 mL). The final reaction mixture was irradiated in a microwave reactor for 2.5 h at 145° C. The resulting mixture was concentrated under vacuum. The crude product was purified by preparative HPLC to furnish 77.4 mg (60%) of I-34 as a white solid. LCMS (ES, m/z): 487 [M+H]$^+$; $^1$H NMR (400 MHz, DMSO) δ9.03 (br s, 1H), 7.85 (s, 1H), 7.47 (s, 1H), 7.42 (br s, 1H), 4.18 (t, 2H), 4.05-3.92 (m, 1H), 3.64 (t, 2H), 3.57 (br s, 4H), 3.23 (s, 3H), 2.97 (t, 2H), 2.49 (s, 4H), 2.25-2.15 (m, 1H), 1.99 (d, 2H), 1.89 (d, 2H), 1.52-1.42 (m, 2H), 1.40-1.28 (m, 5H).

Example 34

Synthesis of 1-(5-(((1-methyl-1H-pyrazol-4-yl) amino)-7-(((1r,4r)-4-morpholino-cyclohexyl)amino) thiazolo[5,4-d]pyrimidin-2-yl)ethan-1-ol, I-35

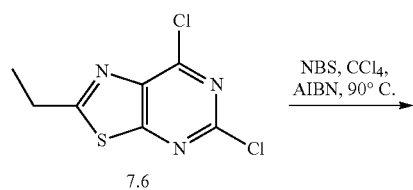

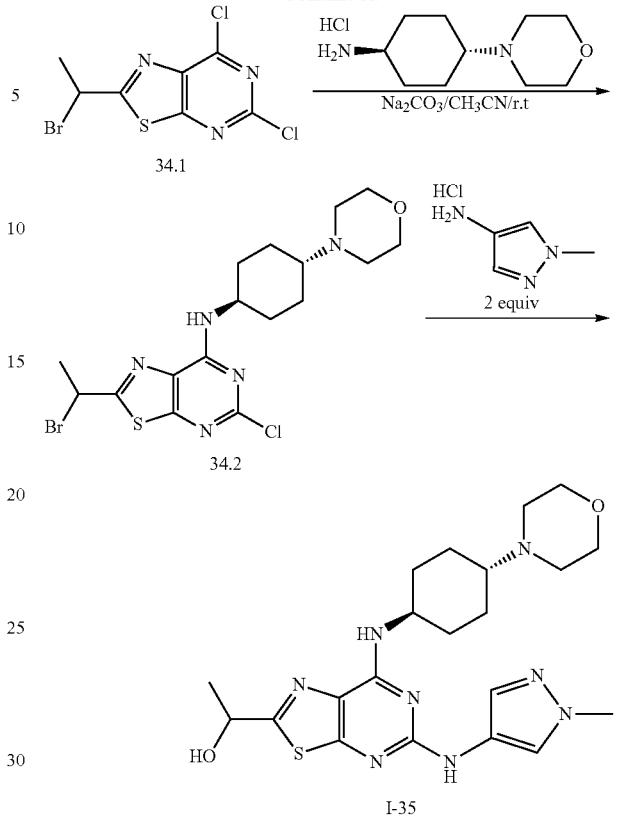

I-35

Synthesis of Intermediate 34.1.

A 100 mL round-bottom flask, was charged with intermediate 7.6 (283 mg, 1.21 mmol, 1.00 equiv) in CCl$_4$ (30 mL), NBS (346 mg, 1.94 mmol, 1.61 equiv), and AIBN (20 mg, 0.12 mmol, 0.10 equiv). The reaction was stirred for 4 h at 90° C. in an oil bath. The crude material was purified using flash column chromatography to afford 220 mg of intermediate 34.1 as (58%) yellow solid.

Synthesis of Intermediate 34.2.

Into a 100 mL round-bottom flask, was placed a solution of intermediate 34.1 (220 mg, 0.70 mmol, 1.00 equiv) in CH$_3$CN (30 mL), (1r,4r)-4-(morpholin-4-yl)cyclohexan-1-amine dihydrochloride (196 mg, 0.76 mmol, 1.08 equiv) and sodium carbonate (147 mg, 1.39 mmol, 1.97 equiv). The reaction was stirred overnight at room temperature. The resulting solution was extracted with 3×30 mL of dichloromethane, and the organic layers were combined and dried over sodium sulfate. Solvents were removed in vacuo to afford the desired intermediate 34.2 (200 mg, 0.43 mmol, 62%) as yellow solid.

Synthesis of Compound I-35.

Into a 100 mL round-bottom flask, was placed a solution of intermediate 34.2 (200 mg, 0.43 mmol, 1.00 equiv) in water (8 mL) and 1-methyl-1H-pyrazol-4-amine hydrochloride (145 mg, 1.09 mmol, 2.50 equiv). The reaction was stirred overnight at 110° C. in an oil bath. The resulting mixture was concentrated under vacuum and crude was purified using flash column chromatography and preparative HPLC to furnish 20 mg (10%) of compound I-35 as a light yellow solid. LCMS (ES, m/z): 459 [M+H]$^+$; $^1$H NMR (400 MHz, CD$_3$OD): δ 7.89 (1H, s), 7.57 (1H, s), 5.038-4.95 (1H, m), 4.07 (1H, s), 3.83 (3H, s), 3.76-3.73 (4H, m), 2.67-2.64 (4H, m), 2.36 (1H, s), 2.26-2.11 (4H, d), 1.61-1.59 (3H, m), 1.52-1.19 (4H, m).

Example 35

Synthesis of compound N5-(1-ethyl-1H-pyrazol-4-yl)-2-methyl-N7-((1r,4r)-4-morpholinocyclohexyl)thiazolo[5,4-d]pyrimidine-5,7-diamine, I-36

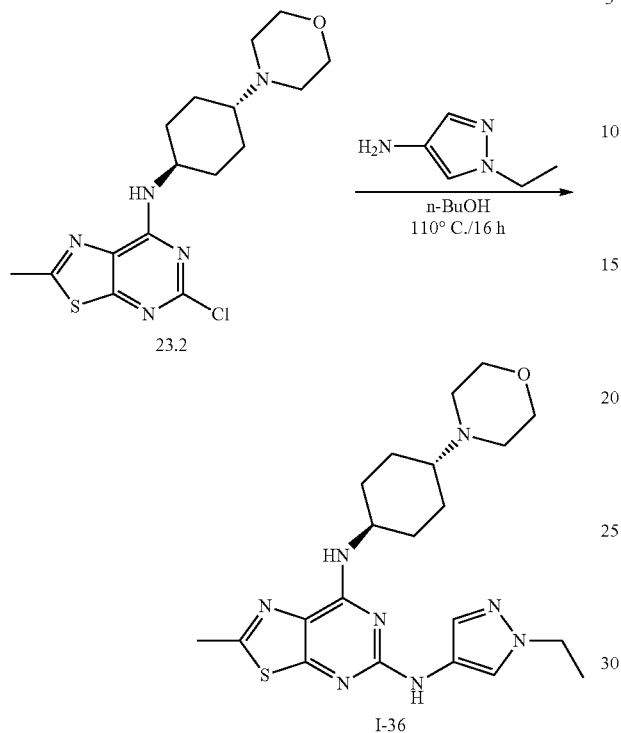

A 50 mL round-bottom flask, was charged with a solution of intermediate 23.2 (150 mg, 0.41 mmol, 1.00 equiv) in n-butanol (10 mL) and 1-ethyl-1H-pyrazol-3-amine (90.49 mg, 0.814 mmol, 2.00 equiv). The reaction was stirred overnight at 110° C. Upon completion of the reaction, the precipitate formed was collected by filtration, washed by n-butanol and dissolved in H$_2$O. The pH value of the solution was adjusted to pH=9 with sodium hydroxide (1 mol/L). The solids formed were collected by filtration and dried under reduced pressure to give 107.5 mg (60%) of compound I-36 as white solid. LCMS (ES, m/z): 443 [M+H]$^+$; $^1$H NMR: (400 MHz, CD$_3$OD): δ 7.91 (s, 1H), 7.59 (s, 1H), 4.20-4.15 (m, 2H), 4.07 (s, 1H), 3.76-3.74 (t, 4H), 2.69-2.68 (d, 7H), 2.38 (s, 1H), 2.27 (s, 2H), 2.17-2.11 (d, 2H), 1.53-1.41 (m, 7H).

Example 36

Synthesis of (5-((1-methyl-1H-pyrazol-4-yl)amino)-7-(((1r,4r)-4-morpholino-cyclohexyl)amino)thiazolo[5,4-d]pyrimidin-2-yl)methanol, I-37

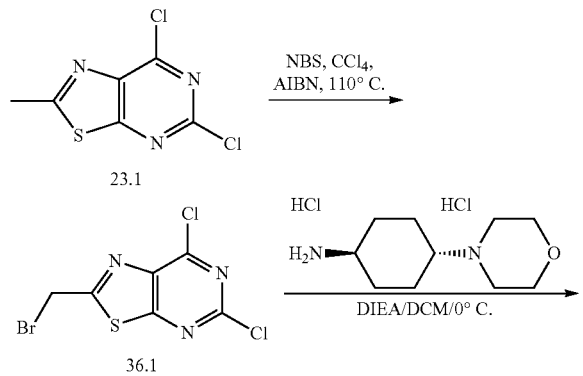

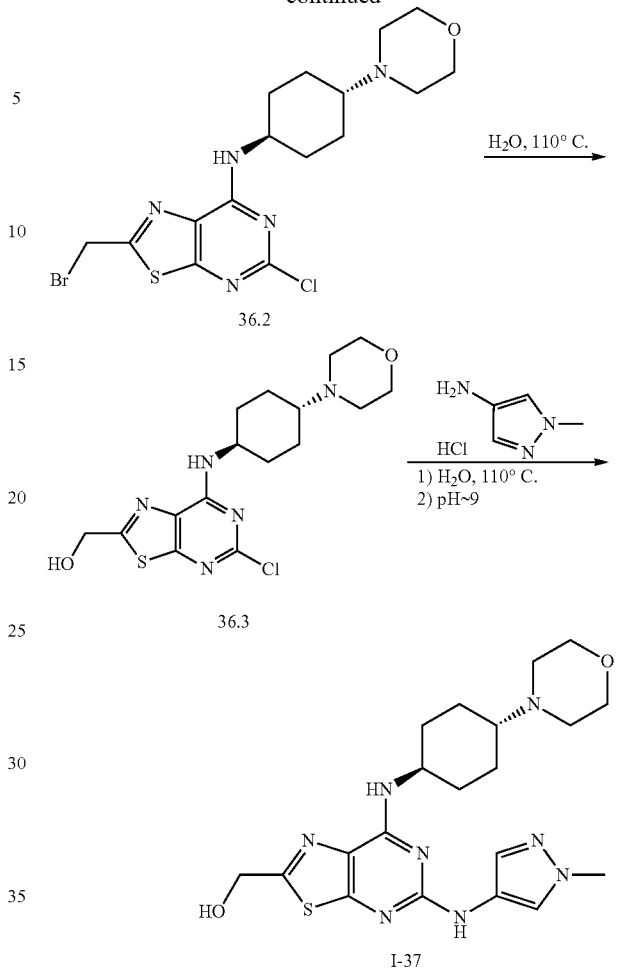

Synthesis of Intermediate 36.1.

A 50 mL round-bottom flask, was charged with compound 23.1 (500 mg, 2.27 mmol, 1.00 equiv), NBS (2000 mg, 11.24 mmol, 4.95 equiv), AIBN (70 mg, 0.43 mmol, 0.19 equiv) and CCl$_4$ (20 mL). The reaction was stirred for 1 h at 90° C. Upon completion of the reaction solvent was removed under vacuum, and crude purified using flash column chromatography to provide 50 mg (7%) of intermediate 36.1 as a yellow solid.

Synthesis of Intermediate 36.2.

Into a 50-mL round-bottom flask, was placed a solution of intermediate 36.1 (50 mg, 0.17 mmol, 1.00 equiv) in dichloromethane (10 mL), (1r,4r)-4-(morpholin-4-yl)cyclohexan-1-amine dihydrochloride (47 mg, 0.18 mmol, 1.09 equiv) and DIEA (67 mg, 0.52 mmol, 3.10 equiv). The reaction was stirred for 4 h at 0° C. Upon completion it was extracted with 3×10 mL of dichloromethane, and the organic layers were combined, dried and concentrated under vacuum to furnish 25 mg crude (33%) of intermediate 36.2 as a light yellow solid.

Synthesis of Intermediate 36.3.

A 25 mL round-bottom flask, was charged with a solution of intermediate 36.2 (20 mg, 0.04 mmol, 1.00 equiv) in water (5 mL). The reaction was stirred for 1 h at 110° C. The resulting solution was extracted with 3×5 mL of dichloromethane, organic layers were combined, dried and concentrated under vacuum to furnish 20 mg of intermediate 36.3 as a light yellow solid.

Synthesis of Compound I-37.

Into a 25 mL round-bottom flask, was placed a solution of intermediate 36.3 (40 mg, 0.10 mmol, 1.00 equiv) in water (5 mL), 1-methyl-1H-pyrazol-4- and amine hydrochloride (27 mg, 0.20 mmol, 1.94 equiv). The reaction was stirred overnight at 110° C. The crude product was purified by preparative HPLC to furnish 1.9 mg (4%) of I-37 as a white solid. LCMS (ES, m/z): 445 [M+H]$^+$; $^1$H NMR (400 MHz, CD$_3$OD): δ 7.93 (1H, s), 7.58 (1H, s), 4.82 (2H, s), 4.07 (1H, br s), 3.89 (3H, s), 3.76-3.66 (4H, m), 2.68-2.65 (4H, m), 2.38-2.36 (1H, br s), 2.30-2.09 (2H, m), 1.94-1.31 (4H, m).

Example 37

Synthesis of 2-methyl-N5-(1-(3-(methylsulfonyl)propyl)-1H-pyrazol-4-yl)-N7-((1r,4r)-4-morpholino-cyclohexyl)thiazolo[5,4-d]pyrimidine-5,7-diamine, I-38

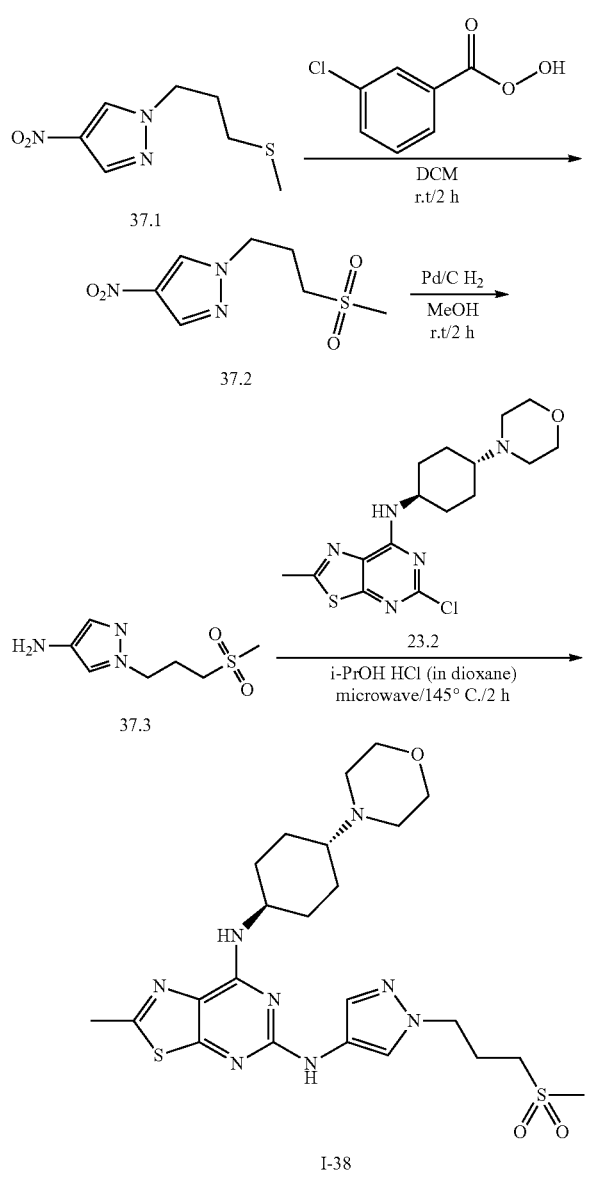

Synthesis of Intermediate 37.2.

Into a 50 mL round-bottom flask, was placed a solution of compound 37.1 (800 mg, 3.98 mmol, 1.00 equiv) in dichloromethane (15 mL) and 3-chlorobenzene-1-carboperoxoic acid (1.71 g, 9.91 mmol, 2.49 equiv). The resulting solution was stirred for 2 h at room temperature. The reaction was then quenched by the addition of 20 mL of Na$_2$S$_2$O$_3$. The resulting solution was extracted with 3×20 mL of dichloromethane and the organic layers were combined and was washed with 2×50 mL of sat. NaHCO$_3$ followed by 2×50 mL of brine, then dried over anhydrous sodium sulfate and concentrated under vacuum. The crude product was purified using flash column chromatography to furnish 1 g (crude) of intermediate 37.2 as a white solid.

Synthesis of Intermediate 37.3.

Into a 50 mL round-bottom flask, was placed a solution of intermediate 37.2 (200 mg, 0.86 mmol, 1.00 equiv) in methanol (8 mL), and palladium on carbon (50 mg), and H$_2$(g) was introduced. The reaction was stirred for 2 h at room temperature. Solids were filtered out and the filtrate was concentrated under vacuum to give 160 mg (92%) of intermediate 37.3 as a white solid.

Synthesis of Compound I-38.

Into a 50 mL round-bottom flask, was placed a solution of intermediate 23.2 (4 mL), intermediate 37.3 (150 mg, 0.79 mmol, 1.50 equiv), and a solution of hydrogen chloride in dioxane (0.5 mL). The final reaction mixture was irradiated in a microwave reactor for 2 h at 145° C. The solids were collected by filtration and washed with propan-2-ol. The crude product was dissolved in dichloromethane and then precipitated by addition of hexanes. The solids were collected by filtration and dried to give 182.6 mg (63%) of compound I-38 as white solid. LCMS (ES, m/z): 535 [M+H]$^+$; $^1$H NMR (400 MHz, CD$_3$OD): δ 7.980 (s, 1H), 7.622 (s, 1H), 4.327-4.294 (t, 2H), 4.055 (s, 1H), 3.750-3.727 (t, 3H), 3.153-3.100 (m, 2H), 2.984 (s, 3H), 2.693-2.639 (m, 7H), 2.413-2.315 (m, 3H), 2.268-2.247 (d, 2H), 2.110-2.088 (d, 2H), 1.530-1.495 (m, 4H).

Example 38

Synthesis of N7-((1r,4r)-4-(6-azaspiro[2.5]octan-6-yl)cyclohexyl)-2-methyl-N5-(1-methyl-1H-pyrazol-4-yl)thiazolo[5,4-d]pyrimidine-5,7-diamine I-39

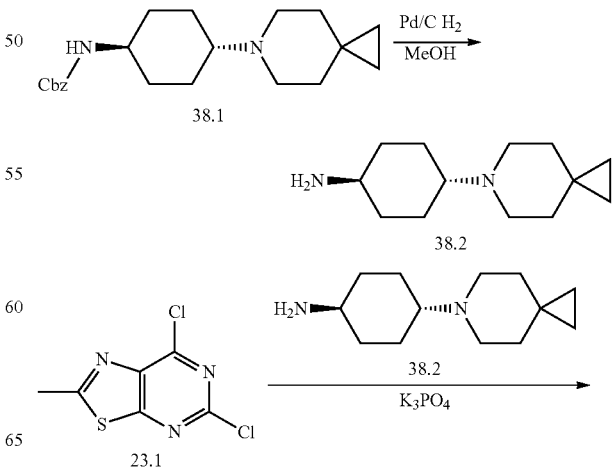

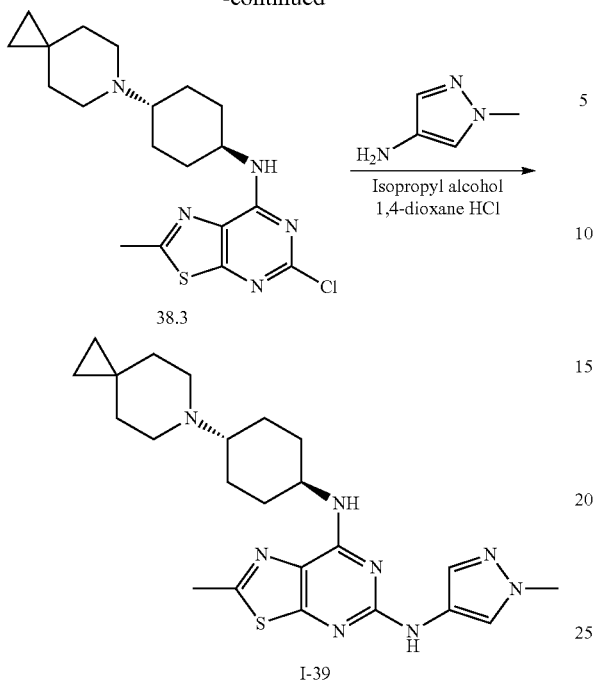

Synthesis of Intermediate 38.2.

Into a 50 mL round-bottom flask, was placed a solution of compound 38.1 (200 mg, 0.58 mmol, 1.00 equiv) in methanol (10 mL), and Pd/C (50 mg). The reaction was stirred for 1.5 h at room temperature under hydrogen atmosphere. The solids were filtered out and the resulting solution was concentrated under vacuum to give 121 mg of crude compound 38.2 as white solid.

Synthesis of Intermediate 38.3.

Into a 50 mL round-bottom flask, was placed a solution of intermediate 38.2 (121 mg, 0.58 mmol, 1.05 equiv) in $CH_3CN$ (10 mL), compound 23.1 (121 mg, 0.55 mmol, 1.00 equiv) and $K_3PO_4$ (352 mg, 1.66 mmol, 3.00 equiv). The reaction was stirred overnight at 80° C. The solids were filtered out and the resulting solution was concentrated under vacuum. The crude was purified using flash column chromatography to give 140 mg (65%) of intermediate 38.3 as a white solid.

Synthesis of Compound I-39.

Into a 5 mL sealed tube, was placed a solution of intermediate 38.3 (140 mg, 0.36 mmol, 1.00 equiv) in dioxane (0.5 mL), and 1-methyl-1H-pyrazol-4-amine (57.6 mg, 0.59 mmol, 1.20 equiv) in isopropyl alcohol (3.5 mL). The reaction was irradiated in a microwave reactor for 2 h at 140° C. The solids were collected by filtration, washed with isopropyl alcohol and dissolved in water. The pH value of the solution was adjusted to 9 with sodium hydroxide (1M). The solids were collected by filtration and dried in an oven under reduced pressure to furnish 83.7 mg (52%) of compound I-39 as a white solid. LCMS (ES, m/z): 453 [M+H]$^+$; $^1$H NMR (400 MHz, $CD_3OD$): δ 7.865 (s, 1H), 7.593 (s, 1H), 4.055 (s, 1H), 3.889 (s, 3H), 2.757 (s, 4H), 2.696 (s, 3H), 2.562 (s, 1H), 2.292-2.263 (d, 2H), 2.118-2.089 (t, 2H), 1.625-1.309 (m, 8H).

Example 39

Synthesis of compound 2-methyl-N5-(1-(2-(methylsulfonyl)ethyl)-1H-pyrazol-4-yl)-N7-((1r,4r)-4-morpholinocyclohexyl)thiazolo[5,4-d]pyrimidine-5,7-diamine I-40

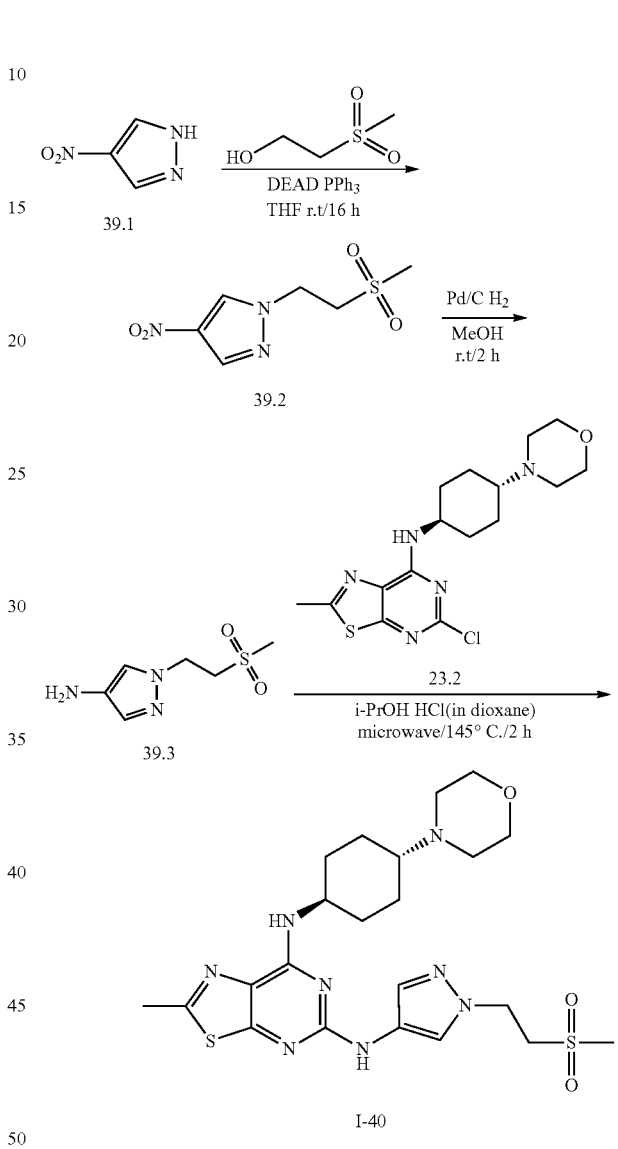

Synthesis of Compound 39.2.

Into a 100 mL round-bottom flask, was placed a solution of compound 39.1 (1 g, 8.84 mmol, 1.00 equiv) in THF (20 mL), triphenylphosphine (4.6 g, 17.54 mmol, 1.98 equiv) and 2-methanesulfonylethan-1-ol (1.1 g, 8.86 mmol, 1.00 equiv). This was followed by the addition of DEAD (2.7 g, 15.50 mmol, 1.75 equiv) dropwise with stirring. The reaction was stirred overnight at room temperature. The resulting solution was diluted with 50 mL of $H_2O$ and extracted with 2×50 mL of ethyl acetate. The organic layers were combined and washed with 2×100 mL of brine, then dried over anhydrous sodium sulfate and concentrated under vacuum. The crude product was purified using flash column chromatography to furnish 0.8 g (41%) of intermediate 39.2 as a yellow solid.

Synthesis of Compound 39.3.

Into a 50 mL round-bottom flask, was placed a solution of intermediate 39.2 (300 mg, 1.37 mmol, 1.00 equiv) in methanol (10 mL) and palladium on carbon (30 mg). To the above mixture H$_2$ (g) was introduced. The reaction was stirred overnight at room temperature. The solid was filtered out and filtrate was concentrated under vacuum to give 200 mg (77%) of compound 39.3 as a yellow solid.

Synthesis of Compound I-40.

Into a 10 mL sealed tube, was placed a solution of intermediate 23.2 (300 mg, 0.82 mmol, 1.00 equiv) in isopropanol (5 mL), intermediate 39.3 (200 mg, 1.06 mmol, 1.30 equiv) and hydrogen chloride (0.5 mL). The reaction was irradiated in a microwave reactor for 2.5 h at 150° C. The resulting mixture was concentrated under vacuum and crude purified using flash column chromatography to furnish 140.8 mg (33%) of compound I-40 as a pink solid. LCMS (ES, m/z): 521 [M+H]$^+$; $^1$H NMR (400 MHz, DMSO): δ 9.068 (s, 1H), 7.950 (s, 1H), 7.557 (s, 1H), 7.481-7.443 (t, 1H), 4.495-4.461 (t, 2H), 3.996-3.975 (d, 1H), 3.685-3.668 (d, 2H), 3.576-3.555 (t, 3H), 2.856 (s, 3H), 2.655 (s, 3H), 2.537-2.496 (m, 4H), 2.203 (s, 1H), 1.990-1.882 (m, 4H), 1.497-1.435 (t, 2H), 1.343-1.245 (m, 3H).

Synthesis of Intermediate 40.2.

Into a 5 mL round-bottom flask, was placed a solution of compound 40.1 (70 mg, 0.18 mmol, 1.00 equiv) in CH$_3$CN (1 mL), (1r,4r)-4-(morpholin-4-yl)cyclohexan-1-amine dihydrochloride (50 mg, 0.19 mmol, 1.09 equiv) and Na$_2$CO$_3$ (38 mg, 0.36 mmol, 1.99 equiv). The reaction was stirred for 4 h at room temperature. Water (1 mL) was added. The reaction was stirred for an additional 2 h at room temperature. Upon completion, the mixture was extracted with 3×5 mL of dichloromethane, and the organic layers were combined, dried and concentrated under vacuum to provide 70 mg (99%) of compound 40.2 as yellow oil.

Synthesis of Compound I-41.

Into a 25 mL round-bottom flask, was placed a solution of intermediate 40.2 (30 mg, 0.08 mmol, 1.00 equiv) in water (7 mL) and 1-methyl-1H-pyrazol-4-amine hydrochloride (19 mg, 0.14 mmol, 1.88 equiv). The reaction was stirred overnight at 110° C. The crude product was purified using preparative HPLC to furnish 3.4 mg (10%) of compound I-41 as a light yellow solid. LCMS (ES, m/z): 457 [M+H]$^+$; $^1$H NMR (300 MHz, DMSO): δ 9.570-9.446 (1H, d), 8.097-7.795 (2H, m), 7.521 (1H, s), 4.097 (1H, s), 3.892-3.812 (3H, m), 3.759-3.589 (4H, m), 2.874-2.798 (3H, d), 2.270-1.971 (5H, m), 1.796-0.854 (8H, m).

Example 40

Synthesis of compound 1-(5-((1-methyl-1H-pyrazol-4-yl)amino)-7-(((1r,4r)-4-morpholinocyclohexyl)amino)thiazolo[5,4-d]pyrimidin-2-yl)ethan-1-one I-41

Example 41

Synthesis of N7-((1r,4r)-4-(2-oxa-7-azaspiro[3.5]nonan-7-yl)cyclohexyl)-2-methyl-N5-(1-methyl-1H-pyrazol-4-yl)thiazolo[5,4-d]pyrimidine-5,7-diamine I-42

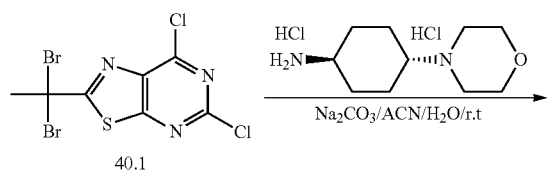

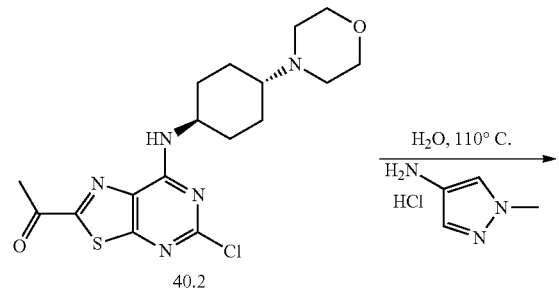

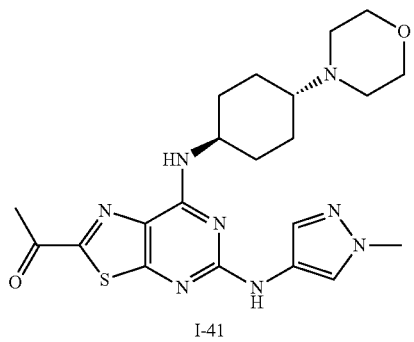

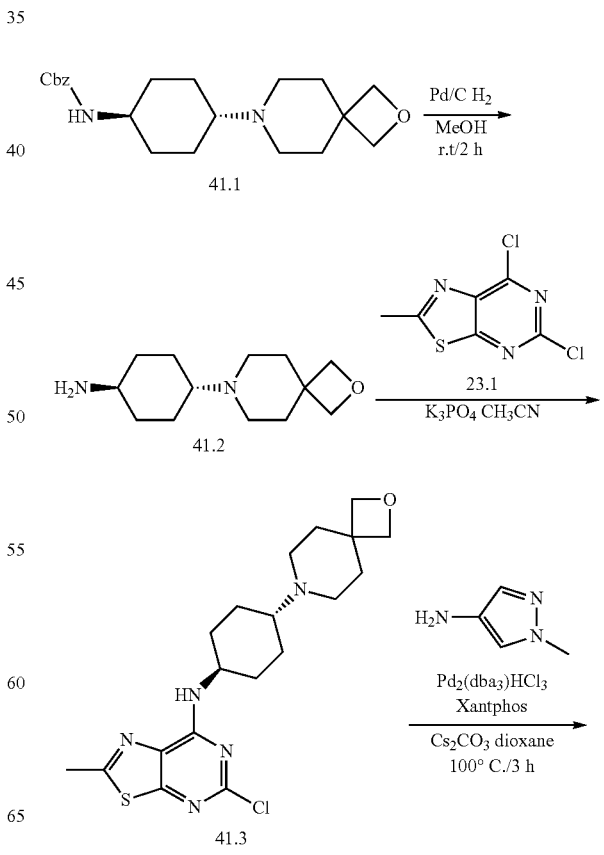

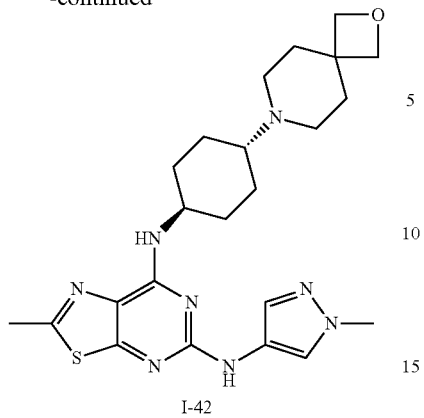

I-42

Synthesis of Compound 41.2.

Into a 50 mL round-bottom flask, was placed a solution of compound 41.1 (200 mg, 0.56 mmol, 1.00 equiv) in methanol (10 mL) and palladium on carbon (50 mg). To the above solution H₂ (g) was introduced. The reaction was stirred for 2 h at room temperature. The solids was filtered out and filtrate was concentrated under vacuum to give 110 mg (88%) of intermediate 41.2 as a colorless oil.

Synthesis of Intermediate 41.3.

A 50-mL round-bottom flask, was charged with a solution of intermediate 41.2 (111 mg, 0.49 mmol, 1.00 equiv) in CH₃CN (10 mL), K₃PO₄ (322 mg, 1.52 mmol, 3.07 equiv), and compound 23.1 (125 mg, 0.57 mmol, 1.15 equiv). The reaction was stirred overnight at 85° C. in an oil bath. Solids were filtered out and solution was concentrated under vacuum. The crude product obtained was purified using flash column chromatography to yield 180 mg (89%) of intermediate 41.3 as a yellow solid.

Synthesis of Compound I-42.

Into a 10 mL round-bottom flask, was placed a solution of intermediate 41.3 (180 mg, 0.44 mmol, 1.00 equiv) in dioxane (2 mL), 1-methyl-1H-pyrazol-4-amine (85.75 mg, 0.88 mmol, 2.00 equiv), Pd₂(dba)₃CHCl₃ (45.54 mg, 0.10 equiv), Xantphos (50.86 mg, 0.09 mmol, 0.20 equiv) and Cs₂CO₃ (432.5 mg, 3.00 equiv). The reaction was stirred overnight at 100° C. in an oil bath. The solids were filtered out, resulting solution was diluted with water and extracted with 3×5 mL of dichloromethane. The organic layers were combined and dried over anhydrous sodium sulfate and concentrated under vacuum. The crude product was purified using flash column chromatography to give 62.5 mg (30%) of compound I-42 as a yellow solid. LCMS (ESI, m/z): 469 [M+H]⁺; ¹H NMR (400 MHz, CD₃OD): δ 7.893-7.857 (d, 1H), 7.592-7.557 (d, 1H), 4.453 (s, 4H), 4.061-4.036 (d, 1H), 3.888 (s, 3H), 2.692 (s, 3H), 2.594-2.457 (m, 5H), 2.264-2.236 (d, 2H), 2.054-2.024 (d, 2H). 1.941 (s, 4H), 1.555-1.308 (m, 4H).

Example 42

Synthesis of compound 2-methyl-N7-((1r,4r)-4-morpholinocyclo-hexyl)thiazolo[5,4-d]pyrimidine-5,7-diamine I-43

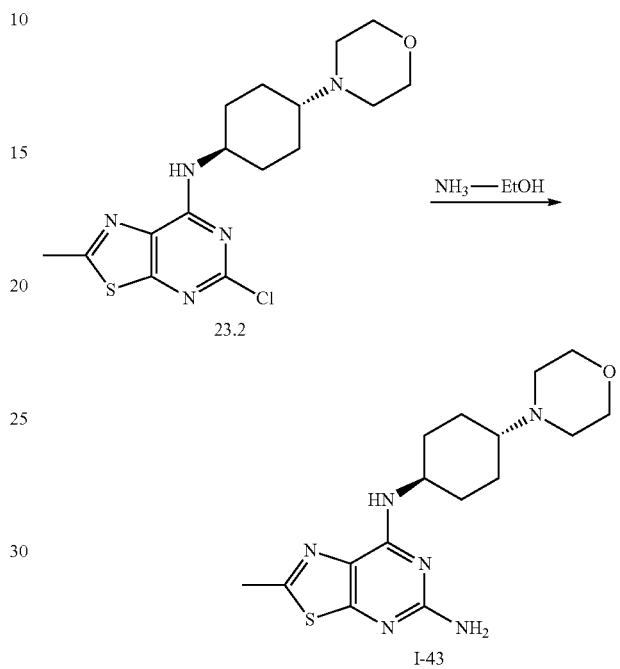

A 5 mL round-bottom flask, was charged with a solution of intermediate 23.2 (500 mg, 1.36 mmol, 1.00 equiv) in NH₃-EtOH (2 mL). The reaction mixture was irradiated in a microwave reactor for 2 hrs at 140° C. The crude product was purified using flash column chromatography to furnish 23.2 mg (5%) of compound I-43 as a yellow solid. LCMS (ES, m/z): 349 [M+H⁺]; ¹H NMR (300 MHz, CDCl₃): δ 5.612 (1H, d), 5.301 (2H, s), 4.752 (1H, s), 4.011-3.984 (4H, m), 2.666 (3H, s), 2.594 (4H, s), 2.277-2.197 (3H, m), 2.019-1.978 (2H, m), 1.497-1.218 (4H, m).

Example 43

Synthesis of N5-(1-methyl-1H-pyrazol-4-yl)-N7-((1r,4r)-4-morpholino-cyclohexyl)-2-(trifluoromethyl)thiazolo[5,4-d]pyrimidine-5,7-diamine, I-44

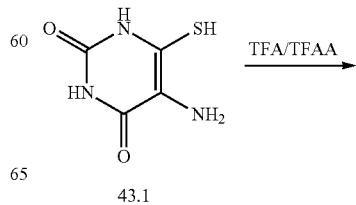

43.1

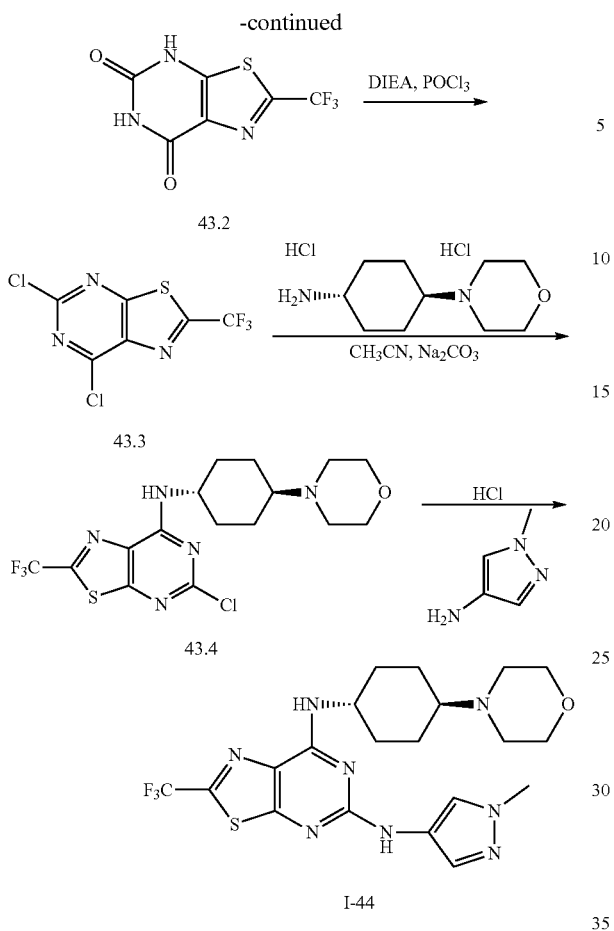

Synthesis of Compound I-44.

A 5 mL microwave tube, was charged with a solution of intermediate 43.3 (100 mg, 0.24 mmol, 1.00 equiv) in isopropanol (2 ml), 1-methyl-1H-pyrazol-4-amine (37.90 mg, 0.39 mmol, 1.20 equiv) and hydrogen chloride (14.4 mg, 1.68 equiv). The final reaction mixture was irradiated in a microwave reactor for 2 h at 145° C. The resulting mixture was concentrated under vacuum and residue was dissolved in 2 mL of H₂O. The pH value of the solution was adjusted to 10 with sodium hydroxide (1 mol/L). The solids were collected by filtration and dried in an oven to furnish 50.7 mg (44%) of I-44 as a white solid. LCMS (ES, m/z): 483.4 [M+H]$^+$; $^1$H NMR (400 MHz, CD₃OD, ppm): δ 7.90 (1H, s), 7.60 (1H, s), 4.13 (1H, s), 3.90 (3H, s), 3.78 (4H, t), 2.78 (4H, s), 2.52 (1H, s), 2.16-2.24 (4H, m), 1.50-1.58 (4H, m).

Example 44

Synthesis of 2-(difluoromethyl)-N5-(1-methyl-1H-pyrazol-4-yl)-N7-((1r,4r)-4-morpholinocyclohexyl)thiazolo[5,4-d]pyrimidine-5,7-diamine, I-45

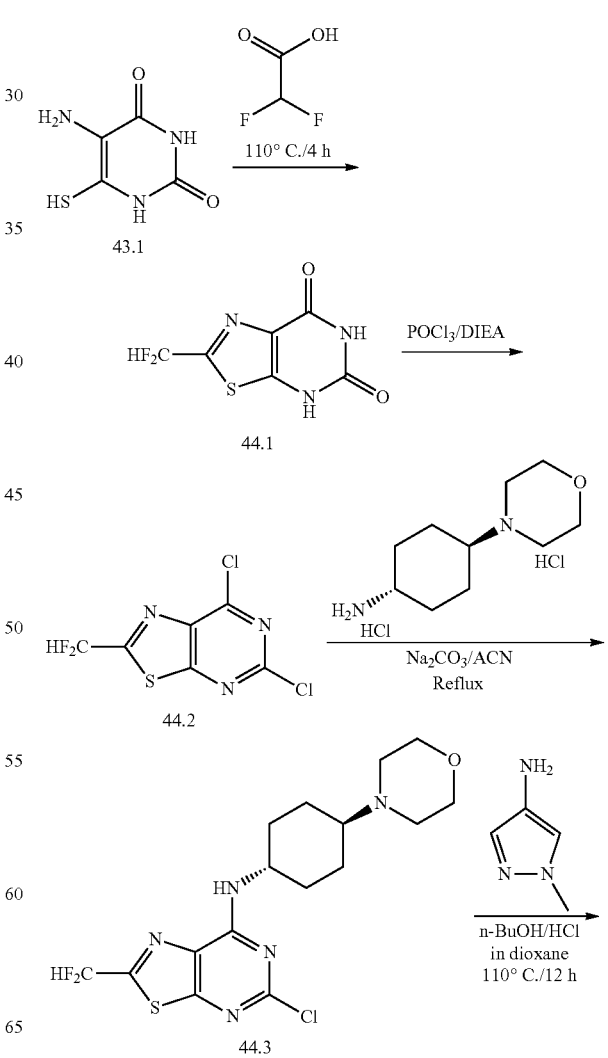

Synthesis of Intermediate 43.2.

A 5 mL vial, was charged with compound 43.1 (200 mg, 1.26 mmol, 1.00 equiv), trifluoroacetic acid (2 mL) and TFAA (0.5 mL). The reaction was stirred for 4 h at 80° C. The resulting mixture was concentrated under vacuum was washed with 1×5 mL of methylene chloride. The solids were collected by filtration to provide 200 mg (67%) of intermediate 43.2 as a yellow solid.

Synthesis of Intermediate 43.3.

Into a 10 mL round-bottom flask, were placed intermediate 43.2 (100 mg, 0.42 mmol, 1.00 equiv), DIEA (0.5 mL) and POCl₃ (2 mL). The reaction was stirred for 12 h at 100° C. The resulting mixture was concentrated under vacuum and crude purified via flash column chromatography to provide 100 mg of intermediate 43.3 as a yellow oil.

Synthesis of Intermediate 43.4.

Into a 10 mL round-bottom flask, was placed intermediate 43.3 (100 mg, 0.36 mmol, 1.00 equiv), (1r,4r)-4-(morpholin-4-yl)cyclohexan-1-amine 2 HCl (112.5 mg, 0.44 mmol, 1.20 equiv), sodium carbonate (78.4 mg, 0.74 mmol, 2.00 equiv) in CH₃CN (5 mL). The reaction was stirred for 4 h at 80° C. Upon completion of the reaction the residue was dissolved in water and the resulting solution was extracted with dichloromethane. Organic layers were combined and concentrated under vacuum to furnish 100 mg (65%) of intermediate 43.4 as a off-white solid.

141
-continued

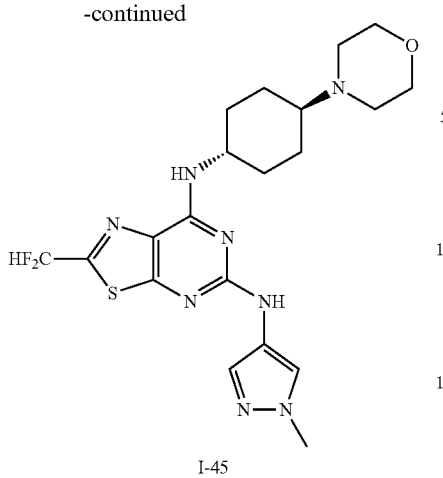

I-45

Synthesis of Compound 44.1.

A 5 mL vial, was charged with compound 43.1 (200 mg, 1.26 mmol, 1.00 equiv) in 2,2-difluoroacetic acid (2 mL). The reaction was stirred for 6 h at 110° C. The resulting mixture was concentrated under vacuum and crude washed with dichloromethane to furnish 190 mg (69%) of intermediate 44.1 as a yellow solid.

Synthesis of Compound 44.2.

Into a 10 mL round-bottom flask, were placed intermediate 44.1 (180 mg, 0.82 mmol, 1.00 equiv), DIEA (1 mL) and POCl$_3$ (4 mL). The reaction was stirred for 12 h at 100° C. The resulting mixture was concentrated under vacuum and the crude product was purified via flash column chromatography to furnish 190 mg (90%) of 44.2 as yellow oil.

Synthesis of Compound 44.3.

A 10 mL round-bottom flask, was charged with intermediate 44.2 (190 mg, 0.74 mmol, 1.00 equiv), (1r,4r)-4-(morpholin-4-yl)cyclohexan-1-amine 2 HCl (227 mg, 1.23 mmol, 1.20 equiv), sodium carbonate (159 mg, 1.50 mmol, 2.00 equiv) and CH$_3$CN (5 mL). The resulting solution was stirred for 3 h at 80° C. The residue was dissolved in water and the resulting solution was extracted with dichloromethane. The organic layers were combined and concentrated under vacuum to give 300 mg (crude) of compound 44.3 as a yellow solid.

Synthesis of Compound I-45.

Into a 25 mL round-bottom flask, were placed intermediate 44.3 (300 mg, 0.74 mmol, 1.00 equiv), 1-methyl-1H-pyrazol-4-amine hydrochloride (119 mg, 0.89 mmol, 1.20 equiv), hydrogen chloride in dioxane (0.5 mL) and n-BuOH (5 mL). The reaction was stirred for 12 h at 110° C. Upon completion of the reaction resulting mixture was concentrated under vacuum. The solution was adjusted to pH 9-10 with sodium hydroxide (2M) and resulting solids were collected by filtration. The crude product was purified by re-crystallization from methanol to furnish 208.8 mg (61%) of compound I-45 as a yellow solid. LCMS (ES, m/z): 465.4[M+H]$^+$; $^1$H NMR (300 MHz, CD$_3$OD): δ 7.86 (1H, s), 7.54 (1H, s), 6.75-7.11 (1H, t), 4.05 (1H, s), 3.85 (3H, s), 3.78 (4H, t), 2.60 (4H, s), 2.08-2.32 (5H, m), 1.29-1.47 (4H, m).

142
Example 45

Synthesis of N5-(1-methyl-1H-pyrazol-4-yl)-N7-((1r,4r)-4-morpholinocyclo-hexyl)thiazolo[5,4-d]pyrimidine-5,7-diamine, I-46

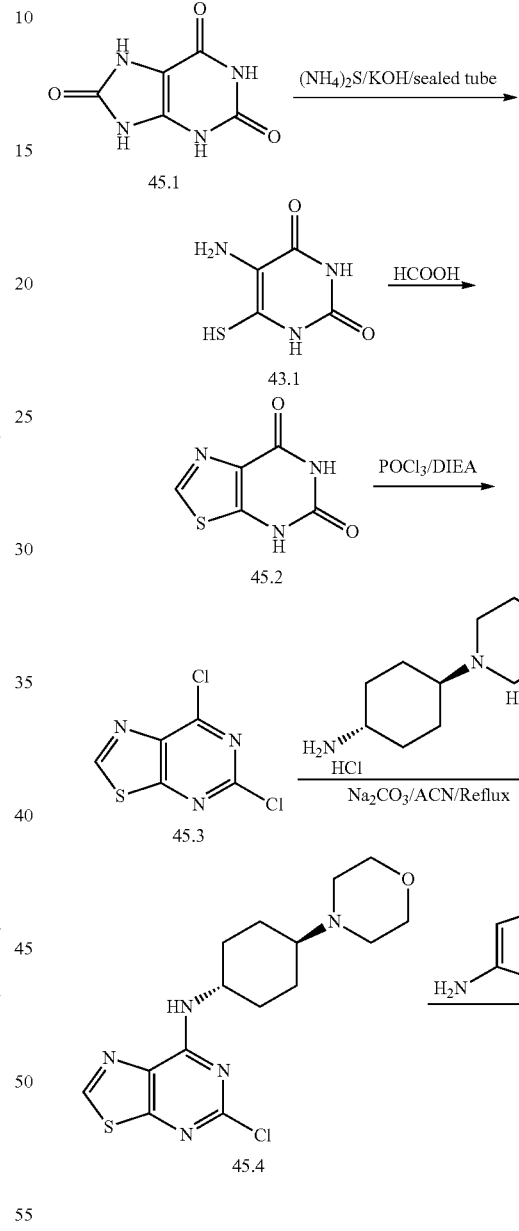

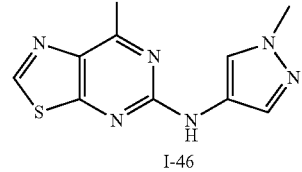

I-46

Synthesis of Compound 43.1.

Into a 100 mL sealed tube, was placed compound 45.1 (3 g, 17.63 mmol, 1.00 equiv), water (10 mL), potassium hydroxide (1 g, 17.86 mmol, 1.00 equiv), and $(NH_4)_2S$ (aq) (50 mL). The reaction was stirred for 6 h at 180° C. The reaction mixture was cooled to 0° C. with an ice/salt bath, solids were collected by filtration and washed with ethanol. This resulted in 2.5 g (89%) of compound 43.1 as a yellow solid.

Synthesis of Intermediate 45.2.

A 10 mL round-bottom flask, was charged with compound 43.1 (200 mg, 1.26 mmol, 1.00 equiv) in formic acid (1 mL). The reaction was stirred for 6 h at 80° C. The reaction mixture was cooled to 25° C. with a water/ice bath and the solids formed were collected by filtration, which resulted in 200 mg (94%) of intermediate 45.2 as an off-white solid.

Synthesis of Intermediate 45.3.

Into a 10 mL round-bottom flask, were placed intermediate 45.2 (100 mg, 0.59 mmol, 1.00 equiv), DIEA (0.5 mL) and $POCl_3$ (2 mL). The reaction was stirred for 12 h at 100° C. The resulting mixture was concentrated under vacuum and the crude product was purified using flash column chromatography to provide 100 mg (82%) of intermediate 45.3 as yellow oil.

Synthesis of Intermediate 45.4.

A 10 mL round-bottom flask was charged with intermediate 45.3 (50 mg, 0.24 mmol, 1.00 equiv.), (1r,4r)-4-(morpholin-4-yl)cyclohexan-1-amine dihydrochloride (75 mg, 0.29 mmol, 1.20 equiv.), and sodium carbonate (52 mg, 0.49 mmol, 2.00 equiv.) in $CH_3CN$ (3 mL). The reaction was stirred for 5 h at 80° C. The residue was dissolved in $H_2O$ and extracted with dichloromethane. The organic layers were combined and concentrated under vacuum to provide 80 mg (93%) of intermediate 45.4 as a yellow solid.

Synthesis of Compound I-46.

Into a 5 mL vial, were placed intermediate 45.4 (60 mg, 0.17 mmol, 1.00 equiv.), 1-methyl-1H-pyrazol-4-amine hydrochloride (27 mg, 0.20 mmol, 1.20 equiv.), n-BuOH (2 mL) and hydrogen chloride in dioxane (0.3 mL). The final reaction mixture was irradiated in a microwave reactor for 2 h at 135° C. The resulting mixture was concentrated under vacuum and crude was purified using flash column chromatography to provide 16.6 mg (24%) of compound I-46 as a brown solid. LCMS (ES, m/z): 415.3 [M+H]$^+$; $^1$H NMR (400 MHz, $CD_3OD$): δ 7.86 (1H, s), 7.54 (1H, s), 6.93 (1H, t), 4.76 (1H, m), 3.85 (3H, s), 3.67 (4H, t), 2.60 (4H, s), 2.18-2.50 (5H, m), 1.29-1.46 (4H, m).

Example 46

Synthesis of 2-isopropyl-N5-(1-methyl-1H-pyrazol-4-yl)-N7-((1r,4r)-4-morpholinocyclohexyl)thiazolo[5,4-d]pyrimidine-5,7-diamine, I-47

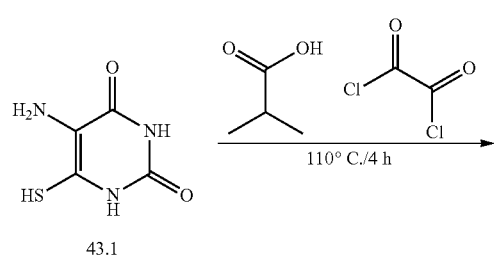

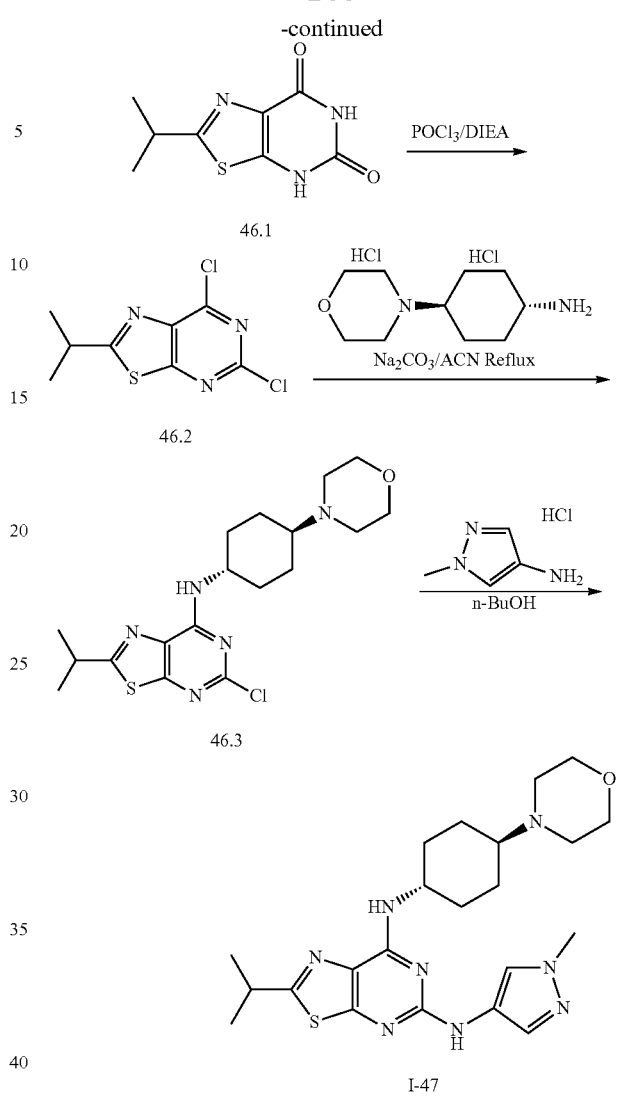

Synthesis of Intermediate 46.1.

Into a 5 mL vial, were placed 2-methylpropanoic acid (1 mL), oxalic dichloride (0.2 mL), and compound 43.1 (200 mg, 1.26 mmol, 1.00 equiv). The reaction was stirred for 4 h at 110° C. The solids were collected by filtration to furnish 150 mg (57%) of intermediate 46.1 as a yellow solid.

Synthesis of Intermediate 46.2.

Into a 10 mL round-bottom flask, were placed intermediate 46.1 (150 mg, 0.71 mmol, 1.00 equiv), DIEA (0.5 mL), $POCl_3$ (2.5 mL). The reaction was stirred for 12 h at 100° C. The resulting mixture was concentrated under vacuum and the crude product was purified using flash column chromatography to furnish 110 mg (62%) of intermediate 46.2 as yellow oil.

Synthesis of Intermediate 46.3.

A 25 mL round-bottom flask was charged with intermediate 46.2 (67 mg, 0.27 mmol, 1.00 equiv), $CH_3CN$ (3 mL), $Na_2CO_3$ (67 mg, 0.63 mmol, 2.00 equiv), and (1r,4r)-4-(morpholin-4-yl)cyclohexan-1-amine hydrochloride (97 mg, 0.38 mmol, 1.20 equiv). The reaction was stirred for 16 hours at 80° C. in an oil bath. Upon completion solvents were removed under vacuum and resulting mixture was diluted with 5 mL of water and extracted with 3×20 mL of ethyl acetate. The organic layers were combined, dried over anhydrous sodium sulfate and concentrated under vacuum to furnish 100 mg (94%) of intermediate 46.3 as an orange solid.

Synthesis of Compound I-47.

A 25 mL round-bottom flask was charged with intermediate 46.3 (462 mg, 1.17 mmol, 1.00 equiv), n-BuOH (5 mL), 1-methyl-1H-pyrazol-4-amine hydrochloride (187 mg, 1.40 mmol, 1.20 equiv) and HCl in 1,4-dioxane (0.5 ml). The reaction was stirred for 16 hours at 110° C. in an oil bath. The resulting mixture was concentrated under vacuum and diluted with 0.5 mL of sodium carbonate (1 mol/L). To this mixture was added 1 mL of methanol, and the resulting solution was extracted with 3×20 mL of $CHCl_3/IPA=3:1$. The organic layers were combined and dried over anhydrous sodium sulfate and concentrated under vacuum. The crude product was purified using preparative HPLC to furnish 45.7 mg (9%) of compound I-47 as a white solid. LCMS (ES, m/z): 457 [M+H]$^+$, $^1$H NMR (300 MHz, CD$_3$OD): δ 7.869 (1H, s), 7.564 (1H, s), 4.868~4.597 (1H, s), 4.045~4.054 (1H, s), 3.888 (3H, s) 3.736 (4H, t), 2.559~2.658 (4H, s), 2.206~2.423 (3H, s), 2.041~2.103 (2H, m), 1.311~1.534 (10H, m).

Example 47

Synthesis of 2-(1,1-difluoroethyl)-N5-(1-methyl-1H-pyrazol-4-yl)-N7-((1r,4r)-4-morpholinocyclohexyl)thiazolo[5,4-d]pyrimidine-5,7-diamine, I-48

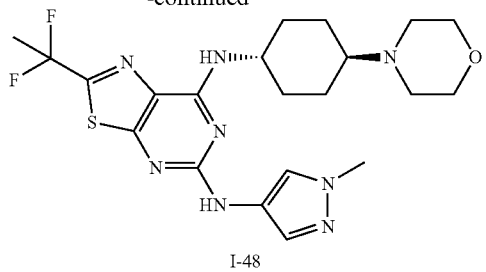

I-48

Synthesis of Compound 47.1.

Into a 5 mL vial were placed intermediate 43.1 (150 mg, 0.94 mmol, 1.00 equiv), 2,2-difluoropropanoic acid (1 mL) and oxalyl chloride (0.5 mL). The reaction was stirred for 4 h at 110° C. The solids were collected by filtration to yield 100 mg (46%) of intermediate 47.1 as an off-white solid.

Synthesis of Compound 47.2.

A 10 mL round-bottom flask was charged with intermediate 47.1 (100 mg, 0.43 mmol, 1.00 equiv), DIEA (0.3 mL) and POCl$_3$ (1 mL). The reaction was stirred for 12 h at 100° C. The resulting mixture was concentrated under vacuum and the crude product was purified using flash column chromatography to furnish 65 mg (56%) of intermediate 47.2 as an off-white solid.

Synthesis of Intermediate 47.3.

Into a 10 mL round-bottom flask were placed intermediate 47.2 (50 mg, 0.19 mmol, 1.00 equiv), (1r,4r)-4-(morpholin-4-yl)cyclohexan-1-amine (57 mg, 0.31 mmol, 1.20 equiv), sodium carbonate (39 mg, 2.00 equiv) and CH$_3$CN (2 mL). The reaction was stirred for 4 h at 80° C. The resulting residue was dissolved in water and extracted with dichloromethane. The organic layers were combined and concentrated under vacuum to provide 80 mg (crude) of intermediate 47.3 as an off-white solid.

Synthesis of Compound I-48.

A 10 mL round-bottom flask was charged with intermediate 47.3 (60 mg, 0.14 mmol, 1.00 equiv), 1-methyl-1H-pyrazol-4-amine hydrochloride (23 mg, 0.17 mmol, 1.20 equiv), hydrogen chloride in dioxane (0.1 mL) and n-BuOH (2 mL). The reaction was stirred for 12 h at 110° C. The resulting mixture was concentrated under vacuum and the crude product was purified using preparative HPLC to furnish 8.8 mg (13%) of compound I-48 as a yellow solid. LCMS: (ES, m/z): 479.2 [M+H]$^+$; $^1$H NMR: (400 MHz, CD$_3$OD): δ 7.90 (1H, s), 7.59 (1H, s), 4.12-4.17 (1H, m), 3.94 (3H, s), 3.77 (4H, t), 2.74 (4H, m), 2.46 (1H, m), 2.05-2.24 (7H, m), 1.44-1.57 (4H, m).

Example 48

Synthesis of compound 2-cyclopropyl-N5-(1-methyl-1H-pyrazol-4-yl)-N7-((1r,4r)-4-morpholinocyclohexyl)thiazolo[5,4-d]pyrimidine-5,7-diamine I-49

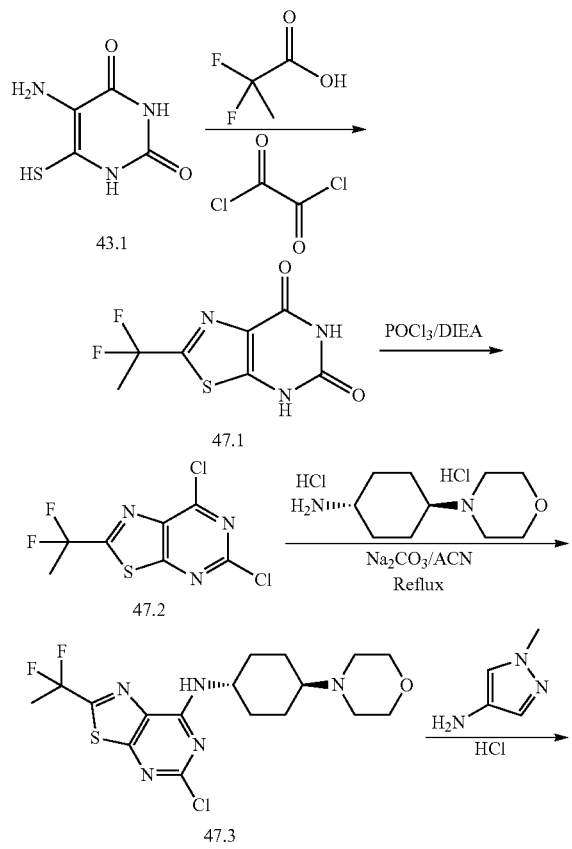

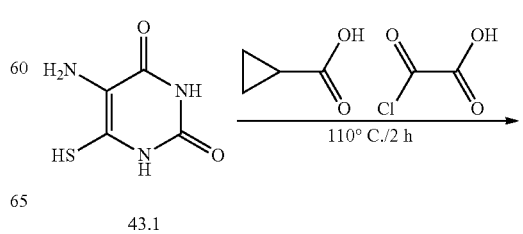

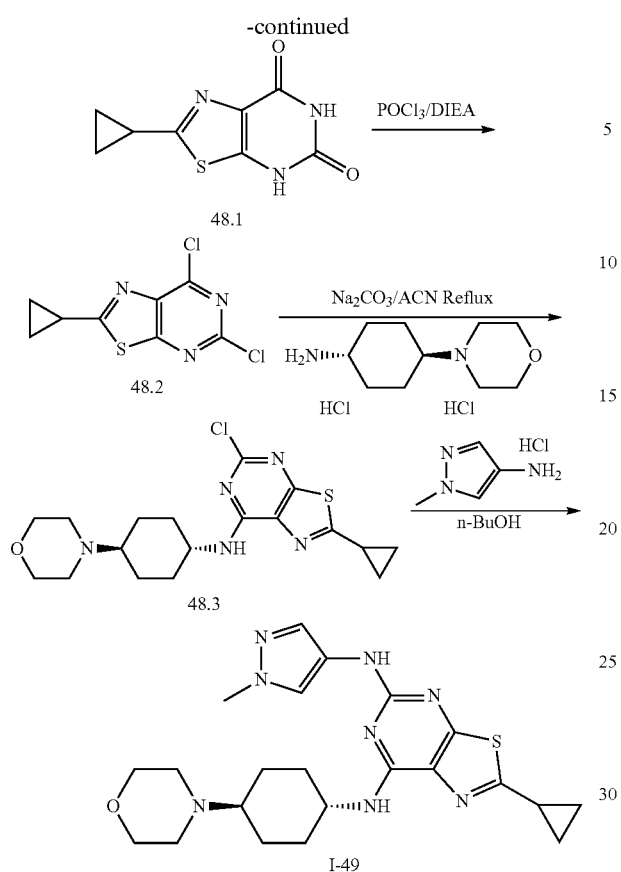

Synthesis of Compound I-49.

Into a 25 mL round-bottom flask were placed intermediate 48.3 (330 mg, 0.84 mmol, 1.00 equiv), n-BuOH (10 mL) and 1-methyl-1H-pyrazol-4-amine hydrochloride (170 mg, 1.27 mmol, 1.20 equiv). The reaction was stirred overnight at 110° C. in an oil bath. The resulting mixture was concentrated under vacuum, diluted with sodium carbonate (1 mol/L) and extracted with 3×20 mL of DCE/IPA (3:1). The organic layers were combined, dried over anhydrous sodium sulfate and concentrated under vacuum. The crude product was purified by preparative HPLC to furnish 81.7 mg (21%) of compound I-49 as an off-white solid. LCMS: 455 [M+H]$^+$; $^1$H NMR: (300 MHz, CD$_3$OD): δ 7.518-7.817 (2H, s), 3.998 (1H, s), 3.836 (1H, d), 3.888 (4H, s), 3.508~3.781 (4H, t), 2.606~2.636 (4H, t), 2.206~2.321 (6H, m), 1.174~1.490 (8H, m).

Example 49

Synthesis of 3-ethyl-N-((1r,4r)-4-morpholinocyclohexyl)isothiazolo[5,4-d]pyrimidin-4-amine, I-20

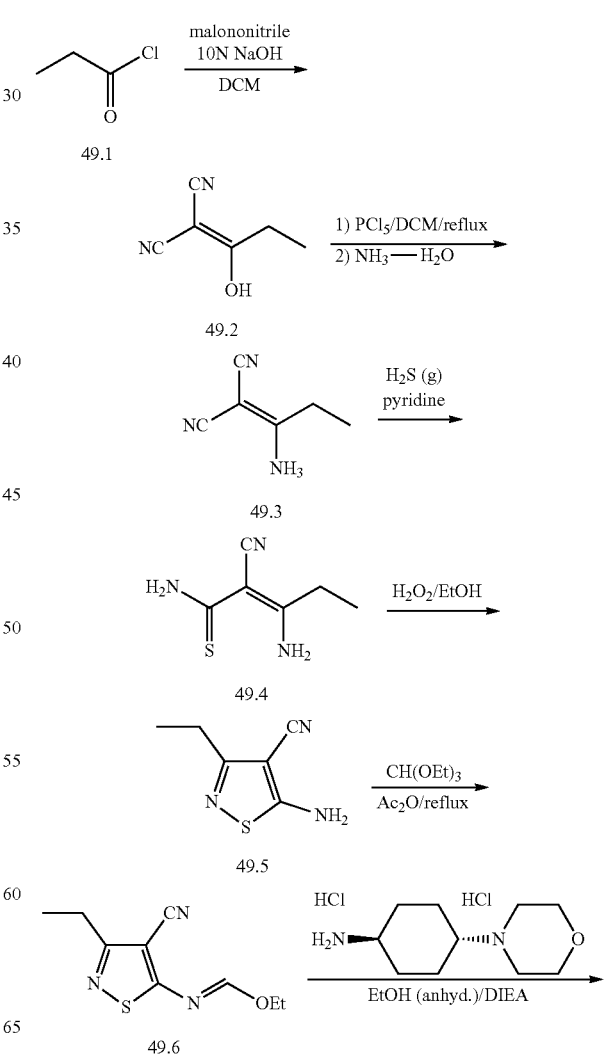

Synthesis of Intermediate 48.1.

Into a 25 mL round-bottom flask were placed intermediate 43.1 (500 mg, 3.14 mmol, 1.00 equiv), cyclopropanecarboxylic acid (5 mL) and oxalic dichloride (1.25 mL). The reaction was stirred for 2 h at 110° C. in an oil bath. Solids were collected and washed with methanol to furnish 350 mg (53%) of intermediate 48.1 as an orange solid.

Synthesis of Intermediate 48.2.

Into a 25 mL round-bottom flask were placed intermediate 48.1 (350 mg, 1.67 mmol, 1.00 equiv), DIEA (1.25 mL) and POCl$_3$ (10 mL). The reaction was stirred overnight at 110° C. in an oil bath. The resulting mixture was concentrated under vacuum and diluted with 30 mL of sodium bicarbonate (2M). The resulting solution was extracted with 3×20 mL of dichloromethane, and the organic layers were combined, dried over anhydrous sodium sulfate and concentrated under vacuum. The crude product was purified using flash column chromatography to furnish 250 mg (61%) of intermediate 48.2 as an orange solid.

Synthesis of Intermediate 48.3.

Into a 25 mL round-bottom flask were placed intermediate 48.2 (250 mg, 1.02 mmol, 1.00 equiv), CH$_3$CN (10 mL), Na$_2$CO$_3$ (216 mg, 2.02 mmol, 2.00 equiv) and (1r,4r)-4-(morpholin-4-yl)cyclohexan-1-amine (313 mg, 1.70 mmol, 1.20 equiv). The reaction was stirred overnight at 80° C. in an oil bath. The resulting mixture was concentrated under vacuum and diluted with 10 mL of water. The resulting solution was extracted with 3×50 mL of ethyl acetate, and the organic layers were combined, dried over anhydrous sodium sulfate and concentrated under vacuum to give 330 mg (82%) of intermediate 48.3 as a reddish solid.

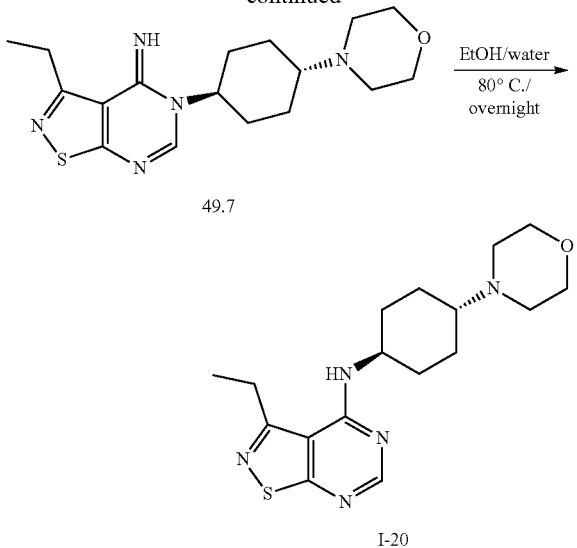

49.7

I-20

Synthesis of Intermediate 49.2.

Malononitrile (7.1 g, 1.00 equiv) was added to a 10 M sodium hydroxide (21.6 mL, 2.00 equiv) at 0° C. and stirred for 1 h at this temperature. A solution of compound 49.1 (10.0 g, 108.08 mmol, 1.00 equiv) in dichloromethane (200 mL) was added dropwise with stirring at 0° C. and stirred overnight at room temperature. The solution was adjusted to pH ~5.0 with 2 M hydrochloric acid, and extracted with 3×200 mL of ethyl acetate. The combined organic layers were dried over anhydrous sodium sulfate and concentrated under vacuum to give 7 g (crude) of product. The aqueous layer was concentrated and washed with 3×100 mL ethyl acetate, and the organic layers were combined and concentrated under reduced pressure to give 4.78 g pure intermediate 49.2.

Synthesis of Intermediate 49.3.

To a solution of intermediate 49.2 (4.78 g, 39.14 mmol, 1.00 equiv) in dichloromethane (50 mL) was added $PCl_5$ (12.2 g, 58.59 mmol, 1.50 equiv) at room temperature. The reaction was stirred overnight at 50° C. in an oil bath under nitrogen. The resulting mixture was concentrated under vacuum to give 5.0 g (crude) of 2-(1-chloropropylidene)propanedinitrile as light yellow oil. The crude 2-(1-chloropropylidene)propanedinitrile (5.0 g) was added to 300 mL of ammonia and stirred for 30 min at room temperature. The resulting solution was extracted with 3×100 mL of dichloromethane. The combined organic layers were dried over anhydrous sodium sulfate and concentrated under reduced pressure to afford 3.08 g (crude) of intermediate 49.3 as a light yellow solid; $^1$H NMR (300 MHz, DMSO) δ 8.63 (s, 1H), 8.41 (s, 1H), 2.36 (q, 2H), 1.14 (t, 3H).

Synthesis of Intermediate 49.4.

$H_2S$ (g) was passed for 2 h into a solution of intermediate 49.3 (300 mg, 2.48 mmol, 1.00 equiv) in pyridine (5 mL) and TEA (0.35 mL, 1.00 equiv) at 40° C. Upon completion of the reaction the resulting solution was poured into 100 mL of cooled water and extracted with 3×20 mL of ethyl acetate. The organic layers were combined, dried over anhydrous sodium sulfate, and concentrated under vacuum to give 330 mg (crude) of intermediate 49.4 as a light yellow solid; $^1$H NMR (400 MHz, DMSO) δ 11.62 (s, 1H), 8.93 (s, 1H), 8.55 (s, 1H), 7.75 (s, 1H), 2.46 (q, 2H), 1.18 (t, 3H).

Synthesis of Intermediate 49.5.

A solution of intermediate 49.4 (2.43 g, 15.66 mmol, 1.00 equiv) in ethanol (20 mL) was added 37% $H_2O_2$ (1.96 g) and the resulting solution was stirred for 3 h at room temperature. The resulting solution was diluted with $H_2O$, and extracted with 3×80 mL of ethyl acetate. Combined organic layers were washed with saturated aqueous $NaHSO_3$, brine and dried over sodium sulfate and concentrated under vacuum to give 2.4 g (crude) of intermediate 49.5 as a light yellow solid. LCMS (ES, m/z): 154 [M+H]$^+$; $^1$H NMR (300 MHz, DMSO) δ 7.98 (br s, 2H), 2.59 (q, 2H), 1.17 (t, 3H).

Synthesis of Intermediate 49.6.

To a solution of intermediate 49.5 (200 mg, 1.31 mmol, 1.00 equiv) in acetyl acetate (2 mL) was added triethoxymethane (1 mL) and the resulting solution was stirred for 3 h at 85° C. in an oil bath. The resulting mixture was concentrated under vacuum and the residue was washed with petroleum ether. The solids were collected by filtration to give 130 mg (48%) of intermediate 49.6 as a brown solid.

Synthesis of Intermediate 49.7.

Into a 50-mL round-bottom flask containing a solution of intermediate 49.6 (130 mg, 0.62 mmol, 1.00 equiv) in ethanol (2 mL) was added trans-4-(morpholin-4-yl)cyclohexan-1-amine dihydrochloride (172.6 mg, 0.67 mmol, 1.07 equiv) and triethylamine (2 mL). The reaction was stirred for 2 h at room temperature. The resulting mixture was concentrated under vacuum and the crude product was purified by preparative HPLC to give 70 mg (33%) of intermediate 49.7 as a white solid. LCMS (ES, m/z): 348 [M+H]$^+$; $^1$H NMR (300 MHz, CDCl$_3$) δ 7.83 (s, 1H), 7.25 (br s, 1H), 5.08-4.92 (m, 1H), 3.73 (t, 4H), 3.07 (q, 2H), 2.59 (t, 4H), 2.45-2.30 (m, 1H), 2.17 (d, 2H), 2.10 (d, 2H), 1.64-1.45 (m, 4H), 1.40 (t, 3H).

Synthesis of Compound I-20.

A solution of intermediate 49.7 (70 mg, 0.20 mmol, 1.00 equiv) in ethanol (5 mL) and water (10 mL) was stirred overnight at 80° C. The resulting solution was concentrated under vacuum and the crude product was purified by preparative HPLC to give 40 mg (57%) of compound I-20 as a white solid. LCMS (ES, m/z): 348 [M+H]$^+$; $^1$H NMR 300 MHz, CD$_3$OD) δ 8.41 (s, 1H), 4.35-4.22 (m, 1H), 3.73 (t, 4H), 3.23 (q, 2H), 2.64 (t, 4H), 2.45-2.32 (m, 1H), 2.21 (d, 2H), 2.09 (d, 2H), 2.05 (d, 2H), 1.65-1.42 (m, 4H), 1.41 (t, 3H).

Example 50

Synthesis of compound 2-(tert-butyl)-N5-(1-methyl-1H-pyrazol-4-yl)-N7-((1r,4r)-4-morpholinocyclohexyl)thiazolo[5,4-d]pyrimidine-5,7-diamine, I-50

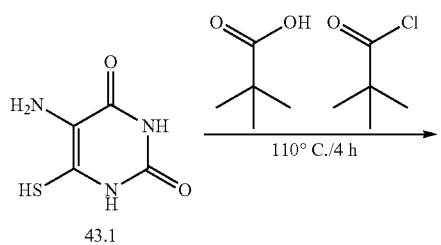

43.1

-continued

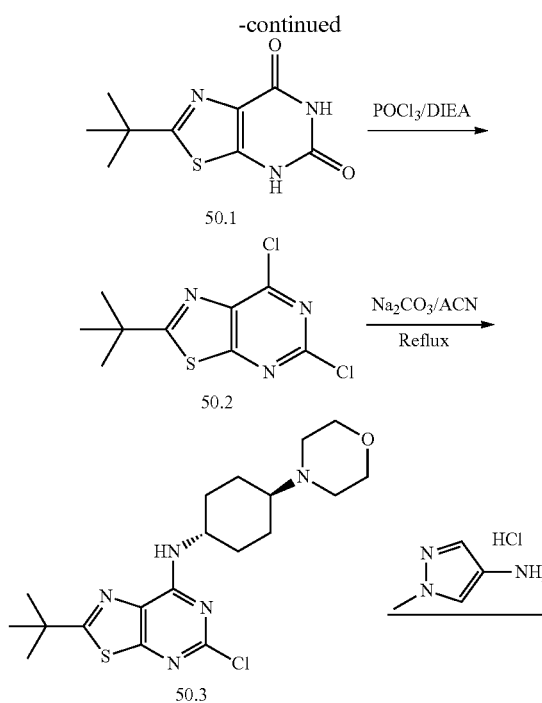

Synthesis of Intermediate 50.1.

Into a 25 mL round-bottom flask, were placed compound 43.1 (150 mg, 0.94 mmol, 1.00 equiv), 2,2-dimethylpropanoic acid (2 mL) and 2,2-dimethyl-propanoyl chloride (0.25 mL). The reaction was stirred for 2 h at 110° C. in an oil bath. The solids were collected by filtration and washed with dichloromethane to provide 130 mg (61%) of compound 50.1 as an orange solid.

Synthesis of Intermediate 50.2.

Into a 25 mL round-bottom flask, was placed intermediate 50.1 (130 mg, 0.58 mmol, 1.00 equiv), DIEA (3 mL) and phosphoroyl trichloride (0.3 mL). The reaction was stirred overnight at 110° C. in an oil bath. The resulting solution was diluted with NaHCO₃ (2M), extracted with dichloromethane, dried, and concentrated under vacuum. The crude was purified using flash column chromatography to give 57 mg (38%) of intermediate 50.2 as an orange solid.

Synthesis of Intermediate 50.3.

Into a 25 mL round-bottom flask, was placed intermediate 50.2 (57 mg, 0.22 mmol, 1.00 equiv), Na₂CO₃ (46 mg, 0.43 mmol, 2.00 equiv), (1r,4r)-4-(morpholin-4-yl)cyclohexan-1-amine dihydrochloride (67 mg, 0.36 mmol, 1.20 equiv) and acetonitrile (3 mL). The reaction was stirred overnight at 80° C. in an oil bath. The resulting mixture was concentrated under vacuum then washed with 1×10 mL of water. The resulting solution was extracted with 3×20 mL of dichloromethane, and the organic layers were combined and concentrated under vacuum to provide 83 mg (93%) of intermediate 50.3 as an orange solid.

Synthesis of Compound I-50.

Into a 20 mL round-bottom flask under nitrogen, were placed intermediate 50.3 (83 mg, 0.21 mmol, 1.00 equiv), butan-1-ol (2 mL) and 1-methyl-1H-pyrazol-4-amine hydrochloride (32 mg, 0.39 mmol, 1.20 equiv). The reaction was stirred overnight at 110° C. in an oil bath, then concentrated under vacuum. The resulting solution was diluted with 0.5 mL of sodium bicarbonate and concentrated under vacuum. The resulting solution was extracted with DCM/IPA (3/1), and the organic layers were combined and concentrated under vacuum. The crude product was purified using flash column chromatography to furnish 11.4 mg (12%) of compound I-50 as a brown solid. LCMS; (ES, m/z): 471 [M+H]⁺; ¹H NMR (400 MHz, CD₃OD): δ 7.828 (s, 1H), 7.526 (s, 1H), 3.842 (s, 3H), 3.679-3.710 (m, 4H), 2.596-2.626 (m, 4H), 2.216 (s, 3H), 2.067-2.082 (d, 2H), 1.395-1.460 (m, 13H).

Example 51

Synthesis of N7-((1r,4r)-4-morpholinocyclohexyl)-N5-(1-(tetrahydro-2H-pyran-4-yl)-1H-pyrazol-4-yl) thiazolo[5,4-d]pyrimidine-5,7-diamine I-51

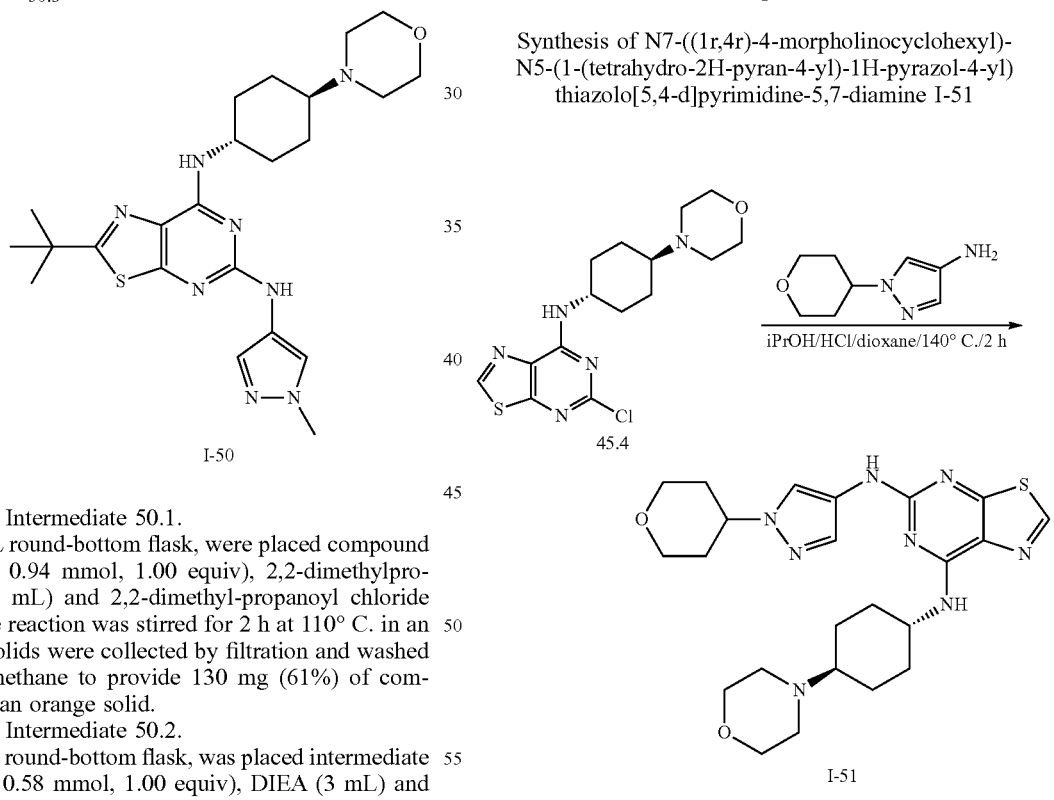

A 5 ml, sealed tube, was charged with a solution of intermediate 45.4 (150 mg, 0.42 mmol, 1.00 equiv) in isopropanol (3.5 mL), 1-(oxan-4-yl)-1H-pyrazol-4-amine (142.8 mg, 0.85 mmol, 2.00 equiv), and a solution of hydrogen chloride (0.1 mL) in dioxane (0.1 mL). The final reaction mixture was irradiated in a microwave reactor for 2 h at 140° C. The resulting solids were collected by filtration. The residue was dissolved in 10 mL of water and the solution was adjusted to pH 9 using sodium carbonate solution (1M). The solids were collected by filtration, washed by methanol and dried in an oven under reduced pressure to furnish 72.6 mg (35%) of compound I-51 as an off-white solid. LCMS (ES, m/z): 485 [M+H]+; 1H NMR (400 MHz, d6-DMSO): δ9.134 (s, 1H), 8.739 (s, 1H), 7.937 (s, 1H), 7.711 (s, 1H), 7.477 (s, 1H), 4.333 (s, 1H), 3.974-3.944 (d, 3H), 3.569-3.558 (d, 4H), 3.468-3.440 (t, 2H), 3.316-3.292 (d, 4H), 2.221-2.211 (t, 1H), 1.956-1.901 (m, 8H), 1.231-1.535 (m, 4H).

Example 52

Synthesis of N7-((1r,4r)-4-morpholinocyclohexyl)-N5-(1-((tetrahydro-2H-pyran-4-yl)methyl)-1H-pyrazol-4-yl)thiazolo[5,4-d]pyrimidine-5,7-diamine, I-52

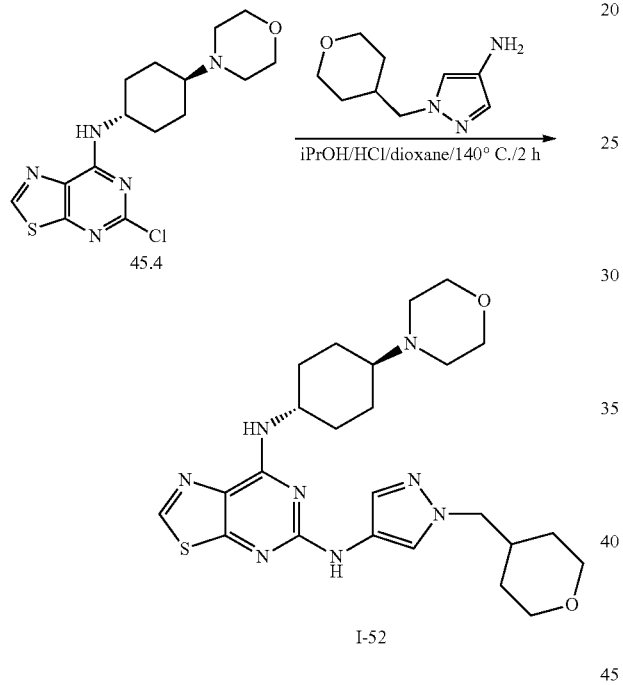

A 5 mL microwave vial, was charged with a solution of intermediate 45.4 (150 mg, 0.42 mmol, 1.00 equiv) in isopropanol (3.5 mL), 1-(oxan-4-ylmethyl)-1H-pyrazol-4-amine (153.8 mg, 0.85 mmol, 2.00 equiv) and a solution of hydrogen chloride in dioxane (0.1 mL). The final reaction mixture was irradiated in a microwave reactor for 3 h at 140° C. The reaction was concentrated under vacuum and the residue was dissolved in 10 mL of water. The solution was adjusted to pH 9 with sodium carbonate (1M). The resulting solution was extracted with 3×30 mL of chloroform, and the organic layers were combined and dried over anhydrous sodium sulfate and concentrated under vacuum. The crude product was purified by preparative HPLC chromatography to give 112.0 mg (53%) of compound I-52 as an off-white solid. LCMS (ES, m/z): 499 [M+H]+; 1H NMR: (400 MHz, d6-DMSO): δ 9.13 (s, 1H), 8.74 (s, 1H), 7.91 (s, 1H), 7.75 (s, 1H), 7.46 (s, 1H), 3.90-4.08 (t, 3H), 3.71-3.89 (d, 2H), 3.18-3.31 (m, 7H), 2.16-2.27 (t, 1H), 1.88-2.08 (m, 4H), 1.13-1.58 (m, 8H).

Example 53

Synthesis of N5-(1-isopropyl-1H-pyrazol-4-yl)-N7-((1r,4r)-4-morpholino-cyclohexyl)thiazolo[5,4-d]pyrimidine-5,7-diamine I-53

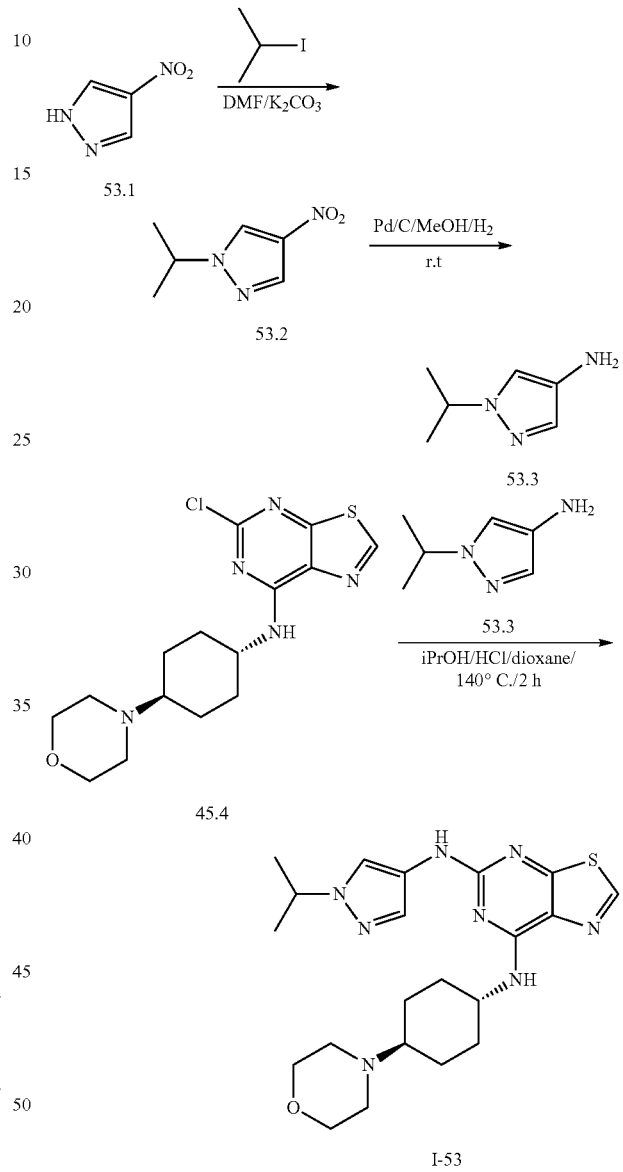

Synthesis of Intermediate 53.2.

A 100 mL round-bottom flask, was charged with a solution of 4-nitro-1H-pyrazole (2 g, 17.69 mmol, 1.00 equiv) in N,N-dimethylformamide (60 mL), 2-iodopropane (4 mL) and K2CO3 (4.88 g, 35.05 mmol, 2.00 equiv). The reaction was stirred for 2 h at 70° C. in an oil bath. The resulting solution was extracted with 5×100 mL of ethyl acetate, and the organic layers were combined and dried over anhydrous sodium sulfate and concentrated under vacuum to give 2.65 g (97%) of intermediate 53.2 as a yellow solid.

Synthesis of Intermediate 53.3.

Into a 25 mL round-bottom flask were placed a solution of intermediate 53.3 (200 mg, 1.29 mmol, 1.00 equiv) in methanol (4 mL) and palladium on charcoal (40 mg). To the above mixture H$_2$ (g) was introduced, and the reaction was stirred for 3 h at room temperature. The solids were filtered and resulting filtrate was concentrated under vacuum to provide 154 mg (95%) of intermediate 53.3 as pink oil.

Synthesis of Compound I-53.

Into a 5 mL microwave vial were placed a solution of intermediate 45.4 (150 mg, 0.42 mmol, 1.00 equiv) in isopropanol (3.5 mL), intermediate 53.3 (106.2 mg, 0.85 mmol, 2.00 equiv) and a solution of hydrogen chloride in dioxane (0.1 mL). The final reaction mixture was irradiated with in a microwave reactor for 3 h at 140° C. The solution was adjusted to pH 9 with sodium carbonate (1M). The resulting mixture was concentrated under vacuum. The crude product was purified using preparative HPLC to furnish 66.7 mg (36%) of compound I-53 as a brown solid. LCMS (ES, m/z): 443 [M+H]$^+$; $^1$H NMR: (400 MHz, d6-DMSO): δ 9.086 (s, 1H), 8.736 (s, 1H), 7.879 (s, 1H), 7.660-7.619 (s, 1H), 7.478 (s, 1H), 4.482-4.416 (m, 1H), 4.038-4.012 (t, 1H), 3.578 (s, 4H), 2.502 (s, 4H), 2.268-2.235 (d, 1H), 2.019-1.894 (m, 4H), 1.559-1.521 (d, 2H), 1.479-1.423 (d, 3H), 1.401-1.345 (d, 3H), 1.307-1.266 (d, 2H).

Example 54

Synthesis of 2-(4-((7-(((1r,4r)-4-morpholinocyclohexyl)amino)thiazolo[5,4-d]pyrimidin-5-yl)amino)-1H-pyrazol-1-yl)ethan-1-ol, I-54

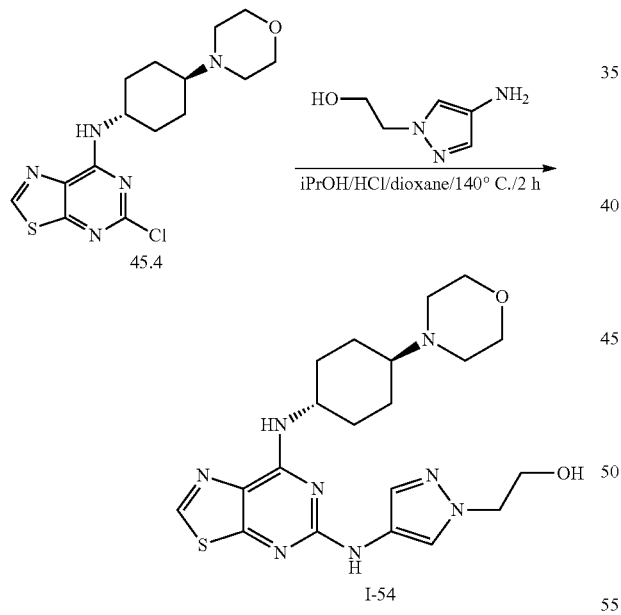

Into a 5 mL microwave vial were placed a solution of intermediate 45.4 (150 mg, 0.42 mmol, 1.00 equiv) in isopropanol (3.5 mL), 2-(4-amino-1H-pyrazol-1-yl)ethan-1-ol (107.9 mg, 0.85 mmol, 2.00 equiv) and a solution of hydrogen chloride in dioxane (0.1 mL). The final reaction mixture was irradiated in a microwave reactor for 3 h at 140° C. The resulting mixture was concentrated under vacuum and the residue was dissolved in 10 mL of water. The solution was adjusted to pH 9 with sodium carbonate (1M). The resulting solution was extracted with 3×30 mL of chloroform: isopropanol=3:1, and the organic layers were combined and dried over anhydrous sodium sulfate and concentrated under vacuum. The crude product was purified using preparative HPLC to provide 81.0 mg (43%) of compound I-54 as a brown solid. LC MS (ES, m/z): 445; [M+H]$^+$; $^1$H NMR (400 MHz, d6-DMSO): δ 9.104 (s, 1H), 8.738 (s, 1H), 7.894 (s, 1H), 7.657 (s, 1H), 7.504 (s, 1H), 4.881 (s, 1H), 4.103-4.008 (m, 3H), 3.717 (s, 2H), 3.580 (s, 4H), 2.502 (s, 4H), 2.266-2.234 (d, 1H), 1.988-1.890 (m, 4H), 1.554-1.472 (t, 2H), 1.436-1.369 (t, 2H).

Example 55

Synthesis of 2-methyl-N-(1-methyl-1H-pyrazol-4-yl)-7-(((1r,4r)-4-morpholino-cyclohexyl)oxy)thiazolo[5,4-d]pyrimidin-5-amine, I-55

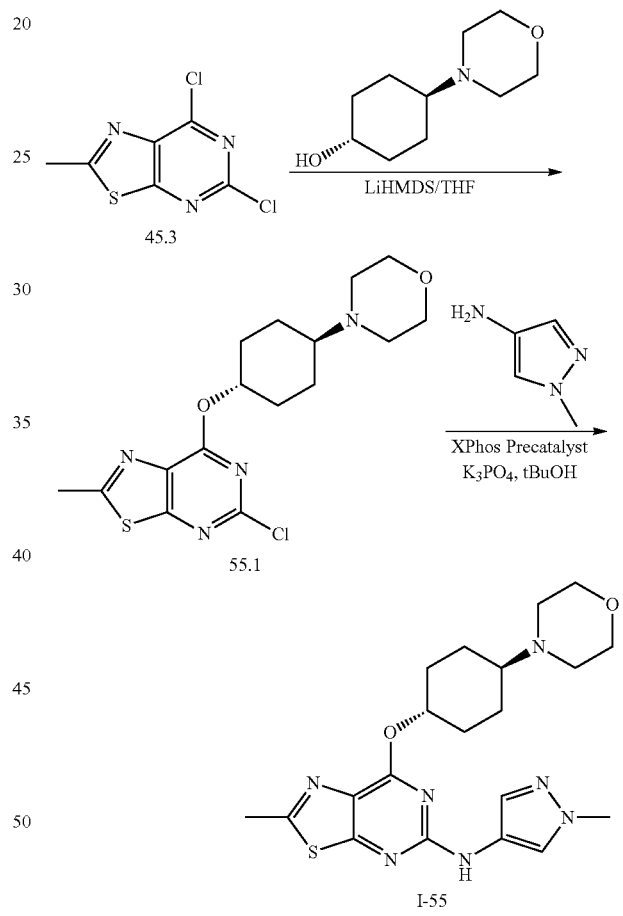

Synthesis of Intermediate 55.1.

Into a 250 mL 3-necked round-bottom flask purged and maintained with an inert atmosphere of nitrogen, was placed LiHDMS (10 mL, 1.00 equiv), 4-(morpholin-4-yl)cyclohexan-1-ol (1.86 g, 10.04 mmol, 1.00 equiv), and tetrahydrofuran (60 mL). The above mixture was stirred for 1 hour. Intermediate 45.3 (2.2 g, 10.00 mmol, 1.00 equiv) was added. The reaction was stirred overnight at room temperature. The resulting mixture was concentrated under vacuum and crude purified using flash column chromatography to furnish 1.6 g (43%) of intermediate 55.1 as a dark green solid.

Synthesis of Compound I-55.

Into a 100 mL round-bottom flask under inert atmosphere were placed intermediate 55.1 (200 mg, 0.54 mmol, 1.00 equiv), 2-methylpropan-2-ol (10 mL), potassium phosphate (346 mg, 1.63 mmol, 3.00 equiv), 1-methyl-1H-pyrazol-4-amine hydrochloride (109 mg, 1.12 mmol, 1.50 equiv), and $3^{rd}$ generation xphos precatalyst (43 mg, 0.05 mmol, 0.10 equiv). The resulting solution was stirred overnight at room temperature. The resulting mixture was concentrated under vacuum and crude was purified using preparative HPLC to furnish 84.4 mg (36%) of compound I-55 as a pink solid. LCMS (ES, m/z): 430 [M+H]$^+$; $^1$H NMR (400 MHz, CD$_3$OD): δ 7.531 (s, 1H), 7.877~7.913 (d, 1H), 5.156~5.225 (m, 1H), 3.850~3.886 (d, 3H), 3.676~3.707 (t, 4H), 2.682~2.725 (d, 3H), 2.585~2.616 (t, 4H), 2.289~2.360 (m, 3H), 2.069~2.113 (d, 2H), 1.504~1.596 (t, 2H), 1.596~1.681 (t, 2H).

Example 56

Synthesis of N-(1-ethyl-1H-pyrazol-4-yl)-2-methyl-7-(((1r,4r)-4-morpholino-cyclohexyl)oxy)thiazolo[5,4-d]pyrimidin-5-amine, I-56

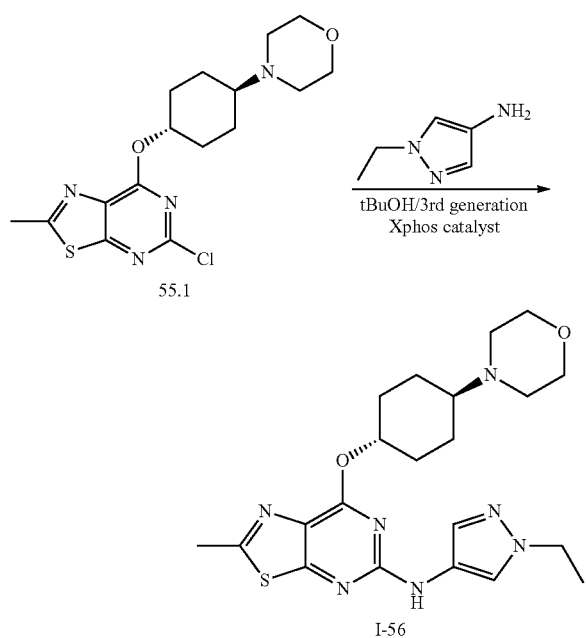

Into a 25 mL round-bottom flask purged and maintained with an inert atmosphere of nitrogen, were placed intermediate 55.1 (200 mg, 0.54 mmol, 1.00 equiv), potassium phosphate (346 mg, 1.63 mmol, 3.00 equiv), 1-ethyl-1H-pyrazol-4-amine hydrochloride (120 mg, 0.82 mmol, 1.50 equiv), 2-methylpropan-2-ol (5 mL) and Xphos precatalyst (43 mg, 0.05 mmol, 0.10 equiv). The reaction was stirred overnight at room temperature. The resulting mixture was concentrated under vacuum and the crude product was purified using preparative HPLC to furnish 38.1 mg (16%) of compound I-56 as a pink solid. LCMS (ES, m/z): 444 [M+H]$^+$; $^1$H NMR (400 MHz, CDCl$_3$): δ 7.553 (s, 1H), 7.903 (s, 1H), 5.152~5.227 (m, 1H), 4.100~4.184 (m, 2H), 3.674~3.739 (m, 4H), 2.681~2.724 (d, 2H), 2.580~2.610 (t, 4H), 2.288~2.325 (d, 3H), 2.065~2.103 (d, 2H), 1.479~1.677 (m, 7H).

Example 57

Synthesis of N-(1-isopropyl-1H-pyrazol-4-yl)-2-methyl-7-(((1r,4r)-4-morpho-linocyclohexyl)oxy)thiazolo[5,4-d]pyrimidin-5-amine I-57

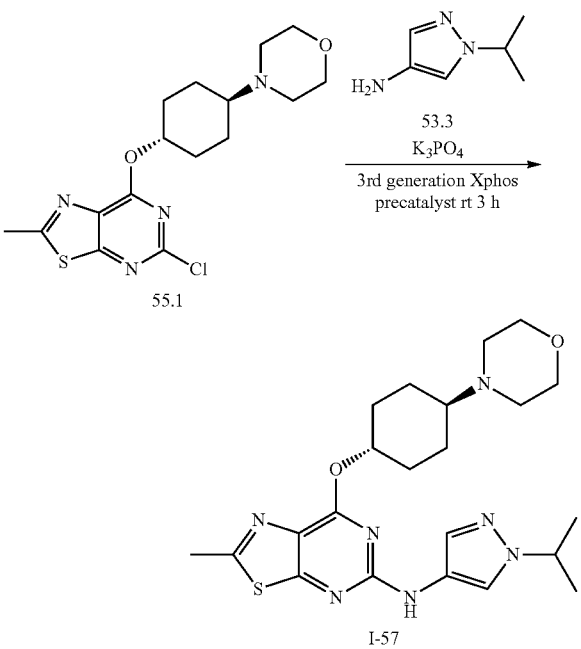

Into a 50 mL round-bottom flask, were placed a solution of intermediate 55.1 (200 mg, 0.54 mmol, 1.00 equiv) in tert-butanol (4 mL), compound 53.3 (135.87 mg, 1.09 mmol, 2.00 equiv), potassium phosphate (345.65 mg, 1.63 mmol, 3.00 equiv) and 3rd Generation Xphos precatalyst (22.99 mg, 0.05 equiv). The resulting solution was stirred for 3 h at room temperature. The resulting mixture was concentrated under vacuum and resulting crude was purified using preparative HPLC to furnish 101.8 mg (41%) of compound I-57 as a pink solid. LCMS (ES, m/z): 458 [M+H]$^+$; $^1$H NMR (400 MHz, d6-DMSO): δ 9.481 (s, 1H), 7.876 (s, 1H), 7.505 (s, 1H), 5.184-5.117 (m, 1H), 4.511-4.422 (m, 1H), 3.595-3.567 (m, 4H), 2.753 (s, 3H), 2.496 (s, 4H), 2.325-2.196 (m, 3H), 1.956-1.916 (d, 2H), 1.454-1.617 (m, 2H), 1.355-1.483 (m, 8H).

Example 58

Synthesis of 2-(methyl-d3)-N5-(1-methyl-1H-pyrazol-4-yl)-N7-((1r,4r)-4-morpholinocyclohexyl)thiazolo[5,4-d]pyrimidine-5,7-diamine I-58

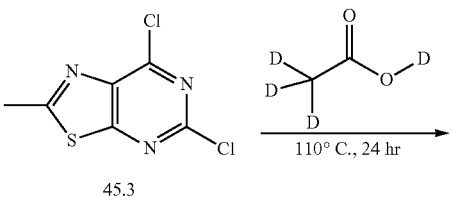

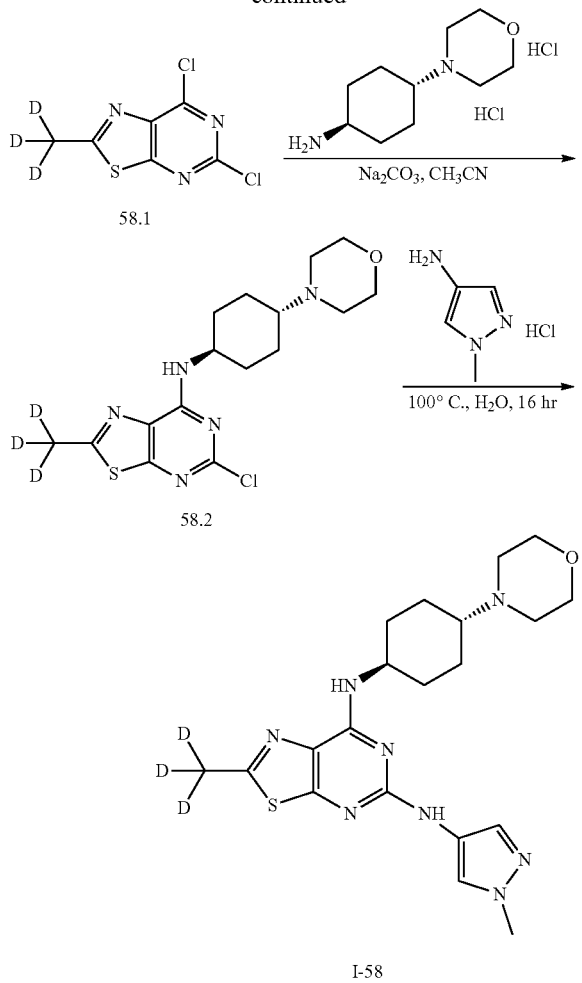

Synthesis of Intermediate 58.1.

A 10 mL round-bottom flask, was charged with compound 45.3 (500 mg, 2.27 mmol, 1.00 equiv) and acetic acid-d$_4$ (5 mL). The reaction was stirred for 24 hours at 110° C. The solids were filtered out and solvents were removed under reduced pressure to provide 450 mg (89%) of intermediate 58.1 as a yellow solid.

Synthesis of Intermediate 58.2.

A 25 mL round-bottom flask, was charged with intermediate 58.2 (444 mg, 1.99 mmol, 1.00 equiv), (1r,4r)-4-(morpholin-4-yl)cyclohexan-1-amine dihydrochloride (614 mg, 2.39 mmol, 1.20 equiv), Na$_2$CO$_3$ (424 mg, 4.00 mmol, 2.00 equiv) and CH$_3$CN (4 mL). The reaction was stirred for 3 hours at 80° C. Upon completion reaction mixture was diluted with water and extracted with CH$_2$Cl$_2$. The organic layers were combined and concentrated under vacuum. The crude product was triturated with hexanes to provide 500 mg (68%) of intermediate 58.2 as a yellow solid.

Synthesis of Compound I-58.

A 25 mL round-bottom flask was charged with intermediate 58.2 (65 mg, 0.18 mmol, 1.00 equiv), water (5 mL) and 1-methyl-1H-pyrazol-4-amine hydrochloride (47 mg, 0.35 mmol, 2.00 equiv). The reaction was stirred overnight at 100° C. in an oil bath. Upon completion the solution was adjusted to pH 9.0 with sodium carbonate. The resulting solids were collected by filtration, washed with CH$_3$CN (2×5 mL) and dried under vacuum to furnish 37.2 mg (49%) of compound I-58 as an off-white solid. LC-MS (ES, m/z): [M+H]$^+$=432.3; $^1$H NMR (CDCl$_3$, ppm): 7.866 (1H, s), 7.558 (1H, s), 4.013-4.017 (1H, m), 3.877 (3H, s), 3.715-3.746 (4H, m), 2.626-2.657 (4H, m), 2.041-2.334 (5H, m), 1.293-1.519 (4H, m).

Example 59

IRAK-4 Assay

| Assay Materials | | |
|---|---|---|
| Material | Vendor | Catalog number |
| HEPES | Amresco | 0511 |
| Brij-35 | Sigma | B4184-100mL |
| Coating Reagent #3 | Caliper | |
| EDTA | Sigma | E5134-1KG |
| ATP | Sigma | A7699-1G |
| MgCl$_2$ | Sigma | 63068-250G |
| MnCl$_2$ | Sigma | M8054-100G |
| Peptide 8 | GL bioscience | 112396 |
| IRAK4 | CARNA Bioscience | 09-145 |
| 384-wellplate | Corning | 3573 |

A 1× kinase base buffer was prepared from 50 mM HEPES, pH 7.5 and 0.0015% Brij-35. A stop buffer was prepared from 100 mM HEPES, pH 7.5, 0.015% Brij-35, 0.2% Coating Reagent #3, and 50 mM EDTA.

Test compound was diluted to 50× of the final desired highest inhibitor concentration in reaction by 100% DMSO. 100 ul of this compound dilution was transferred to a well in a 96-well plate. For example, if desired highest inhibitor concentration in IC50 determination is 100 uM, then prepare 5000 uM of compound DMSO solution in this step.

Test compound was serially diluted by transferring 30 μl to 60 μl of 100% DMSO in the next well and so forth for a total of 10 concentrations. 100 μl of 100% DMSO was added to two empty wells for no compound control and no enzyme control in the same 96-well plate.

A new 96-well plate was marked as intermediate plate. 5 μl of compound serial dilution was transferred from source plate to the corresponding wells of the intermediate plate. 45 μl of 1× kinase base buffer (KB buffer) was added to each well of the intermediate plate. The intermediate plate was placed for 10 min on a shaker.

5 μl of each well was transferred from the 96-well intermediate plate to a 384-well plate in duplicates. For example, A1 of the 96-well plate is transferred to A1 and A2 of the 384-well plate. A2 of the 96-well plate is transferred to A3 and A4 of the 384-well plate, and so on.

IRAK4 and DTT in 1× kinase base buffer was added. The 2.5× enzyme mix contained 8.8 nM IRAK4 and 5 mM DTT.

Peptide 8, ATP, MgCl$_2$ and MnCl$_2$ were added in the 1× kinase base buffer. The 2.5× peptide mix contained 3.75 μM peptide 8, 92.5 μM ATP, 12.5 mM MgCl$_2$ and 2.5 mM MnCl$_2$.

Assay plate already contained 5 μl of compound in 10% DMSO. Added 10 μl of 2.5× enzyme solution to each well of the 384-well assay plate, except no enzyme control wells. The final concentration of IRAK4 in reaction was 3.5 nM. Added 10 μl of 1× kinase base buffer to no enzyme control wells in the assay plate. Incubated at room temperature for 10 min.

Added 10 μl of 2.5× peptide solution to each well of the 384-well assay plate. The final concentration of Peptide 8 and ATP was 1.5 μM and 37 μM, respectively. Incubated at 28° C. for 40 minutes. Added 25 μl of stop buffer to stop reaction. Collected data on Caliper.

Copied conversion % data from Caliper program. Converted conversion % values to percent inhibition values. Percent inhibition=(max-conversion %)/(max-min)*100, where "max" means the conversion % of DMSO control and "min" means the conversion % of no enzyme control.

Table 2 shows the activity of selected compounds of this invention in the IRAK-4 activity inhibition assay. The compound numbers correspond to the compound numbers in Table 1. Compounds having an activity designated as "A" provided an $IC_{50} \leq 1$ µM; compounds having an activity designated as "B" provided an $IC_{50}$ of 1-5 µM; compounds having an activity designated as "C" provided an $IC_{50}$ of $\geq 5$ µM. "NA" stands for "not assayed."

TABLE 2

IRAK-4 Activity Inhibition Data

| Cpd # | IRAK-4 |
|---|---|
| I-1 | B |
| I-2 | B |
| I-3 | C |
| I-4 | B |
| I-5 | B |
| I-6 | C |
| I-7 | A |
| I-8 | A |
| I-9 | A |
| I-10 | A |
| I-11 | B |
| I-12 | A |
| I-13 | A |
| I-14 | A |
| I-15 | A |
| I-16 | A |
| I-17 | A |
| I-18 | A |
| I-19 | A |
| I-20 | B |
| I-21 | A |
| I-22 | A |
| I-23 | A |
| I-24 | A |
| I-25 | A |
| I-26 | A |
| I-27 | A |
| I-28 | A |
| I-29 | A |
| I-30 | A |
| I-31 | C |
| I-32 | A |
| I-33 | A |
| I-34 | A |
| I-35 | A |
| I-36 | A |
| I-37 | A |
| I-38 | A |
| I-39 | A |
| I-40 | A |
| I-41 | A |
| I-42 | A |
| I-43 | C |
| I-44 | A |
| I-45 | A |
| I-46 | A |
| I-47 | A |
| I-48 | A |
| I-49 | A |
| I-50 | B |
| I-51 | A |
| I-52 | A |
| I-53 | A |
| I-54 | A |
| I-57 | A |
| I-58 | A |

Provided compounds were also assayed as inhibitors of IRAK-1. In certain embodiments, a provided compound inhibits IRAK-1 with an $IC_{50} \leq 5$ µM. In some embodiments, a provided compound inhibits IRAK-1 with an $IC_{50}$ of 5-20 µM. In other embodiments, a provided compound inhibits IRAK-1 with an $IC_{50}$ of 20-50 µM.

Provided compounds were also assayed in a panel of 334 kinases and were found to be highly selective for IRAK4. Provided compounds were also assayed for inhibition of IL-1-induced IRAK1 degradation in MRC5 cells, LPS- and R848 (TLR-7 agonist)-induced cytokine expression in human whole blood, and found to be potent inhibitors in those assays.

Provided compounds were also assayed to determine their $K_i$ versus IRAK-4 using a Reaction Biology radioactive kinase assay. All of compounds I-1 through I-25 were found to have $K_i$ values within the range from about 1 nM to about 100 nM.

Example 60

Cytokine Production Assay

Provided compounds were also assayed in an LPS (Lipopolysacharide) or R848 (TLR-7 agonist) induced cytokine (TNFα and IL8) production assay in THP-1 cells, human white blood cells (hWBC), and whole blood. The exemplary protocol for this assay in THP-1 cells was as follows below.

THP-1 cells from ATCC (TIB-202) were cultured in RPMI Medium 1640 (Invitrogen, Cat No. A10491-01), 10% fetal bovine serum (Invitrogen, Cat No. 10099141, Lot No. 8172882) containing 100 U/mL Penicillin, 100 µg/mL streptomycin (Invitrogen, Cat No. 15140-122), and 50 uM 2-Mercaptoethanol (Invitrogen, Cat No. 21985023). LPS-EK ultra pure (Invivogen, Cat No. tlrl-peklps) was used to induce IL8 and TNFα production, that was detected in the cell culture supernatant by IL8 HTRF kit (Cisbio, Cat No. 62IL8PEB) and TNFα HTRF kit (Cisbio, Cat No. 62TNF-PEB), as per manufacturer instructions. Cells were cultured in 96 well assay plates at 100,000 cells per well, and compounds diluted in final 0.3% DMSO were pre-incubated with cells for 1 hour prior to stimulation with 300 ng/mL LPS. Cytokine production in cell supernatant was measured at 5 hours for TNFα and IL8 production, and for 16 hours for IL8 production and assessment of cell viability.

Table 3 shows the activity of selected compounds of this invention in the TNFα and IL8 production assay. The compound numbers correspond to the compound numbers in Table 1. Compounds having an activity designated as "A" provided an $IC_{50} \leq 0.25$ µM; compounds having an activity designated as "B" provided an $IC_{50}$ of 0.25-0.5 µM; and compounds having an activity designated as "C" provided an $IC_{50}$ of $\geq 0.5$ µM. "NA" stands for "not assayed."

TABLE 3

TNF and IL8 Production Assay

| Cpd # | TNFα | IL8 (16 h) |
|---|---|---|
| I-7 | A | A |
| I-8 | A | A |
| I-9 | A | A |
| I-10 | A | A |
| I-12 | B | B |
| I-19 | A | NA |
| I-21 | A | A |
| I-22 | B | A |
| I-26 | A | A |
| I-23 | B | A |
| I-24 | C | B |

TABLE 3-continued

TNF and IL8 Production Assay

| Cpd # | TNFα | IL8 (16 h) |
|---|---|---|
| I-25 | A | A |
| I-27 | B | A |
| I-28 | B | A |
| I-29 | C | A |
| I-18 | A | A |
| I-14 | A | A |
| I-13 | A | A |
| I-16 | A | NA |
| I-30 | C | NA |
| I-17 | A | NA |
| I-32 | A | A |
| I-33 | A | A |
| I-34 | A | A |
| I-35 | C | C |
| I-36 | B | A |
| I-37 | C | C |
| I-38 | C | B |
| I-39 | B | B |
| I-40 | A | B |
| I-42 | B | B |

Example 61

In Vitro LPS/R848/CpG-Induced Cytokine Production Assays in hWBC or Whole Blood Compounds of the present invention were also studied in in vitro LPS/R848/CpG-induced cytokine production assays. Exemplary protocols follow.

Whole Blood (LPS): 13 mL of whole blood solution was prepared by combining whole blood in no serum medium with a ratio of 1:1. Cells were seeded in a 96-well plate with 130 ul/well of the cell suspension according to the plate map. 9 ul of 30 mM compound solution was added into the wells in the assigned rows, then serial solutions with 4× dilutions were made. That is, add 9 uL of 100% DMSO into each of the rest wells and take 3 uL of compound solution from the one-step higher concentration solution and mix well with the DMSO. For the second compound master plate, 196 uL of the growth medium (no serum media) were added into each of the wells and 4 uL of the compound solution from the first compound master plate was added and mixed with the media. Cells were treated for 0.5 h by adding 20 uL of the compound and the control solutions prepared in the second master plate to each well according to the plate map. Cells were stimulated with a) 0.1 ug/mL of LPS overnight for whole blood assay; b) 0.01 ug/mL of LPS overnight for hWBC assay. Plates were sealed with sealing films and the plates were centrifuged at 3000 rpm at 4 degrees C. for 5 min. The supernatants were transferred, and 100 ul of working Capture antibody solution was added to each well. The plates were sealed and incubated overnight at RT. IL-6, IFN-α or TNF-α detection antibody labeled with biotin: Added 100 uL of the Detection Antibody solution to each well. Covered the plate and incubated for 2 h at RT. Added 100 uL of Streptavidin-HRP solution to each well. Covered the plate and incubate for 20 min at RT in dark. Added 100 uL of Substrate Solution to each well. Incubated for 20 min at RT in dark. Added 50 uL of Stop Solution to each well. Gently tapped the plate to ensure thorough mixing. Determined the optical density of each well immediately, using a microplate reader set to 450 nm and also read at 540 nm or 570 nm for correction if wavelength correction is not available.

For R848-induced or CpG-induced assays, the same procedure as above was followed except that 1 uM R848 for 20 h for TNF-α production, and for 5 hr for INF-α production in whole blood; 1 uM R848 for 5 h for hWBC cytokine production; or 0.5 uM or 0.1 uM CpG or 1 ng/mL IL-1-β overnight for hWBC cytokine production were used as indicated in Table 5, instead of LPS. Data from the whole blood and hWBC cytokine production assays is shown in Table 4. Compounds having an activity designated as "A" provided an $IC_{50} \leq 0.25$ μM; compounds having an activity designated as "B" provided an $IC_{50}$ of 0.25-1.0 μM; compounds having an activity designated as "C" provided an $IC_{50}$ of 1.0-5.0 μM; and compounds having an activity designated as "D" provided an $IC_{50} \geq 5.0$ μM.

TABLE 4

Results of in vitro cytokine production assays

| | | | | Test Compound | | |
|---|---|---|---|---|---|---|
| Cells | Stimulant | Conc. | Cytokine | I-7 | I-9 | I-24 |
| Whole Blood | LPS | 0.1 uM | TNF-α | D | C | D |
| | R848 | 1 uM | TNF-α | C | B | C |
| WBC | CPG | 0.5 uM | IFN-α | A | A | A |
| | LPS | 0.1 uM | TNF-α | B | A | A |
| | R848 | 1 uM | TNF-α | B | A | A |

Example 62

In Vivo LPS-Induced Cytokine Production

Compounds of the present invention were also assayed in vivo to determine their inhibitory effect on LPS-induced cytokine production. In vivo studies of LPS-induced cytokine production was conducted in female Lewis rats (n=10 each). Rats were dosed with compound at 30, 10, 3, or 1 mg/kg, 5 mg/kg dexamethasone, or vehicle, dosed PO in 0.5% methylcellulose. After 2 hours, rats were administered LPS in PBS at 0.1 mg/mL, 1 mL/kg. One hour later, rats were bled and serum was analyzed for TNF-α produced by ELISA (eBioscience).

Certain compounds of the invention inhibit ~50% of the LPS induced TNF production in vivo, at average drug concentrations greater than 2 uM and higher. Compounds I-7, I-9 and I-24 inhibited LPS induced TNF production in vivo in rats at a minimal efficacious dose of 10 mg/kg, corresponding to drug concentrations of 1.6 uM, 1.05 uM and 6.6 uM respectively.

While we have described a number of embodiments of this invention, it is apparent that our basic examples may be altered to provide other embodiments that utilize the compounds and methods of this invention. Therefore, it will be appreciated that the scope of this invention is to be defined by the appended claims rather than by the specific embodiments that have been represented by way of example.

We claim:

1. A compound of formula I:

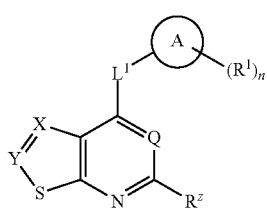

or a pharmaceutically acceptable salt thereof, wherein:

Q is N;
X is N and Y is C—$R^x$;
Ring A is a 3-7 membered saturated or partially unsaturated carbocyclic ring;
$R^1$ is Cy;
each $R^{1'}$ is independently —$R^2$, halogen, —CN, —$NO_2$, —OR, —SR, —$N(R)_2$, —$S(O)_2R$, —$S(O)_2N(R)_2$, —S(O)R, —C(O)R, —C(O)OR, —C(O)N(R)_2, —C(O)N(R)OR, —N(R)C(O)OR, —N(R)C(O)N(R)_2, Cy, or —N(R)S(O)_2R;
each Cy is an optionally substituted ring selected from a 3-7 membered saturated or partially unsaturated carbocyclic ring or a 4-10 membered saturated or partially unsaturated heterocyclic ring having 1-3 heteroatoms independently selected from nitrogen, oxygen, or sulfur;
each R is independently hydrogen, or an optionally substituted group selected from $C_{1-6}$ aliphatic, phenyl, 4-7 membered saturated or partially unsaturated heterocyclic having 1-2 heteroatoms independently selected from nitrogen, oxygen, or sulfur, or 5-6 membered heteroaryl ring having 1-4 heteroatoms independently selected from nitrogen, oxygen, or sulfur, or:

two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, or sulfur;

each $R^2$ is independently an optionally substituted group selected from $C_{1-6}$ aliphatic, phenyl, 4-7 membered saturated or partially unsaturated heterocyclic having 1-2 heteroatoms independently selected from nitrogen, oxygen, or sulfur, or 5-6 membered heteroaryl ring having 1-4 heteroatoms independently selected from nitrogen, oxygen, or sulfur;

$R^x$ is hydrogen, —$R^2$, —CN, —$NO_2$, halogen, —C(O)N(R)_2, —C(O)OR, —C(O)R, —$N(R)_2$, —NH[Ar], —OR, or —$S(O)_2N(R)_2$;

$R^z$ is hydrogen, —$N(R)_2$, or —NH[Ar];

[Ar] is a 5-membered heteroaromatic ring substituted by m instances of $R^{1'}$;

$L^1$ is a covalent bond or a $C_{1-6}$ bivalent hydrocarbon chain wherein one or two methylene units of the chain are optionally and independently replaced by —N(R)—, —N(R)C(O)—, —C(O)N(R)—, —N(R)S(O)_2—, —S(O)_2N(R)—, —O—, —C(O)—, —OC(O)—, —C(O)O—, —S—, —S(O)— or —$S(O)_2$—;

m is 0-4; and
n is 1.

2. The compound of claim 1 of Formula IV-i:

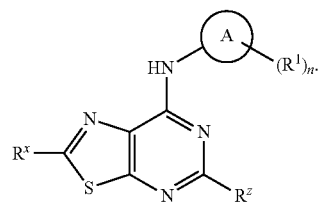

3. The compound of claim 1 of Formula VI:

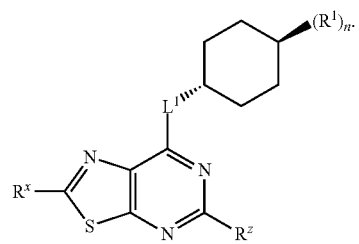

4. The compound of claim 1 wherein $R^z$ is —NH[Ar].

5. A compound of formula I:

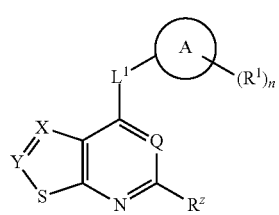

or a pharmaceutically acceptable salt thereof, wherein:
Q is N;
X is N and Y is C—$R^x$;
Ring A is a cyclohexyl ring;
each $R^1$ and $R^{1'}$ is independently —$R^2$, halogen, —CN, —$NO_2$, —OR, —SR, —$N(R)_2$, —$S(O)_2R$, —$S(O)_2N(R)_2$, —S(O)R, —C(O)R, —C(O)OR, —C(O)N(R)_2, —C(O)N(R)OR, —N(R)C(O)OR, —N(R)C(O)N(R)_2, Cy, or —N(R)S(O)_2R; or $R^1$ is selected from one of the following formulas:

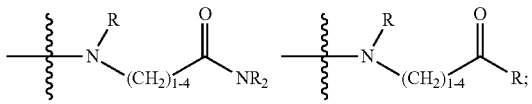

or
two $R^1$ groups are taken together with their intervening atoms to form an optionally substituted 4-7 membered fused, spiro-fused, or bridged bicyclic ring having 0-2 heteroatoms independently selected from nitrogen, oxygen, or sulfur;
each Cy is an optionally substituted ring selected from a 3-7 membered saturated or partially unsaturated carbocyclic ring or a 4-10 membered saturated or partially unsaturated heterocyclic ring having 1-3 heteroatoms independently selected from nitrogen, oxygen, or sulfur;
each R is independently hydrogen, or an optionally substituted group selected from $C_{1-6}$ aliphatic, phenyl, 4-7 membered saturated or partially unsaturated heterocyclic having 1-2 heteroatoms independently selected from nitrogen, oxygen, or sulfur, or 5-6 membered heteroaryl ring having 1-4 heteroatoms independently selected from nitrogen, oxygen, or sulfur, or:

two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, or sulfur;

each $R^2$ is independently an optionally substituted group selected from $C_{1-6}$ aliphatic, phenyl, 4-7 membered saturated or partially unsaturated heterocyclic having 1-2 heteroatoms independently selected from nitrogen, oxygen, or sulfur, or 5-6 membered heteroaryl ring having 1-4 heteroatoms independently selected from nitrogen, oxygen, or sulfur;

$R^x$ is hydrogen, —$R^2$, —CN, —$NO_2$, halogen, —C(O)N(R)$_2$, —C(O)OR, —C(O)R, —N(R)$_2$, —NH[Ar], —OR, or —S(O)$_2$N(R)$_2$;

$R^z$ is hydrogen, —N(R)$_2$, or —NH-pyrazolyl, wherein the pyrazolyl ring is substituted with m instances of $R^{1'}$;

[Ar] is a phenyl or heteroaromatic ring substituted by m instances of $R^{1'}$;

$L^1$ is —N(R)— or —O—;

m is 0-4; and n is 0-4.

6. A compound selected from any one of the following, or a pharmaceutically acceptable salt thereof:

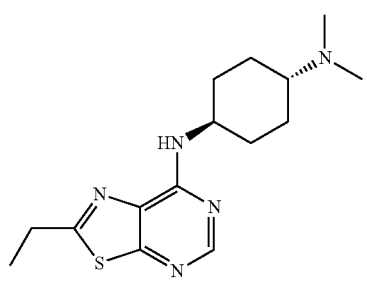

I-1

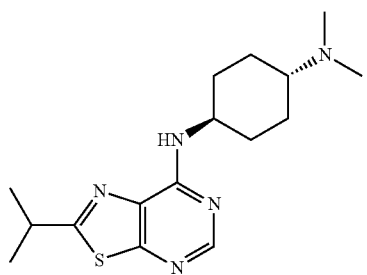

I-2

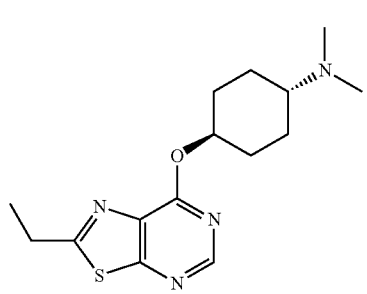

I-3

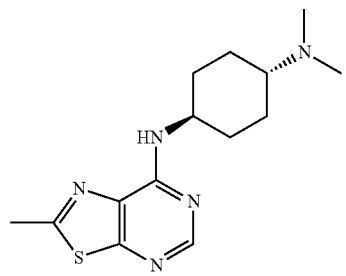

I-4

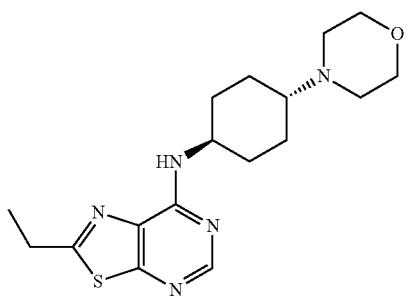

I-5

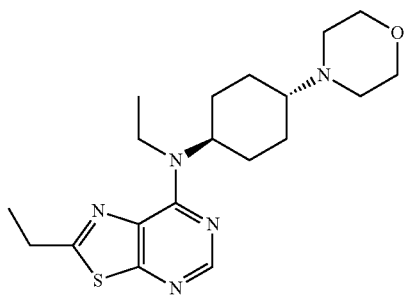

I-6

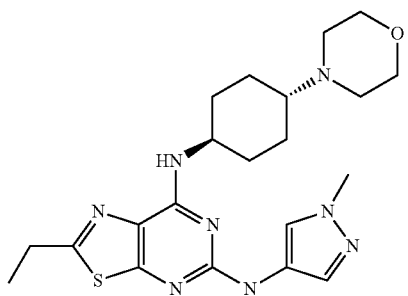

I-7

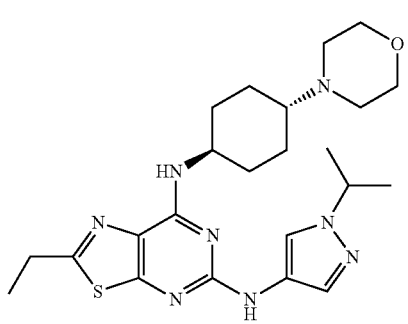

I-8

-continued
I-9
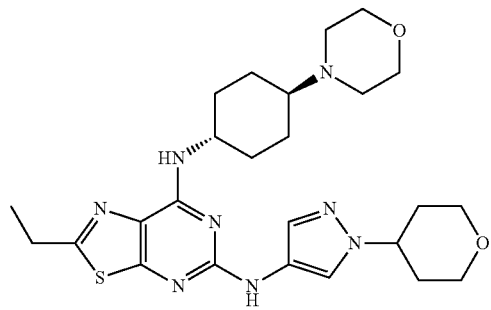
I-10
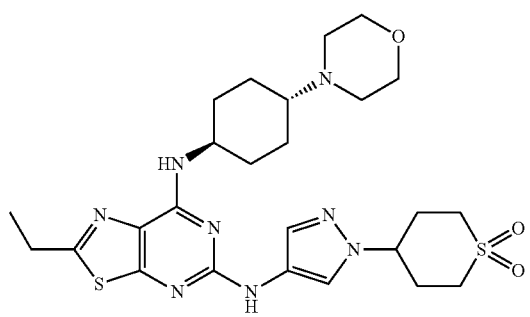
I-11
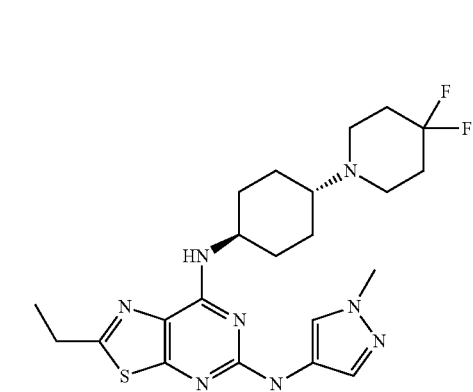
I-12
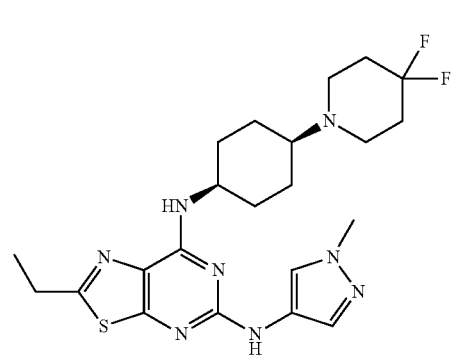
-continued
I-13
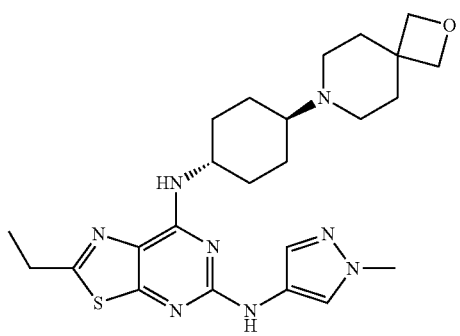 [SMILES: CCc1nc2c(N[C@H]3CC[C@H](N4CCC5(CC4)COC5)CC3)nc(Nc3cnn(C)c3)nc2s1]
I-14
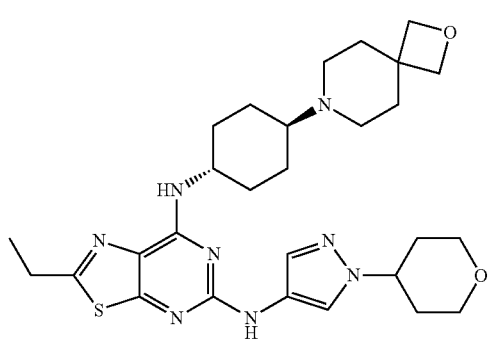 [SMILES: CCc1nc2c(N[C@H]3CC[C@H](N4CCC5(CC4)COC5)CC3)nc(Nc3cnn(C4CCOCC4)c3)nc2s1]
I-15
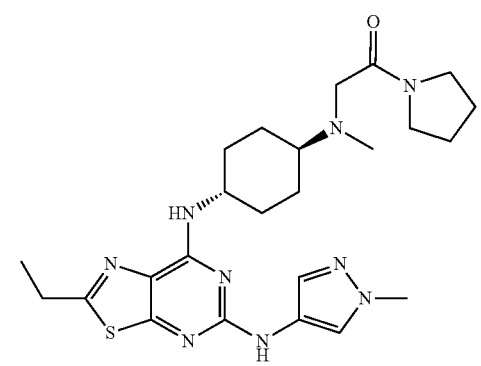 [SMILES: CCc1nc2c(N[C@H]3CC[C@H](N(C)CC(=O)N4CCCC4)CC3)nc(Nc3cnn(C)c3)nc2s1]
I-16
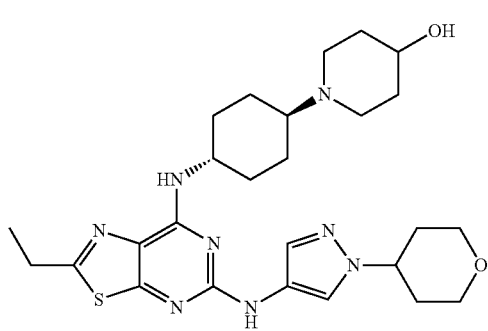 [SMILES: CCc1nc2c(N[C@H]3CC[C@H](N4CCC(O)CC4)CC3)nc(Nc3cnn(C4CCOCC4)c3)nc2s1]

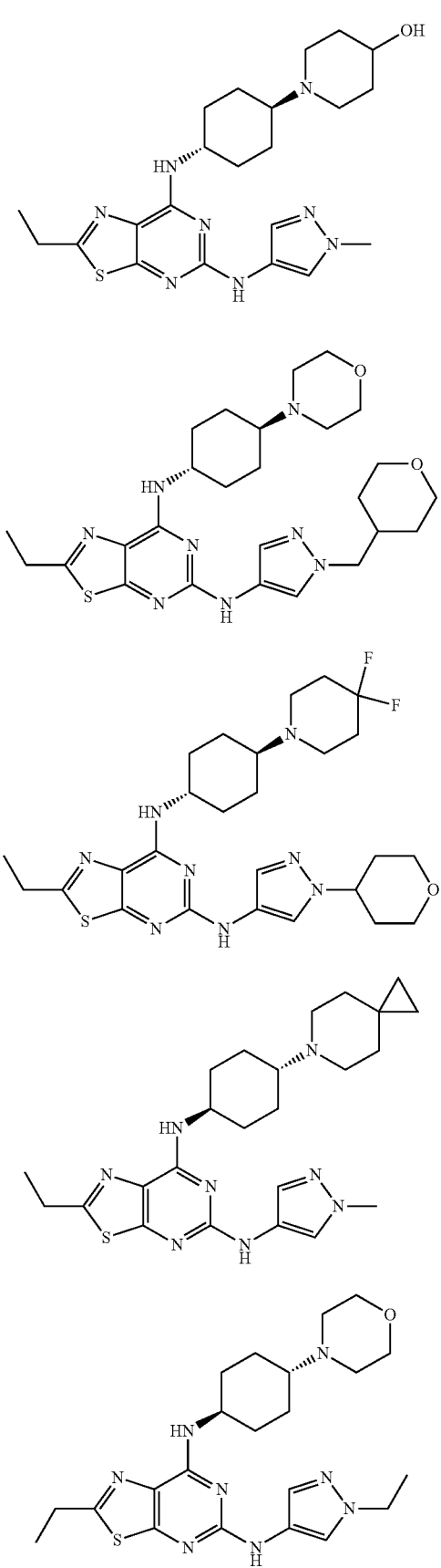
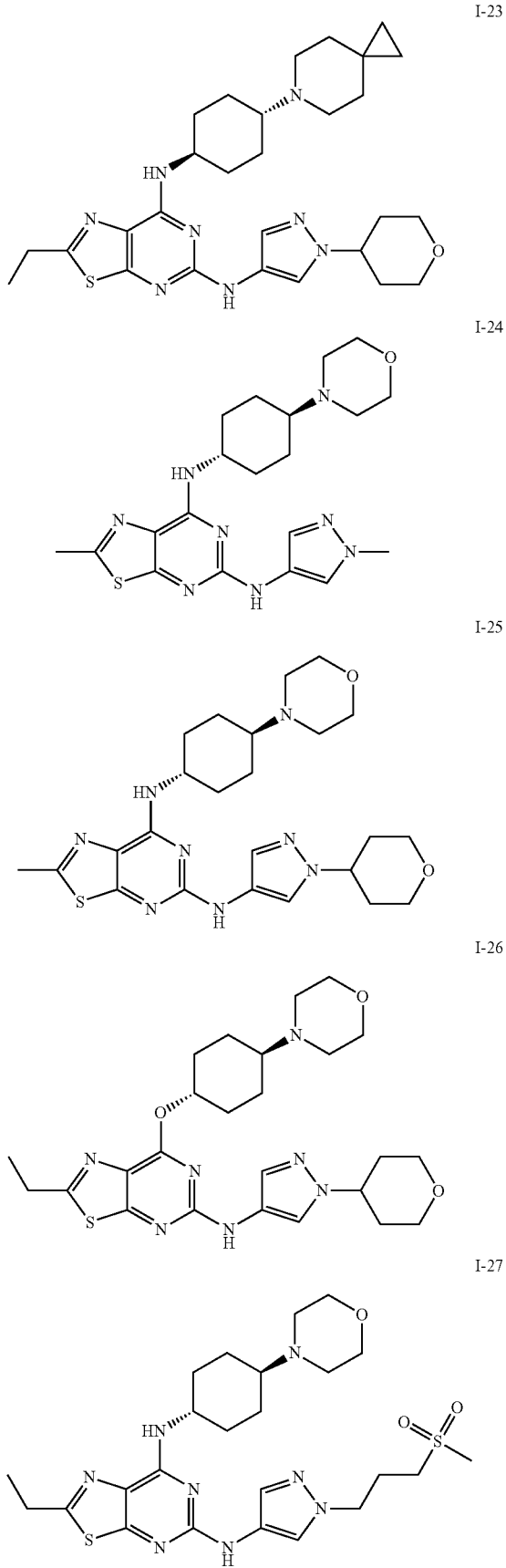

I-28
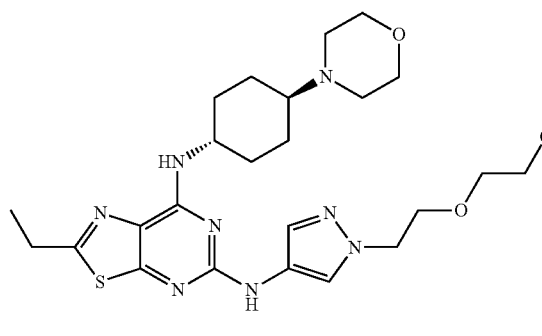
I-29
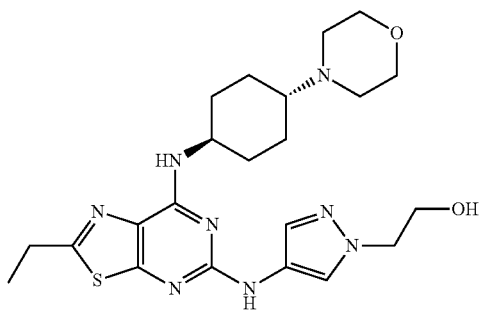
I-30
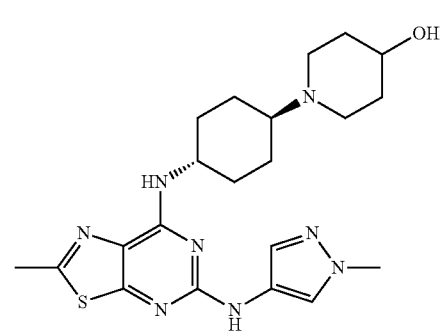 [SMILES: Cc1nc2c(N[C@H]3CC[C@H](N4CCC(O)CC4)CC3)nc(Nc3cnn(C)c3)nc2s1]
I-31
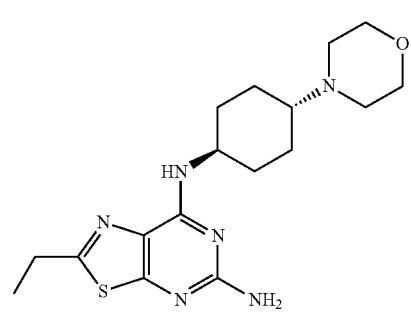 [SMILES: CCc1nc2c(N[C@H]3CC[C@H](N4CCOCC4)CC3)nc(N)nc2s1]
I-32
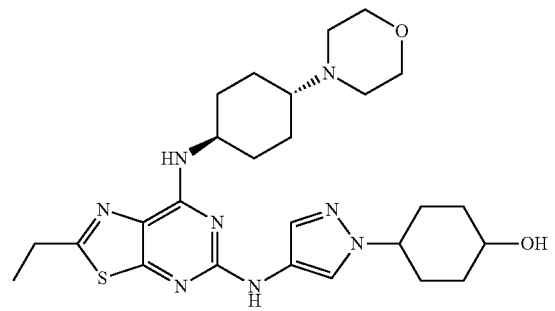
I-33
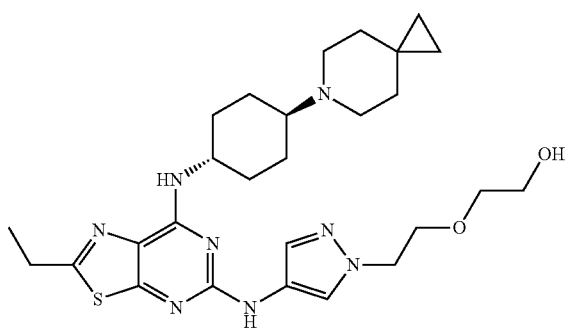
I-34
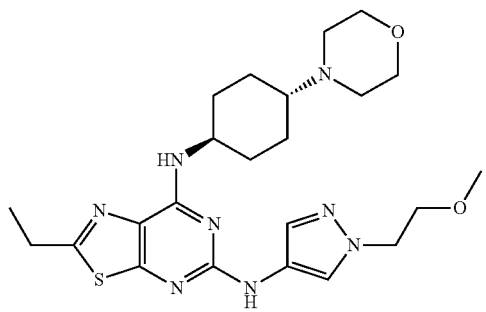
I-35
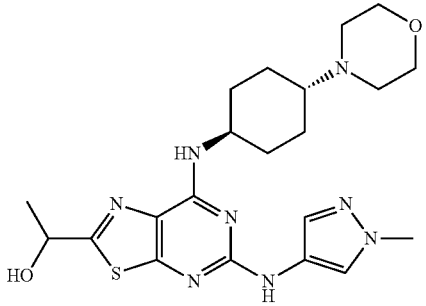 [SMILES: CC(O)c1nc2c(N[C@H]3CC[C@H](N4CCOCC4)CC3)nc(Nc3cnn(C)c3)nc2s1]
I-36
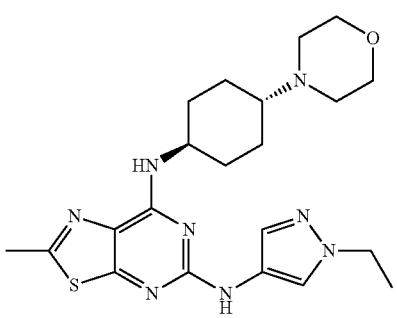
I-37
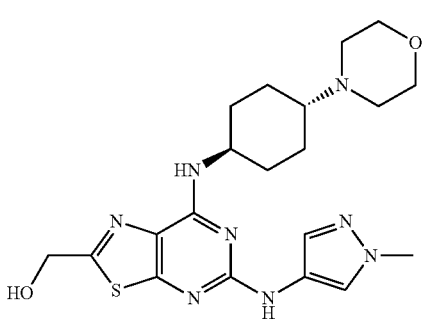 [SMILES: Cn1cc(Nc2nc(N[C@H]3CC[C@H](N4CCOCC4)CC3)c3nc(CO)sc3n2)cn1]

I-38
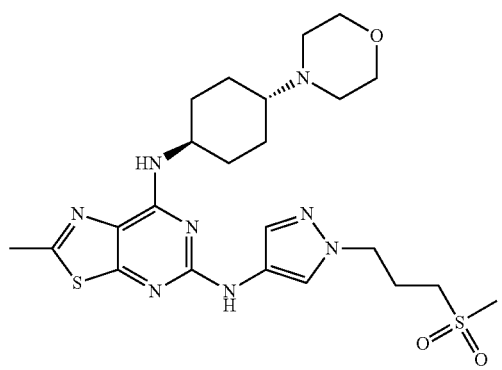
I-39
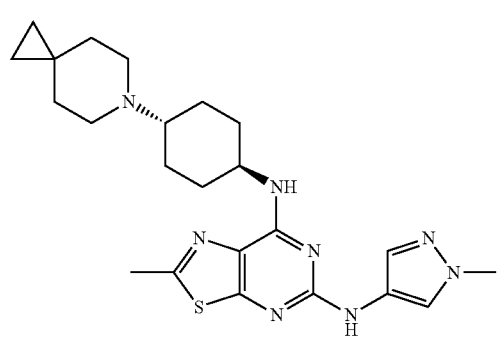 [SMILES: Cc1nc2c(N[C@H]3CC[C@H](N4CCC5(CC4)CC5)CC3)nc(Nc3cnn(C)c3)nc2s1]
I-40
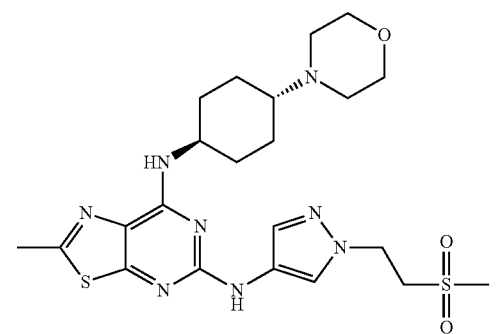
I-41
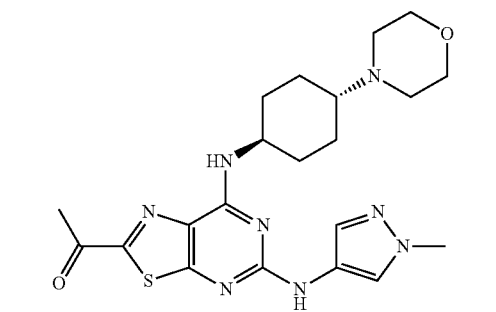 [SMILES: CC(=O)c1nc2c(N[C@H]3CC[C@H](N4CCOCC4)CC3)nc(Nc3cnn(C)c3)nc2s1]
I-42
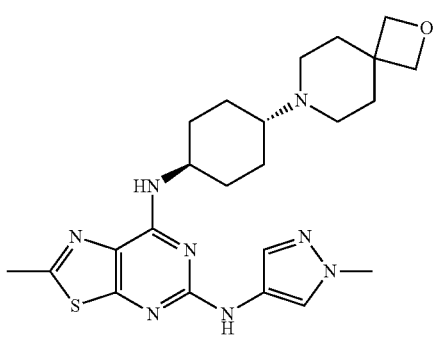
I-43
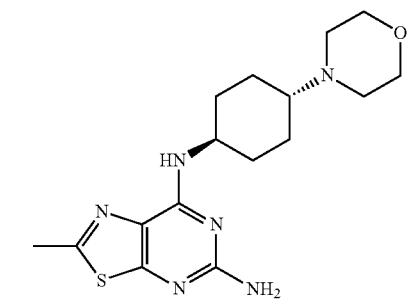 [SMILES: Cc1nc2c(N[C@H]3CC[C@H](N4CCOCC4)CC3)nc(N)nc2s1]
I-44
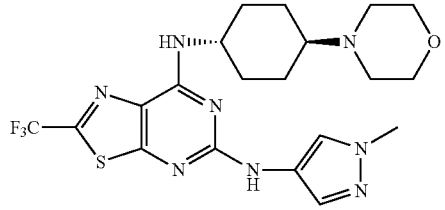 [SMILES: Cn1cc(Nc2nc(N[C@H]3CC[C@H](N4CCOCC4)CC3)c3nc(C(F)(F)F)sc3n2)cn1]
I-45
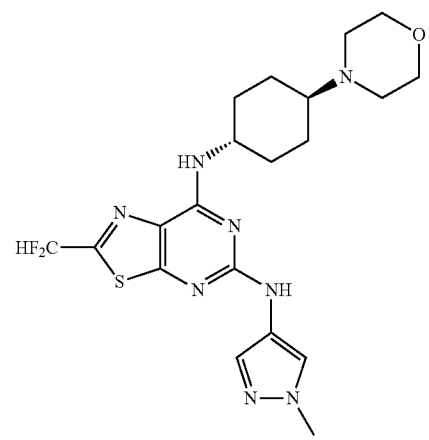
I-46
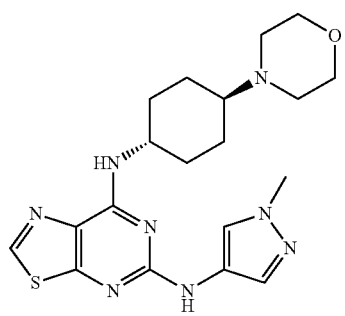 [SMILES: Cn1cc(Nc2nc(N[C@H]3CC[C@H](N4CCOCC4)CC3)c3ncsc3n2)cn1]

I-47 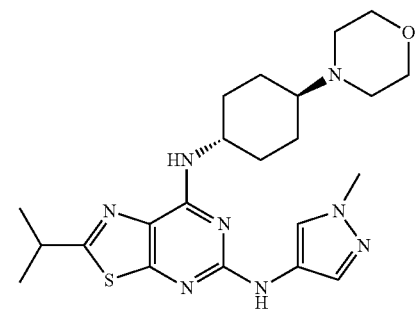 [SMILES: CC(C)c1nc2c(N[C@H]3CC[C@H](N4CCOCC4)CC3)nc(Nc3cnn(C)c3)nc2s1]
I-48 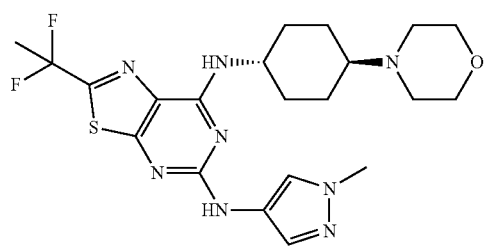 [SMILES: Cn1cc(Nc2nc(N[C@H]3CC[C@H](N4CCOCC4)CC3)c3nc(C(C)(F)F)sc3n2)cn1]
I-49 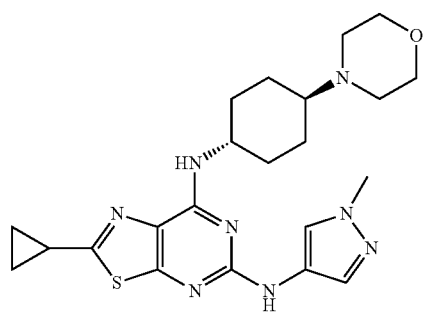 [SMILES: Cn1cc(Nc2nc(N[C@H]3CC[C@H](N4CCOCC4)CC3)c3nc(C4CC4)sc3n2)cn1]
I-50 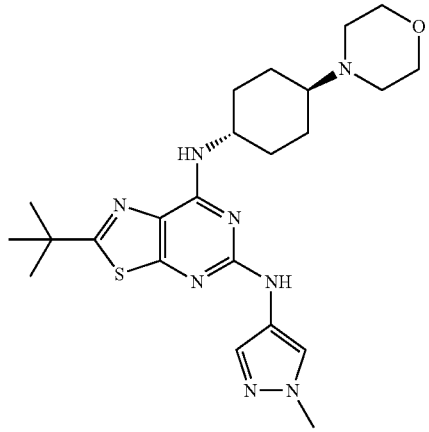 [SMILES: Cn1cc(Nc2nc(N[C@H]3CC[C@H](N4CCOCC4)CC3)c3nc(C(C)(C)C)sc3n2)cn1]
I-51 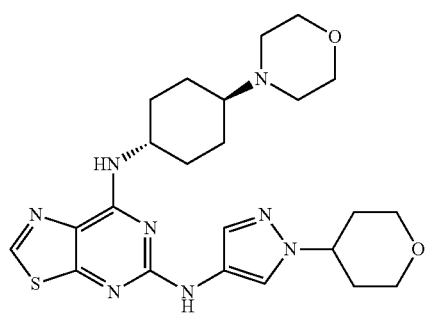
I-52 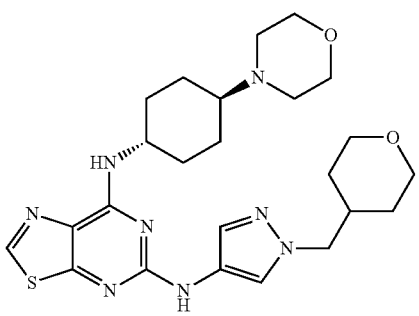
I-53 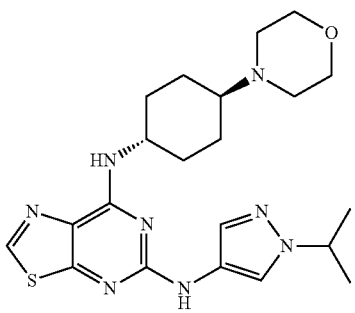 [SMILES: CC(C)n1cc(Nc2nc(N[C@H]3CC[C@H](N4CCOCC4)CC3)c3ncsc3n2)cn1]
I-54 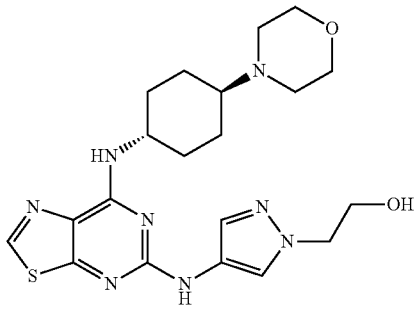 [SMILES: OCCn1cc(Nc2nc(N[C@H]3CC[C@H](N4CCOCC4)CC3)c3ncsc3n2)cn1]
I-55 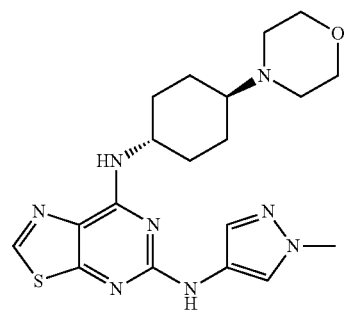
I-56 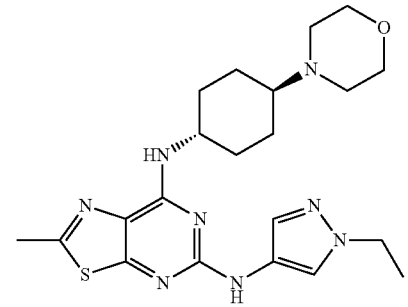 [SMILES: CCn1cc(Nc2nc(O[C@H]3CC[C@H](N4CCOCC4)CC3)c3nc(C)sc3n2)cn1]

-continued

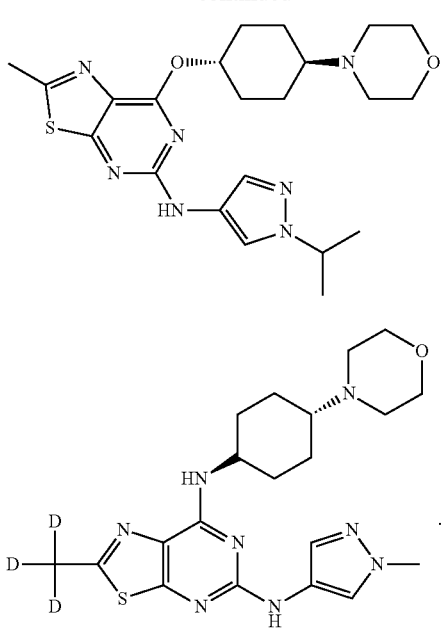

I-57

I-58

7. The compound of claim 1 wherein m is 1 and $R^{1'}$ is an optionally substituted group selected from $C_{1-6}$ aliphatic, phenyl, 4-7 membered saturated or partially unsaturated heterocyclic having 1-2 heteroatoms independently selected from nitrogen, oxygen, or sulfur, or 5-6 membered heteroaryl ring having 1-4 heteroatoms independently selected from nitrogen, oxygen, or sulfur.

8. The compound of claim 7 wherein $R^{1'}$ is optionally substituted $C_{1-6}$ aliphatic.

9. The compound of claim 7 wherein $R^{1'}$ is an optionally substituted 4-7 membered saturated or partially unsaturated heterocyclic having 1-2 heteroatoms independently selected from nitrogen, oxygen, or sulfur.

10. The compound of claim 5 wherein n is 1 and $R^1$ is Cy.

11. The compound of claim 5 wherein m is 1 and $R^{1'}$ is an optionally substituted group selected from $C_{1-6}$ aliphatic, phenyl, 4-7 membered saturated or partially unsaturated heterocyclic having 1-2 heteroatoms independently selected from nitrogen, oxygen, or sulfur, or 5-6 membered heteroaryl ring having 1-4 heteroatoms independently selected from nitrogen, oxygen, or sulfur.

12. The compound of claim 11 wherein $R^{1'}$ is an optionally substituted 4-7 membered saturated or partially unsaturated heterocyclic having 1-2 heteroatoms independently selected from nitrogen, oxygen, or sulfur.

13. The compound of claim 11 wherein $R^{1'}$ is $C_{1-3}$ alkyl.

14. A pharmaceutical composition comprising a compound according to claim 1, and a pharmaceutically acceptable carrier, adjuvant, or vehicle.

* * * * *